(12) United States Patent
Daly

(10) Patent No.: US 11,542,450 B2
(45) Date of Patent: Jan. 3, 2023

(54) BIOLOGICAL BUFFERS WITH WIDE BUFFERING RANGES

(71) Applicant: Thomas Daly, Arlington Heights, IL (US)

(72) Inventor: Thomas Daly, Arlington Heights, IL (US)

(73) Assignee: TPAT IP LLC, Chicago, IL (US)

( * ) Notice: Subject to any disclaimer, the term of this patent is extended or adjusted under 35 U.S.C. 154(b) by 53 days.

(21) Appl. No.: 16/661,822

(22) Filed: Oct. 23, 2019

(65) Prior Publication Data

US 2021/0147756 A1    May 20, 2021

Related U.S. Application Data

(63) Continuation of application No. 15/606,757, filed on May 26, 2017, now abandoned, which is a (Continued)

(51) Int. Cl.
*C10L 1/2387* (2006.01)
*C10L 1/233* (2006.01)
(Continued)

(52) U.S. Cl.
CPC .......... *C10L 1/2387* (2013.01); *C07C 205/15* (2013.01); *C07C 205/40* (2013.01); *C07C 215/08* (2013.01); *C07C 217/08* (2013.01); *C07C 217/28* (2013.01); *C07C 217/48* (2013.01); *C07C 219/06* (2013.01); *C07C 219/22* (2013.01); *C07C 229/12* (2013.01); *C07C 229/22* (2013.01); *C07C 309/14* (2013.01); *C07D 213/74* (2013.01); *C07D 295/088* (2013.01); *C07D 295/15* (2013.01); *C07F 9/091* (2013.01); *C07F 9/3808* (2013.01); *C07F 9/3817* (2013.01); *C07F 9/58* (2013.01); *C09K 3/00* (2013.01); *C10L 1/10* (2013.01); *C10L 1/22* (2013.01); *C10L 1/2222* (2013.01); *C10L 1/2225* (2013.01); *C10L 1/238* (2013.01); *C10L 1/2335* (2013.01); *C10L 1/2437* (2013.01); *C10L 1/2608* (2013.01); *C10L 1/2633* (2013.01); *C11D 1/66* (2013.01)

(58) Field of Classification Search
CPC ...................................................... C10L 1/2387
See application file for complete search history.

(56) References Cited

U.S. PATENT DOCUMENTS 4,568,358 A * 2/1986 Courtney ................ C10L 10/04
                                                          44/434
4,604,103 A * 8/1986 Campbell ............. C10L 1/2225
                                                          44/434

(Continued)

*Primary Examiner* — Ellen M McAvoy
*Assistant Examiner* — Ming Cheung Po
(74) *Attorney, Agent, or Firm* — Clifford H. Kraft

(57) ABSTRACT

Amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

13 Claims, 134 Drawing Sheets

Related U.S. Application Data continuation-in-part of application No. 15/255,654, filed on Sep. 2, 2016, now abandoned, which is a continuation of application No. 14/810,106, filed on Jul. 27, 2015, now Pat. No. 9,447,310, which is a continuation-in-part of application No. 14/079,369, filed on Nov. 13, 2013, now Pat. No. 9,090,638, which is a continuation-in-part of application No. 13/588,530, filed on Aug. 17, 2012, now Pat. No. 8,822,728.

(60) Provisional application No. 62/396,871, filed on Sep. 20, 2016, provisional application No. 62/341,850, filed on May 26, 2016, provisional application No. 62/110,331, filed on Jan. 30, 2015, provisional application No. 61/726,417, filed on Nov. 14, 2012, provisional application No. 61/635,023, filed on Apr. 18, 2012, provisional application No. 61/621,862, filed on Apr. 9, 2012, provisional application No. 61/606,063, filed on Mar. 2, 2012, provisional application No. 61/566,259, filed on Dec. 2, 2011, provisional application No. 61/561,993, filed on Nov. 21, 2011, provisional application No. 61/553,410, filed on Oct. 31, 2011, provisional application No. 61/547,695, filed on Oct. 15, 2011.

(51) Int. Cl.

| | | |
|---|---|---|
| *C10L 1/26* | (2006.01) | |
| *C10L 1/24* | (2006.01) | |
| *C10L 1/222* | (2006.01) | |
| *C07C 205/15* | (2006.01) | |
| *C07C 205/40* | (2006.01) | |
| *C07C 215/08* | (2006.01) | |
| *C07C 217/08* | (2006.01) | |
| *C07C 217/28* | (2006.01) | |
| *C07C 217/48* | (2006.01) | |
| *C07C 219/06* | (2006.01) | |
| *C07C 219/22* | (2006.01) | |
| *C07C 229/12* | (2006.01) | |
| *C07C 229/22* | (2006.01) | |
| *C07C 309/14* | (2006.01) | |
| *C07D 213/74* | (2006.01) | |
| *C07D 295/088* | (2006.01) | |
| *C07D 295/15* | (2006.01) | |
| *C07F 9/09* | (2006.01) | |
| *C07F 9/38* | (2006.01) | |
| *C07F 9/58* | (2006.01) | |
| *C09K 3/00* | (2006.01) | |
| *C10L 1/10* | (2006.01) | |
| *C10L 1/22* | (2006.01) | |
| *C10L 1/238* | (2006.01) | |
| *C11D 1/66* | (2006.01) | |

(56) References Cited

U.S. PATENT DOCUMENTS

2010/0242341 A1\* 9/2010 Tinetti .................. C10L 10/04
  44/434
2011/0041387 A1\* 2/2011 Green .................. A01N 33/08
  44/434

\* cited by examiner

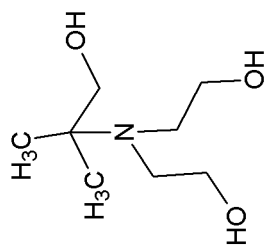
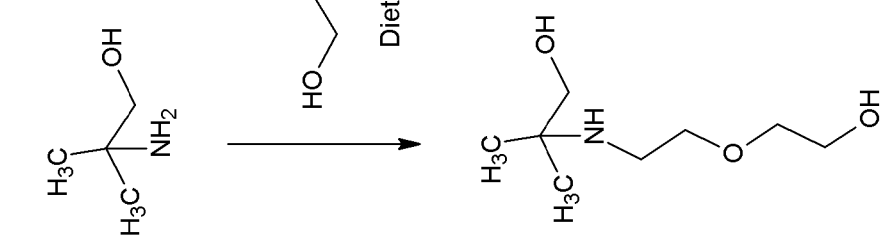
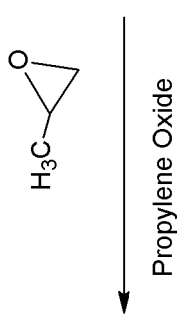
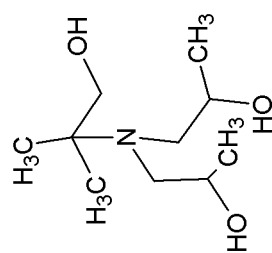
Figure 9

Figure 21
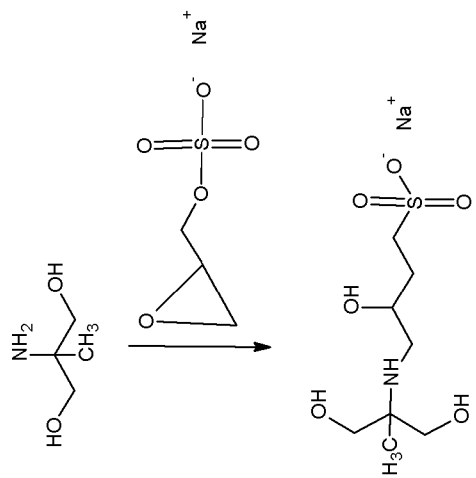
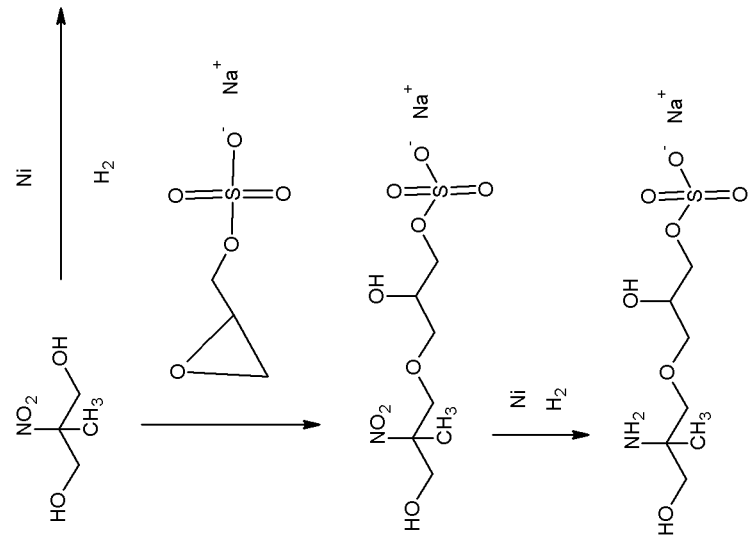

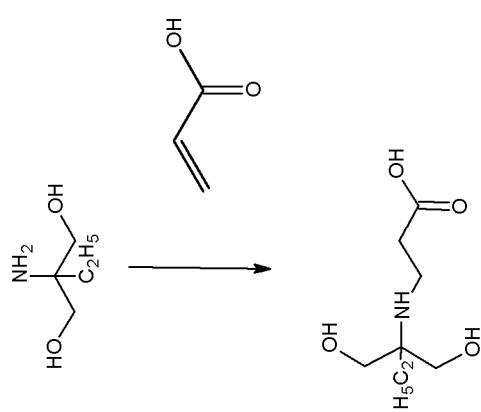
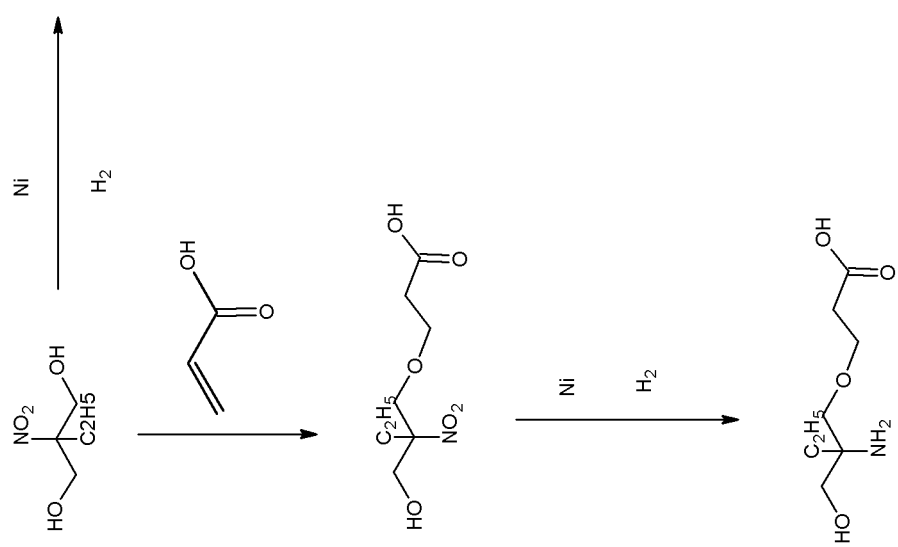
Figure 22

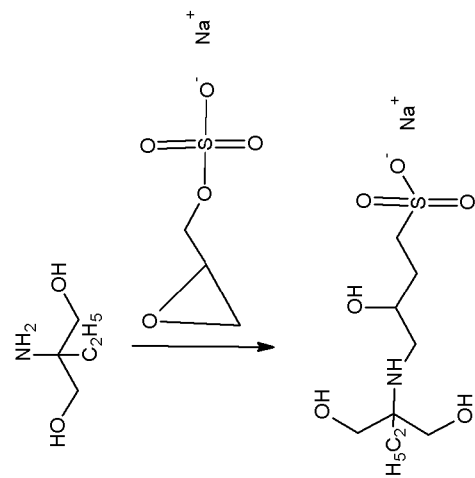
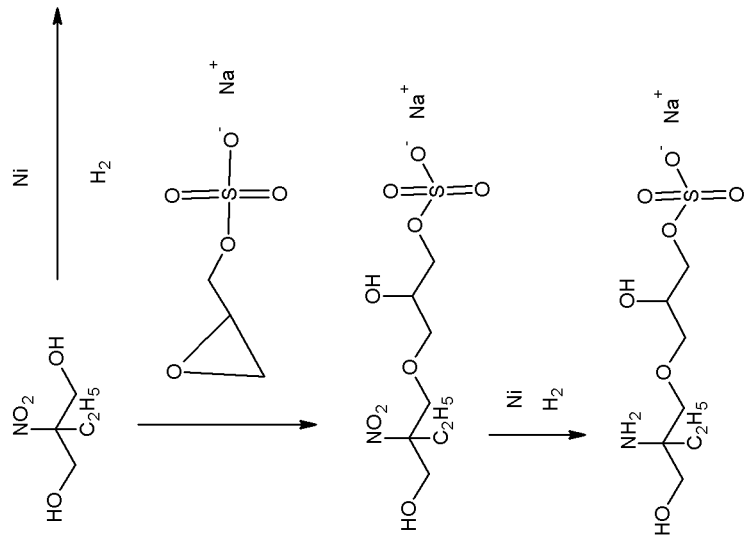
Figure 23

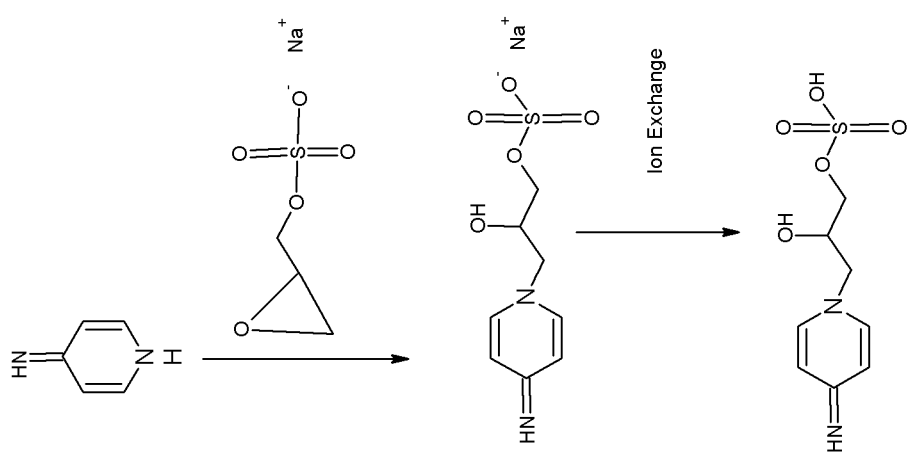
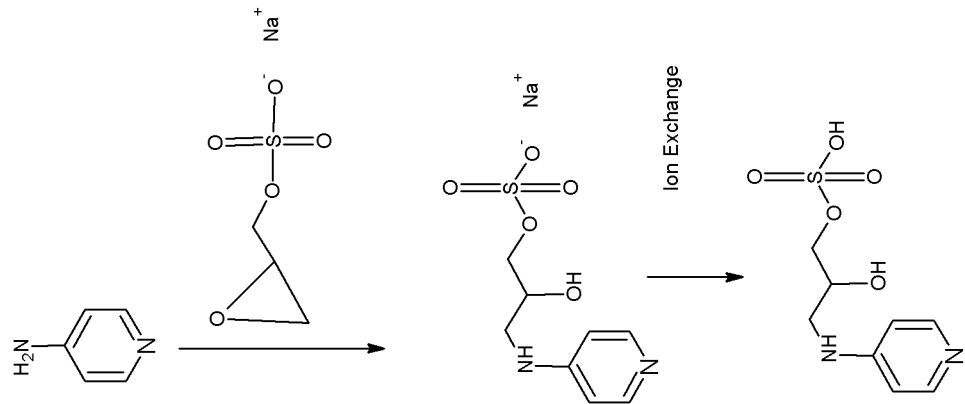
Figure 51

J and L are independantly chosen from -H, -CH3, -CH2CH3, -(CH2CH2O)n-, -(CH2CH(CH3)O)n-, -(CH2CH(CH2CH3)O)n-. G is chosen from -H, -CH3, -OH. n is an integer.

A, D, and E are independantly chosen from; -H, -CH3, -CH2CH3, -CH2OH. J and L are independantly chosen from -H, -CH3, -CH2CH3, -(CH2CH2O)n-, -(CH2CH(CH3)O)n-, -(CH2CH(CH3)CH2O)n-, Q is chosen from -CH3, -CH2CH3.

A, D, and E are independantly chosen from, -H, -CH3, -CH2CH3, -CH2OH. G is chosen from -CH3, -OH, and H.

Where R and R' are chosen from alkyl, alkenyl, alkynl, may be linear or branched, saturated or unsaturated. Additionally, R' may be -H.

A, and D are independantly chosen from, -H, -CH3, -CH2CH3, -CH2OH. G is chosen from -H, -CH3, -CH2CH3, -OH.

A, D, E, M, J and L are independantly chosen from, -H, , -OH, -CH3, -CH2CH3, -CH2OH. G is chosen from the group -H, -OH, -CH2CH3, -CH3.

M, J and L are independantly chosen from, -H, , -OH, -CH3, -CH2CH3, -CH2OH. R is chosen from the group -H, alkyl, alkenal, or alkynal, linear or branched, saturated or unsaturated.

M, J and L are independantly chosen from, -H,, -OH, -CH3, -CH2CH3, -CH2OH. R is chosen from the group -H, alkyl, alkenal, alkynal, linear or branched, saturated or unsaturated.

M, J and L are independantly chosen from; -H, , -OH, -CH3, -CH2CH3, -CH2OH. R is chosen from the group -H, alkyl, alkenal, or alkynal, linear or branched, saturated or unsaturated.

R is alkyl, alkenal, or alkynal, linear or branched, saturated or unsaturated.

A is chosen from, -H, -CH3, -CH2CH3.

A, D, and E are independantly chosen from, -H, -CH3, -CH2CH3, -CH2OH. G is chosen from -H, -CH3, -CH2CH3, -OH. n is an integer greeater than 0. R is -H, -CH3, or -CH2CH3.

G is chosen from -H, -CH3, -CH2CH3, -OH. n and m are integers greater than 0. R is -H, -CH3, or -CH2CH3.

A, D, and E are independently chosen from, -H, -CH3, -CH2CH3, -CH2OH. G is chosen from -H, -CH3, -CH2CH3, -OH. n is 1 or 2.

A, D, and E are independantly chosen from, -H, -CH3, -CH2CH3, -CH2OH. G is chosen from -H, -CH3, -CH2CH3, -OH.

n and m are integers greater than 0, q is 1 or 2. R is -H, -CH3, or -CH2CH3.

A, D, and E are independently chosen from, -H, -CH3, -CH2CH3, -CH2OH. G is chosen from -H, -CH3, -CH2CH3, -OH.

A, D, and E are independently chosen from, -H, -CH3, -CH2CH3, -CH2OH.

A, D, and E are independently chosen from, -H, -CH3, -CH2CH3, -CH2OH. G is chosen from -H, -CH3, -CH2CH3, -OH.

A, D, and E are independantly chosen from, -H, -OH, -CH3, -CH2CH3, -CH2OH. G is chosen from -H, -CH3, -CH2CH3, -OH. n is an integer greeater than 0. R is -H, -CH3, or -CH2CH3.

G is chosen from -H, -CH3, -CH2CH3, -OH. n and m are integers greater than 0. R is -H, -CH3, or -CH2CH3.

A, D, and E are independantly chosen from, -H, -OH, -CH3, -CH2CH3, -CH2OH. G is chosen from -H, -CH3, -CH2CH3, -OH. n is an integer greeater than 0. R is -H, -CH3, or -CH2CH3.

A, D, and E are independantly chosen from, -H, -OH, -CH3, -CH2CH3, -CH2OH. G is chosen from -H, -CH3, -CH2CH3, -OH. n is an integer greeater than 0. R is -H, -CH3, or -CH2CH3.

A, D, and E are independantly chosen from, -H, -OH, -CH3, -CH2CH3, -CH2OH. n and n' are 1 or 2.

A, D, and E are independantly chosen from, -H, -OH, -CH3, -CH2CH3, -CH2OH. G is chosen from -H, -CH3, -CH2CH3, -OH. n is an integer greeater than 0. R is -H, -CH3, or -CH2CH3.

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$.. R, R', R", R''' are independantly chosen from, alkyl, alkenyl, alkynyl, branched or linear. n and m are integers, both may not be zero.

Figure 114

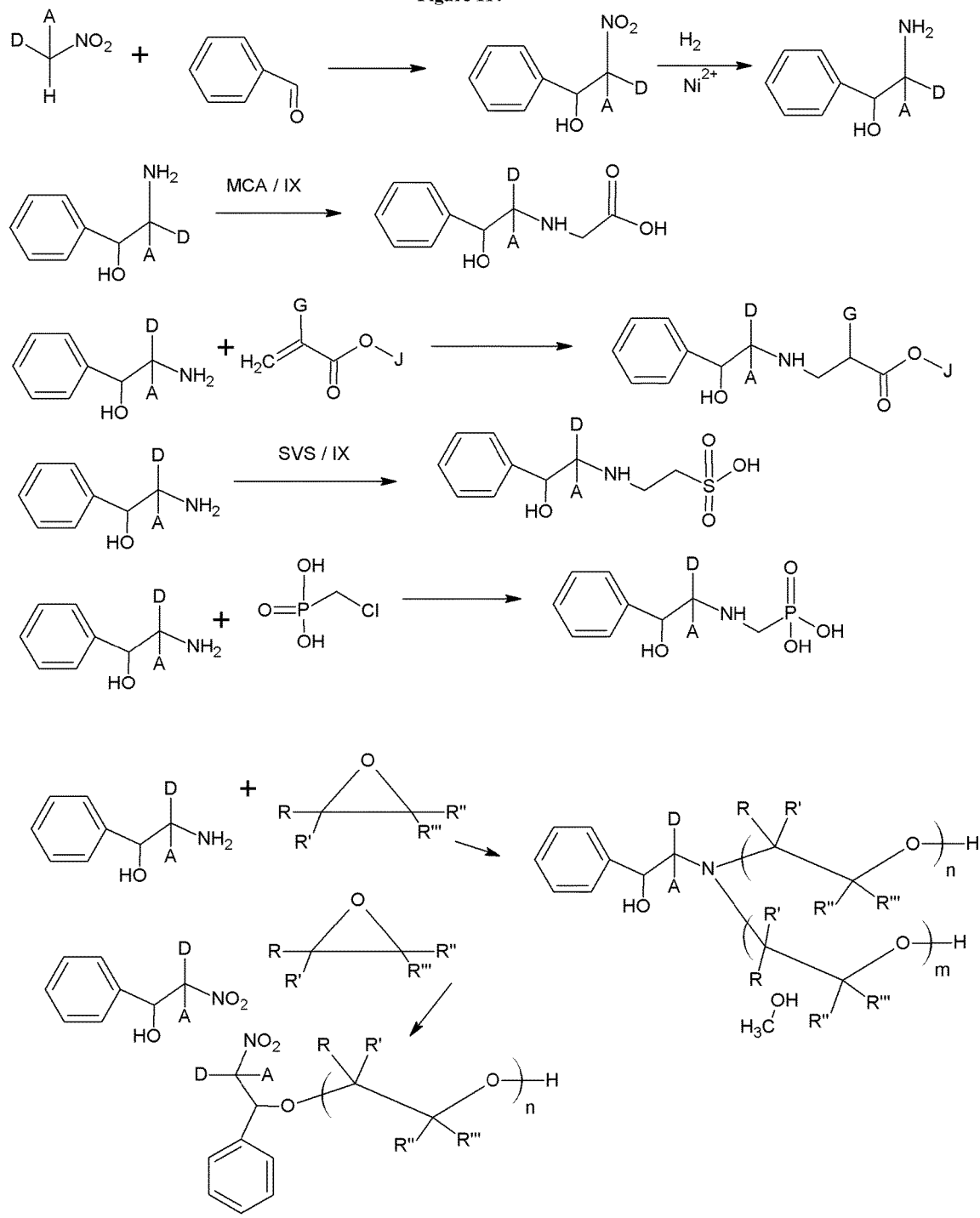

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$.. G is chosen from -H, -CH3, -CH2CH3, -OH. J is chosen from alkyl, alkenyl, alkynyl, branched or linear, -H, -(CH$_2$CH$_2$O)$_n$H, -(CH$_2$CH$_2$CH$_2$0)$_n$H, -(CH$_2$CH(CH$_3$)O)$_n$H, -(CH$_2$C(CH$_3$)$_2$O)$_n$H. R, R', R", R'" are independantly chosen from, alkyl, alkenyl, alkynyl, branched or linear. n and m are integers, both may not be zero.

Figure 115
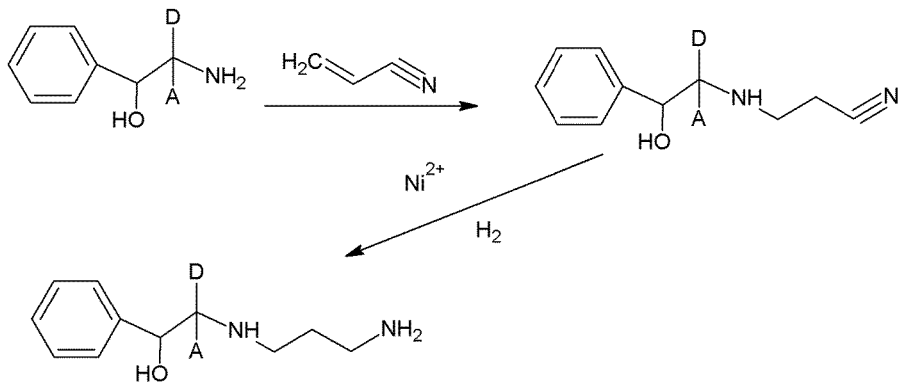
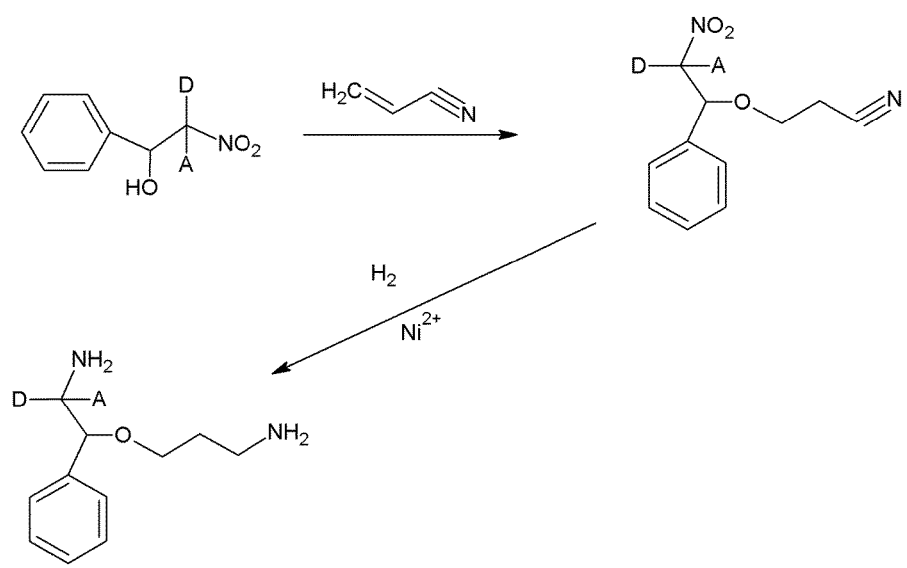
A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$..

A is chosen from -H, -CH3, -CH2CH3, -CH2CH2CH3, -CH2OH, $-CH_2COOH$, $-CH_2CH_2COOH$, $-CH_2CH(CH_3)COOH$, $-CH_2PO(OH)_2$.. E is alkyl, saturated or unsaturated, branched or linear with from 2 - 22 carbons. G is chosen from -H, -CH3, -CH2CH3, -OH. n is the generally accepted designation for the repeating unit of a polymer.

A and D are independantly chosen from -H, -CH3, -CH2CH3, -CH2CH2CH3, -CH2OH, $-CH_2COOH$, $-CH_2CH_2COOH$, $-CH_2CH(CH_3)COOH$, $-CH_2PO(OH)_2$. n is the generally accepted symbol for the repeating unit of a polymer, m is an integer, zero or greater.

A, G, and E are chosen such that 1 is Nitrogen and the remaining are carbon. J is chosen from -H, -OH, -CH$_3$, or -CH$_2$CH$_3$, -CH$_2$COOH. R is -H, -OH, -CH$_3$, or -CH$_2$CH$_3$, -CH$_2$COOH. n is an integer from 1 to 100.

A, D and E are independantly chosen from -H, -CH3, -CH2CH3, -CH2CH2CH3, -CH2OH, -CH2COOH, -CH2CH2COOH, -CH2CH(CH3)COOH, -CH2PO(OH)2. G is chosen from -H, -CH3, -CH2CH3, -OH. L, L', M, M', Q and Q' are independently chosen from N and C. n is an integer from 1 to 3.

A, G and E are independently chosen from N and C. D, L, and J are independently chosen from -H, -OH, -CH3, -CH2CH3, -CH2OH.

Figure 131
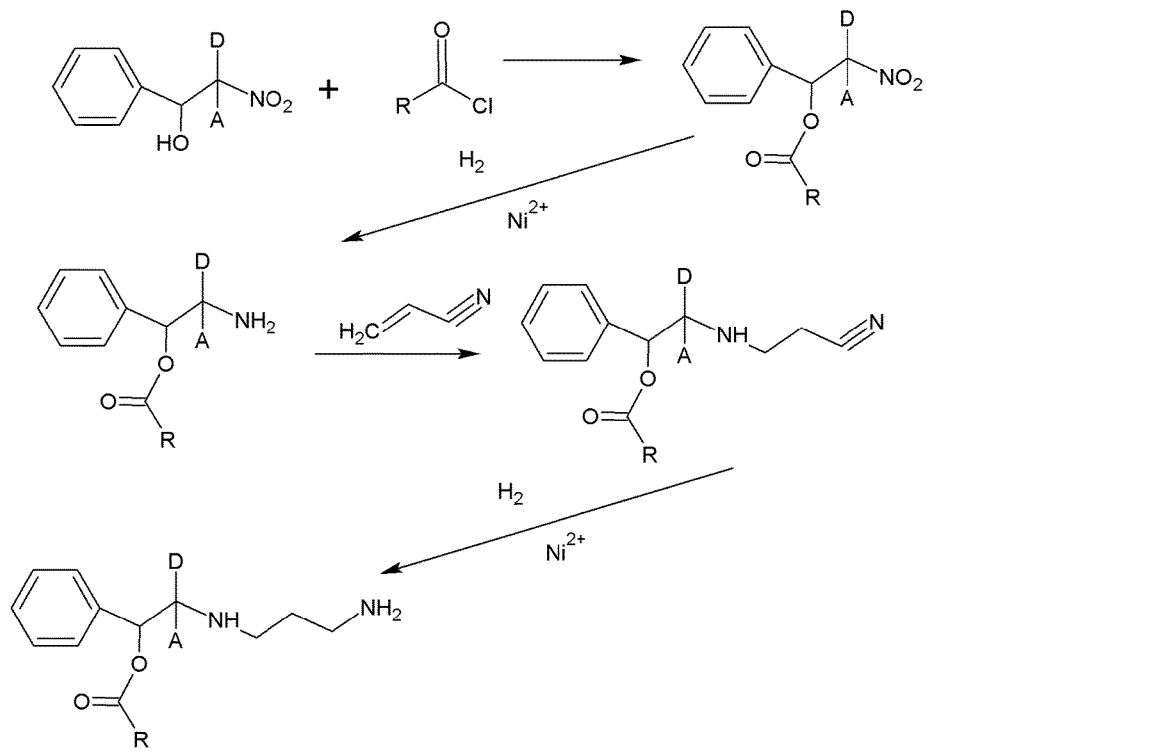
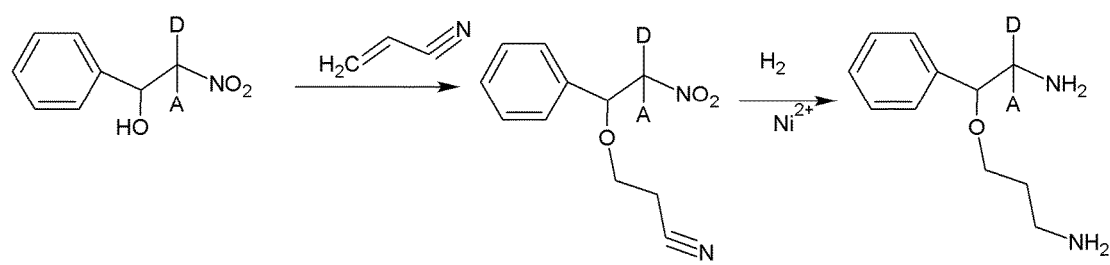
A and D are independantly chosen from -H, -CH3, -CH2CH3, -CH2CH2CH3, -CH2OR, -CH$_2$COOR, -CH$_2$CH$_2$COOR, -CH$_2$CH(CH$_3$)COOR, -CH$_2$PO(OH)$_2$, -CH2CH2CN. R is -H, or alkyl, linear or branched, saturated or unsaturated, cyclic or acyclic from 1 to 22 carbons.

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$. E chosen from -H, or is alkyl, saturated or unsaturated, branched or linear, cyclic or acyclic with from 1 - 22 carbons. n, m and Q are integers.

A and D are independantly chosen from -H, -CH3, -CH2CH3, -CH2CH2CH3, -CH2OH, -CH$_2$COOH, -CH$_2$CH$_2$COOH, -CH$_2$CH(CH$_3$)COOH, -CH$_2$PO(OH)$_2$. E is chosen from -H, or is alkyl, saturated or unsaturated, branched or linear, cyclic or acyclic with from 1 - 22 carbons. n and m are integers.

A and D are independantly chosen from -H, -CH3, -CH2CH3, -CH2CH2CH3, -CH2OH, -O(CH2CH2O)n-(CH2CH(CH3)O)m-(CH2CH(CH2CH3)O)qL, L is chosen from -H, -CH2CH2CN, or -CH2CH2CH2NH2, E is chosn from -H, alkyl, saturated or unsaturated, branched or linear, cyclic or acyclic with from 1 - 22 carbons. J is chosen from -H, -CH3, -CH2CH3. n, m and q are integers..

BIOLOGICAL BUFFERS WITH WIDE BUFFERING RANGES

This is a continuation of application Ser. No. 15/606,757 filed May 26, 2017 application Ser. No. 15/606,757 is hereby incorporated by reference in its entirety.

BACKGROUND

Field of the Invention

The present invention relates generally to the field of amines and more particularly to a classes of amines used as buffers in biological systems.

Description of the Problem Solved by the Invention

Amines are very useful compounds in the buffering of biological systems. Each class of amine has various limitations which require choosing an amine based on multiple factors to select the best amine. For example, pH buffering range is typically most important, but issues of chelation, and pH range stability, and solubility also come into play. Typically, a suboptimal buffer will result in yields that are well below the potential yield. The invention disclosed improves the yields in fermentation and purification, and improves shelf stability of proteins and amino acids.

SUMMARY OF THE INVENTION

The present invention relates to amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

DESCRIPTION OF THE FIGURES

Attention is now directed to the following figures that describe embodiments of the present invention:

FIG. 9 shows FIG. 9 shows alkoxylation of aminomethylpropanol.

FIG. 12 shows the synthesis of a series of buffers with 1-nitropropane as a starting material where n and m are integers where m+n is greater than zero and n is greater than or equal to m.

FIG. 18-25 show the synthesis of families of zwitterionic buffers from nitroalcohols.

FIG. 51 shows the synthesis of zwitterionic sultaines from 4-aminopyridine.

FIG. 114-115 teach the synthesis of banzaldehyde and nitro compounds and their derivatives.

COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R' is chosen from, alkyl, alkenyl, alkynyl, branched or linear. L, M, and Q are chosen from N or C. n is an integer greater than zero.

Figure 126:
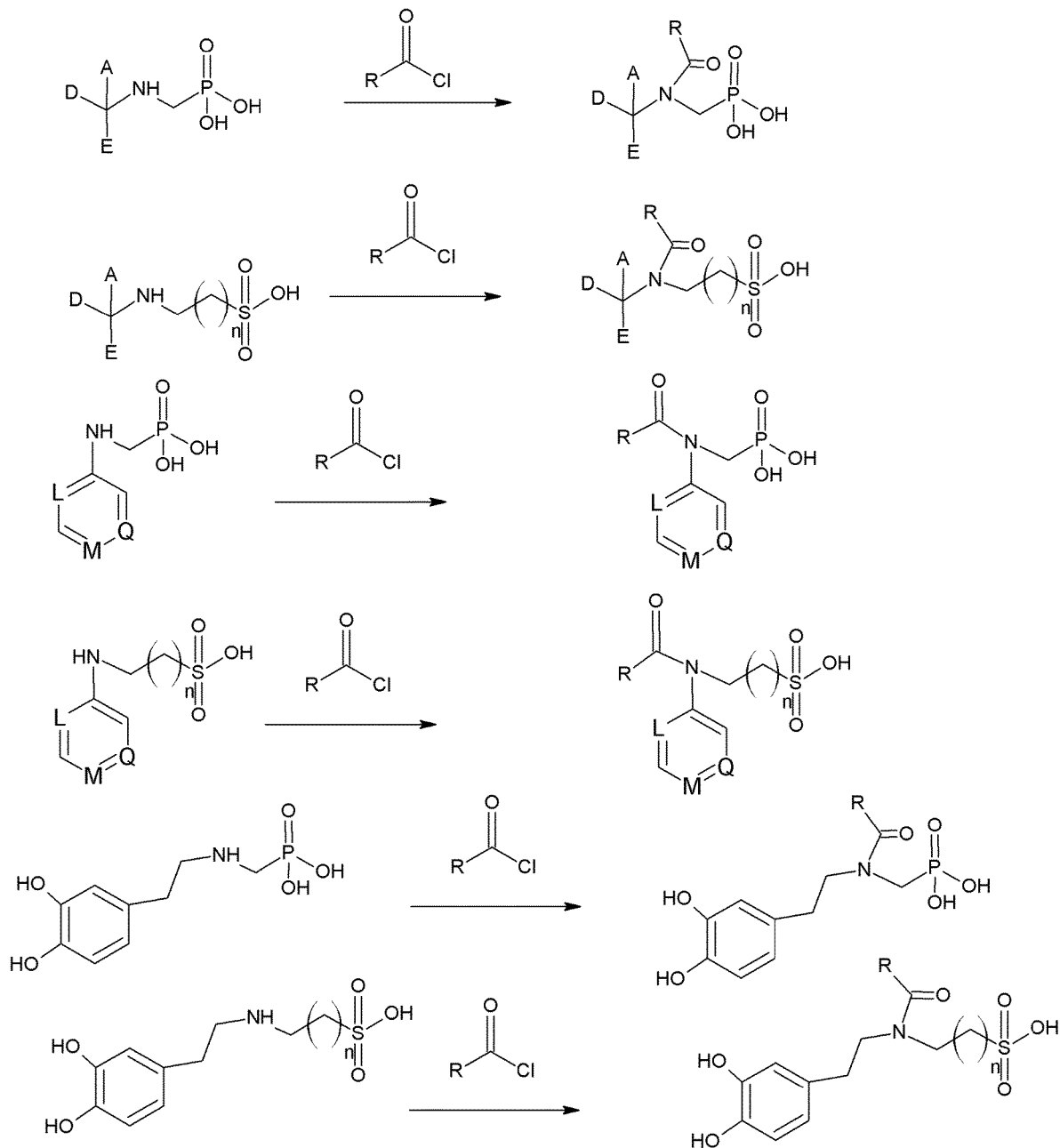

FIG. 126 teaches a series of mild zwitterionic surfactants based on sulfonate and phosphonate chemistries. A, D and E are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R' is chosen from, alkyl, alkenyl, alkynyl, branched or linear. n is an integer from 1 to 6. L, M, and Q are chosen from N or C.

Figure 127:
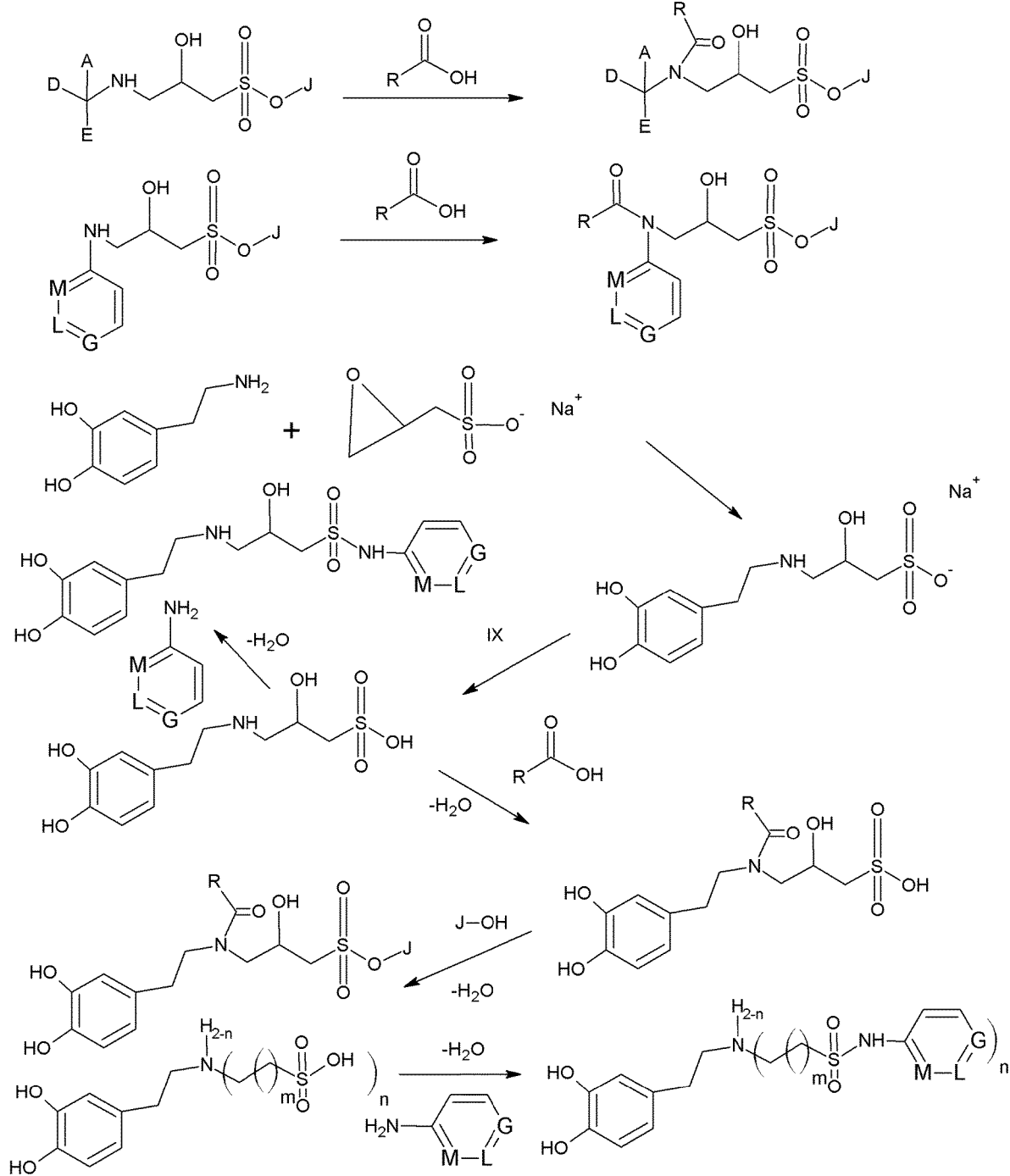

FIG. 127 teaches sultaine buffers and surfactants where A, D and E are independently chosen from —H, —CH3, —CH2CH3, —CH2CH2CH3, —CH2OH, —CH2COOH, —CH2CH2COOH, —CH2CH(CH3)COOH, —CH2PO(OH)2. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R is chosen from —H, alkyl, alkenyl, alkynyl, branched or linear, saturated or unsaturated from 1 to 22 carbons. G, M, and L are chosen such that any one can be Nitrogen, the others Carbon. n is 1 or 2, m is an integer from 1 to 6 inclusive.

Figure 128:
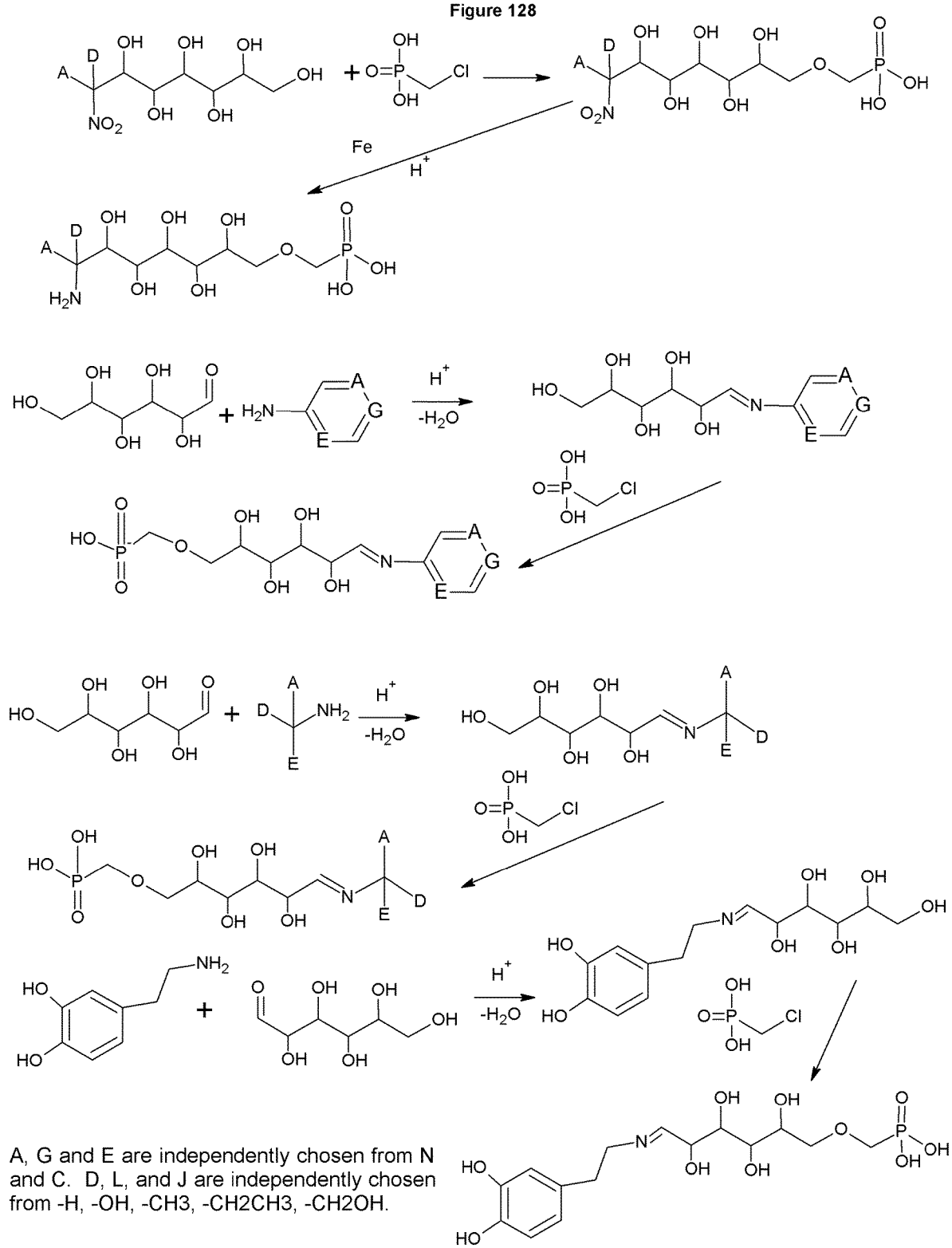

FIG. 128 teaches an amino sugar zwitterionic buffer.

Figure 129:
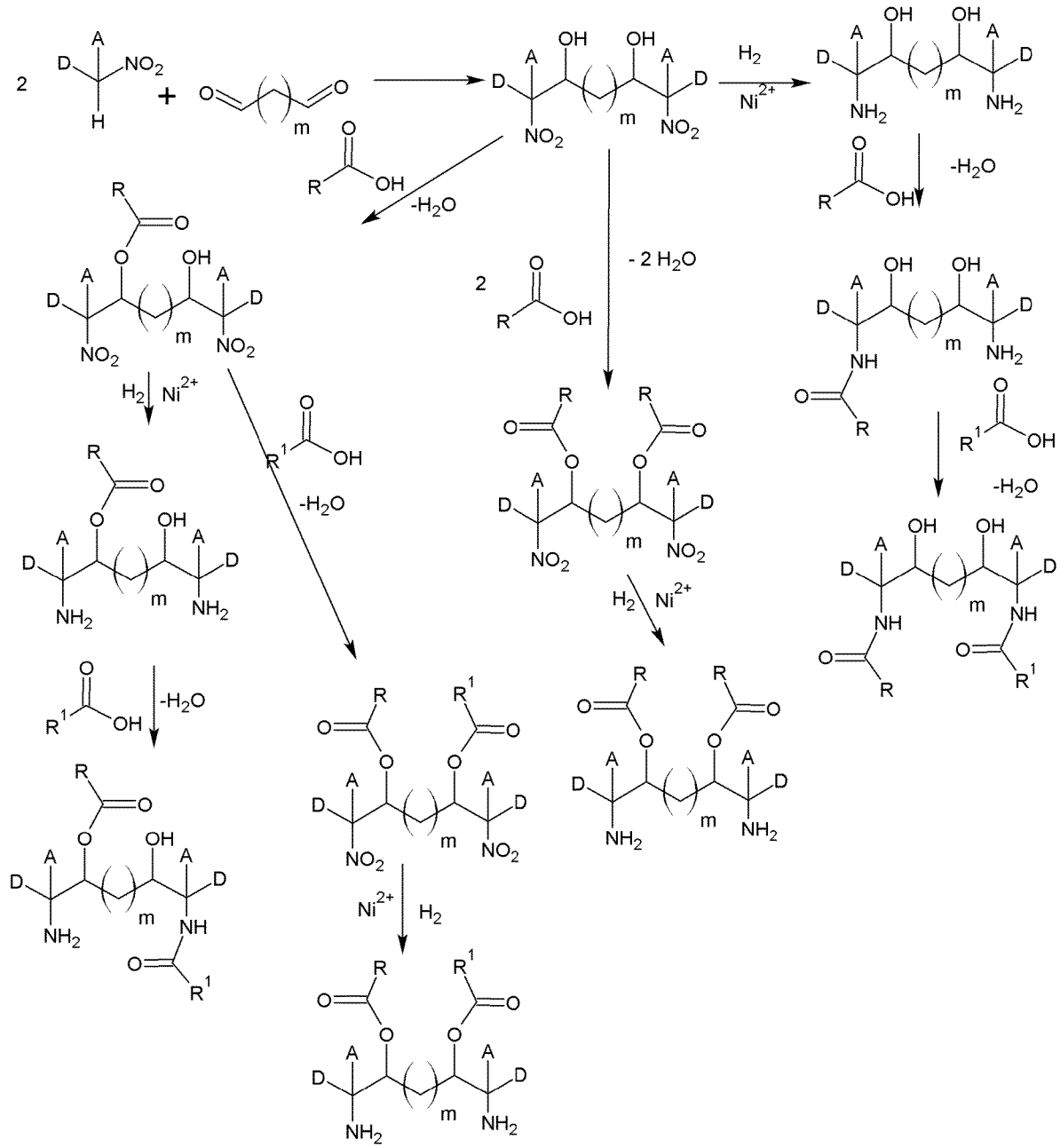

FIG. 129 teaches the synthesis of a range of amino esters and amides that are useful as anti-strips in asphalt and asphalt emulsifiers. A and D are independently chosen from —H, —CH3, —CH2CH3, —CH2CH2CH3, —CH2OH, —CH$_2$COOH, —CH$_2$CH$_2$COOH, —CH$_2$CH(CH$_3$)COOH, —CH$_2$PO(OH)$_2$. n is the generally accepted symbol for the repeating unit of a polymer, m is an integer, zero or greater. R and R1 are alkyl, saturated or unsaturated, linear or branched, cyclic or acyclic from 1 to 22 carbons.

Figure 130:
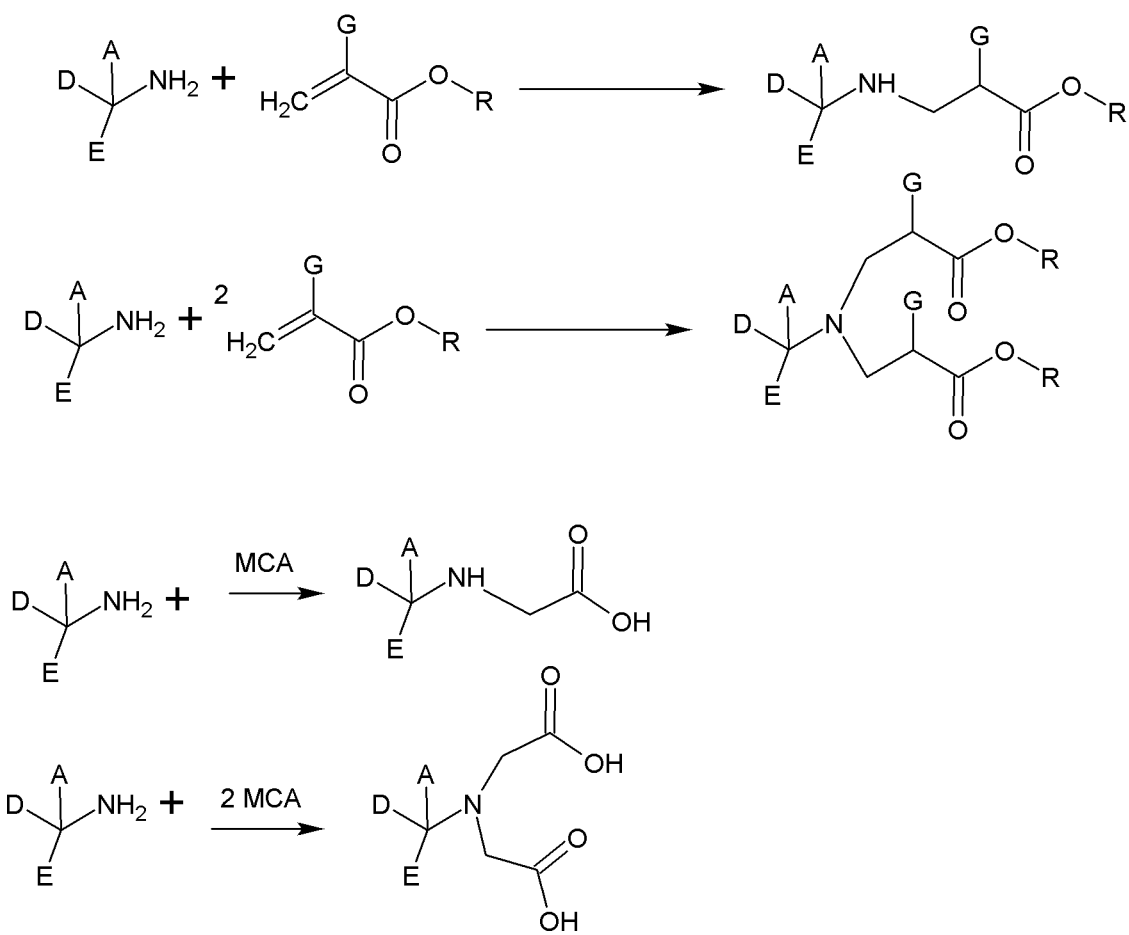

FIG. 130 teaches the synthesis of ether amino acid buffers. A, D and E are independently chosen from —H, —CH3, —CH2CH3, —CH2CH2CH3, —CH2OR, —CH2COOH, —CH2CH2COOH, —CH2CH(CH3)COOH, —CH2PO(OH)2, —CH2CH2CN. G is chosen from —H, —OH, —CH3, or —CH2CH3, —CH2COOH. R is alkyl, linear, branched, saturated or unsaturated, cyclic or acyclic from 1-22 carbons or —H.

FIG. 131 teaches the synthesis of aromatic ring containing mining collectors.

Figure 132:
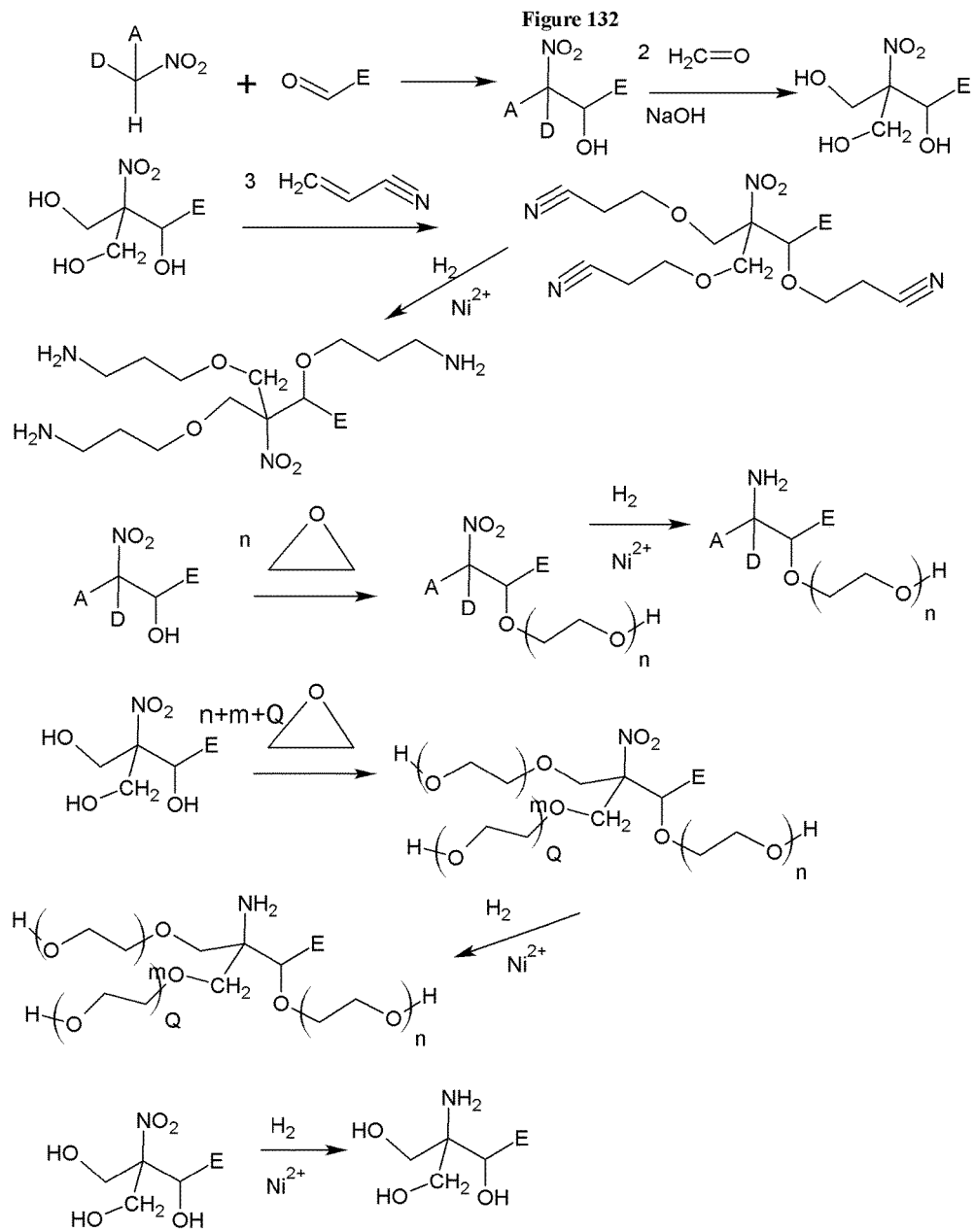
Figure 133:
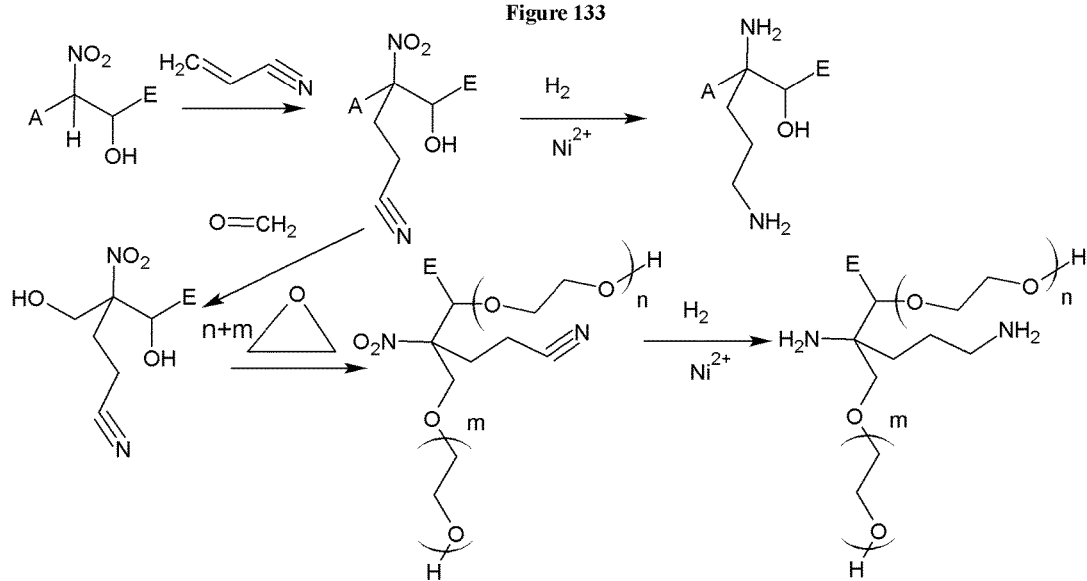

FIGS. 132-133 teach the synthesis of a range of poly primary amines that are useful as mining collectors and asphalt emulsifiers.

Figure 134:
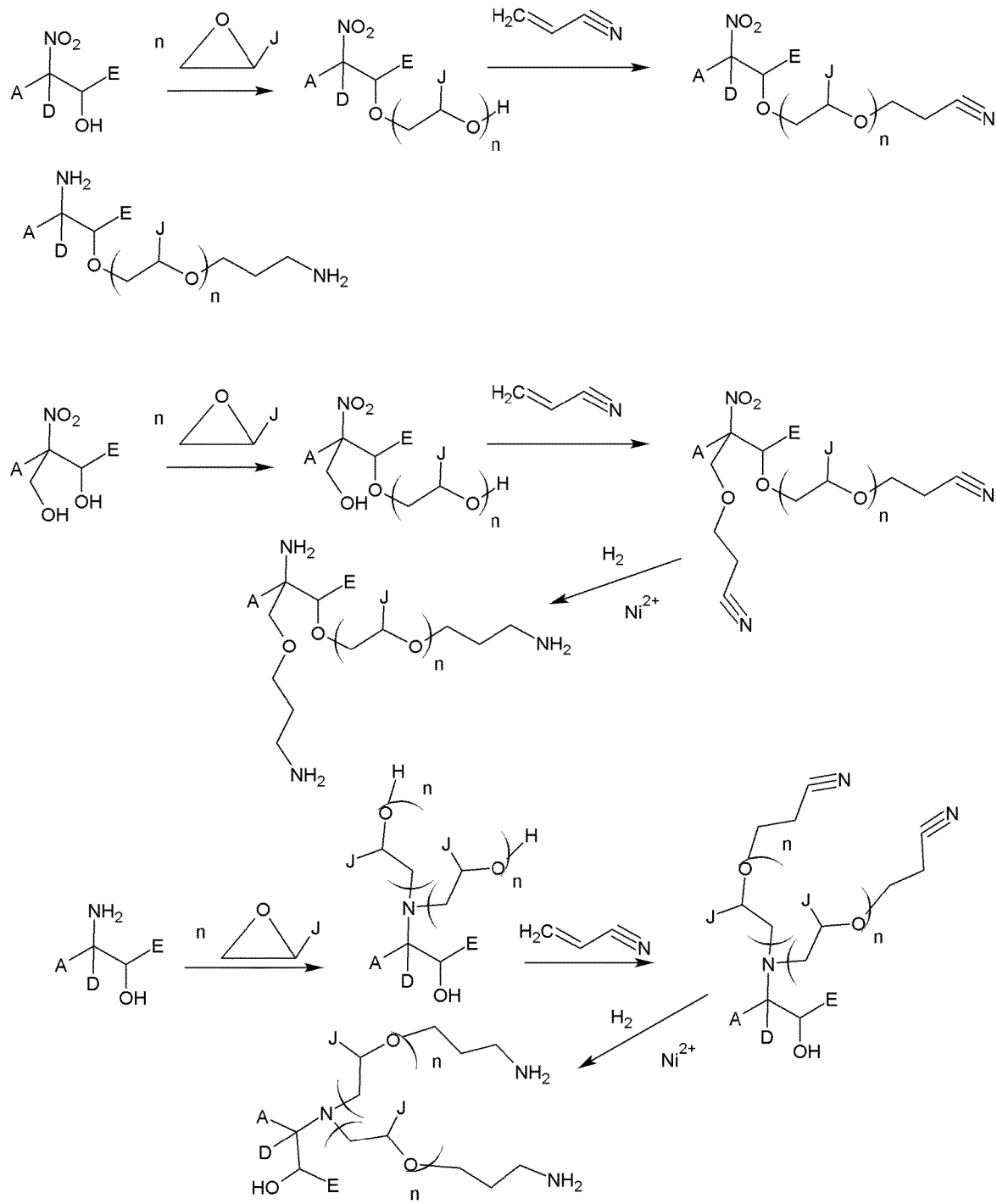

FIG. 134 teaches the synthesis of a range of polyether amines that are useful as mining collectors, asphalt emulsifiers, agricultural adjuvents and fuel additives.

Several drawings and illustrations have been presented to aid in understanding the invention. The scope of the present invention is not limited to what is shown in the figures.

DETAILED DESCRIPTION OF THE INVENTION

Combining amines with monochloroacetic acid (MCA) or sodium vinyl sulfonate (SVS) results in products are zwitterionic buffers that can buffer in both acidic and basic pH conditions. A limited number amines are currently used for this purpose, such as, tromethamine and ammonia. The reaction of amines, alcohols, and aminoalcohols with acrylonitrile (via the Michaels Addition), followed by reduction results in amines and polyamines that have a broad buffering range. The further derivatization of the amines and polyamines with MCA and SVS yields a further crop of amine buffers with desirable properties. One skilled in the art will recognize that MCA and sodium monochloroacetic acid (SMCA) can be used interchangeably.

The reaction of tromethamine as described above yields the products in FIG. 1. In step 1 in FIG. 1 where the acrylonitrile is added to the amine a branched structure wherein the addition of acrylonitrile results in a tertiary amine is shown. In reality, particularly when n is greater than 1, a mixture of products is obtained that is both tertiary and secondary. For the invention disclosed herein, n may equal any integer greater than zero, including 1. Controlling the reaction temperature, pressure and agitation will allow the mixture to be predominately secondary (such as when m=n) or tertiary amine, m can be any integer less than or equal n. Furthermore, this selection can take place in adding acrylonitrile to the amine that results, allowing a progressively more branched product. It is within the scope of the invention disclosed herein to include these additional types of products and their subsequent derivatives described herein.

Figure 1:
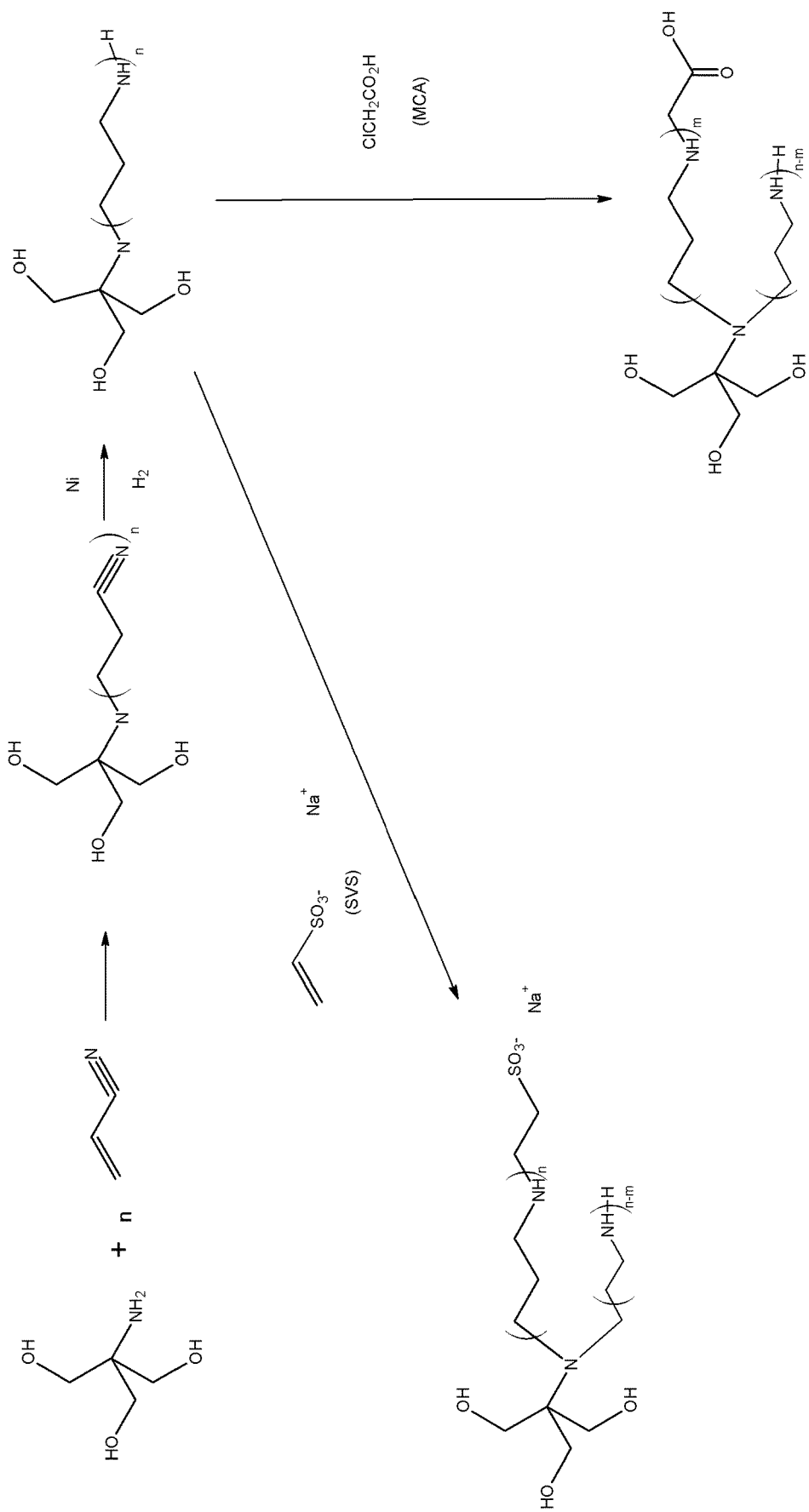
FIG. 1 shows the derivation of polyamines and zwitterionic buffers from tromethamine.

With regard to the reaction of the polyamine resulting from the second step in FIG. 1. FIG. 1 shows the addition of only one mole of SVS or MCA, it is known in the art, that a second mole may be added to obtain a product with a second zwitterionic group. Furthermore, in the case where the product has repeated additions of acrylonitrile and reduction to the amines, the branched products may have many more zwitterionic groups. Also, it is to be noted that, while the sulfonates are shown as sodium salts, other salts and the free acids (non-salted form) are also within the scope of this invention.

Other amines that would make excellent starting materials in place of tromethamine are 2-amino-2-methyl-1-propanol, 2-amino-1-butanol, 2-amino-2-ethyl-1,3-propanediol, 2-amino-2-methyl-1,3-propanediol, and dihydroxymethyl-aminomethane.

Additionally, fatty amines, such as lauryl amine, coco amine, tallow amine, and oleoyl amine, and fatty ether amines, such as bis-(2-hydroxyethyl) isodecyloxypropylamine, when reacted with SVS produce mild surfactants that find utility where zwitterionic surfactants are desired, including personal care.

Figure 2:
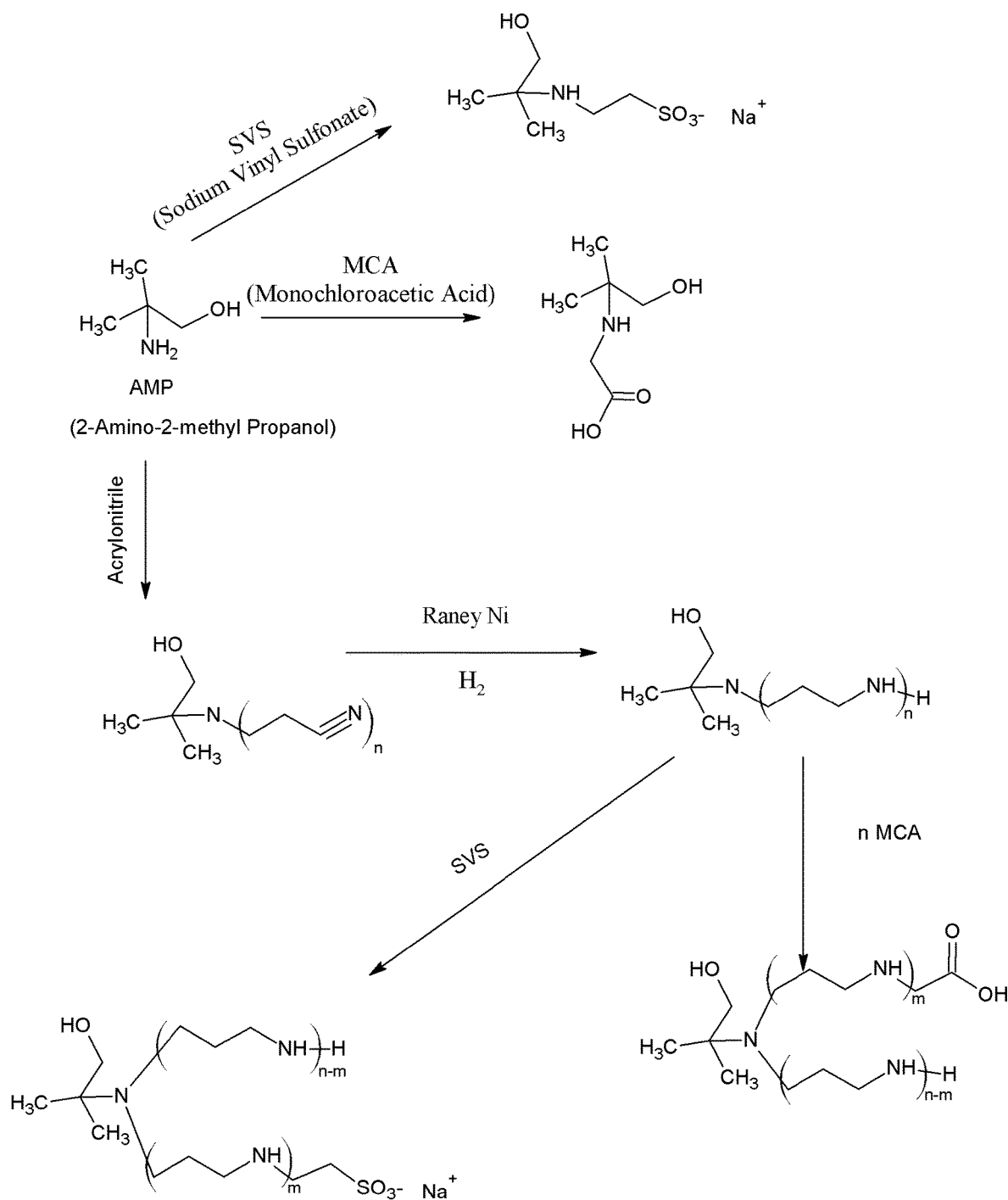
FIG. 2 shows the derivation of zwitterionic buffers and polyamines from aminomethylpropanol.

Other amines that are shown in FIG. 2 are produced via a similar series of reactions, except that FIG. 2 includes zwitterionic buffers from the amine 2-amino-2-methyl-1-propanol, as well as the polyamines derived from the reaction with acrylonitrile and the subsequent derivatives described above. Other amines can be utilized in addition to 2-amino-2-methyl-1-propanol to obtain excellent buffers are 2-amino-1-butanol, 2-amino-2-ethyl-1,3-propanediol, 2-amino-2-methyl-1,3-propanediol, and dihydroxymethyl-aminomethane. Reaction conditions could be created such that the alcohol groups on the amines listed above could be reacted with acrylonitrile as well, and then reduced to the amines and, if desired, reacted with SVS or MCA to impart zwitterionic character.

Polyamines with good properties for use in biological fermentations, purifications, storage and general handling can also be produced through the reaction of nitroalcohols and acrylonitrile, followed by reduction. Additional derivatization with SVS or MCA will result in zwitterionic buffers with a very large buffering range and capacity.

Figure 3:
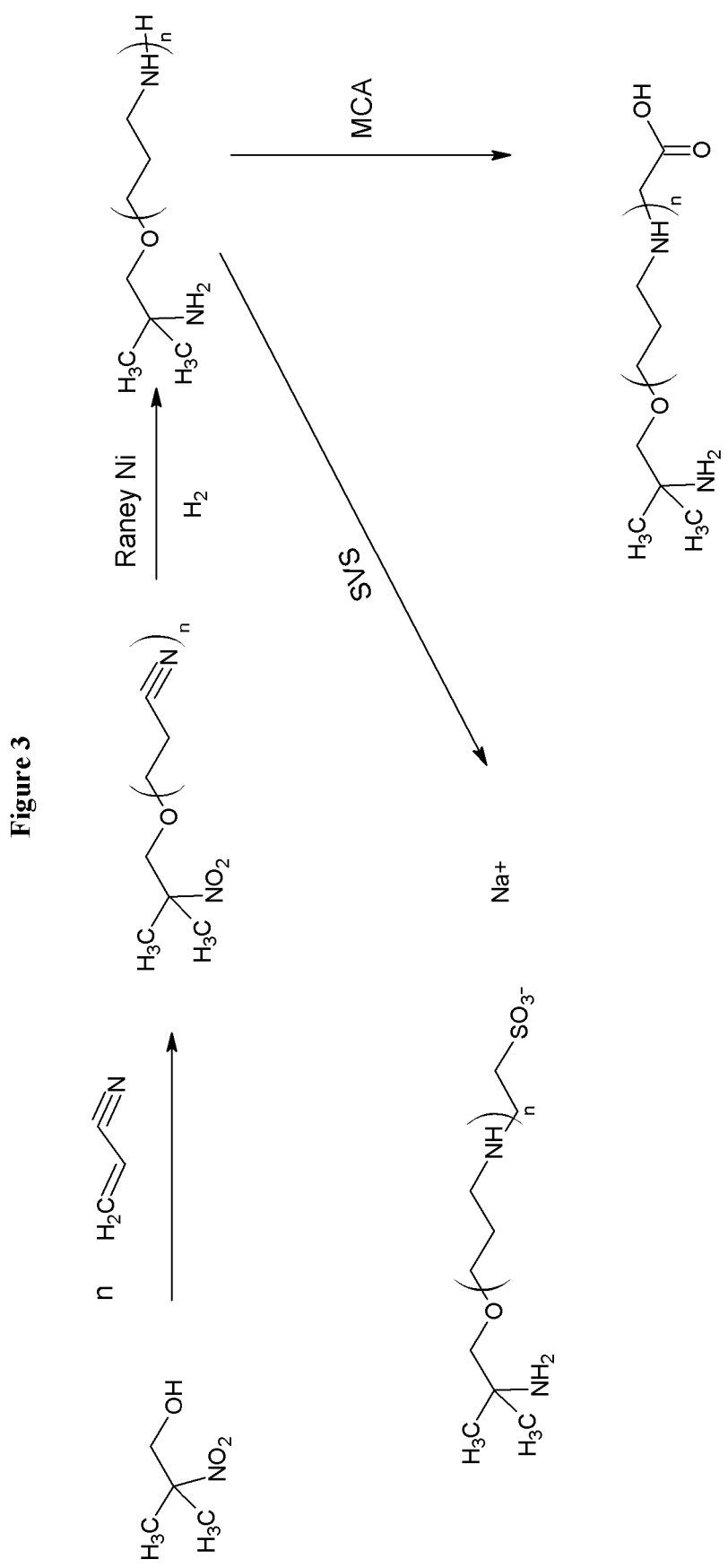
FIG. 3 shows the reaction of 2-methyl-2-nitro-1-propanol with acrylonitrile and its derivatives.

FIG. 3 shows the reaction of 2-methyl-2-nitro-1-propanol with acrylonitrile and its derivatives.

Figure 4:
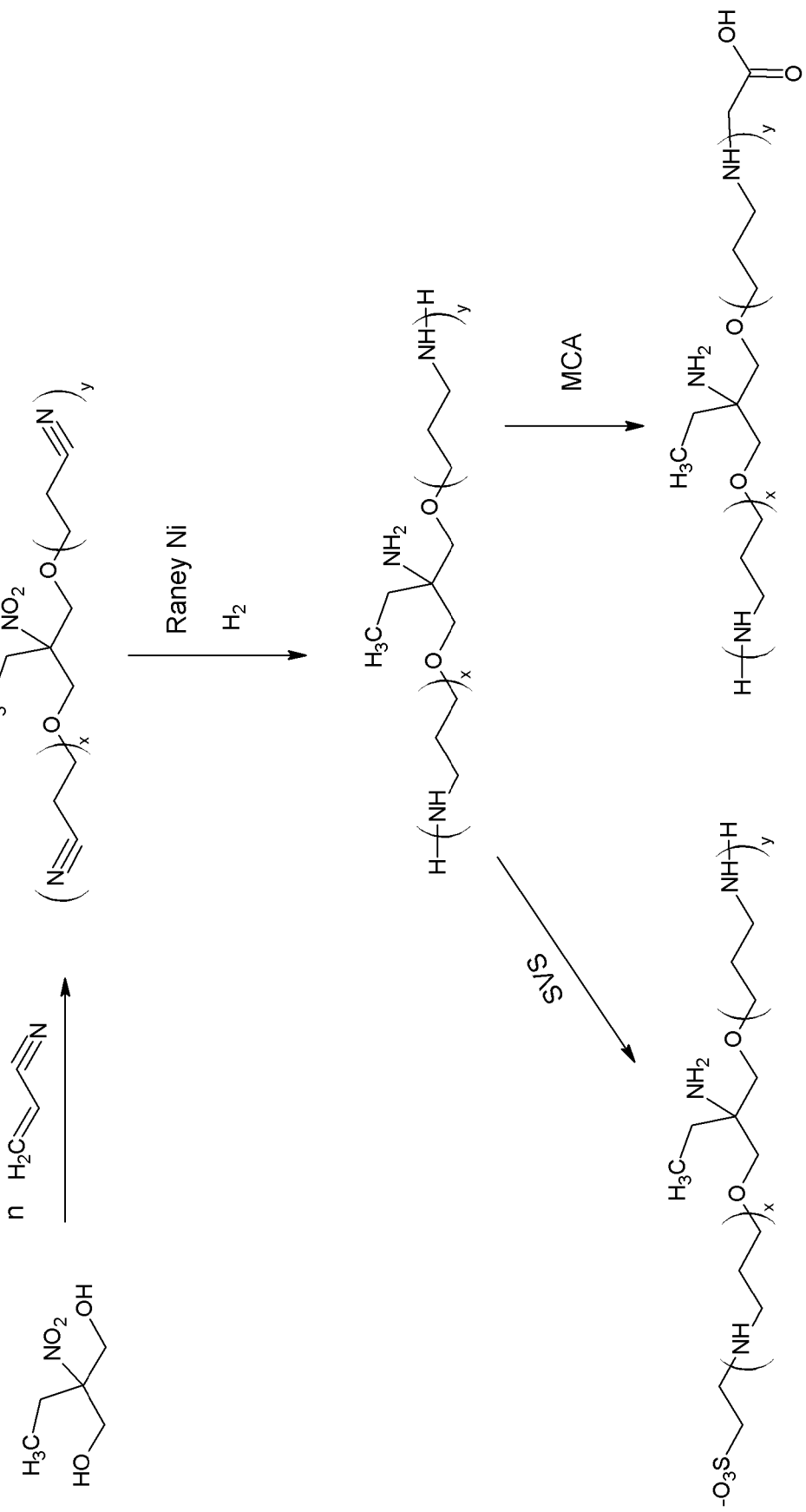
FIG. 4 shows the reaction of 2-nitro-2-ethyl-1,3-propanediol with acrylonitrile and its derivatives where x, y, and n are all integers where x and y are chosen independently, such that x+y=n and n is greater than zero.

FIG. 4 shows the reaction of 2-nitro-2-ethyl-1,3-propanediol with acrylonitrile and its derivatives where x, y, and n are all integers where x and y are chosen independently, such that x+y=n and n is greater than zero.

Figure 5:
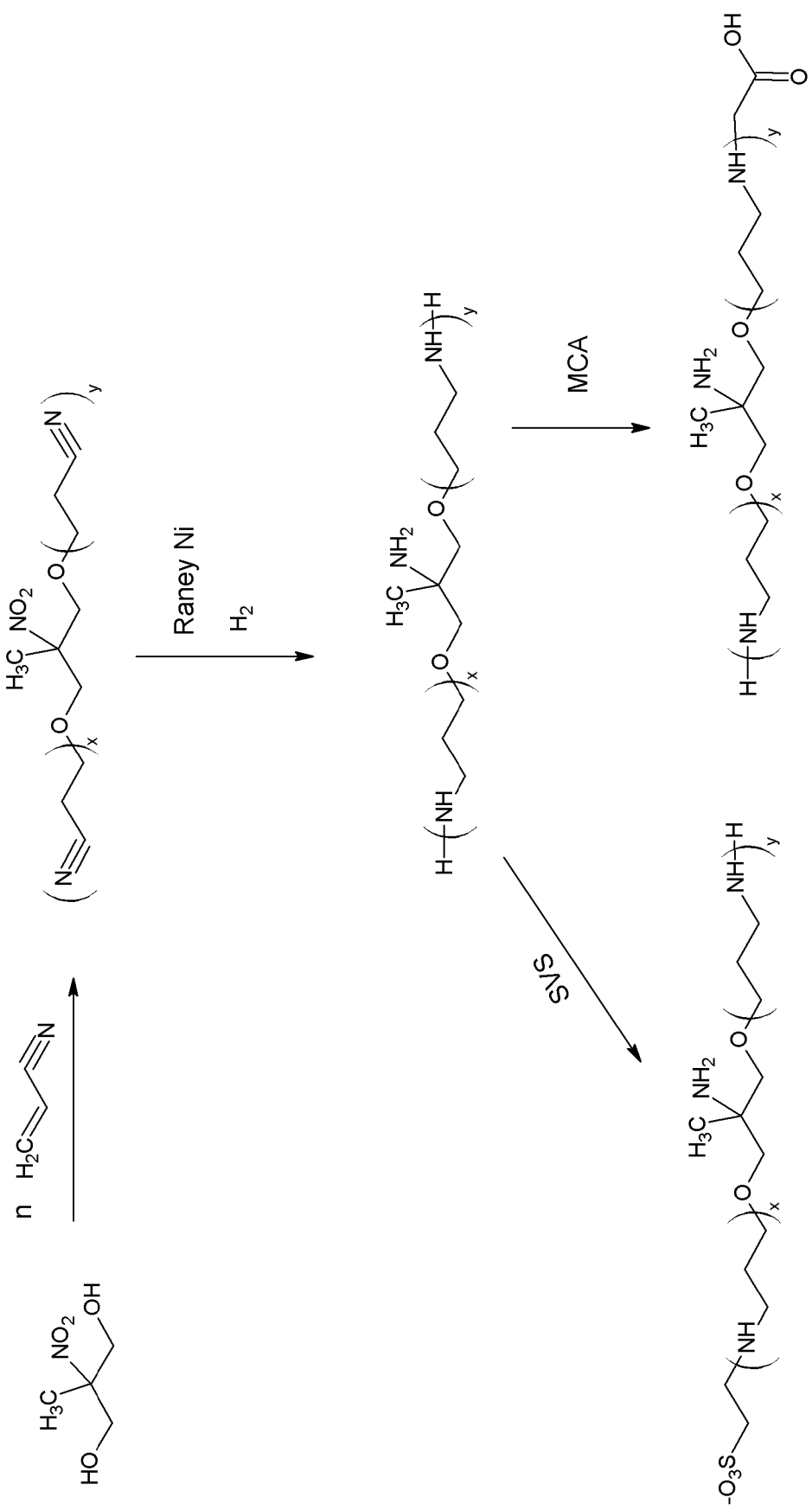
FIG. 5 shows the reaction of 2-nitro-2-methyl-1,3-propanediol with acrylonitrile and its derivatives where x, y, and n are all integers where x and y are chosen independently, such that x+y=n and n is greater than zero.

FIG. 5 shows the reaction of 2-nitro-2-methyl-1,3-propanediol with acrylonitrile and its derivatives where x, y, and n are all integers where x and y are chosen independently, such that x+y=n and n is greater than zero.

Figure 6:
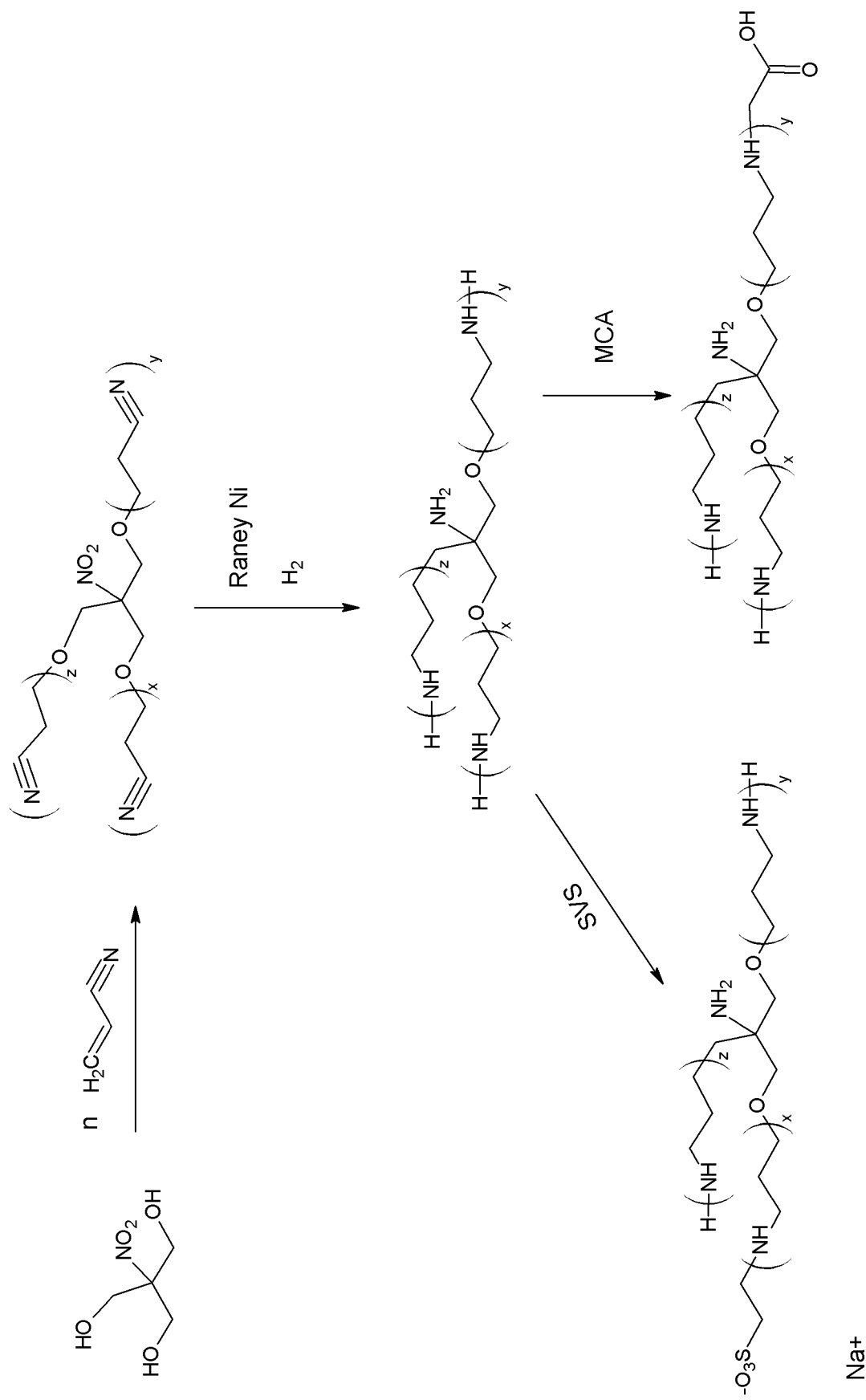
FIG. 6 shows the reaction of tris(hydroxymethyl)nitromethane with acrylonitrile and its derivatives where x, y, z, and n are all integers where x, y and z are chosen independently, such that x+y+z=n and n is greater than zero.

FIG. 6 shows the reaction of tris(hydroxymethyl)nitromethane with acrylonitrile and its derivatives where x, y, z, and n are all integers where x, y and z are chosen independently, such that x+y+z=n and n is greater than zero.

Figure 7:
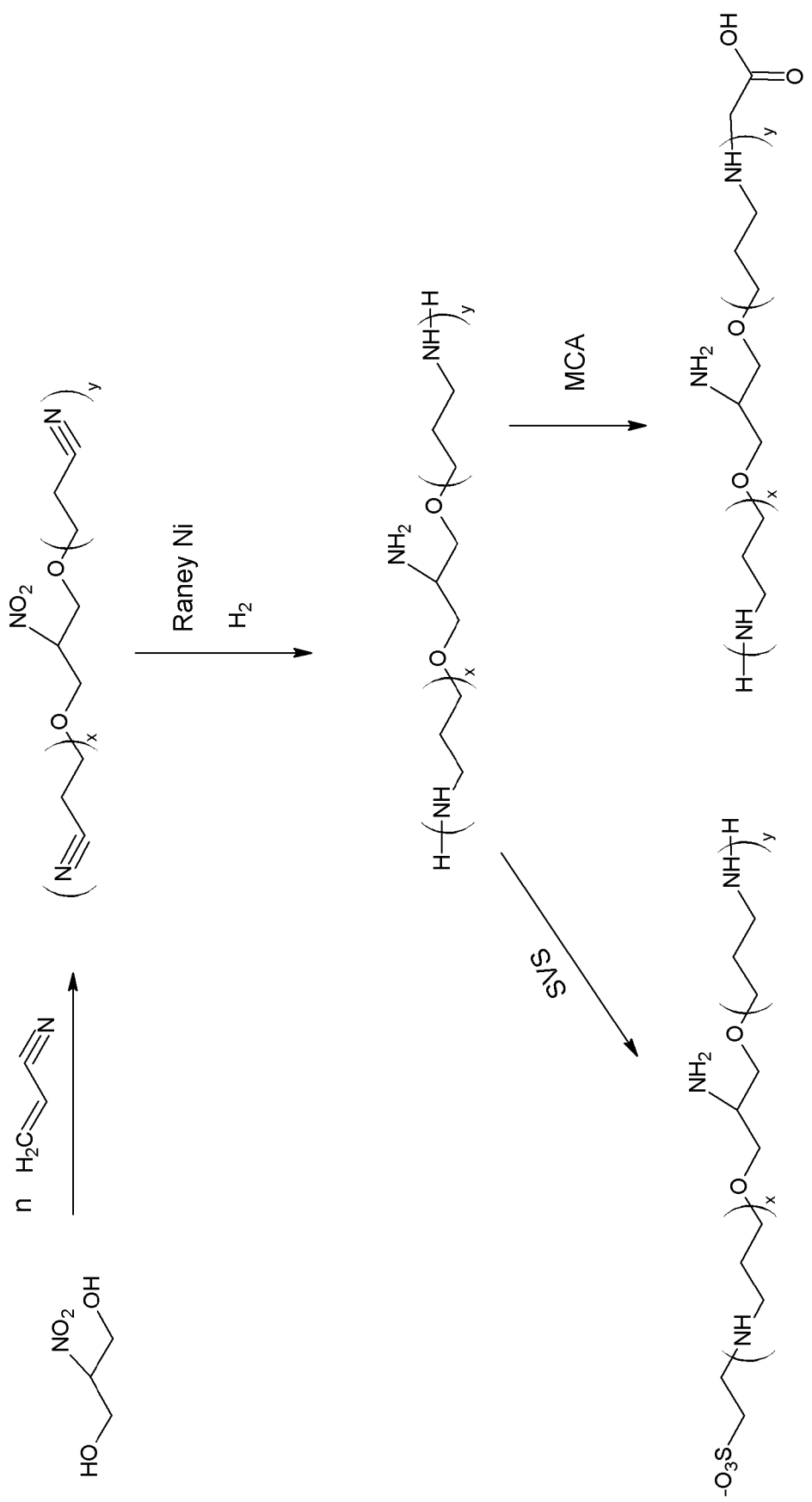
FIG. 7 shows the reaction of 2-nitro-1,3-propanediol with acrylonitrile and its derivatives where x, y, and n are all integers where x and y are chosen independently, such that x+y=n and n is greater than zero.

FIG. 7 shows the reaction of 2-nitro-1,3-propanediol with acrylonitrile and its derivatives where x, y, and n are all integers where x and y are chosen independently, such that x+y=n and n is greater than zero.

Figure 8:
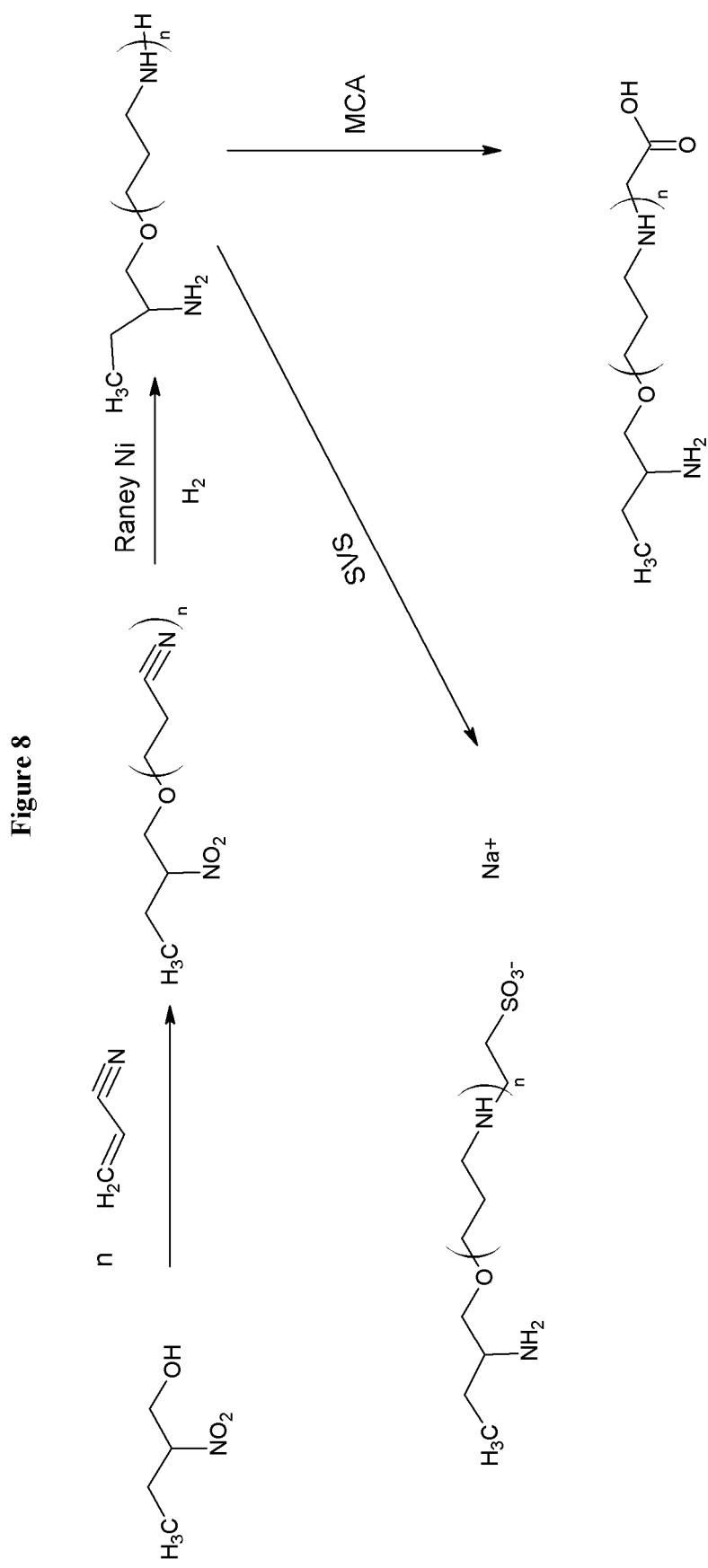
FIG. 8 shows the reaction of 2-nitro-1-butanol with acrylonitrile and its derivatives.

FIG. 8 shows the reaction of 2-nitro-1-butanol with acrylonitrile and its derivatives.

FIGS. 2 through 8 are subject to the same clarifications as FIG. 1 with regard to the cyanoethylation and the formation of a more linear or branched structure as well as the addition of SVS or MCA in molar equivalents of primary amine groups or less than molar equivalents of primary amine groups present.

The buffers described thus far may also be ethoxylated, propoxylated, or butoxylated to modify their properties. Ethoxylation will tend to impart surfactancy to the resulting product. Propoxylation will add surfactancy, but also reduce the water solubility. This is useful in emulsion breaking and reverse emulsion breaking, this will also find utility in breaking up and dissolving biofilms. This is also desired in oil-field applications. Butoxylation will similarly shift the HLB to the hydrophobic. Combinations of ethoxylation, propoxylation, and butoxylation can be tailored to specific emulsion and reverse emulsion forming and breaking requirements. FIG. 9 shows alkoxylation of aminomethylpropanol. The direct 2 mole ethoxylation of 2-amino-2-methyl-1-propanol with 2 moles of ethylene oxide, as shown in FIG. 9 produces an excellent biological buffer with less chelation than 2-amino-2-methyl-1-propanol. The reaction of 2-amino-2-methyl-1-propanol with propylene oxide or butylene oxide yields a similarly less chelating product, as does the reaction with diethylene glycol. The reaction product of 2-amino-2-methyl-1-propanol with 1 mole of diethylene glycol as shown in FIG. 9 produces an ideal amine for gas scrubbing of $H_2S$. This product is particularly useful because it does not bind to carbon dioxide and carbon monoxide in any appreciable amount. Thus making it ideal for tail gas scrubbing and maximizing the capacity of sulfur plants in refineries. Similar performance is seen with the reaction of the following amines 2-amino-1-butanol, 2-amino-2-methyl-1,3-propanediol, 2-amino-2-ethyl-1,3-propanediol, tris(hydroxylmethyl)aminomethane, and 2-amino-1,3-propanediol.

Figure 10A:
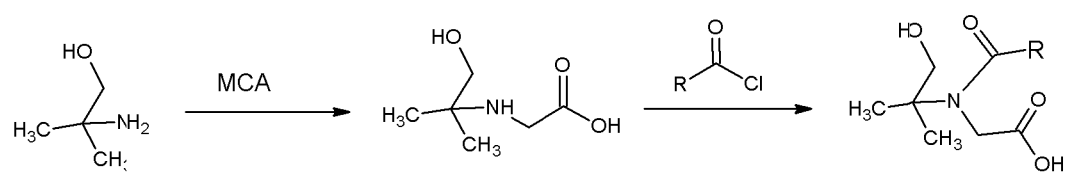
FIG. 10A shows the synthesis of a very mild, high foaming, surfactant derived from MCA.
Figure 10B:
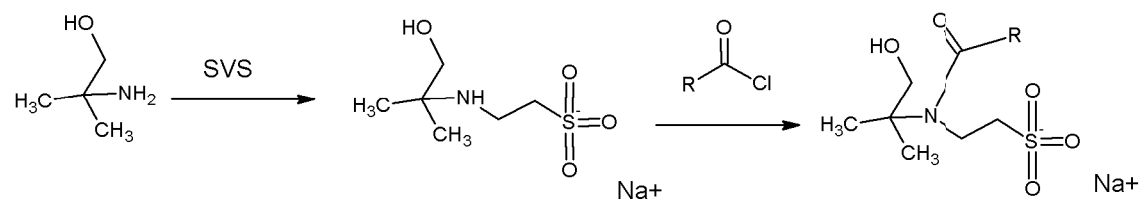
FIG. 10B shows the synthesis of a very mild, high foaming, surfactant derived from SVS.

The buffers described herein also make excellent starting materials for surfactants. FIG. 10 shows the synthesis of 2 very mild, high foaming, surfactants that are well suited for personal care applications were irritation is problematic, such as baby shampoo and face cleansers. Similar results are seen when 2-amino-1-butanol, 2-amino-2-methyl-1,3-propanediol, 2-amino-2-ethyl-1,3-propanediol, tris(hydroxylmethyl)aminomethane, and 2-amino-1,3-propanediol are used as the starting material in place of 2-amino-2-methyl-1-propanol.

Figure 11:
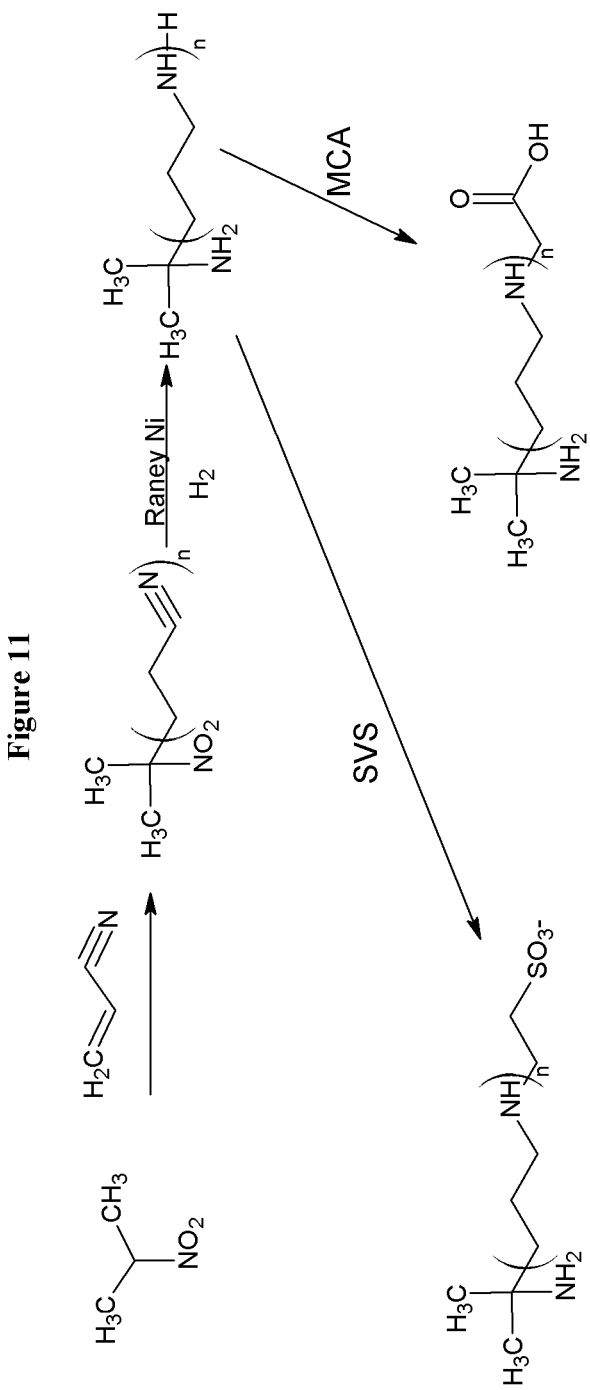
FIG. 11 shows the synthesis of a series of buffers with 2-nitropropane as the starting material.
Figure 12:
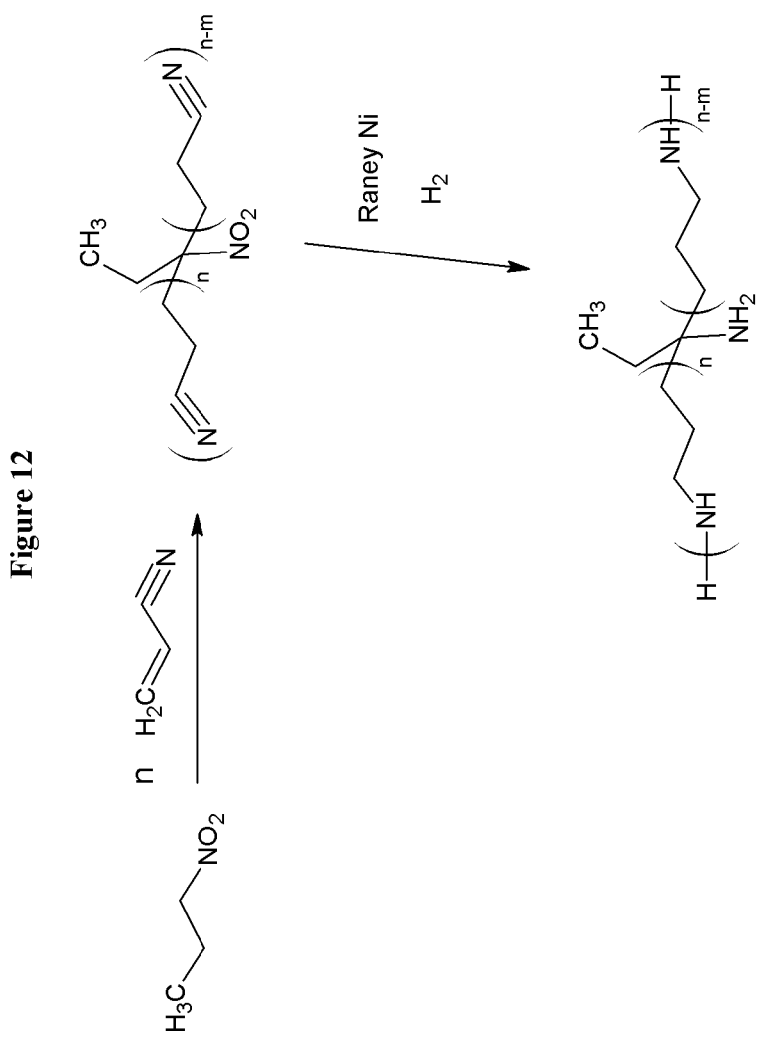
FIG. 12 shows

Polyamines with good properties for use in biological fermentations, purifications, storage and general handling can also be produced through the reaction of nitroalkanes and acrylonitrile, followed by reduction. Additional derivatization with SVS or MCA will result in zwitterionic buffers with a very large buffering range and capacity. FIG. 11 shows the synthesis of a series of buffers with 2-nitropropane as the starting material. FIG. 12 shows the synthesis of a series of buffers with 1-nitropropane as a starting material where n and m are integers where m+n is greater than zero and n is greater than or equal to m. Branching can be imparted on the buffers described in FIGS. 11 through 14 for the polyamines that have greater than 3 amine groups by reducing the resulting nitrile or polynitrile to the polyamine and then reacting with more acrylonitrile and then reducing the resulting nitrile groups to amine groups. This can be done repeatedly. As in FIG. 1, conditions can be chosen such that a more branched product results. A more linear product is produced by simply adding all the acrylonitrile in one step, and then reducing the resulting polynitrile to the polyamine. For FIGS. 12 through 14, the zwitterionic products can be made by adding MCA or SVS as shown in FIGS. 2 through 8.

Figure 13:
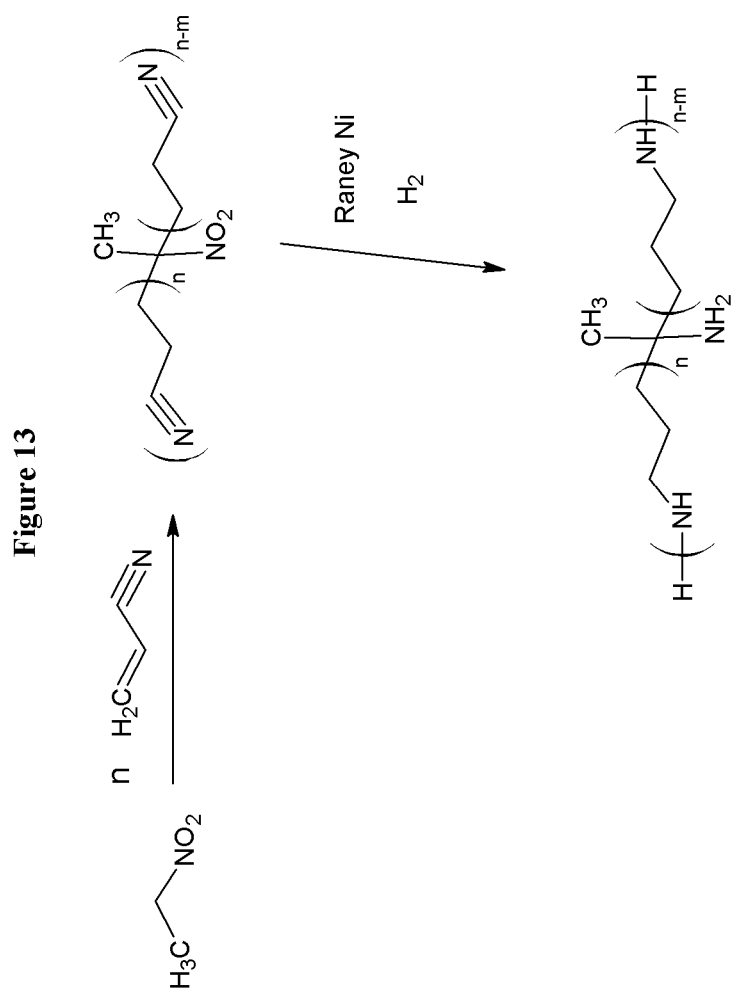
FIG. 13 shows the synthesis of a series of buffers with nitroethane as a starting material where n and m are integers where m+n is greater than zero and n is greater than or equal to m.
Figure 14:
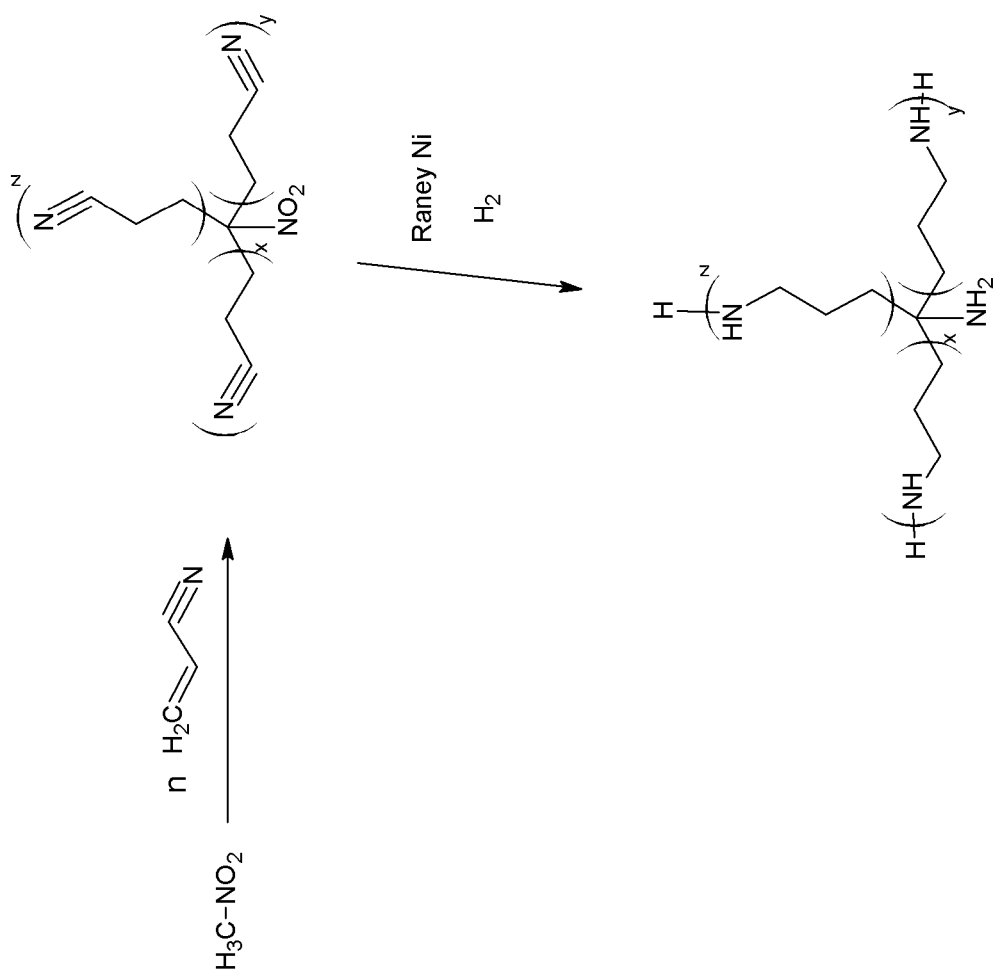
FIG. 14 shows the synthesis of a series of buffers with nitromethane as a starting material where x, y, z and n are integers and x+y+z=n and n is greater than zero.

FIG. 13 shows the synthesis of a series of buffers with nitroethane as a starting material where n and m are integers where m+n is greater than zero and n is greater than or equal to m. FIG. 14 shows the synthesis of a series of buffers with nitromethane as a starting material where x, y, z and n are integers and x+y+z=n and n is greater than zero.

Several descriptions and illustrations have been presented to enhance understanding of the present invention. One skilled in the art will know that numerous changes and variations are possible without departing from the spirit of the invention. Each of these changes and variations are within the scope of the present invention.

Figure 15:
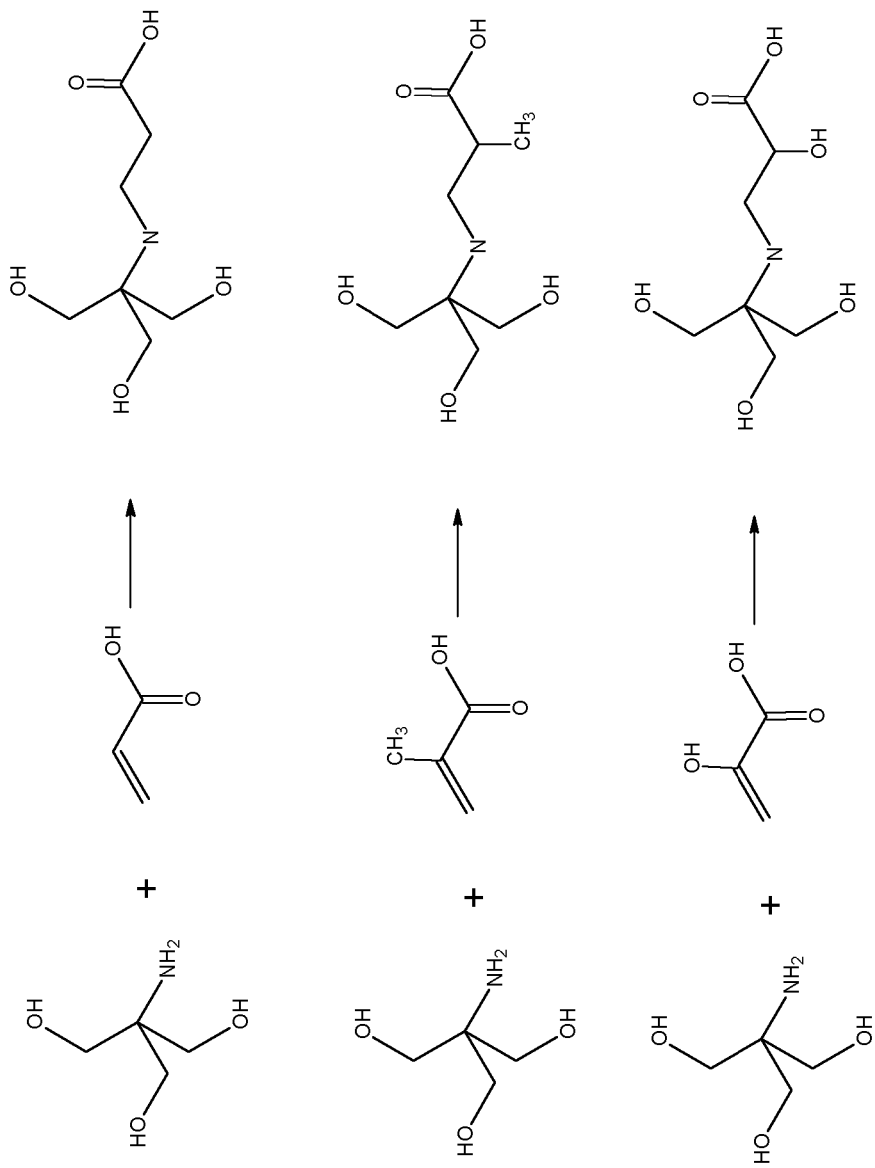
FIG. 15 shows the synthesis of a series of zwitterionic buffers based on acrylic acids.

Another embodiment of the present invention is the synthesis of zwitterionic buffers with vinyl acids. FIG. 15 shows the synthesis of a family of zwitterionic buffers based on members of the acrylic acid family. However, other vinyl acids may be used. Vinyl acids such as acrylic, 3-butenoic acid, 4-pentenoic acid, and other carboxcylic acids with a double bond at the terminus. Carboxcylic acids with a triple bond at the terminus also can be utilized, similarly, an acid where the multiple bond is not at the terminus, such as hex-4-enoic acid, can also be utilized. However, due to the reduced commercial availability of such compounds, the preferred embodiment is the vinyl acid with a double bond at the terminus. One very large benefit of utilizing vinyl acids to make zwitterionic buffers is that the product does not need to be ion exchanged to produce a non-ionized form. In the market, both ionized, or sometimes called salted, and non-ionized forms sometimes called free acid or free base, are required. In situations where ionic strength must be very closely controlled, the non-ionized forms are more popular. For cases where increased water solubility and ease of solution are desired, the salted forms are preferred. It is understood to one skilled in the art, the present invention covers both the ionized and non-ionized forms of the buffers disclosed herein.

Figure 16:
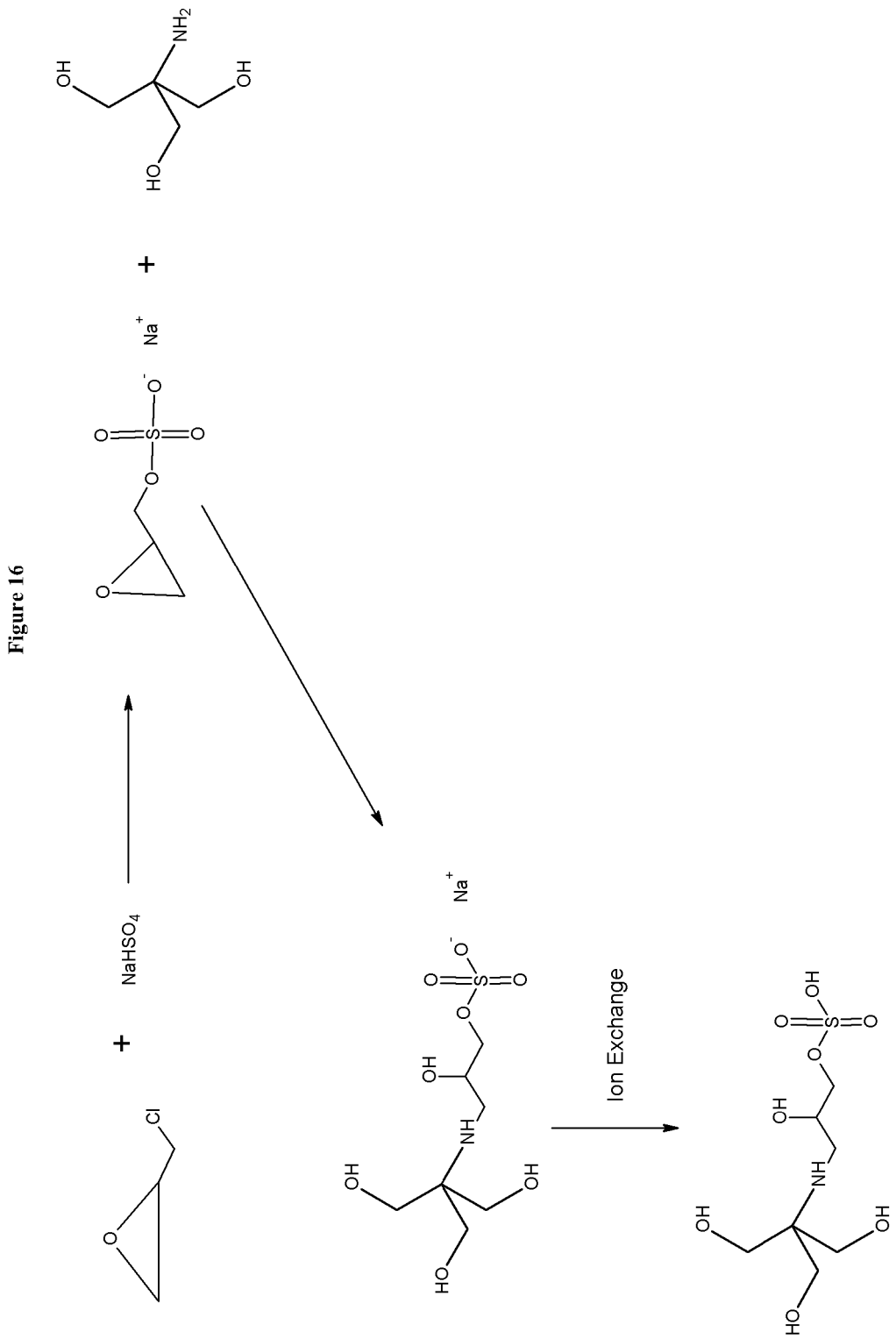
FIG. 16 shows the synthesis of a zwitterionic sulfonate based on tromethamine.
Figure 17:
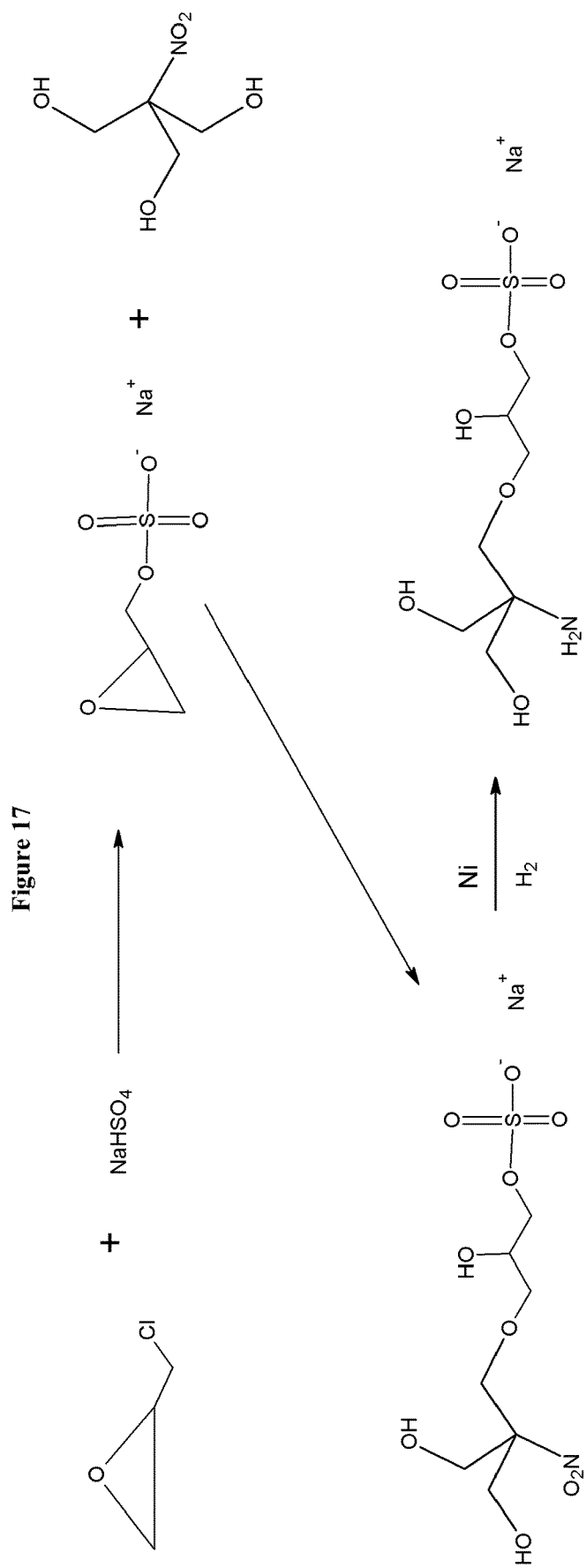
FIG. 17 shows the synthesis of a zwitterionic sulfonate based on aminomethylpropanol.
Figure 18:
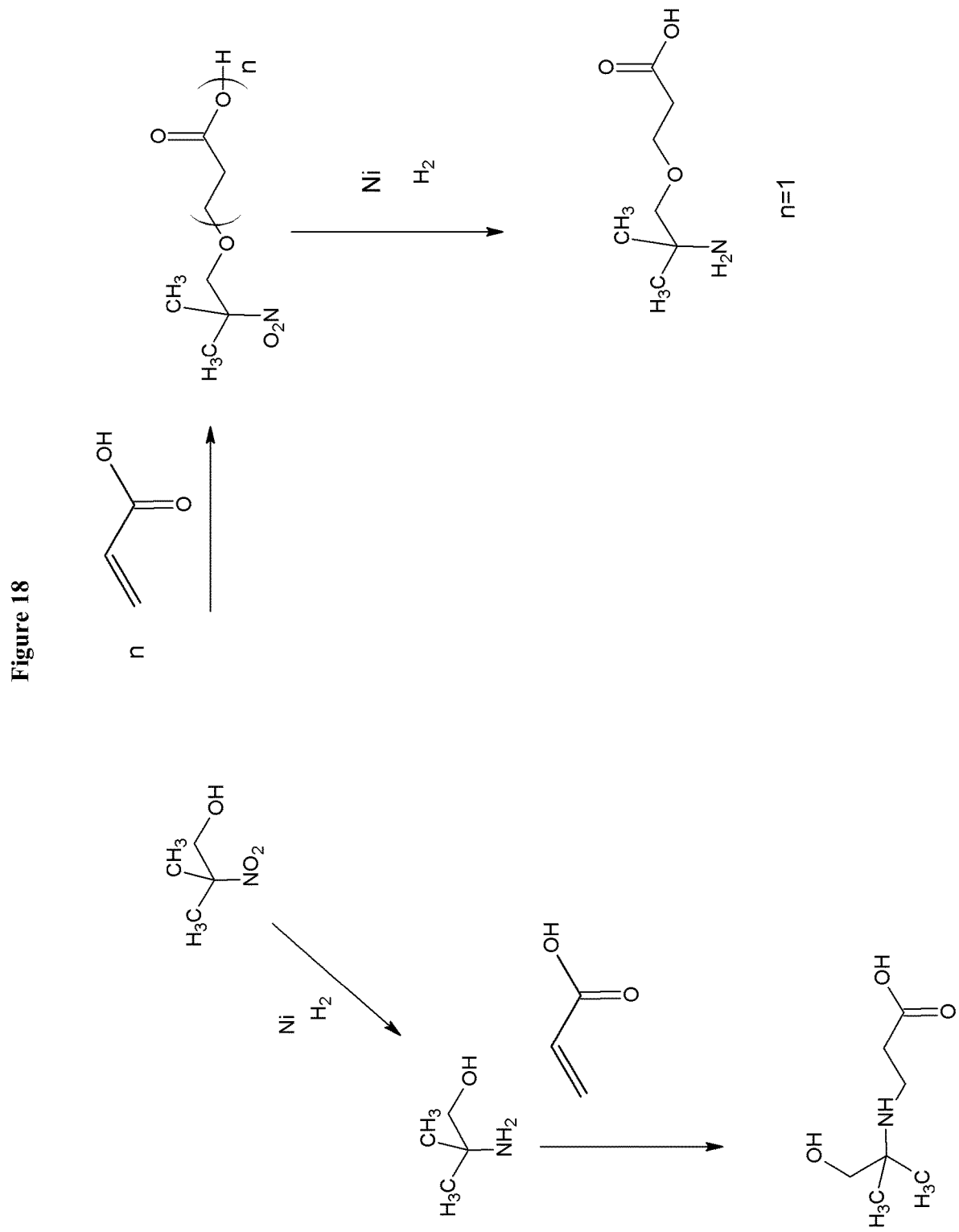
Figure 19:
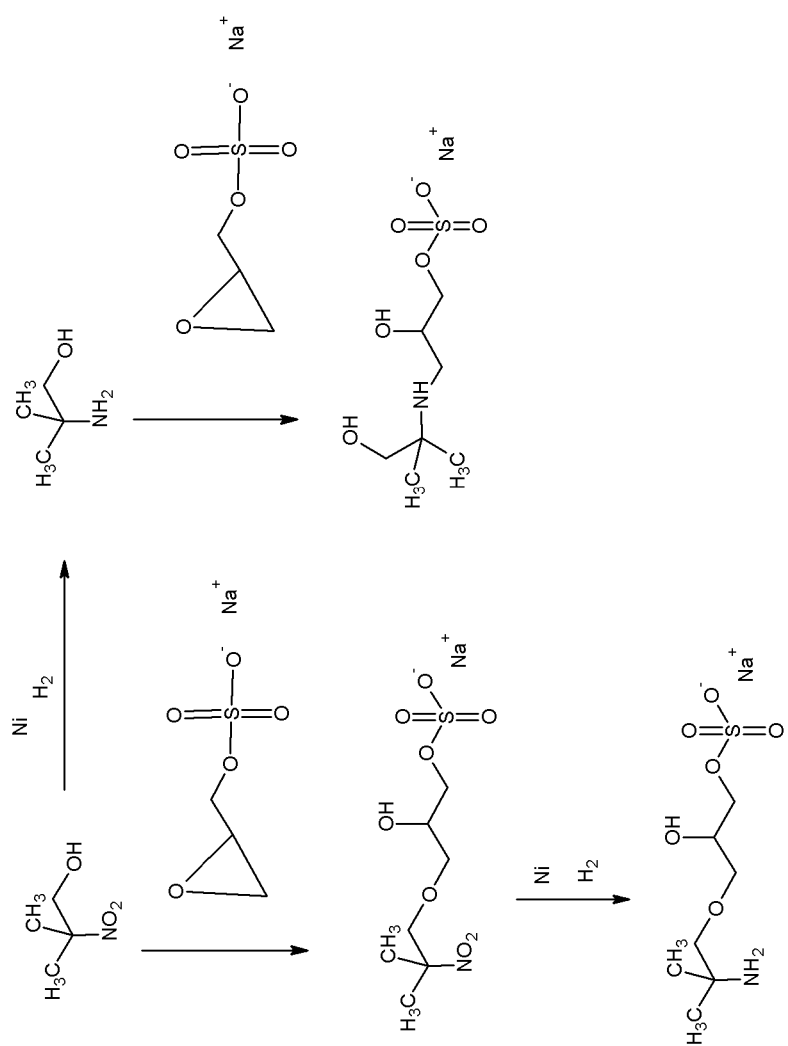
Figure 20:
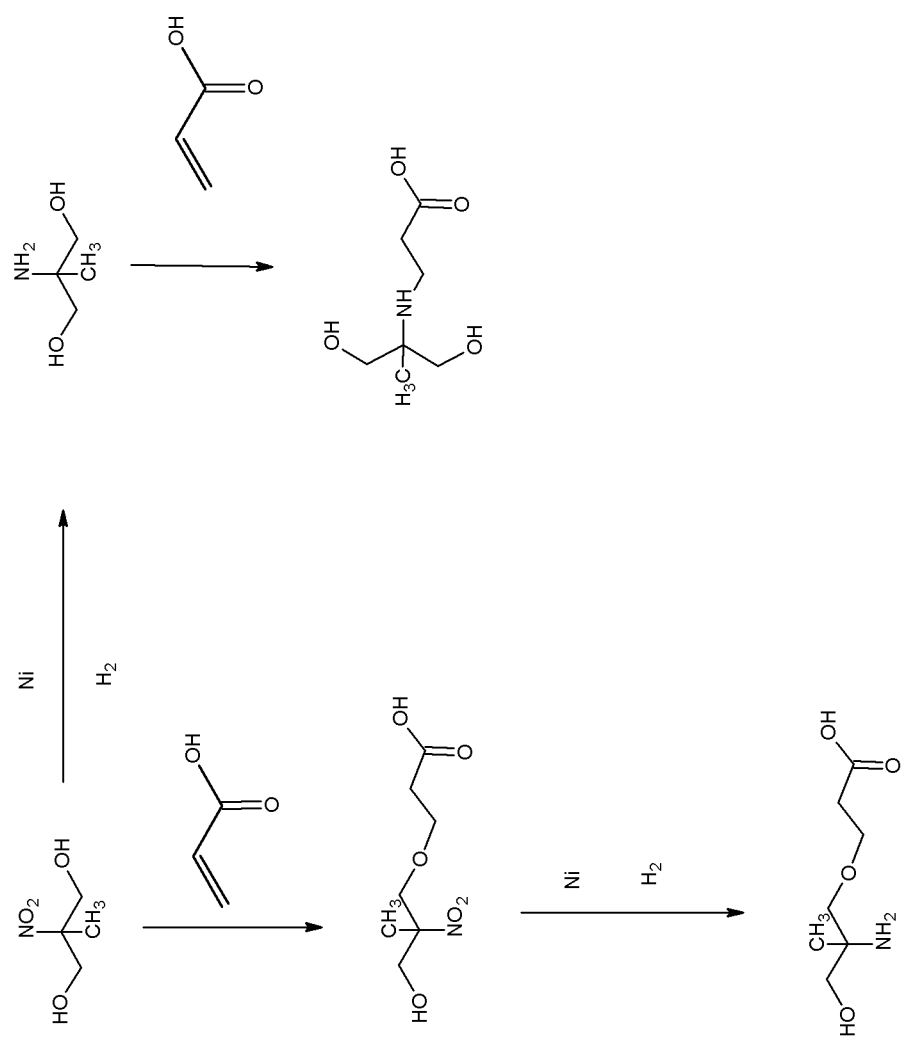
Figure 24:
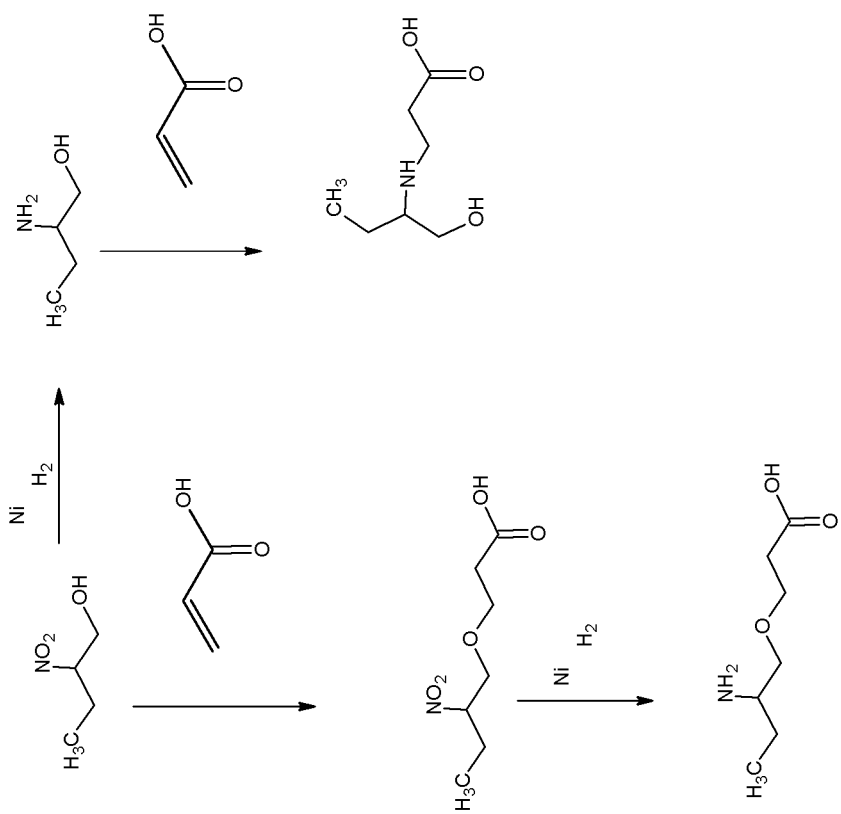
Figure 25:
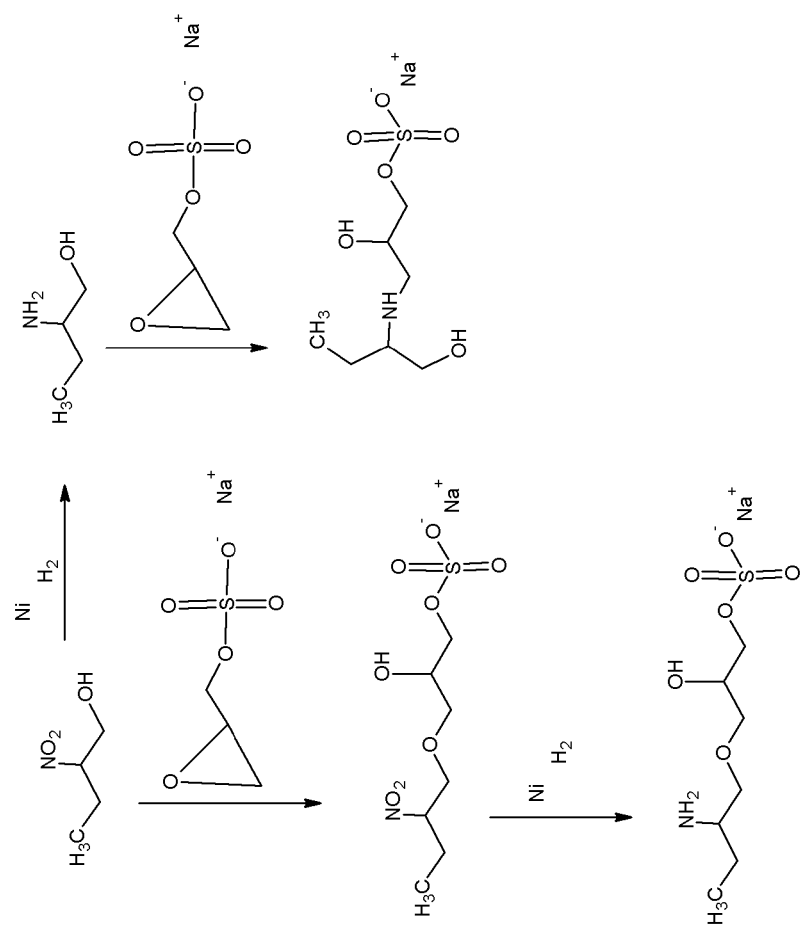

Another embodiment of the present invention is the sulfonate zwitterionic buffers derived from the reaction of an amine with an epichlorohydrin and sodium bisulfate condensate as described in FIG. 16. It is understood by one skilled in the art that other sulfate salts can be utilized to arrive at the desired molecular structure and is included in the present invention. FIGS. 17 through 25 teach the flexibility of the present invention to synthesize a series of a amine sulfonate or amino acid zwitterionic buffers from nitroalcohols or alkanolamines to produce zwitterionic buffers that have primary amino functionality or secondary amino functionality. In cases where there are more than one reactive group, amine, alcohol, or a combination, multiple sulfonate groups or acid groups can be reacted by adding more than one equivalent of the vinyl acid or the oxirane containing sulfonate.

Figure 26:
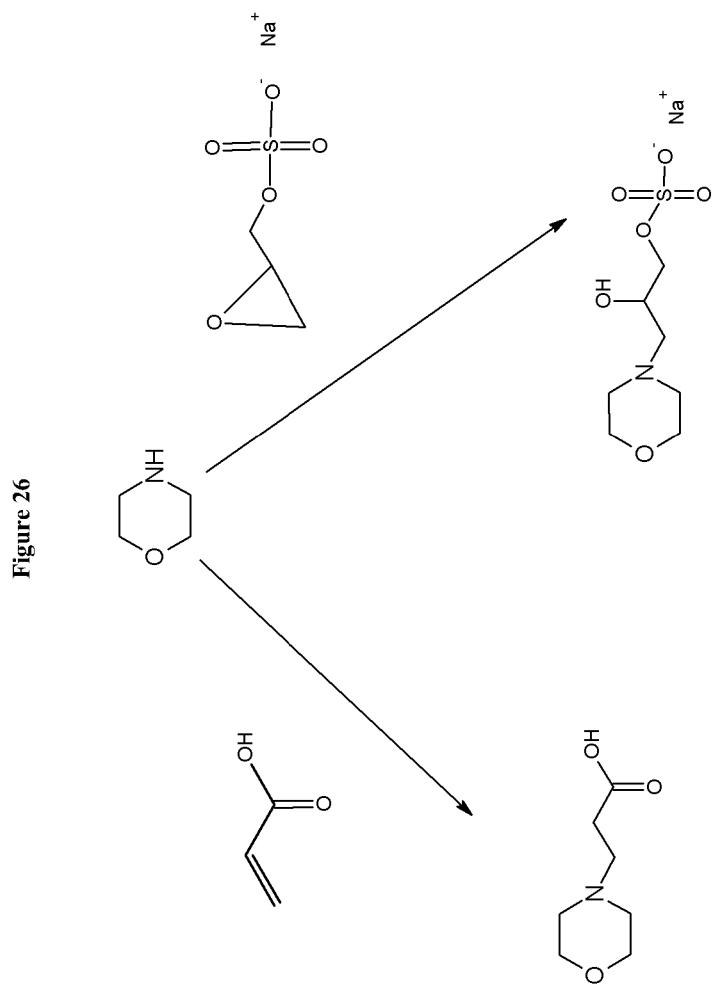
FIG. 26 shows the synthesis of zwitterionic buffers from morpholine.
Figure 27:
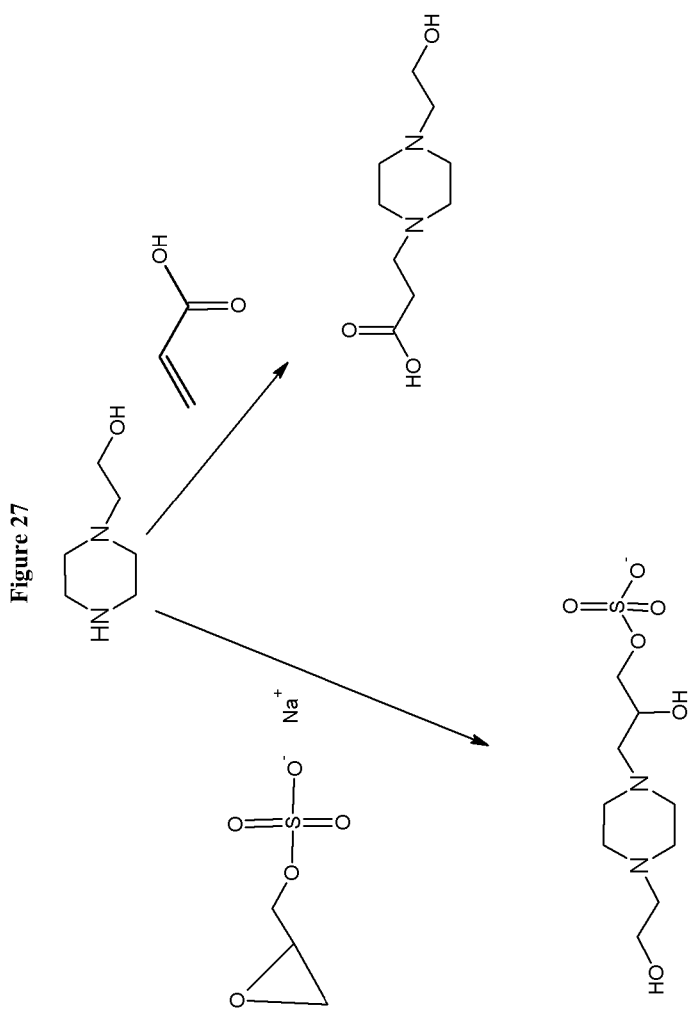
FIG. 27 shows the synthesis of zwitterionic buffers from hydroxyethyl piperazine.
Figure 28:
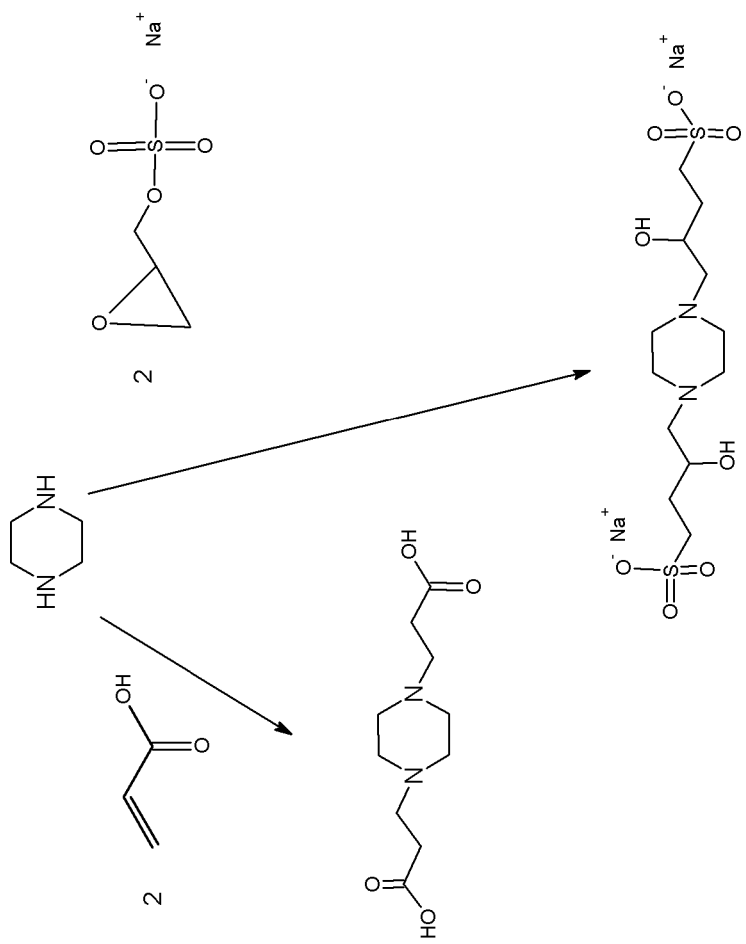
FIG. 28 shows the synthesis of zwitterionic buffers from piperazine.
Figure 29:
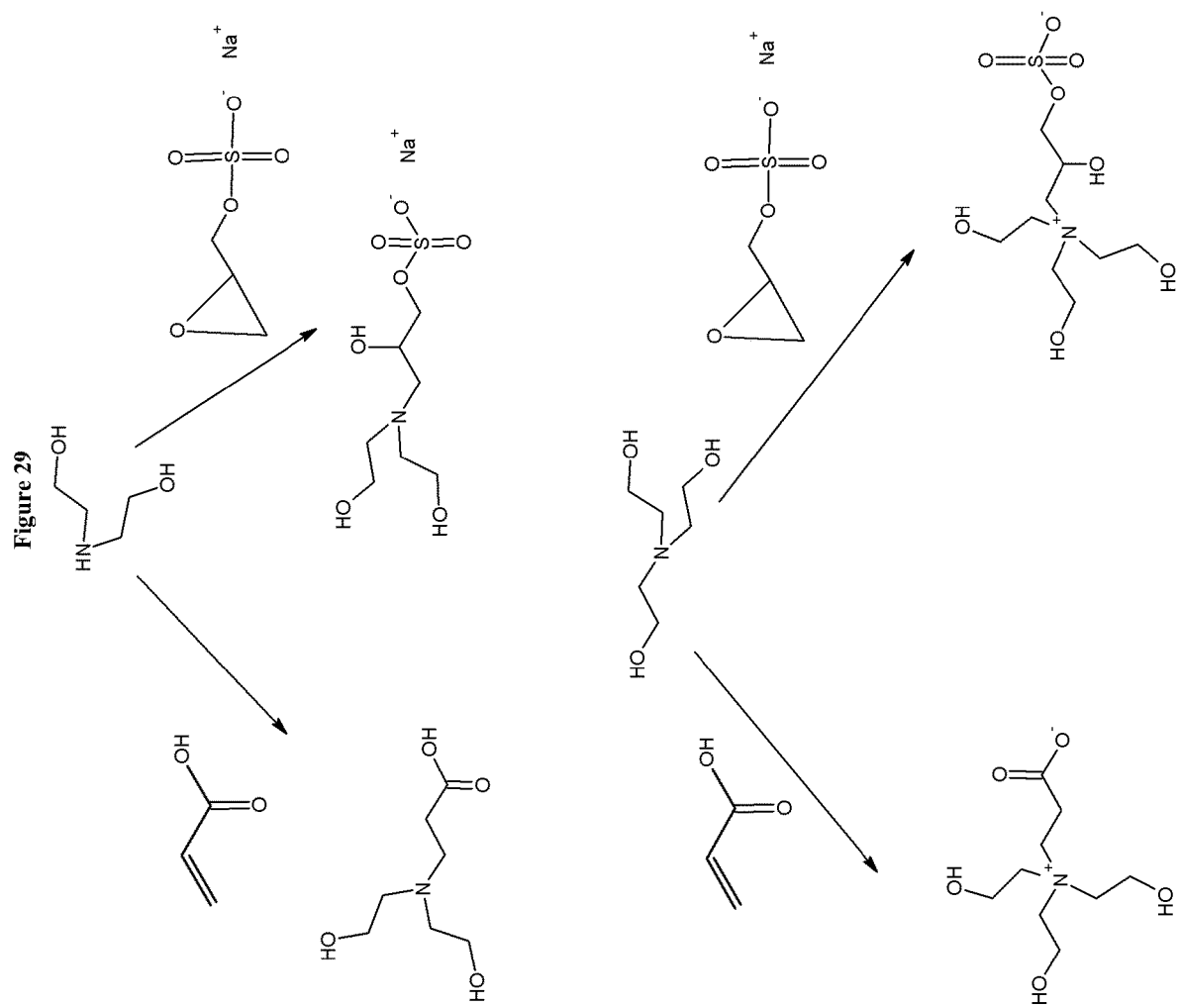
FIG. 29 shows the synthesis of zwitterionic buffers from ethyleneamines.

Another embodiment of the current invention is to make zwitterionic buffers with cylcoamines as the starting material. The cycloamines result in a tertiary amino group that is less chelating and interferes less in biological functions. FIG. 26 shows the reaction of morpholine with a vinyl acid and morpholine with the oxirane sulfonate. FIG. 27 shows similar products, but utilizing hydroxyethyl piperazine. FIG. 28 shows the use of diamines as starting materials by using piperazine as the starting material. This is a good example of a synthesis of polyzwittterionic buffers as discussed earlier. FIG. 29 shows the use of ethylene amines to make zwitterionic buffers through reaction with vinyl acids or oxirane sulfonates. One skilled in the art will recognize that similar compounds can be made by using ethylene amines, such as monoethanolamine and the higher homologs, such as diethylenetriamine and is part of the invention disclosed herein.

Figure 30:
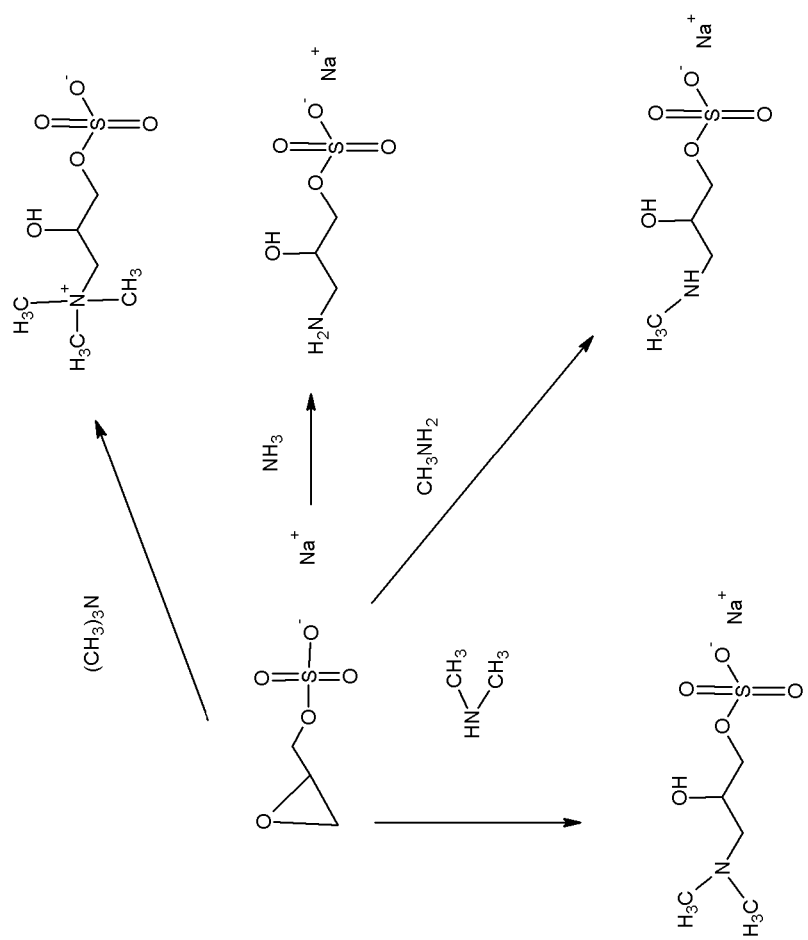
FIG. 30 shows the synthesis of a zwitterionic buffer with primary, secondary, tertiary, or quaternary amine functionality.

Another embodiment of the current invention is the synthesis of zwitterionic amines that have primary, secondary, tertiary, and quaternary amine functionality. FIG. 30 shows this via oxirane sulfonate and amines. One skilled in the art will recognize that any primary, secondary, or tertiary amine can be used in place of the methyamines in FIG. 30. While not shown in the figure, one skilled in the art will recognize that the resulting amines can be reacted further with vinyl acids, monochloroacetic acid, sodium vinyl sulfonate, or an oxirane sulfonate to further add acidic character to the zwitterionic buffer.

Figure 31:
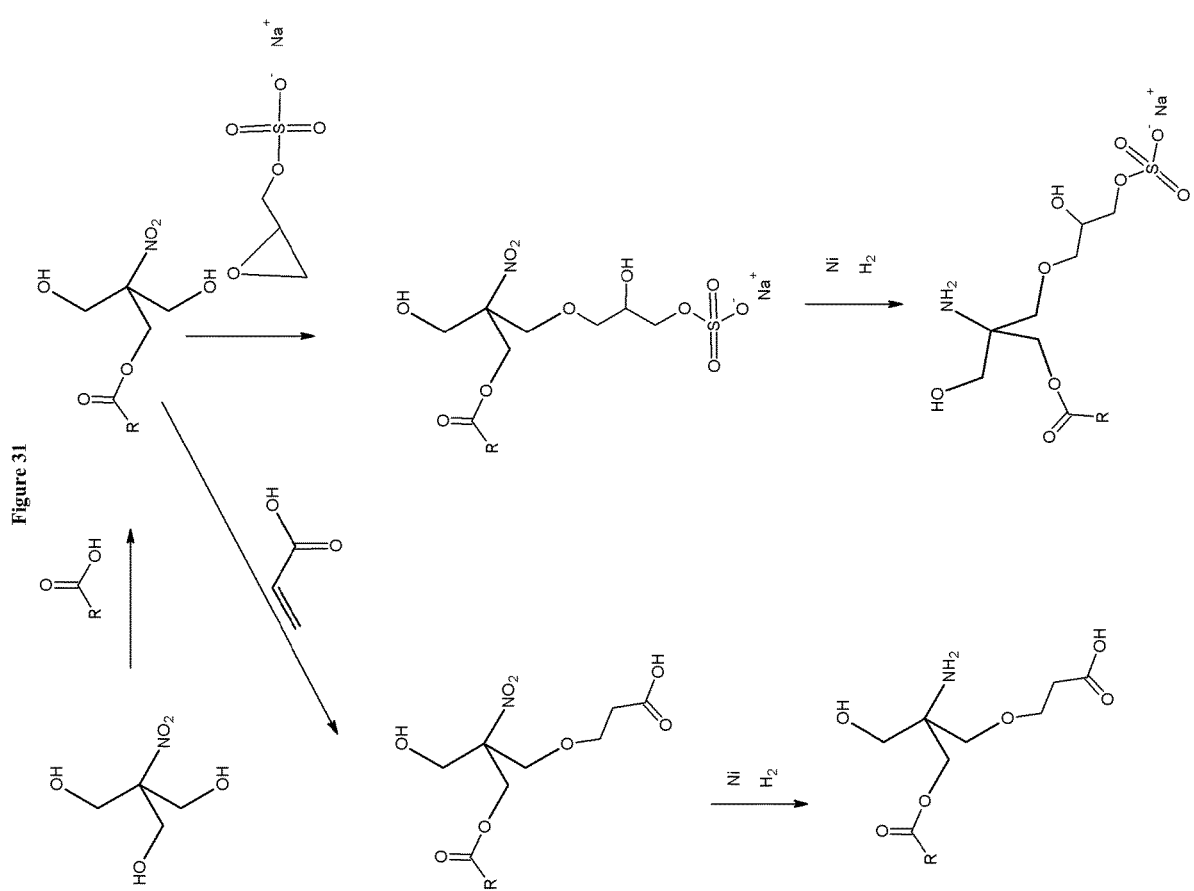
FIGS. 31-33 show the synthesis of mild zwitterionic surfactants from nitroalcohols.
Figure 32:
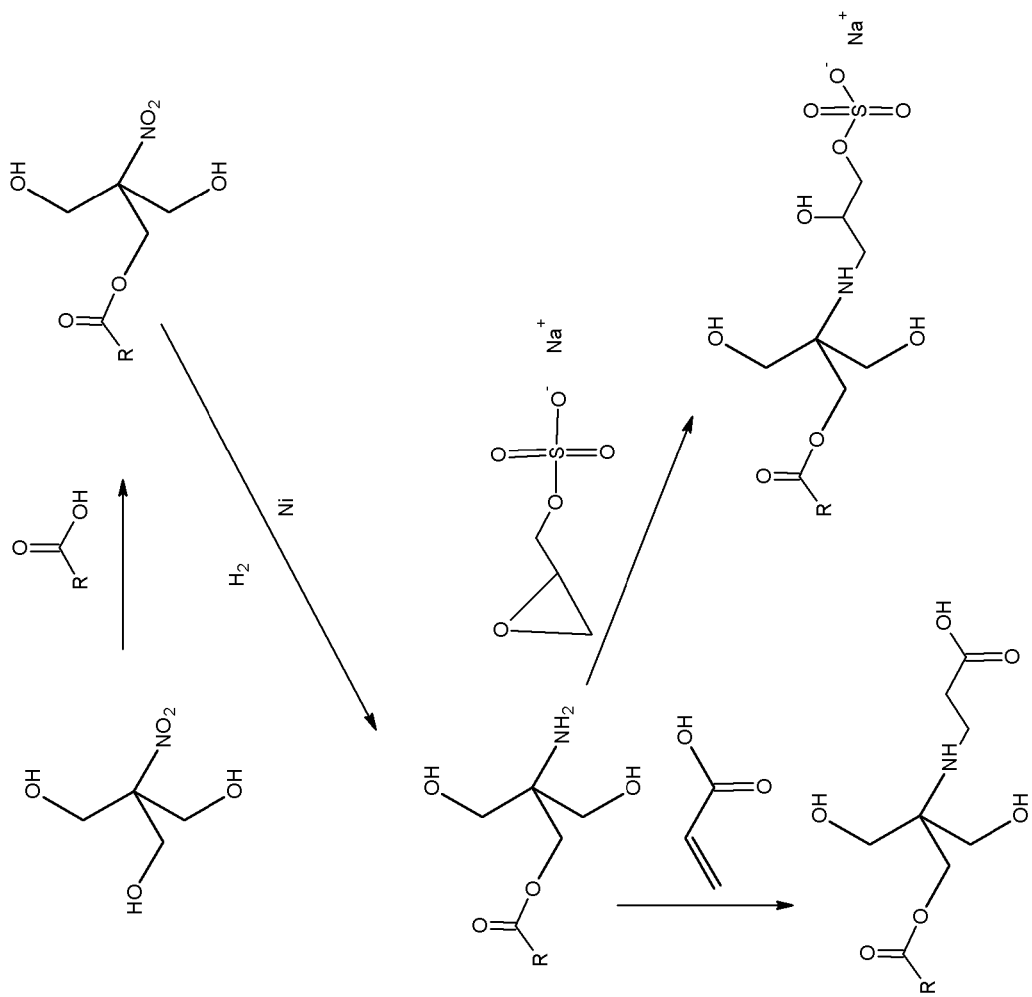
Figure 33:
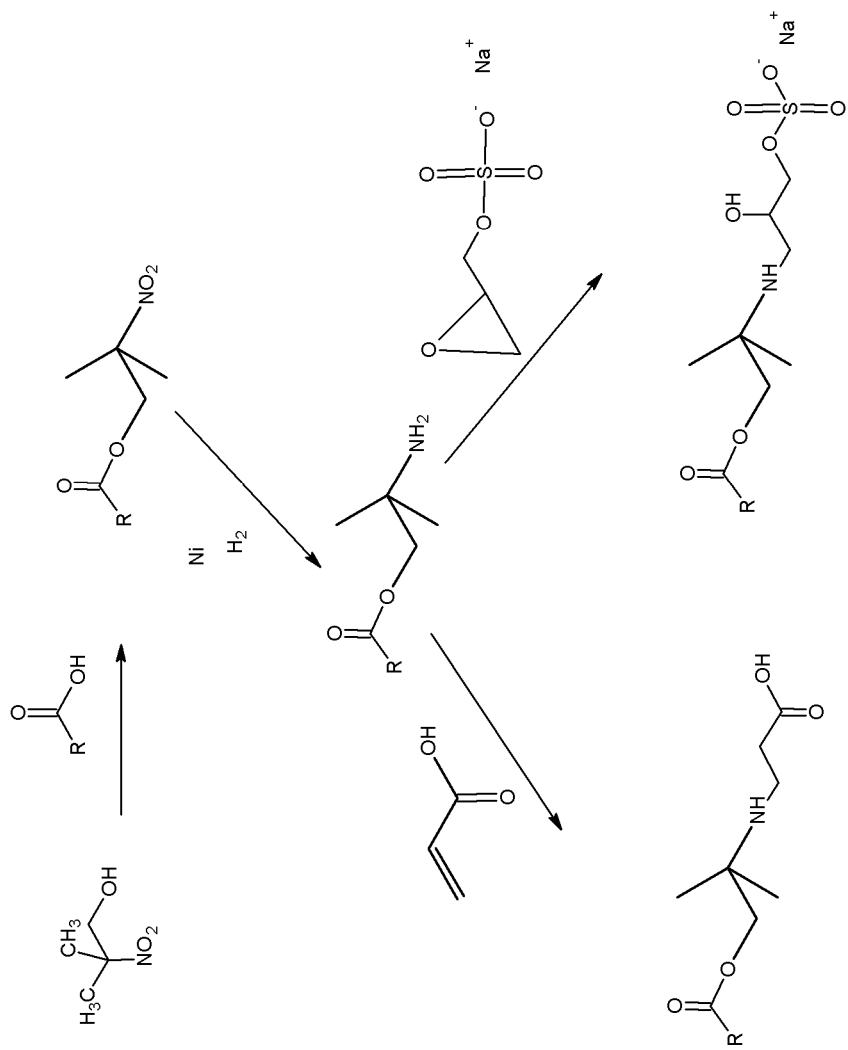

Another embodiment of the current invention is the synthesis of mild surfactants from nitroalcohols. FIGS. 31 through 33 teach the synthesis of these mild surfactants. Lower molecular weight acids produce lower foaming mild surfactants, whereas higher molecular weight carboxcylic acids yield higher foam. Lauric acid is the preferred embodiment for a high foaming, mild surfact. Coconut fatty acid performs similarly, but at a lower cost. A good surfactant with low foam can be made using octanoic acid as the carboxcylic acid.

Figure 34:
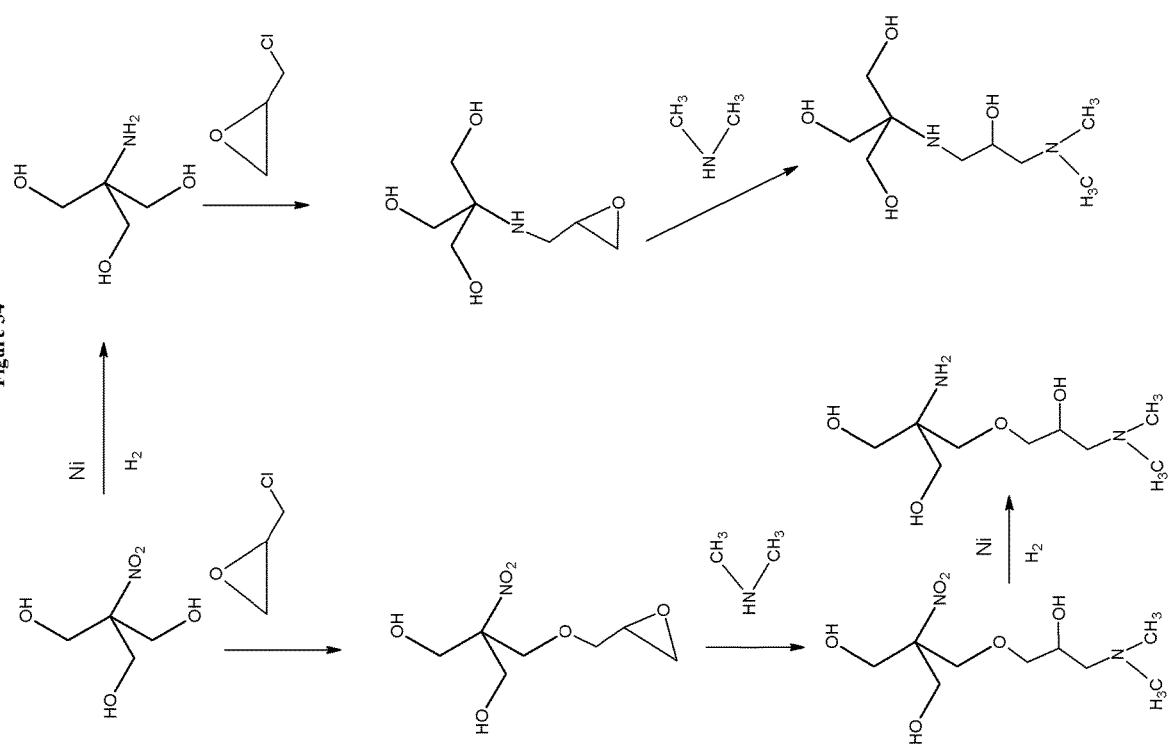
FIG. 34-37 show the synthesis of polyamines from nitroalcohols.
Figure 35:
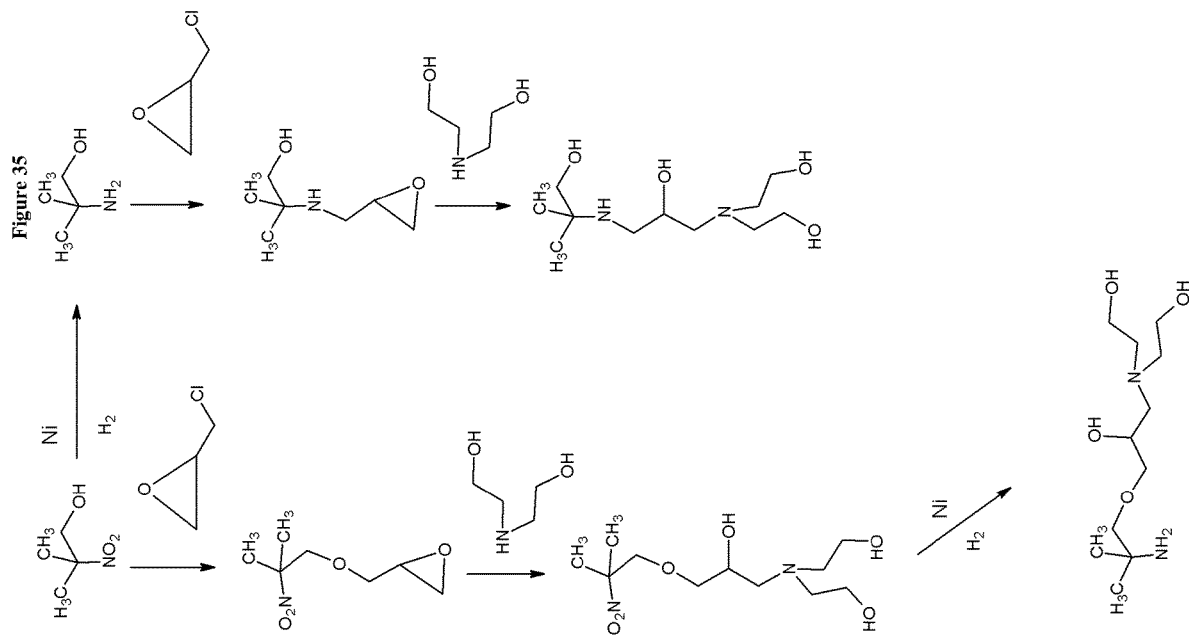
Figure 36:
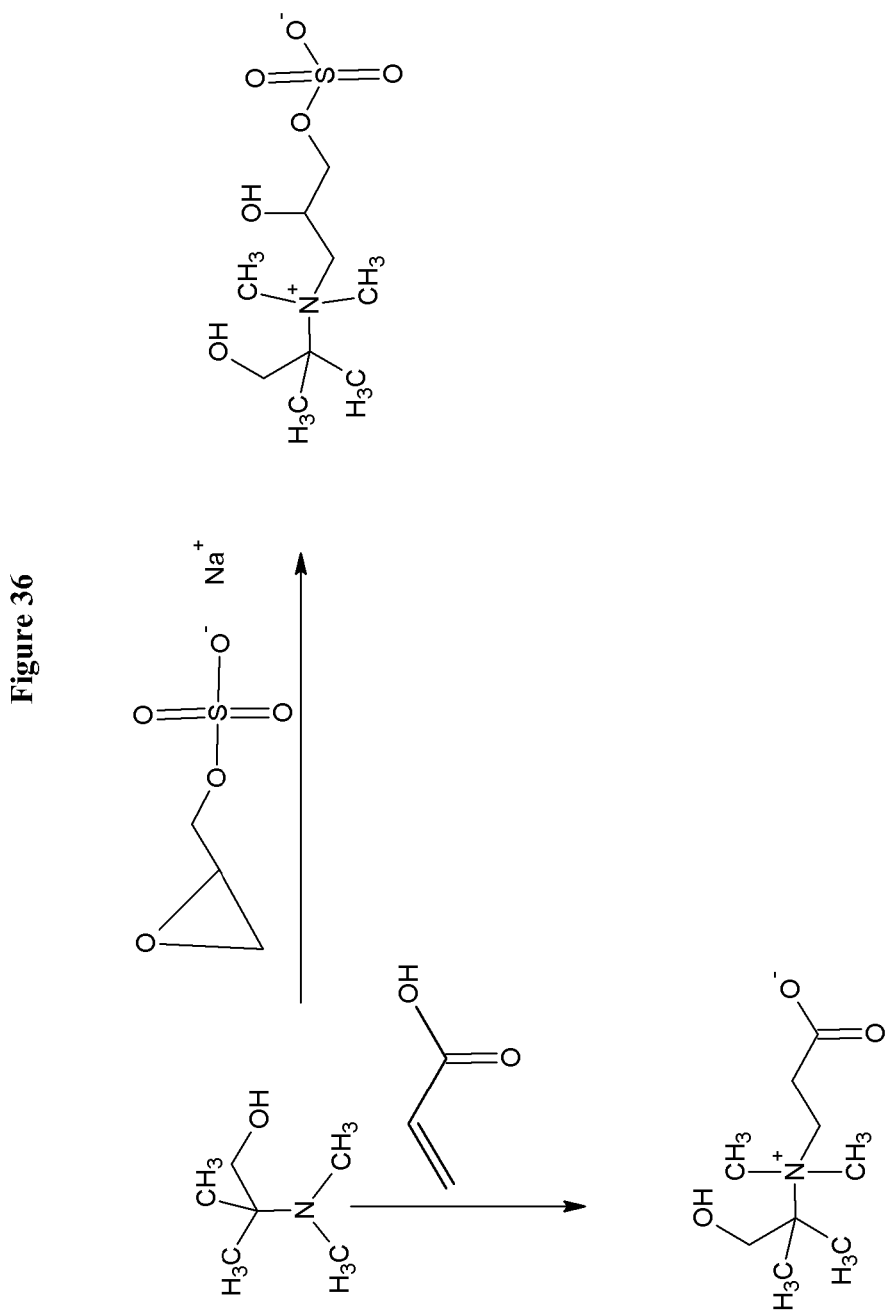
Figure 37:
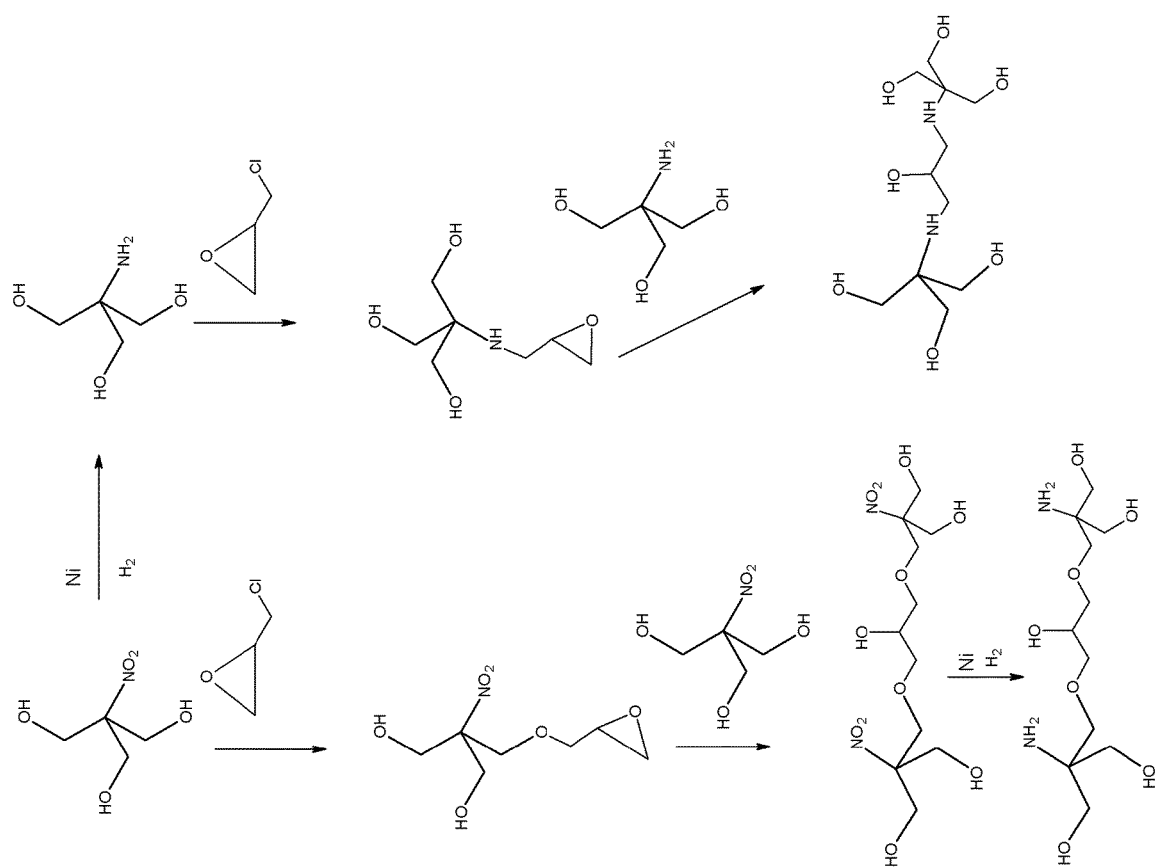
Figure 38:
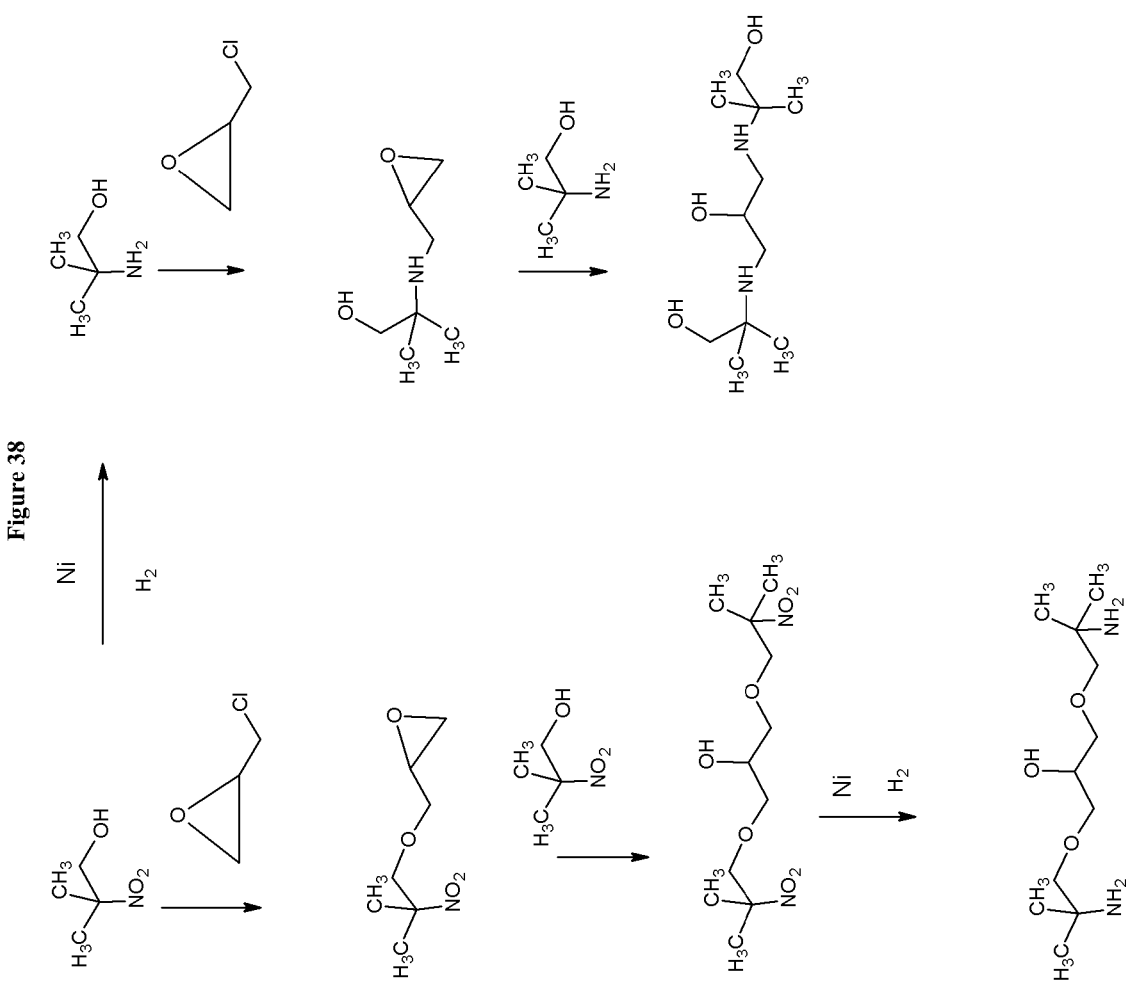
FIG. 38 shows the synthesis of diamines from nitroalcohols and aminoalcohols.
Figure 39:
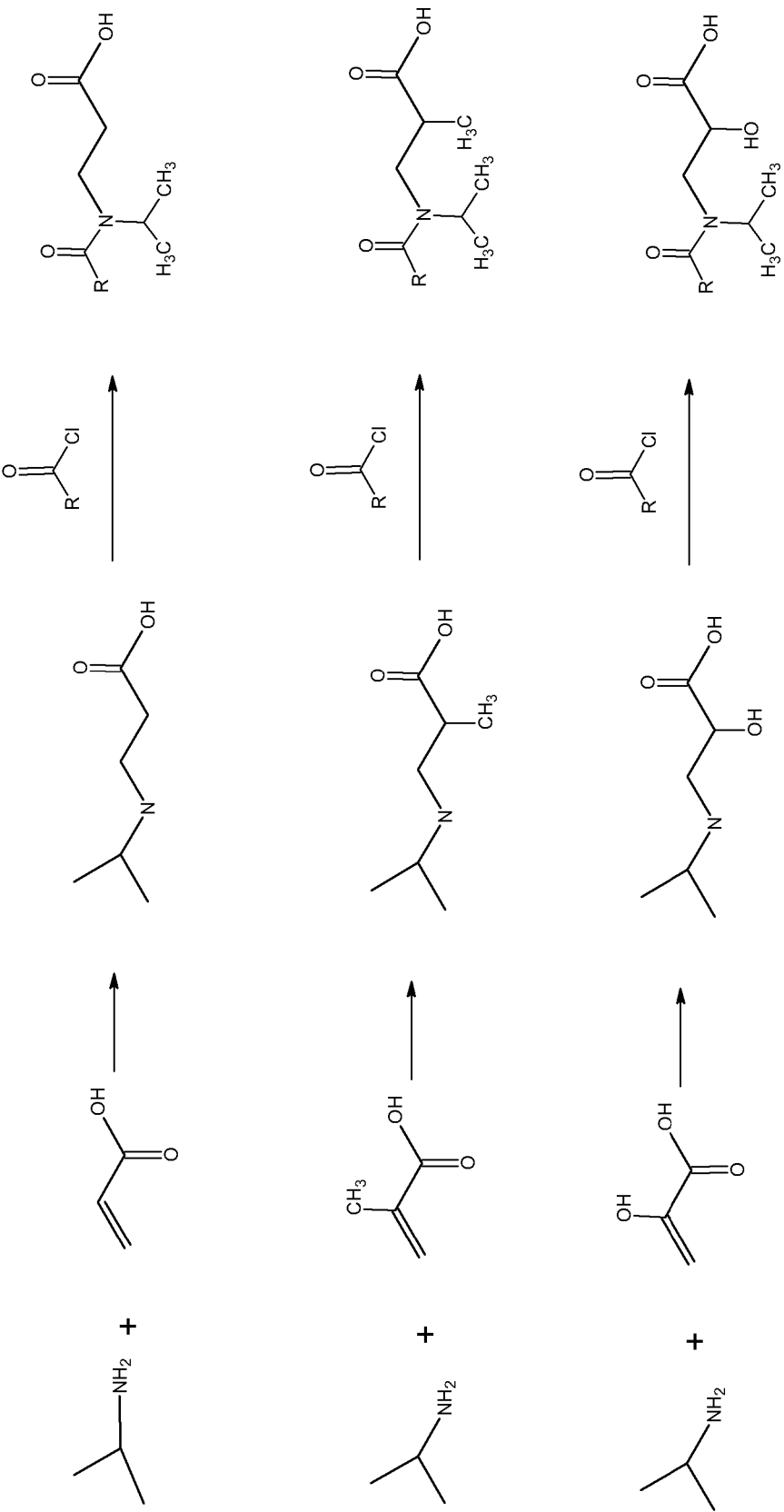
FIG. 39 shows the synthesis of isopropyl amine acrylate buffers and mild surfactants.
Figure 40:
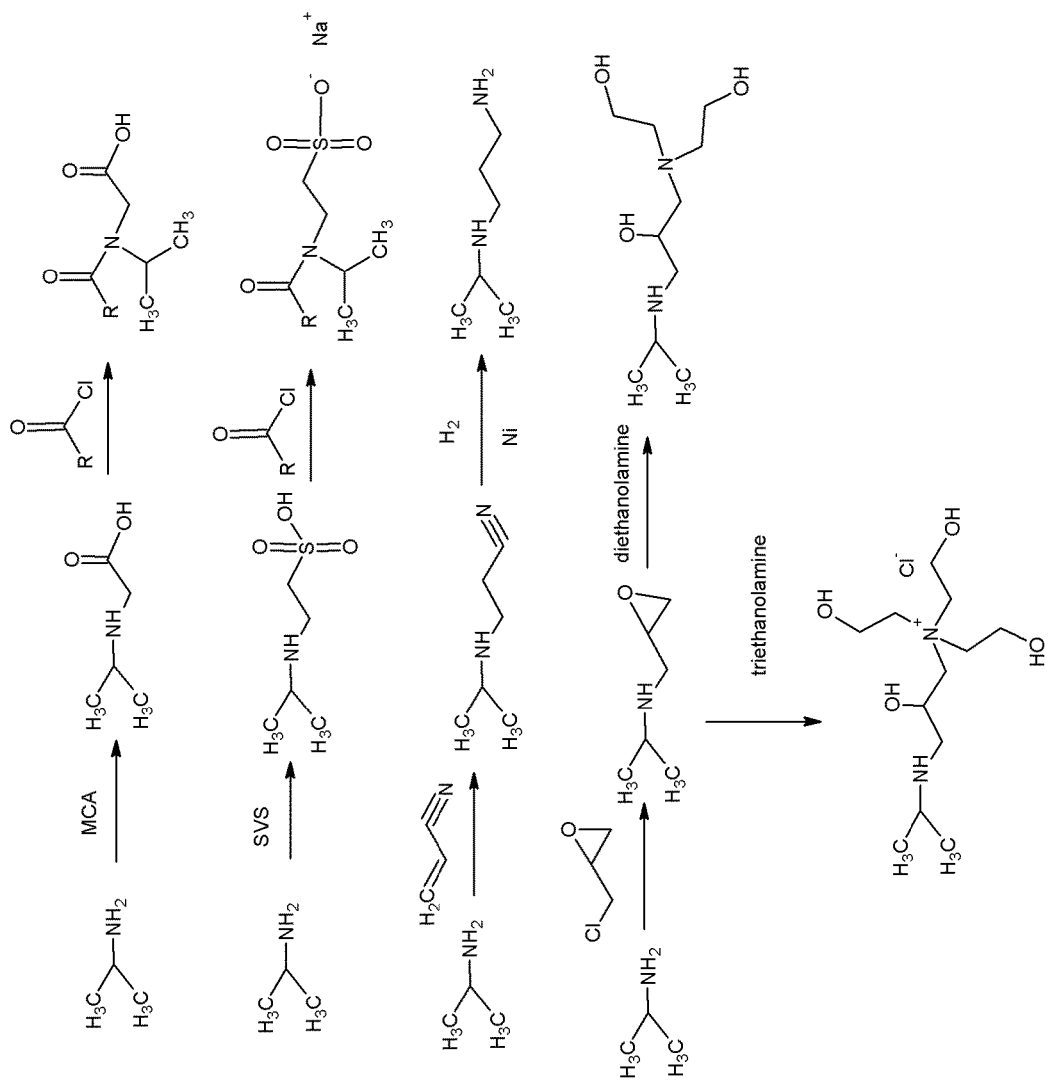
FIG. 40 shows the synthesis of zwitterionic buffers from SVS and MCA derived from isopropyl amine as well as mild surfactants and diamines.
Figure 41:
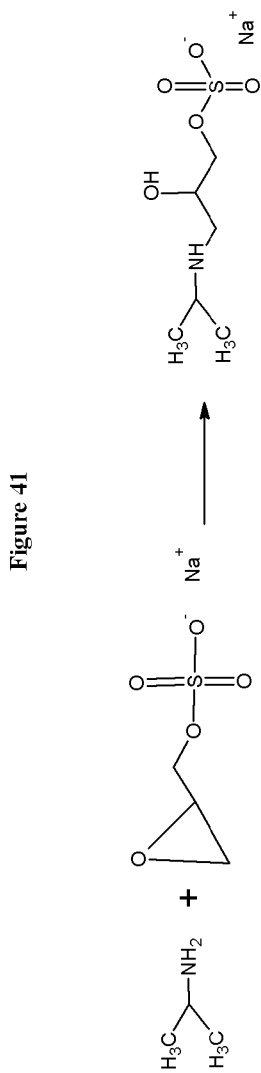
FIG. 41 shows the synthesis of a sultaine zwitterionic buffer of isopropyl amine.

Another embodiment of the current invention is the synthesis of polyamines from nitroalcohols. FIGS. 34 and 35 teach the synthesis of diamines from nitroalcohols. FIG. 34 shows the synthesis with several hydroxyl groups present. It is understood by one skilled in the art that additional amino groups can be added by reacting more than one equivalent of epichlorohydrin to the nitroalcohol, up to the number of hydroxyl groups, and then reacting the same number of equivalents of amine to the oxirane containing amine. In the case where the nitroalcohol is reduced to the amino alcohol in the beginning, the addition of base, such as caustic, to the amino alcohol will assist in the reaction of the epichlorohydrin with the hydroxyl groups. Without the base, the epichlorohydrin will preferably react with the amine as outlined in the 1 equivalent addition depicted in FIG. 34 and FIG. 35. FIG. 36 demonstrates that tertiary amines can be used to make zwitterionic buffers with quaternary amine functionality from tertiary amines. While not explicitly shown, any other tertiary amine can be used as the starting material and is part of the invention described herein. FIG. 37 and FIG. 38 demonstrate that diamines can be made from nitroalcohols by reacting sequentially the nitroalcohol with epichlorohydrin and then the second equivalent of the nitroalcohol, followed by reduction. Also taught is that a reduction step can take place in the beginning to yield a diamine with two secondary amino groups. It is understood by one skilled in the art that the nitroalcohols or alkanolamines do not need to be symmetric, but others may be used in the synthesis of the diamine and is part of the invention disclosed herein.

Figure 42:
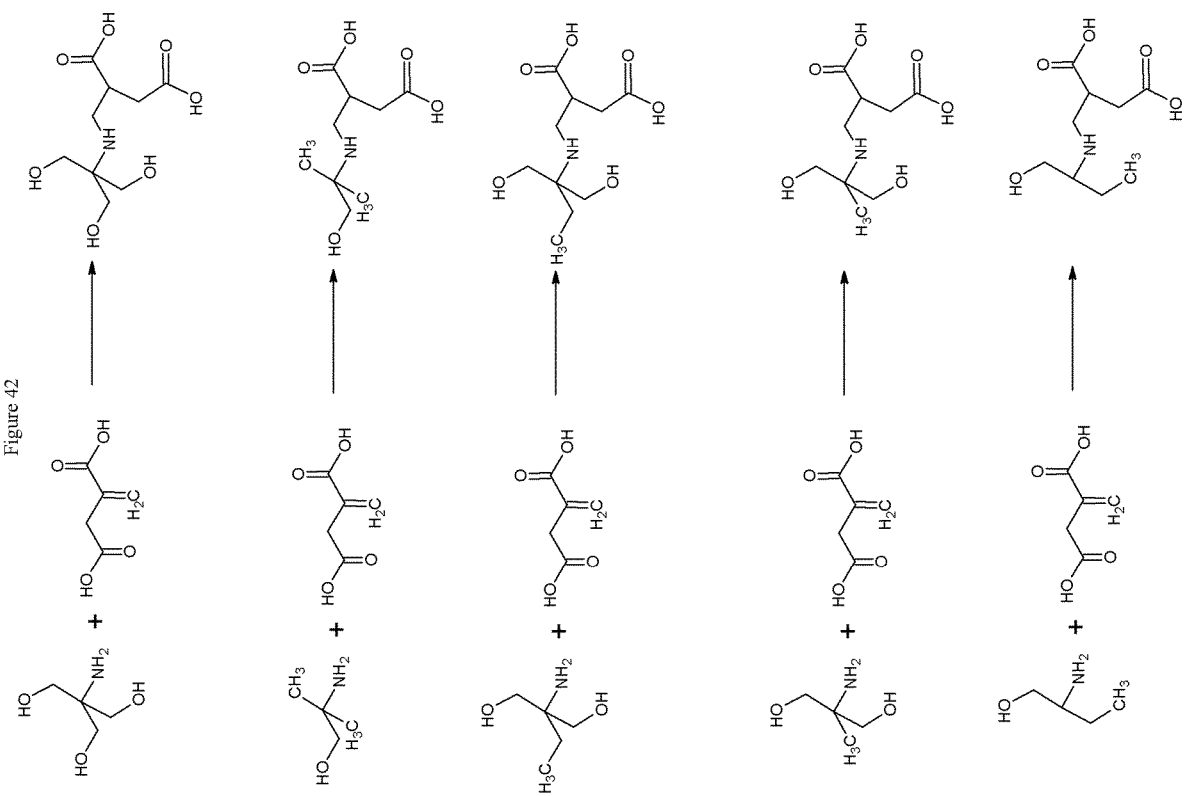
FIG. 42 shows the synthesis of zwitterionic buffers from amino alcohols and itaconic acid.
Figure 43:
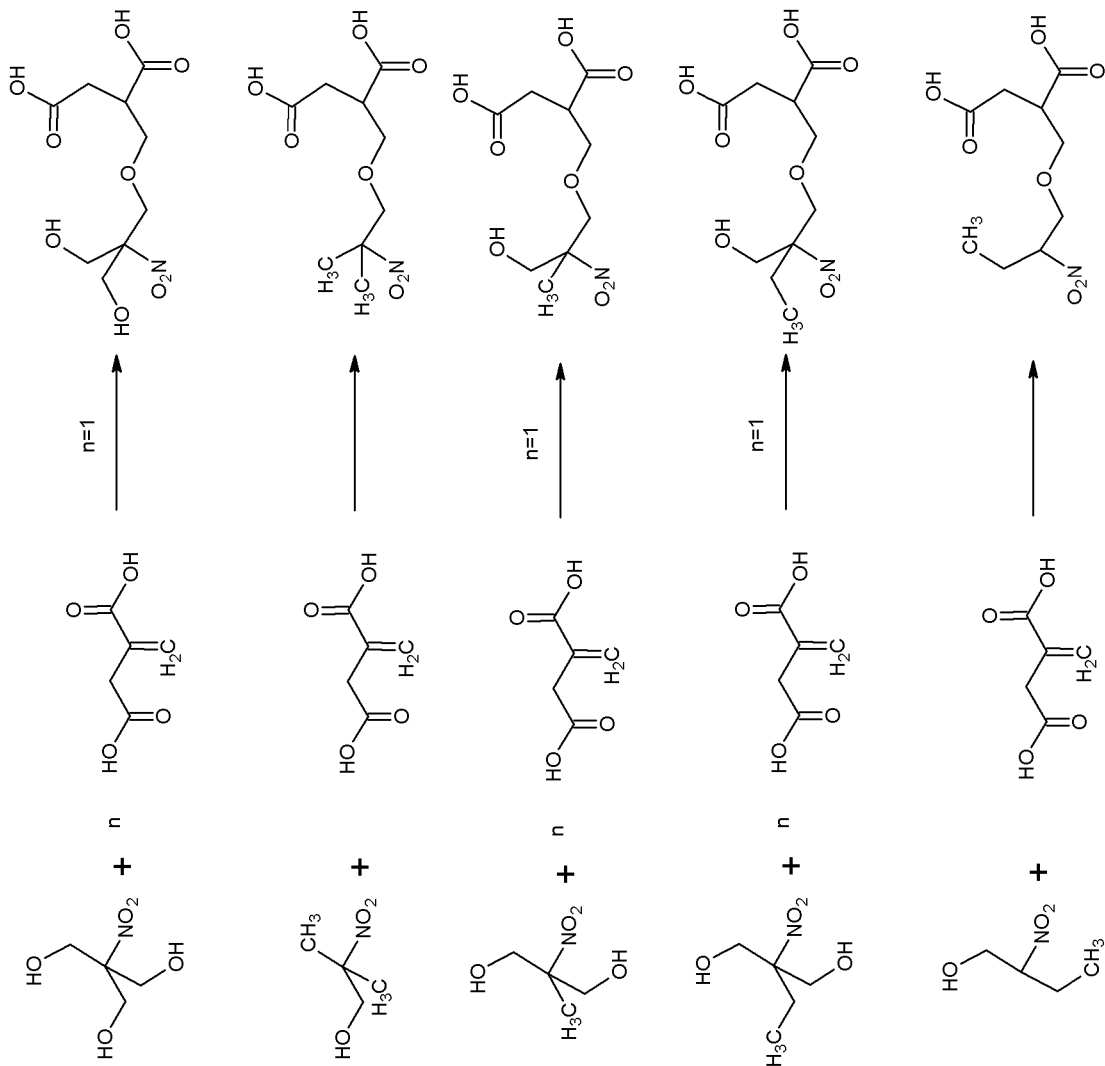
FIG. 43 shows the synthesis of nitro acids from nitroalcohols and itaconic acid.
Figure 44:
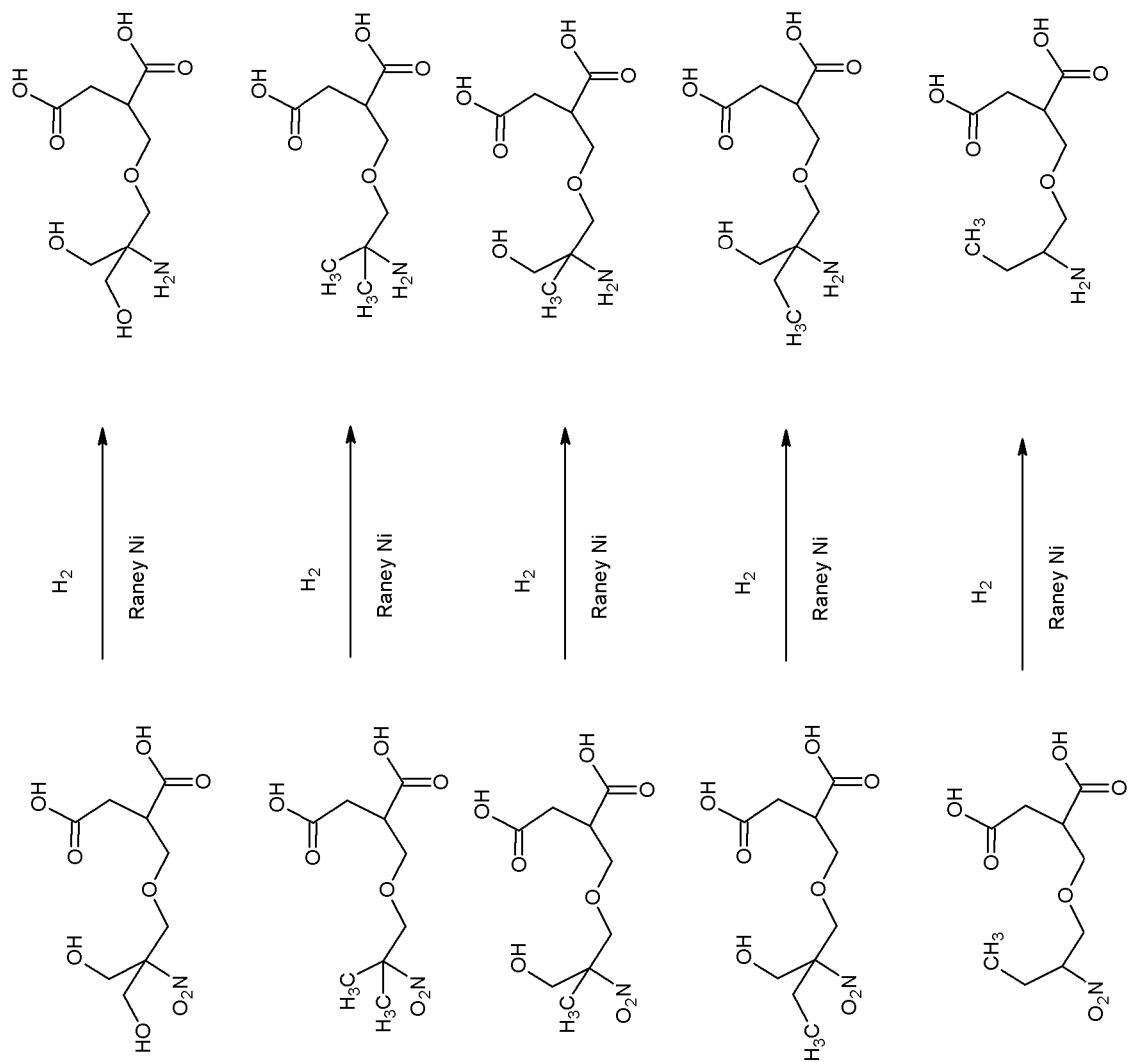
FIG. 44 shows the synthesis of primary amino zwitterionic buffers from nitro acids.

FIG. 42 shows the synthesis of zwitterionic biological buffers from amino alcohols and itaconic acid. These buffers have two acid groups and increased buffering in the acidic range of pH 3-6. FIGS. 43 and 44 show the synthesis of zwitterionic buffers with primary amine groups. These buffers are preferred in applications such as personal care where secondary amines are seen as undesirable. The nitro diacids of FIG. 44 also have great utility as chemical intermediates when synthesizing bioactive molecules.

Figure 45:
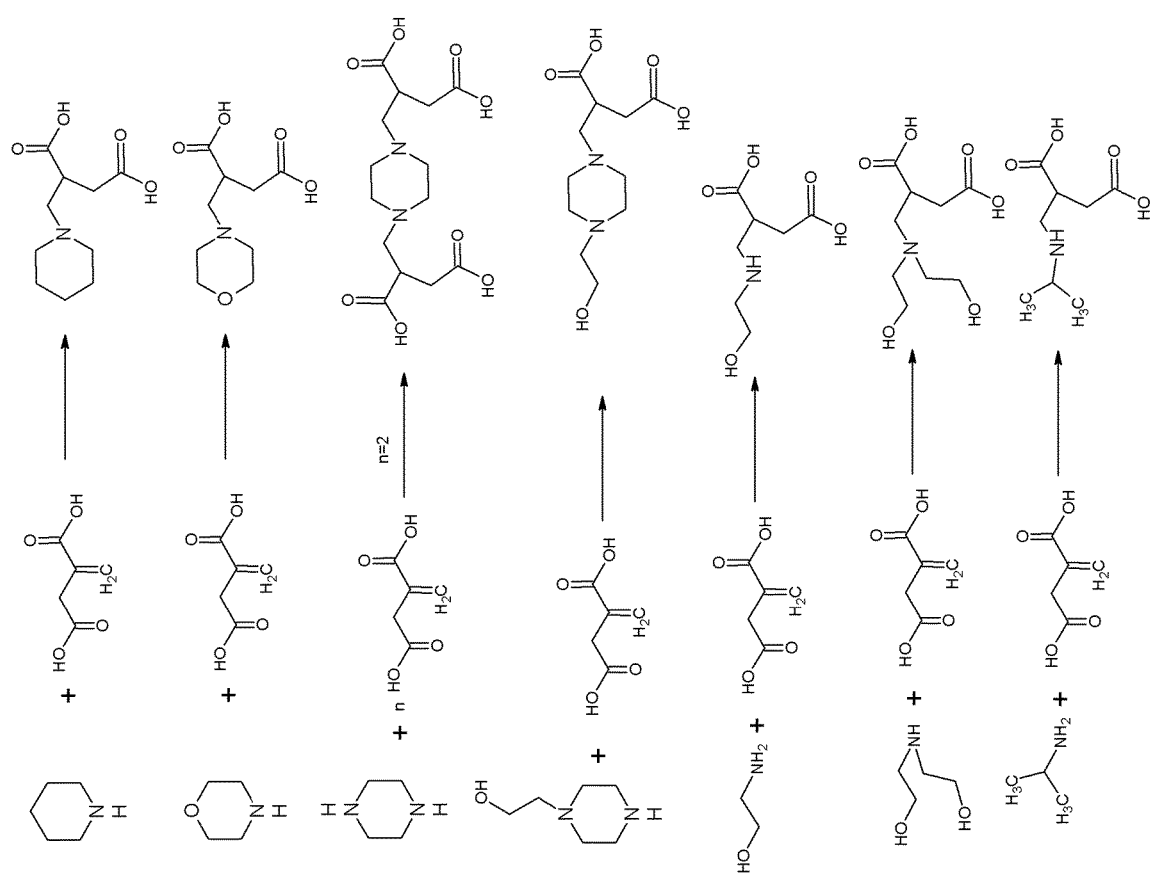
FIG. 45. shows the synthesis of a family of zwitterionic buffers from itaconic acid and amines.

FIG. 45 shows the synthesis of a family of zwitterionic buffers from itaconic acid. The buffers in FIG. 45 are not limited to amino alcohols as starting materials and provide a wide range of molecular size and solubilities.

Figure 46:
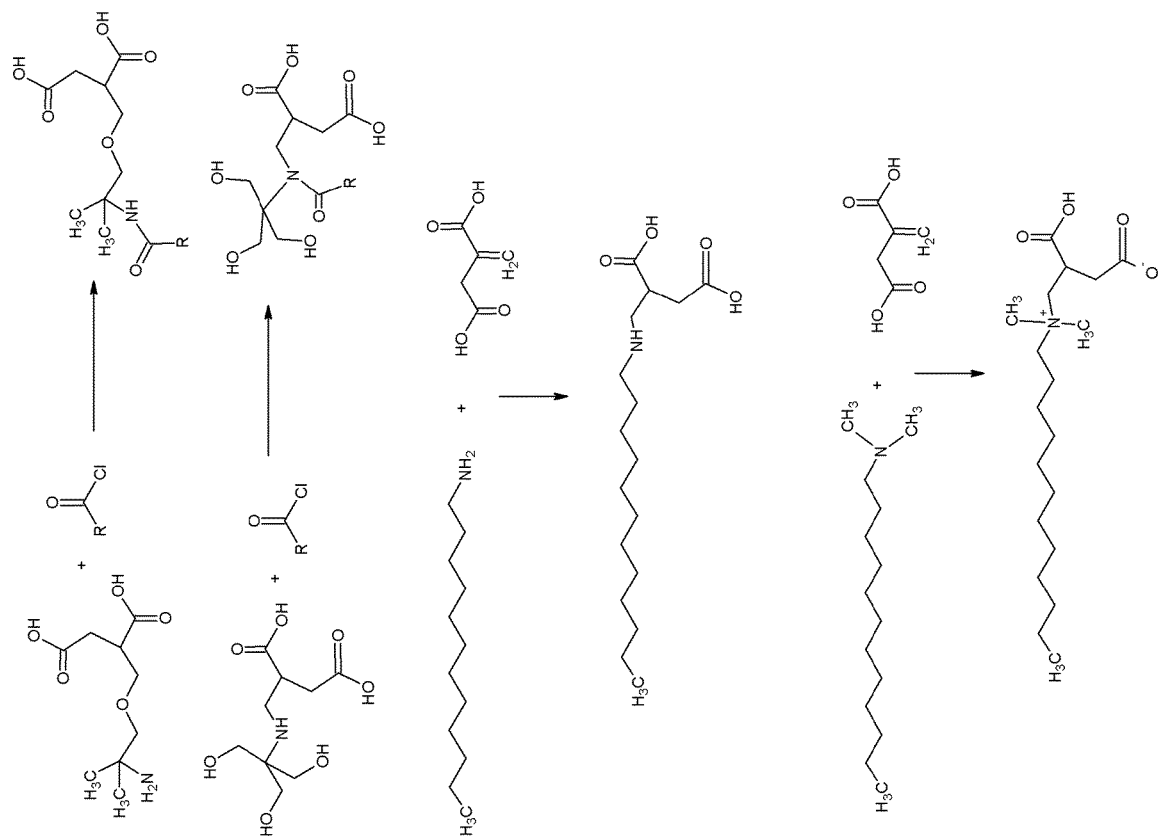
FIG. 46 shows the synthesis of surfactants from amines and itaconic acid intermediates.

FIG. 46 shows the synthesis of a family of amphoteric surfactants. These surfactants are preferred for there mildness, ability to perform in hard water conditions and persistent lather when in the fatty tail is approximately 10-12 carbons in length. The R group in FIG. 46 is to encompass the fatty acid family of carbon chain lengths, generally from about 6 to about 22 carbons. In the specific cases illustrated of lauric amine and lauric dimethyl amine reacted with itaconic acid, it is understood by one in the art that any chain length amine can be used and is in within the scope of the invention herein. Particularly, but not limited to the fatty amines (carbon lengths of about 6 to about 22 carbons, branched and linear, saturated and unsaturated), isopropyl amine and butyl amine. The lower carbon chain lengths produce low foaming hard surface cleaners, while the carbon chains of about 8 to 10 tend to produce the most foam. Higher chain lengths find utility as mineral collectors in floatation processes such as those employed in iron and potash mining.

Figure 47:
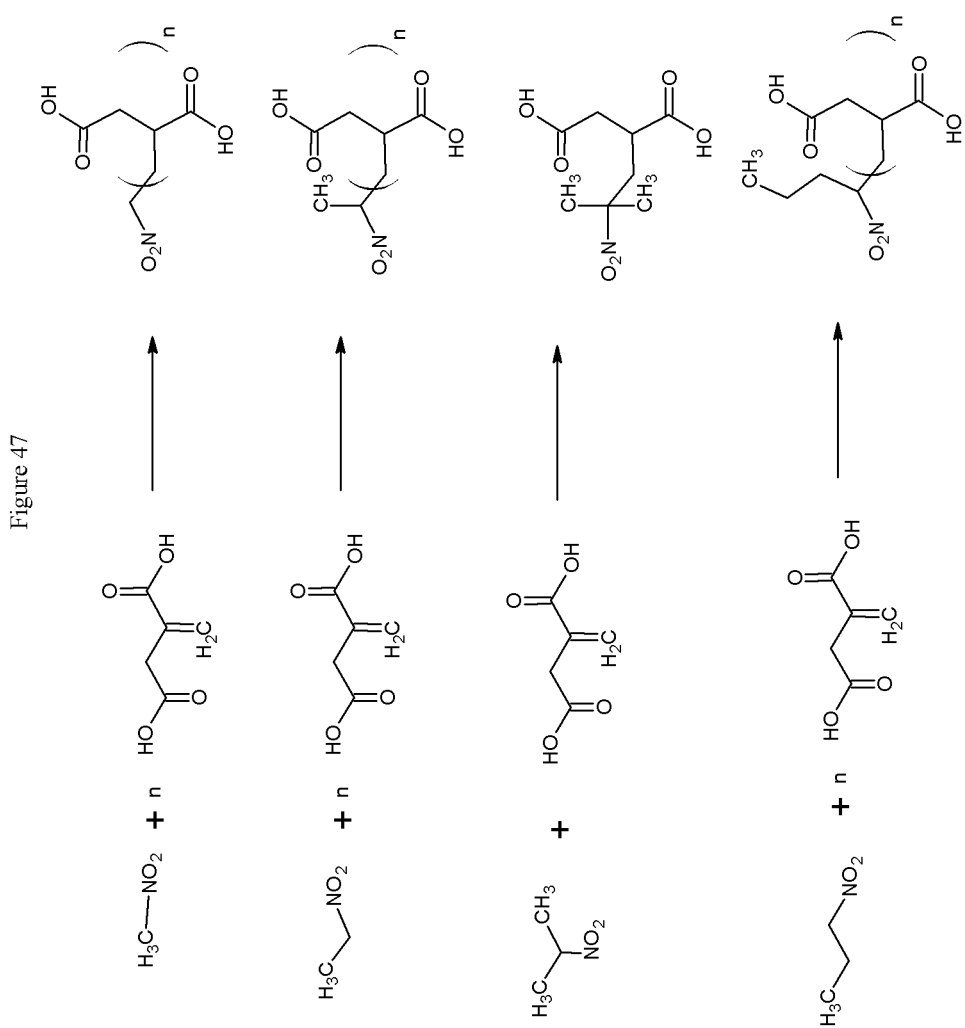
FIG. 47 shows the synthesis of nitroacids from nitroparaffins and itaconic acid.
Figure 48:
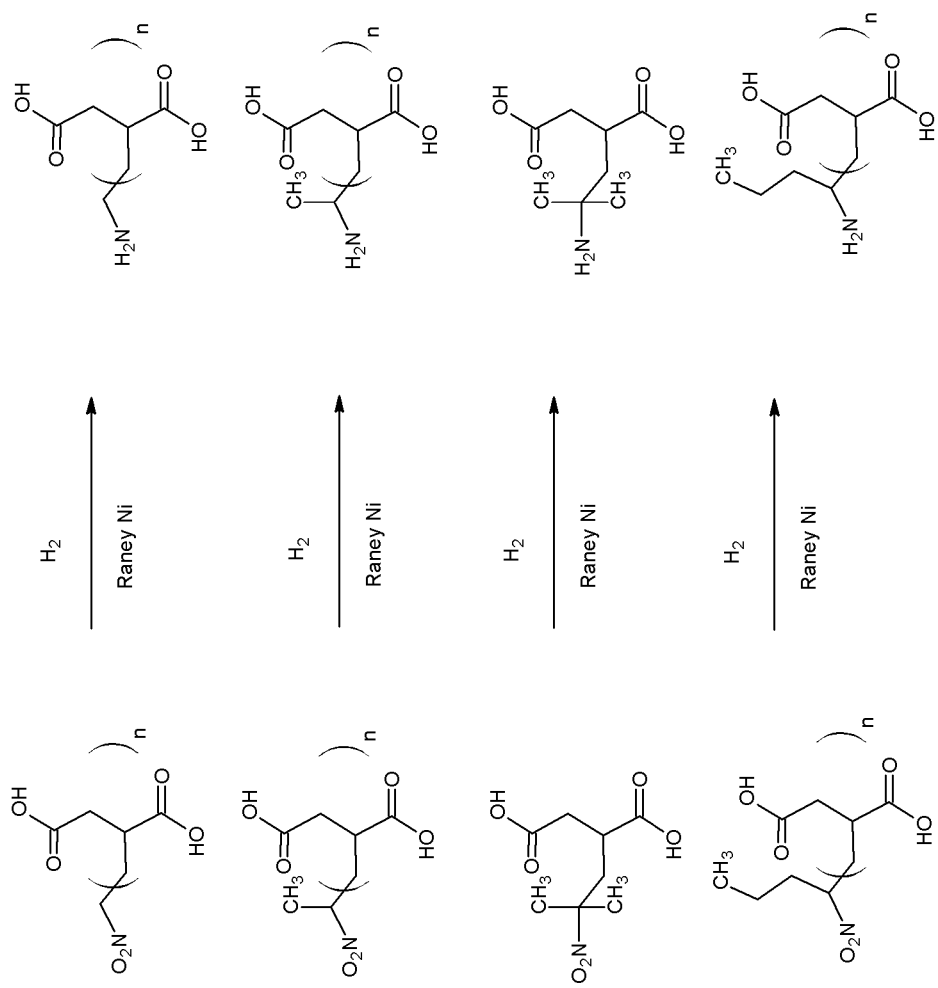
FIG. 48 shows the synthesis of zwitterionic buffers from nitro acids.

FIG. 47 shows the synthesis of nitro acids from nitroparaffins. As stated early, these are very flexible intermediates, particularly when synthesizing bioactive molecules. Reduction of the nitro acids, as shown in FIG. 48 produces zwitterionic buffers with primary amine character. In the case of nitroparaffins that have more than one hydrogen bound to the nitro bound carbon, more than one addition of the itaconic acid can occur. The substitution can occur up to the number of hydrogen atoms bound to the nitro bound carbon.

Figure 49:
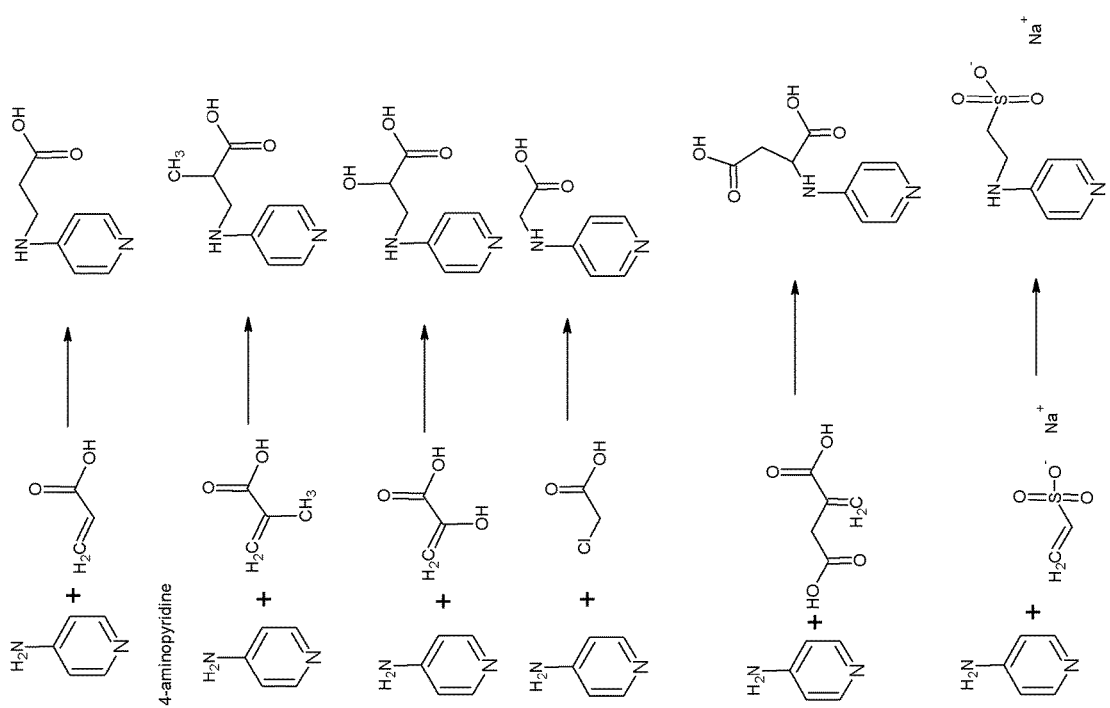
FIG. 49 shows the synthesis of zwitterionic buffers from 4-aminopyridine.
Figure 50:
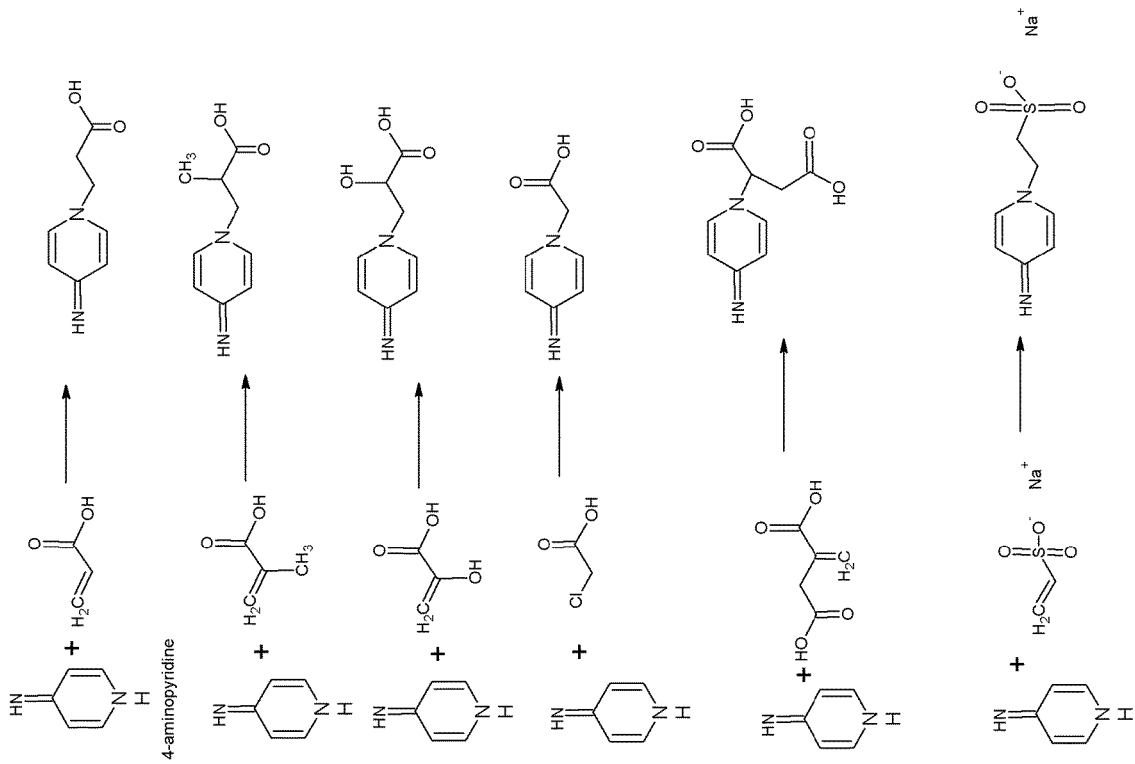
FIG. 50 shows the synthesis zwitterionic buffers from the ketimine conformation of 4-aminopyridine.

FIG. 49 shows the synthesis of zwitterionic buffers from 4-aminopyridine, FIG. 50 shows using the less stable ketimine conformation as the starting material. FIG. 51 shows the synthesis of sultaine type buffers from 4-aminopyridine. Additional buffers can be made by propoxylating and butoxylating 4-aminopyridine. The ethoxylating and propoxylating will reduce the water solubility and reduce the bioavailability. This is one method of extending the time a material is bioavailable by making it available slowly, particularly if the molecule is metabolized. Additionally, a triamine can be made by reacting 2-aminopyridine with acrylonitrile and reducing it to the triamine, or reacting with allylamine to keep the aromatic nature of the six membered ring. The resulting buffers are excellent buffers in their own right, but also have great promise in treatment of multiple sclerosis, and other conditions that can benefit from calcium or other cation inhibition. The anionic components, in particular, are all groups that can chelate cations.

Figure 52:
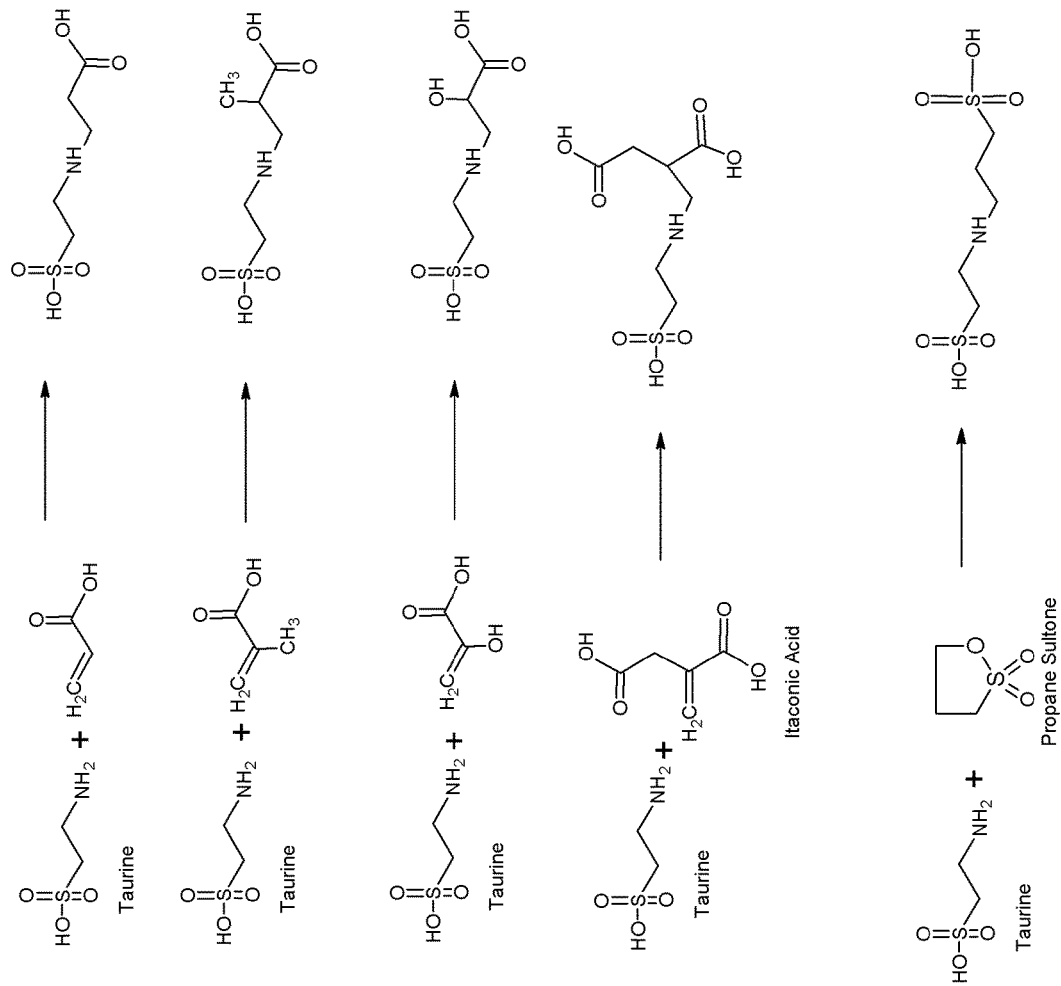
FIG. 52 shows the synthesis of zwitterionic buffers from taurine.
Figure 53:
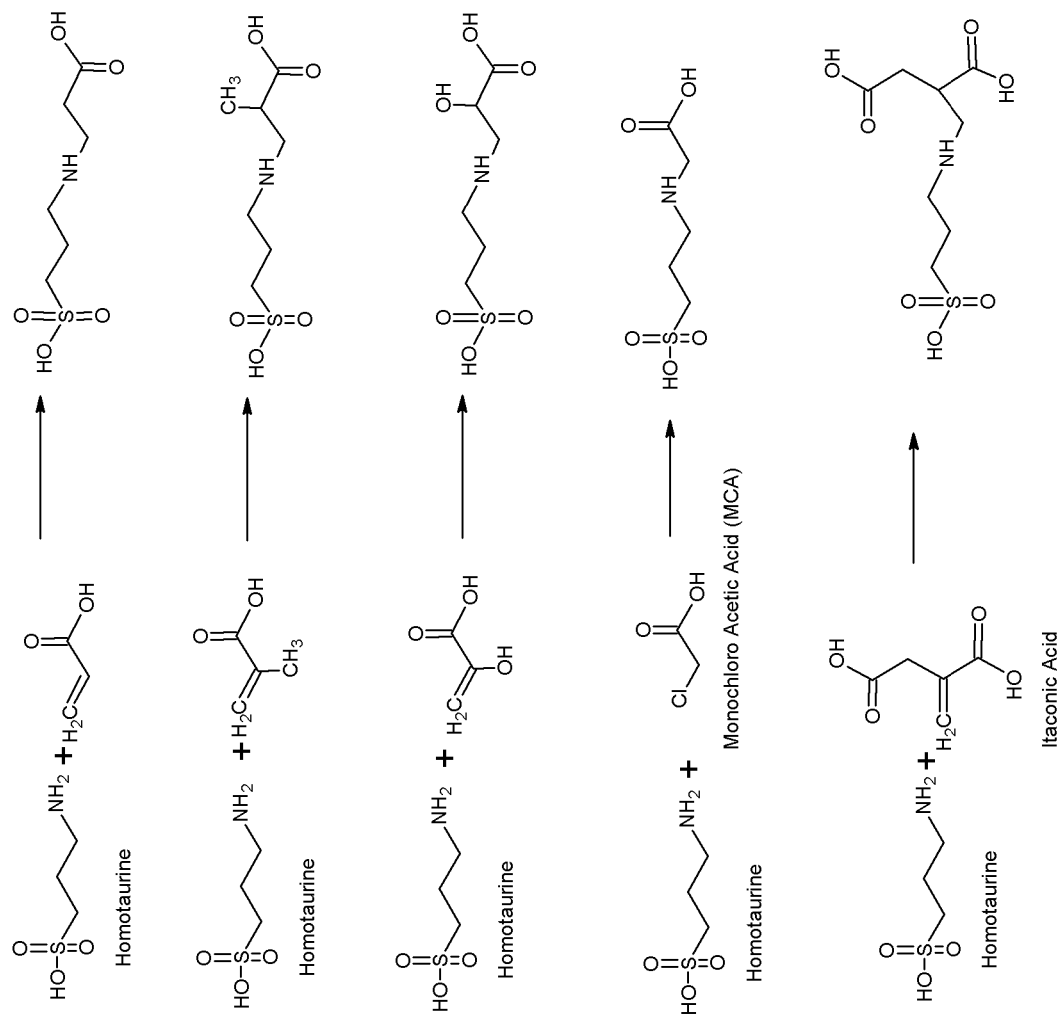
FIG. 53 shows the synthesis of zwitterionic buffers from homotaurine.
Figure 54:
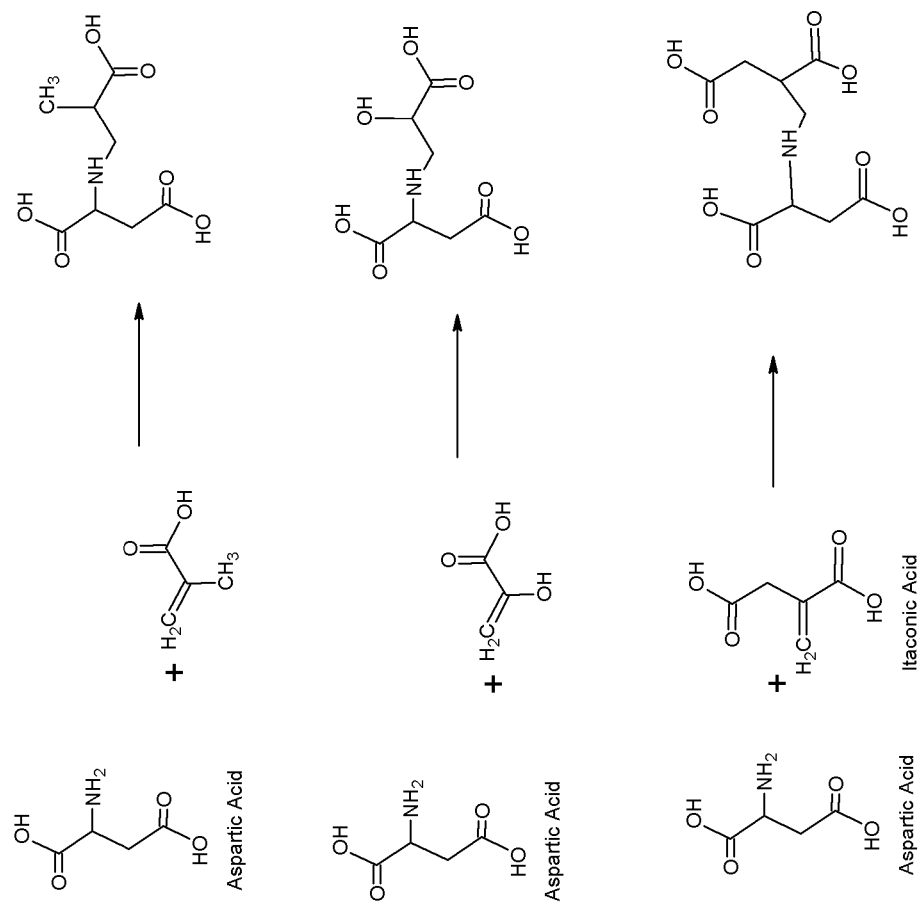
FIG. 54 shows the synthesis of zwitterionic buffers from aspartic acid.
Figure 55:
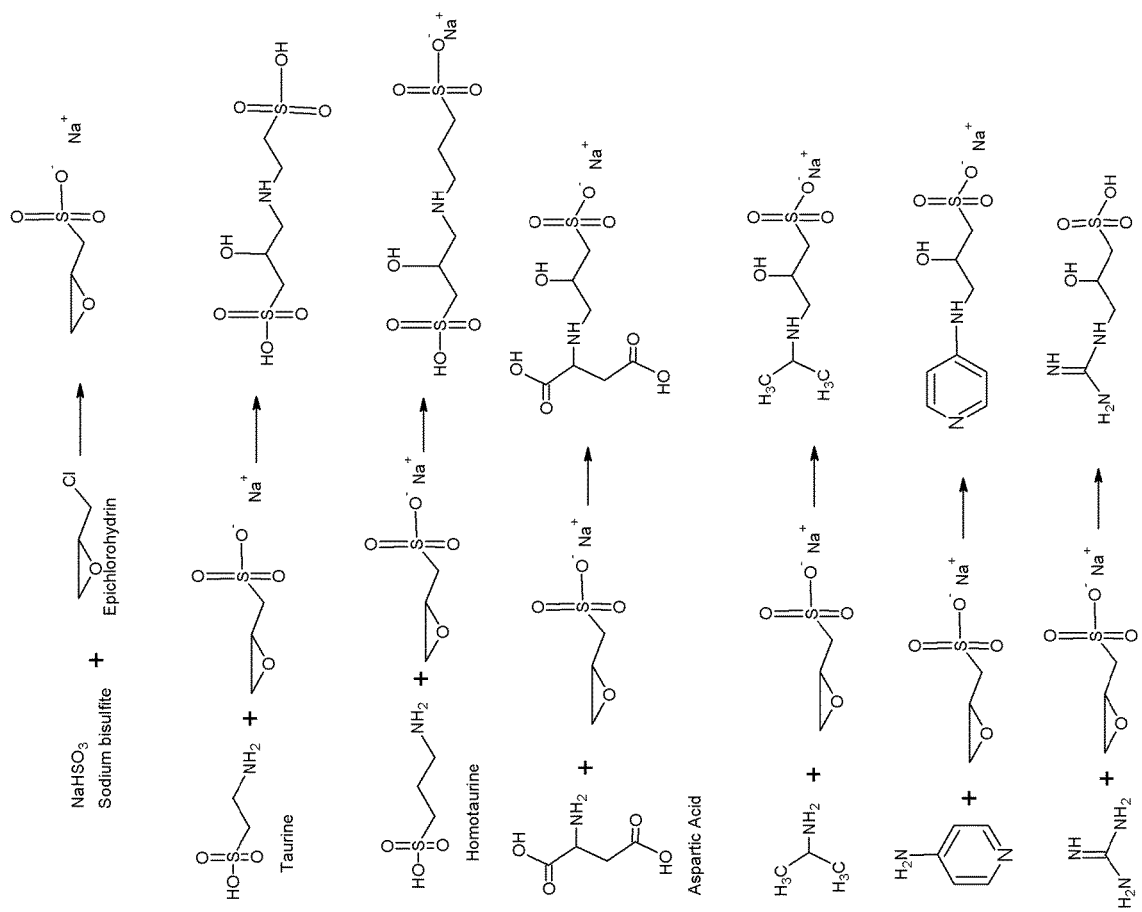
FIG. 55 shows the synthesis of sultaine zwitterionic buffers from sodium bisulfite and epichlorohydrin.
Figure 56:
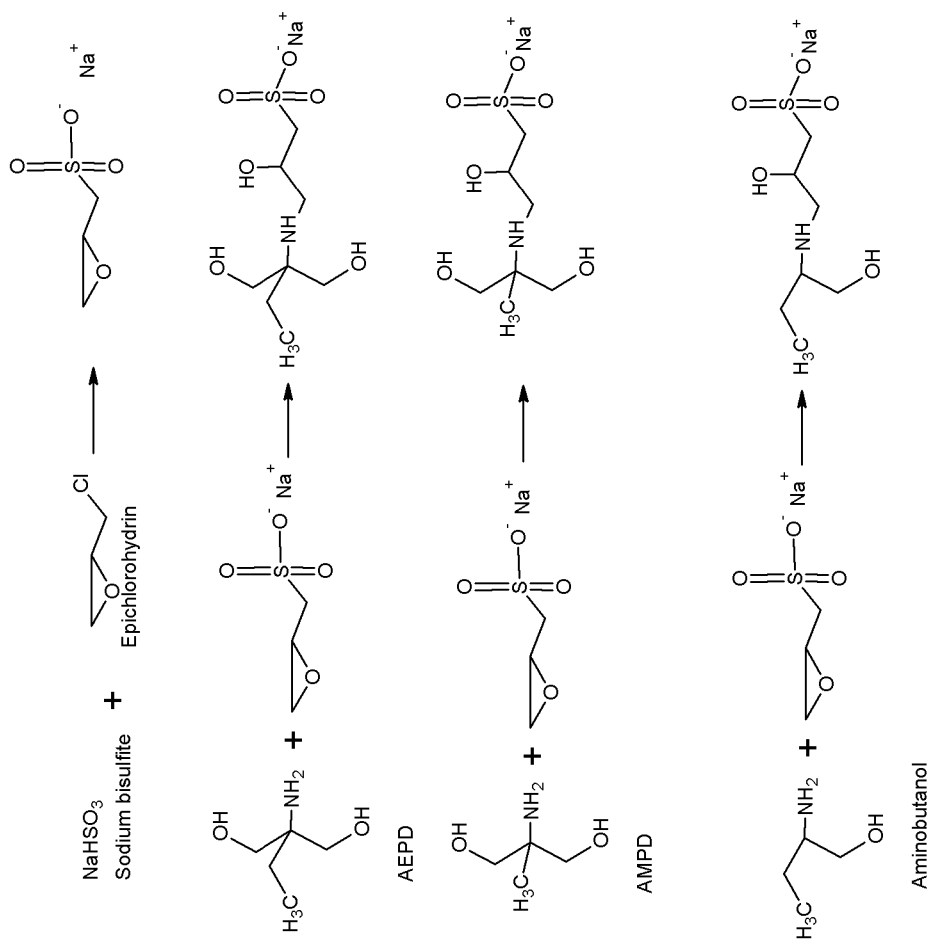
FIG. 56 shows the synthesis of sultaine zwitterionic buffers from sodium bisulfite, epichlorohydrin, and aminoalcohols.
Figure 57:
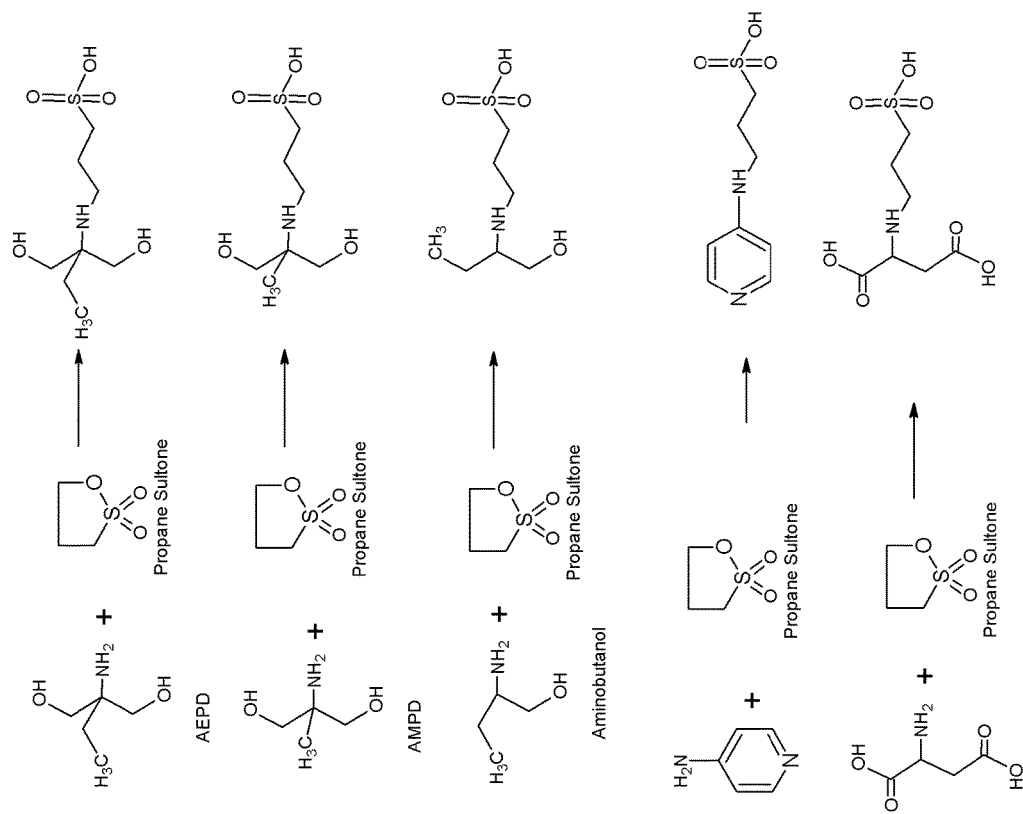
FIG. 57 shows the synthesis of zwitterionic buffers from propane sultone
Figure 58:
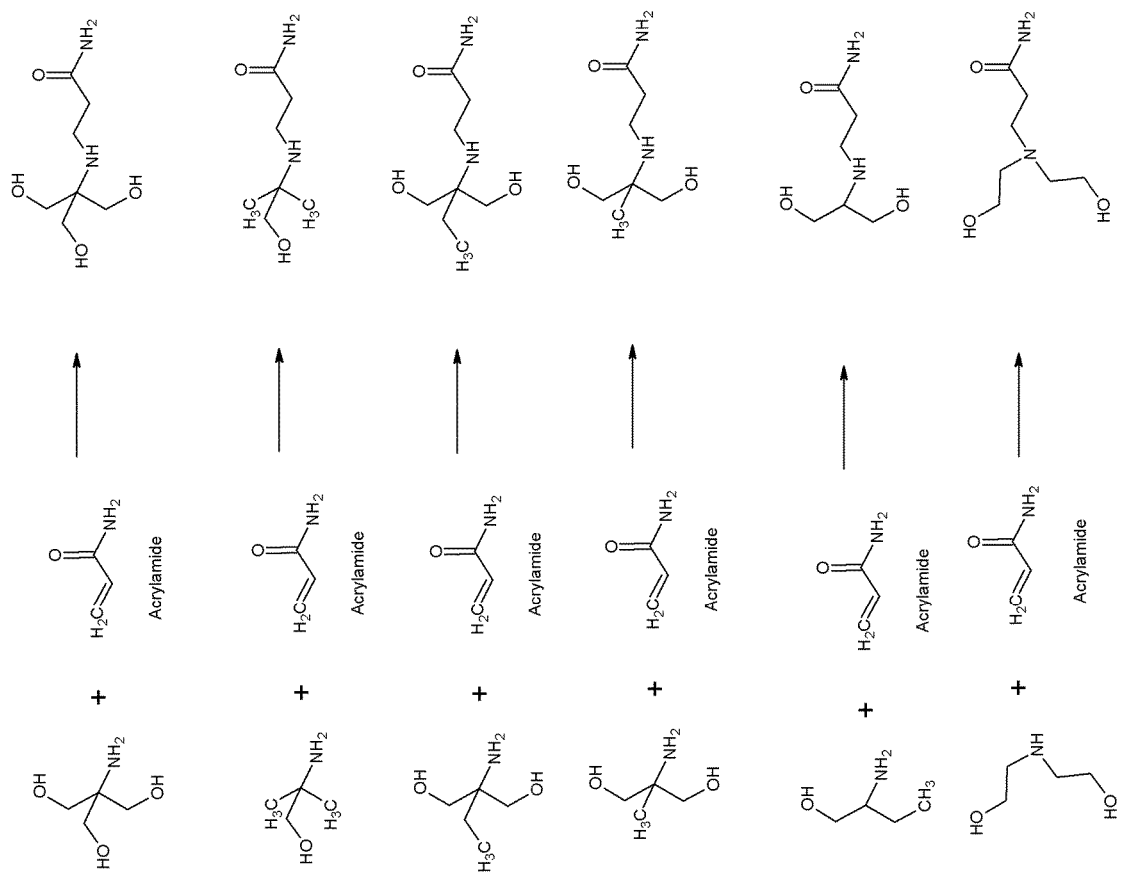
FIG. 58 shows the synthesis of amidoamine buffers from acrylamide.
Figure 59:
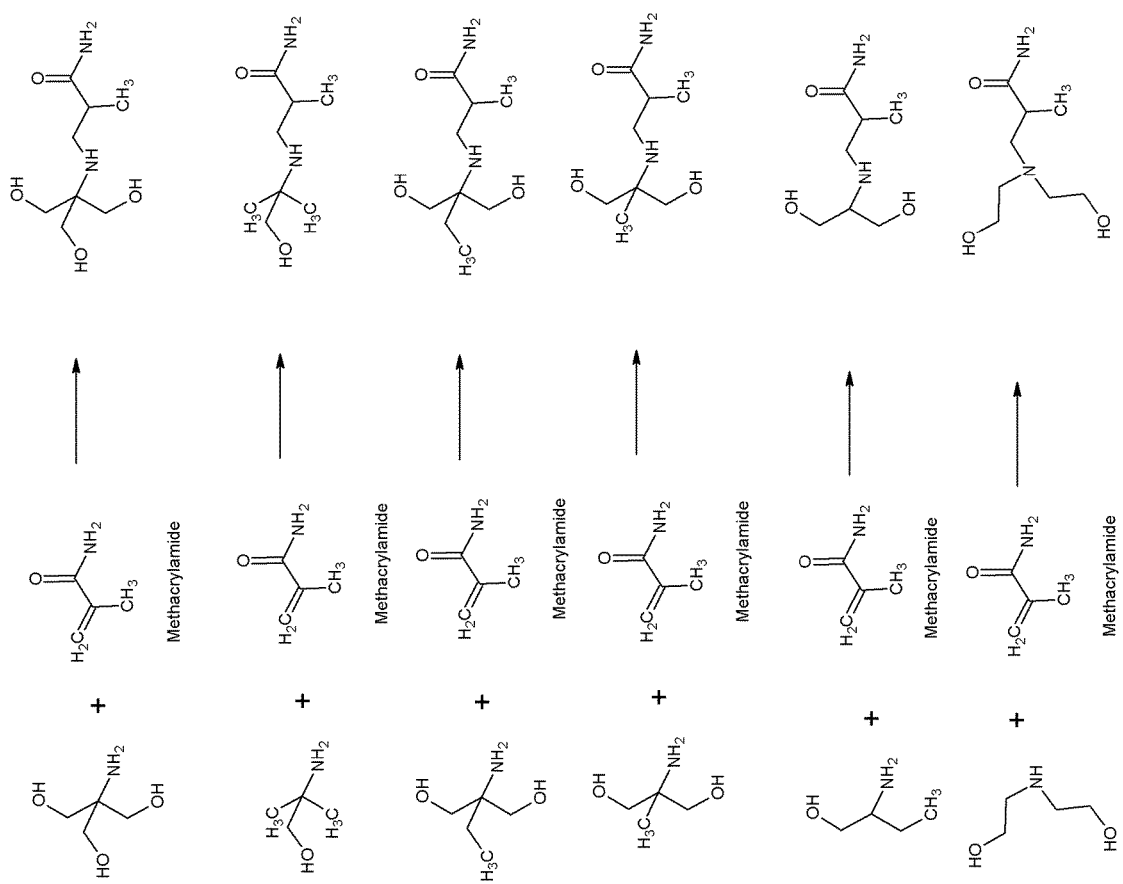
FIG. 59 shows the synthesis of amidoamine buffers from methacrylamide.
Figure 60:
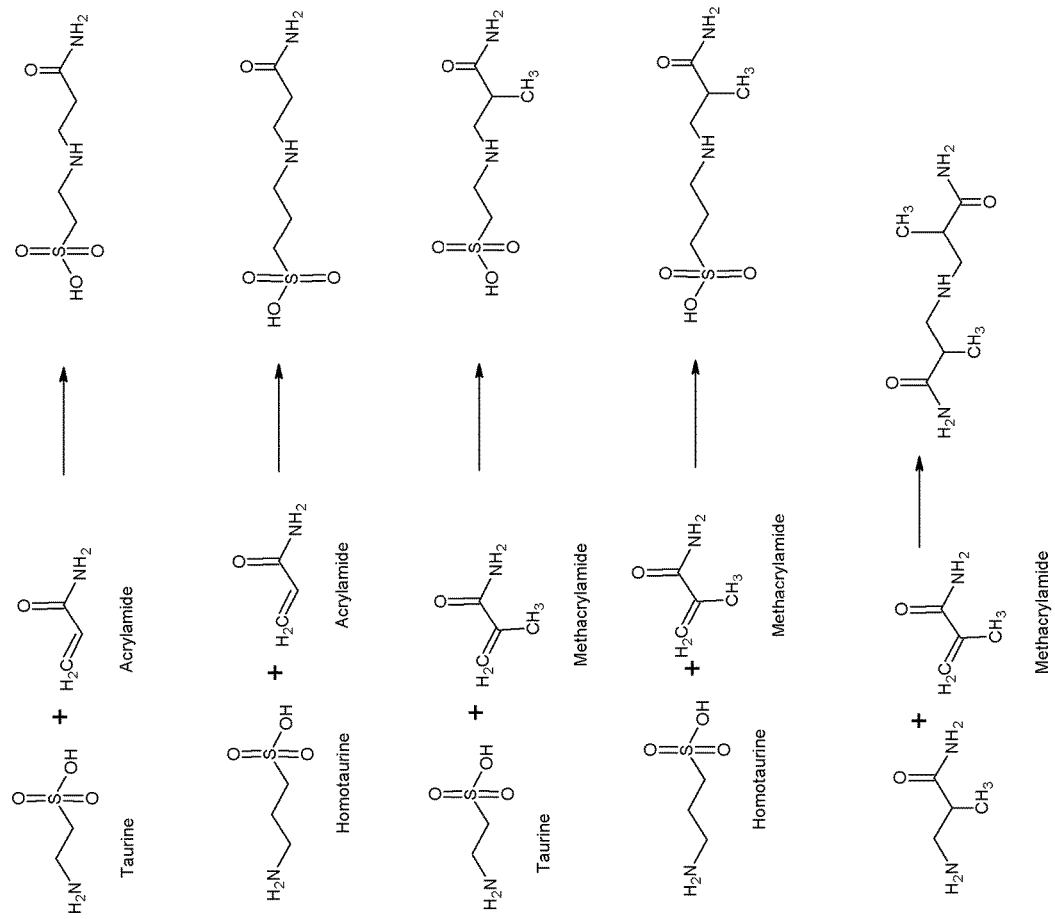
FIG. 60 shows the synthesis of amidoamine buffers from taurines and diamines.
Figure 61:
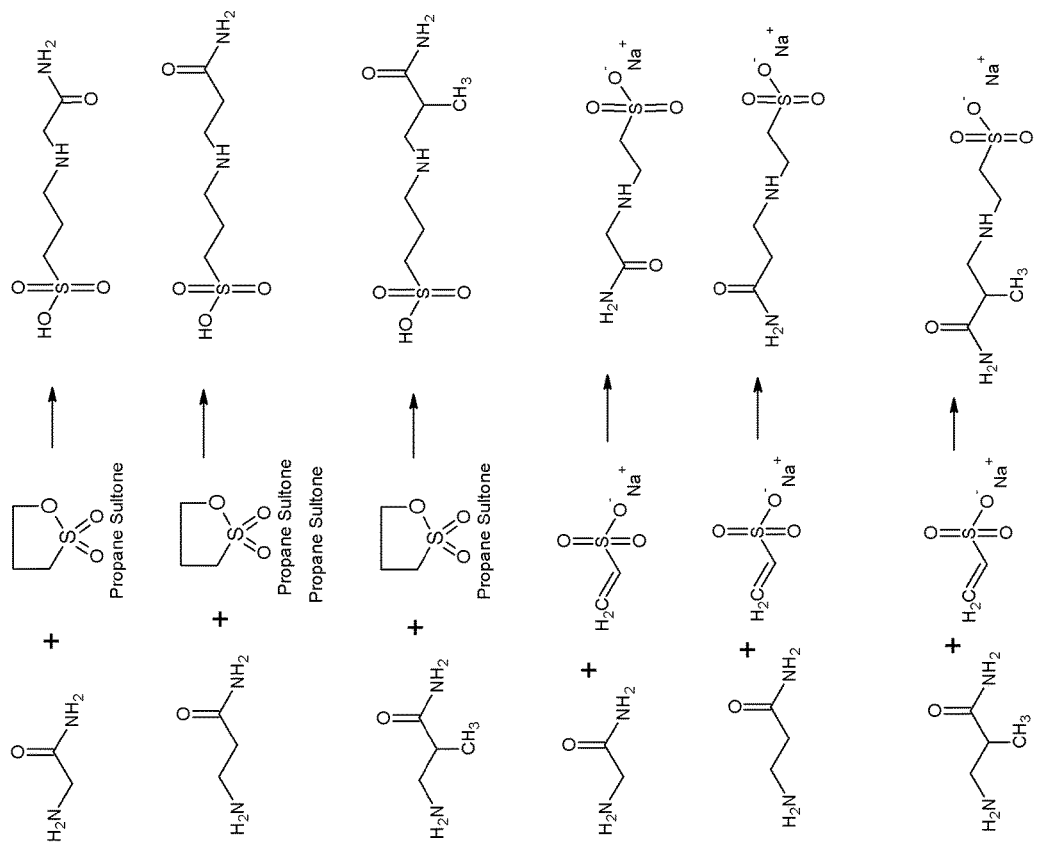
FIG. 61 shows the synthesis of zwitterionic amidoamine buffers from propone sultone and SVS.
Figure 62:
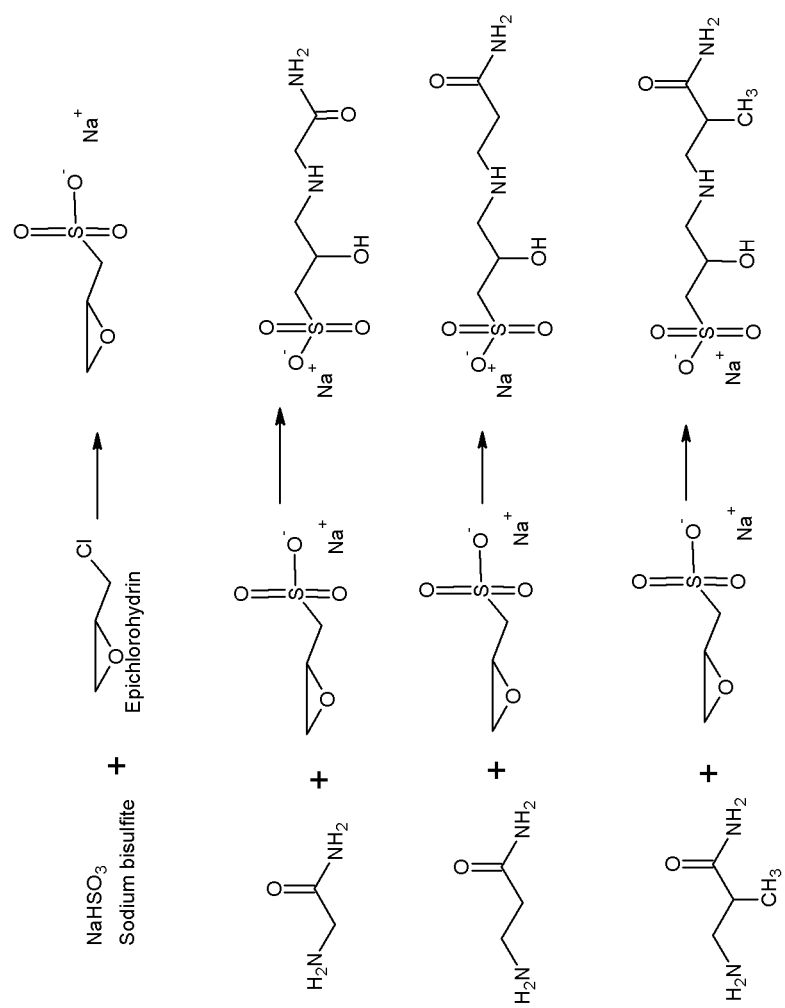
FIG. 62 shows the synthesis of sultaine amidoamine zwitterionic buffers.

FIG. 52 outlines the synthesis of taurine derived zwitterionic buffers. These molecules, along with the products in FIG. 53, homotaurine derived zwitterionic buffers, are expected to find great utility in the purification of proteins and in cell culture media. FIG. 54 shows the synthesis of a series of zwitterionic buffers derived from aspartic acid. These compounds are expected to be very useful in electrophoresis gels as they have a unique charge density and size profile. The sultaine derivatives in FIG. 55 and FIG. 56 are expected to find great utility in cell culture media and in purification due to their zwitterionic nature and pKa range. The zwitterionic buffers of FIG. 57 are expected to be primarily useful in cell culture media. The buffers of FIG. 58 and FIG. 59 are ideally suited for use in electrophoresis gels and in isoelectric focusing. FIG. 60, FIG. 61 and FIG. 62 show the synthesis of zwitterionic amidoamine buffers for use cell culture media and purification.

Figure 63:
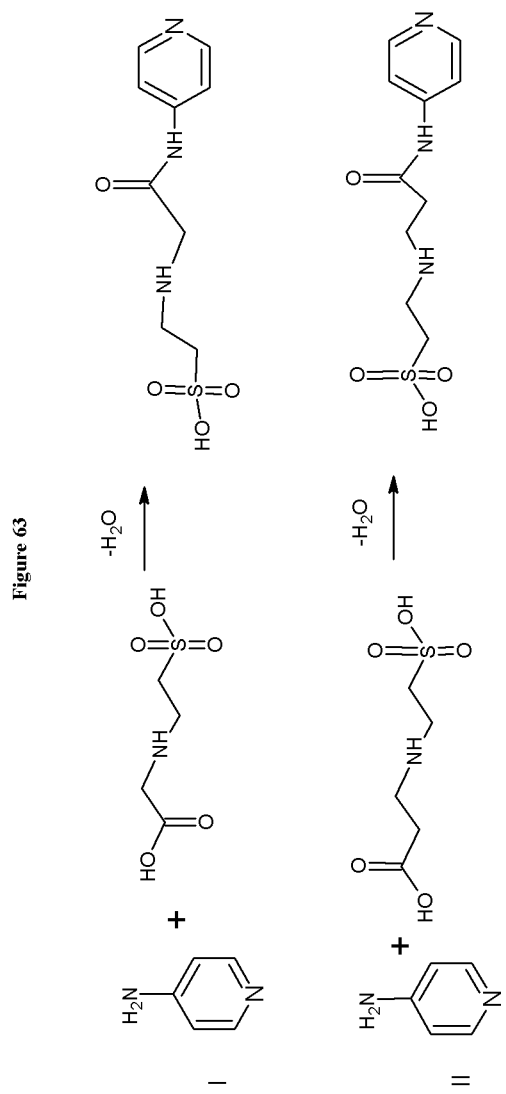
FIG. 63 shows the synthesis of a family of compounds as zwitterionic buffers and products that are expected to be useful as multiple sclerosis and spinal cord injury therapies.
Figure 64:
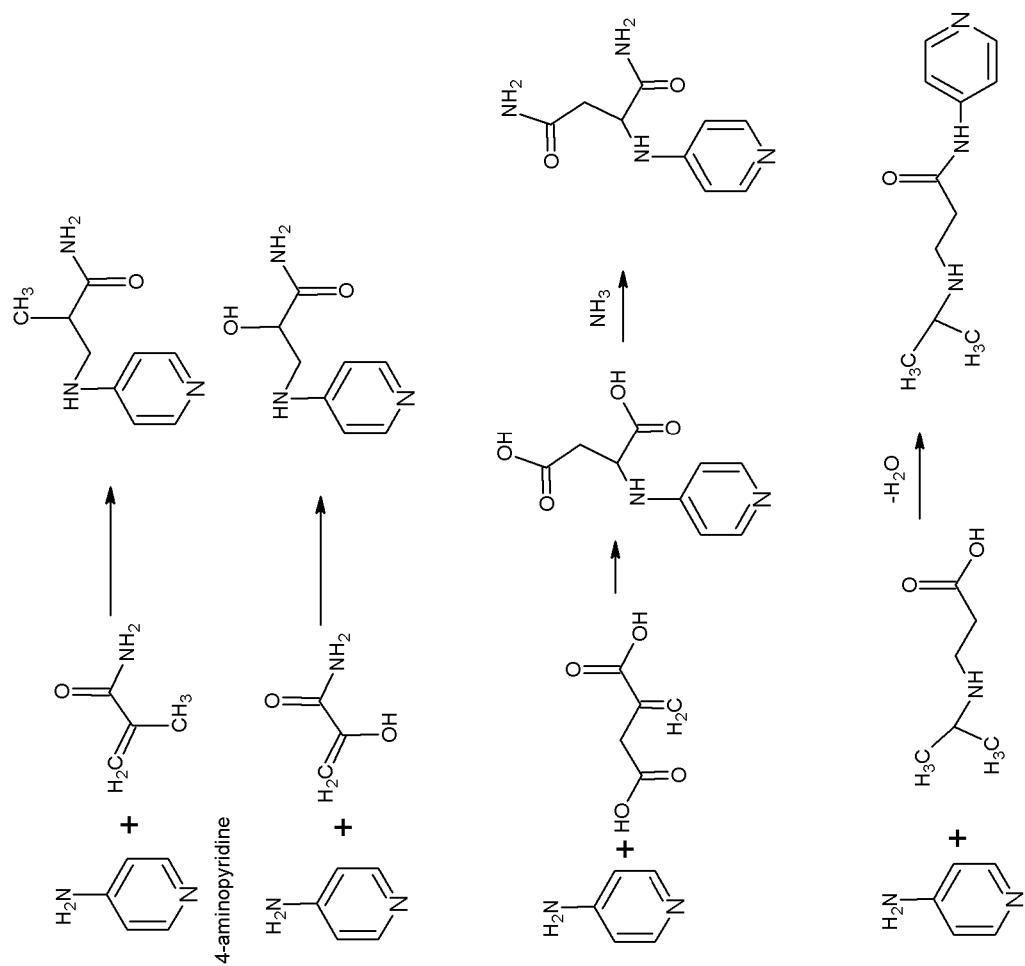
FIG. 64 shows amide based zwitterionic buffers and products that are expected to be useful as multiple sclerosis and spinal cord injury therapies.
Figure 65:
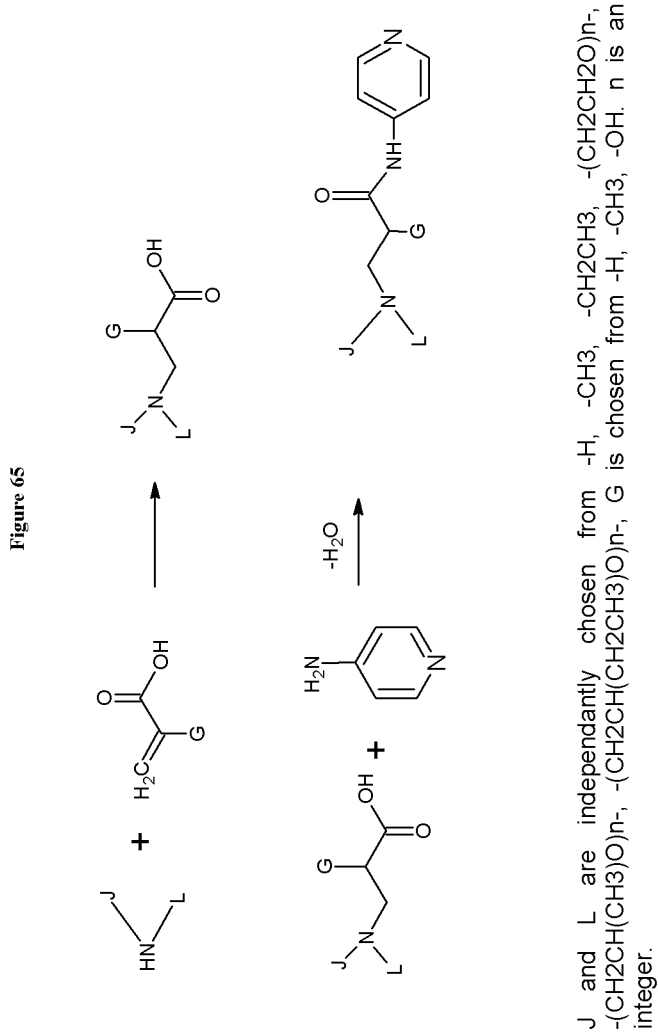
FIG. 65 shows additional zwitterionic buffers based on 4-aminopyridine amides. These products are also expected to be useful as multiple sclerosis and spinal cord injury therapies.
Figure 66:
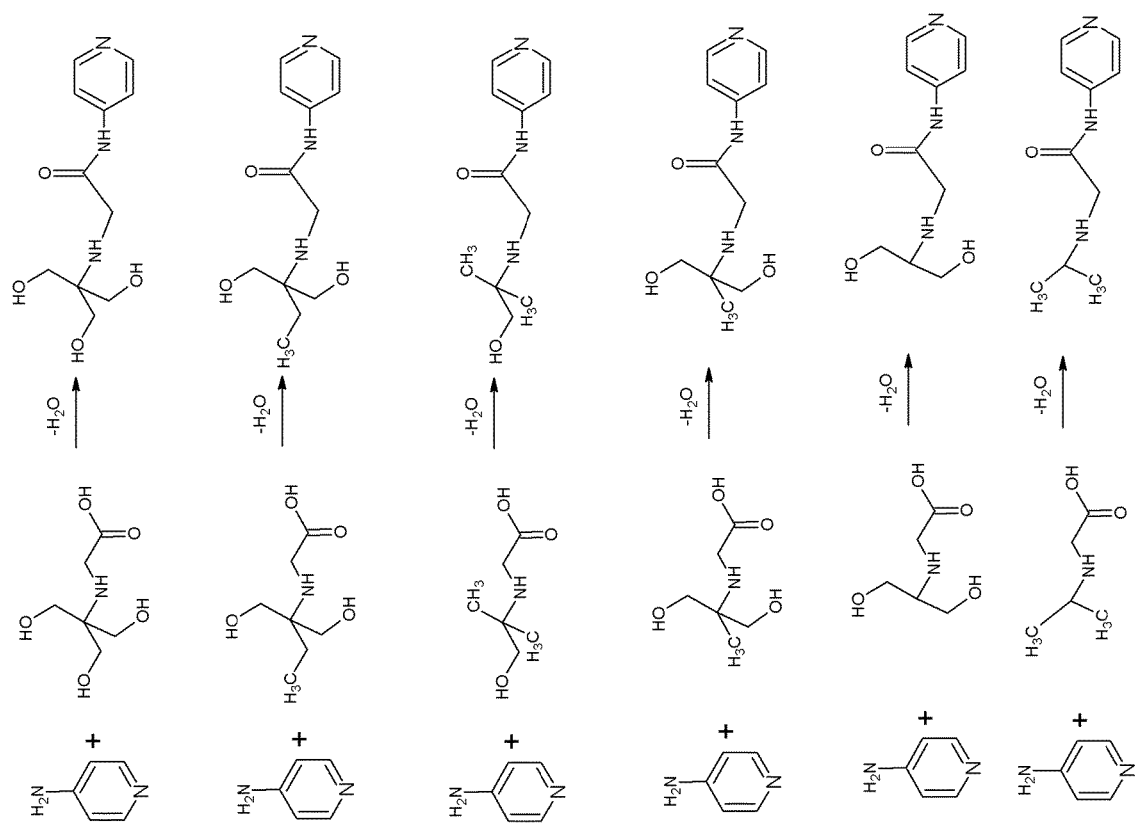
FIG. 66 shows the synthesis of zwitterionic buffers that are also expected to be useful as multiple sclerosis and spinal cord injury therapies. Most of this family has increased hydrogen bonding and is based on the MCA derived zwitterionic buffers disclosed herein.
Figure 67:
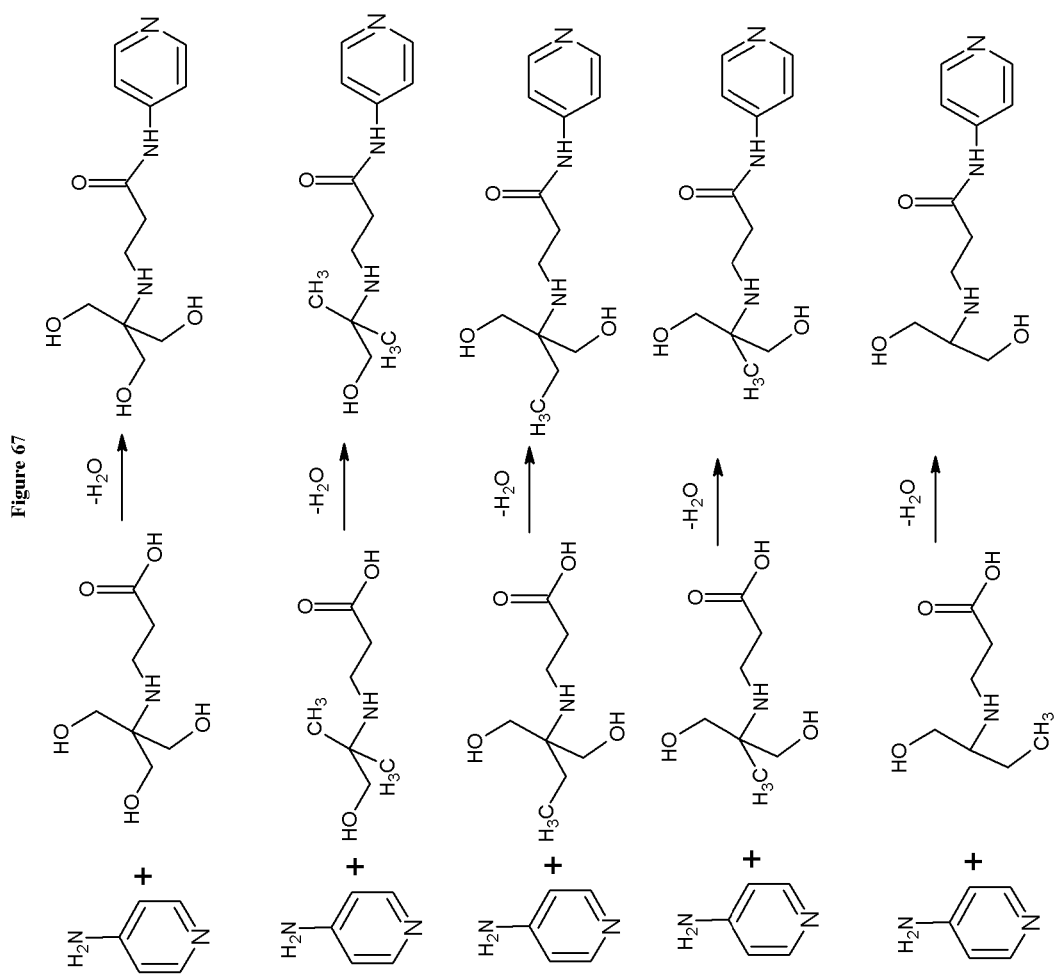
FIG. 67 shows the synthesis of zwitterionic buffers that are also expected to be useful as multiple sclerosis and spinal cord injury therapies. Most of this family has increased hydrogen bonding and is based on the acrylic acid derived zwitterionic buffers disclosed herein.
Figure 68:
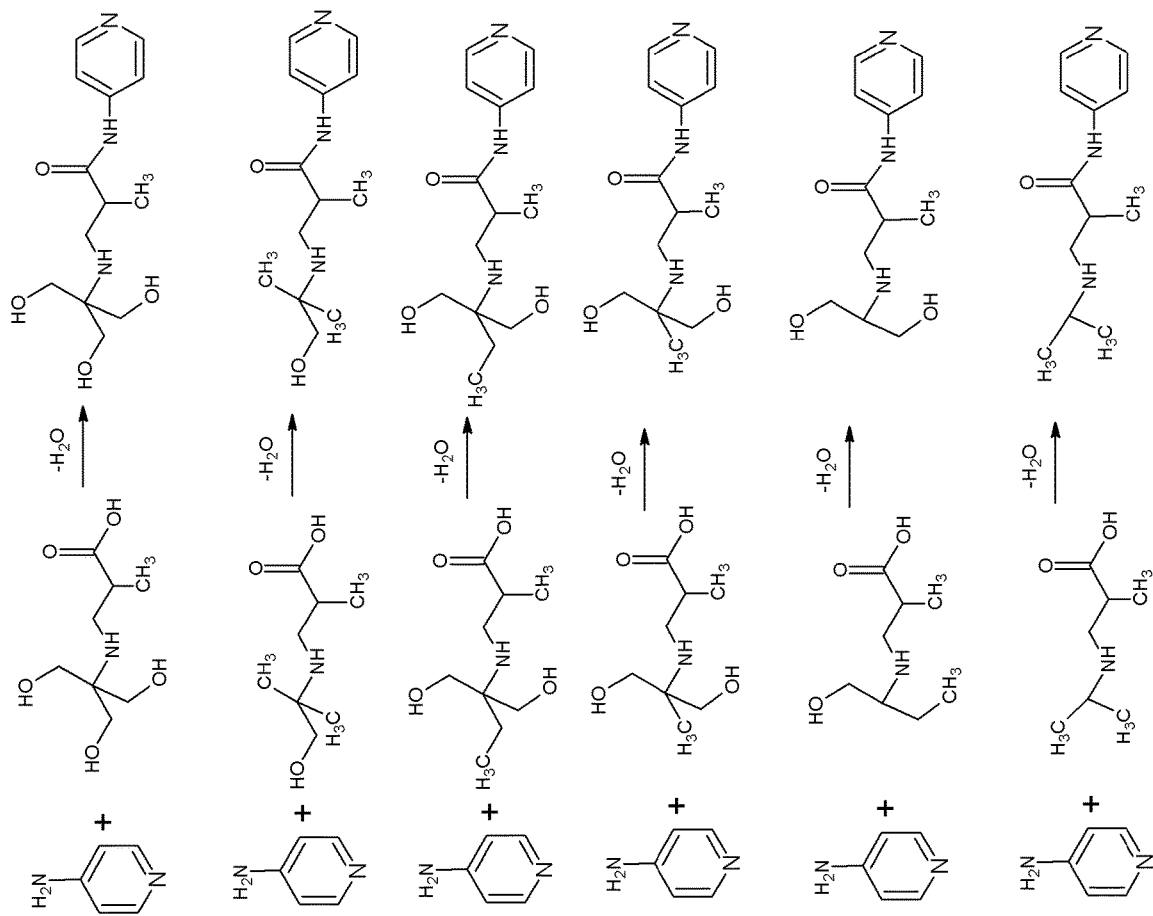
FIG. 68 shows the synthesis of zwitterionic buffers that are also expected to be useful as multiple sclerosis and spinal cord injury therapies. Most of this family has increased hydrogen bonding and is based on the methacrylic acid derived zwitterionic buffers disclosed herein.
Figure 69:
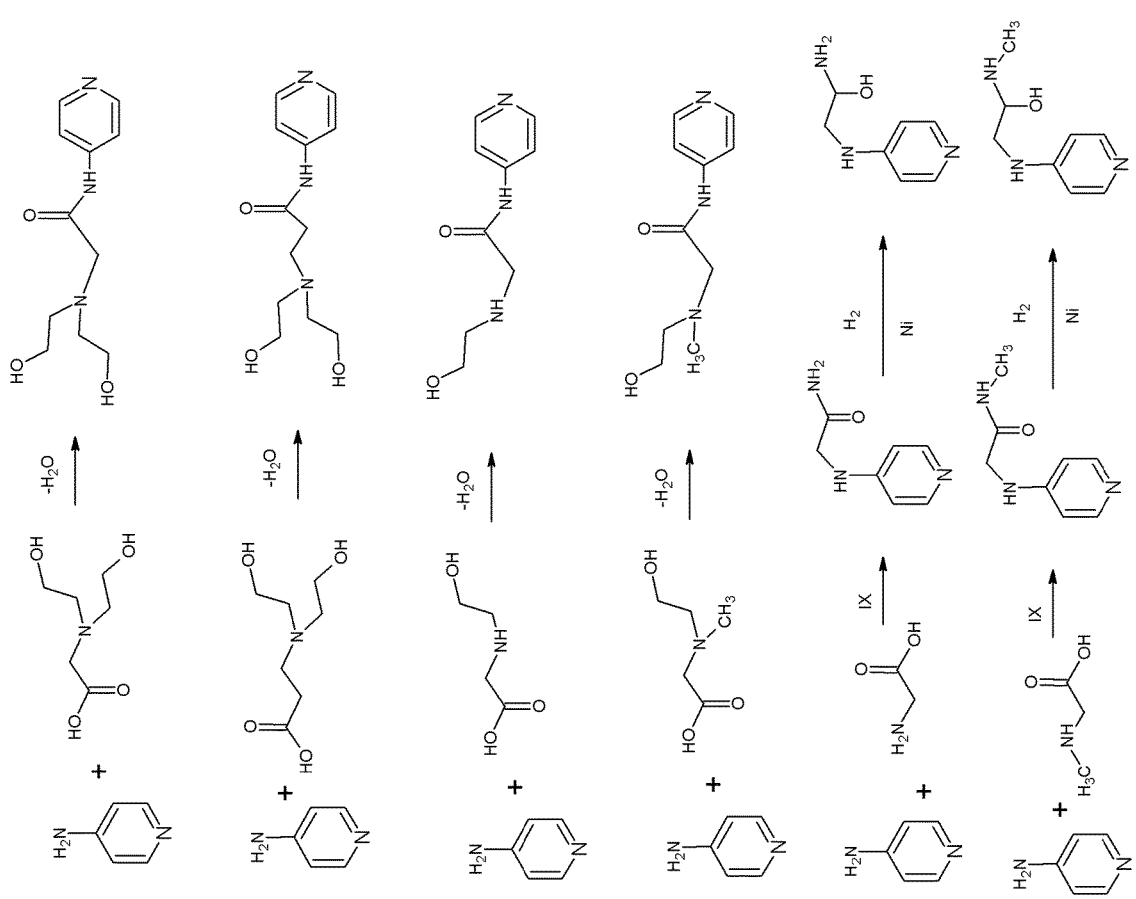
FIG. 69 shows the synthesis of zwitterionic buffers that are also expected to be useful as multiple sclerosis and spinal cord injury therapies. Derived from ethylene amines.
Figure 70:
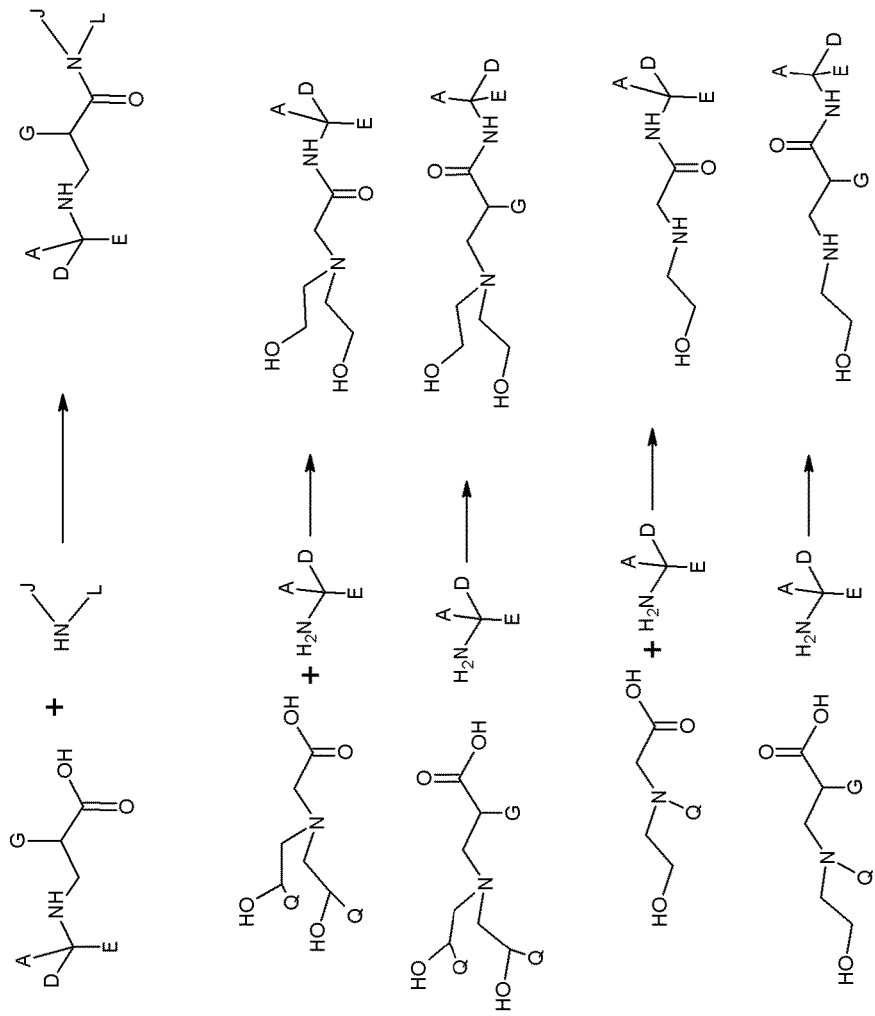
FIG. 70 shows the synthesis of amidoamine buffers that are stearicly hindered.
Figure 71:
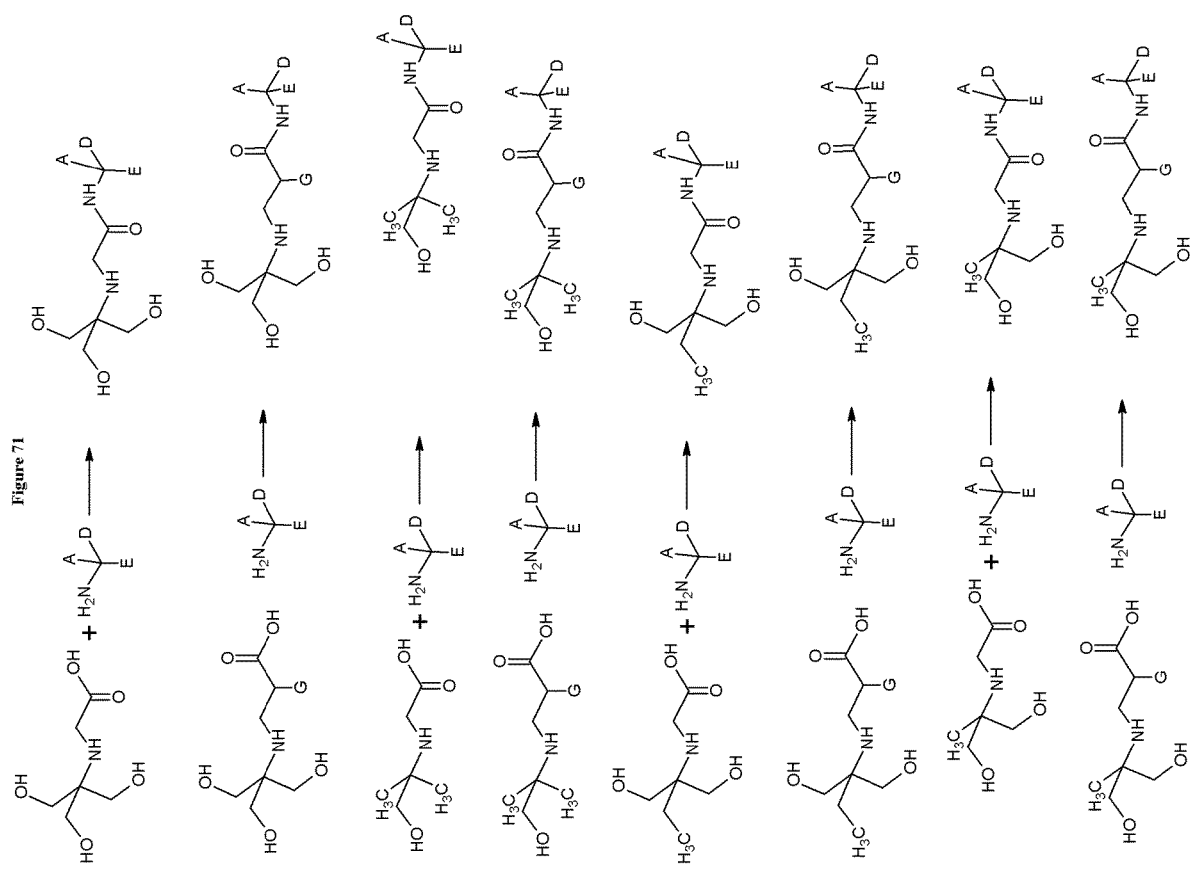
FIG. 71 shows the synthesis of amidoamine buffers that are stearicly hindered with extensive hydrogen bonding.
Figure 72:
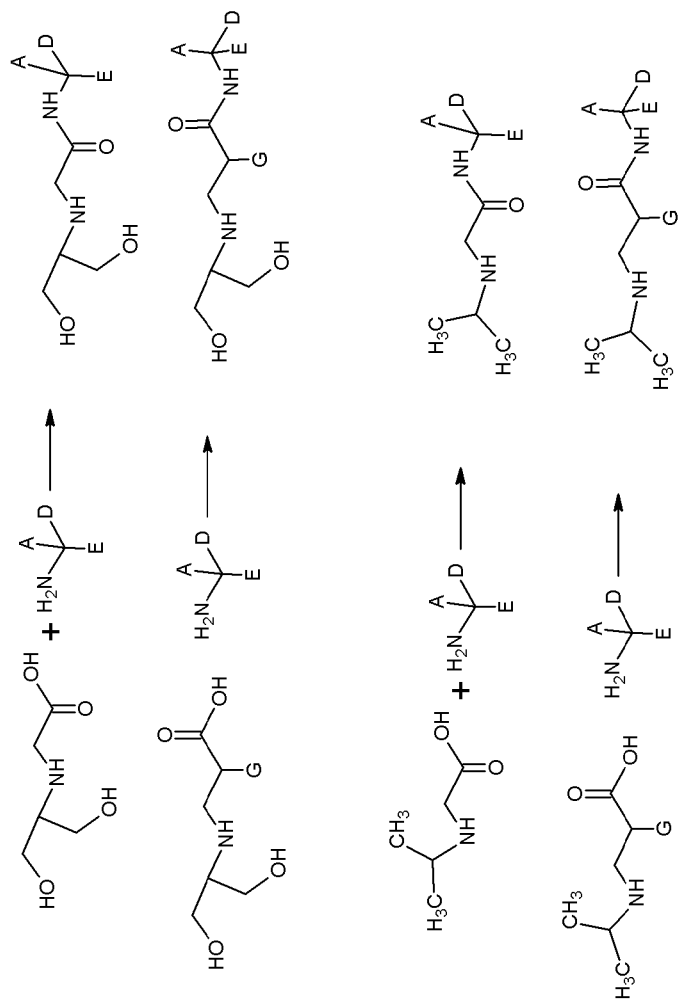
FIG. 72 shows the synthesis of amidoamine buffers.
Figure 73:
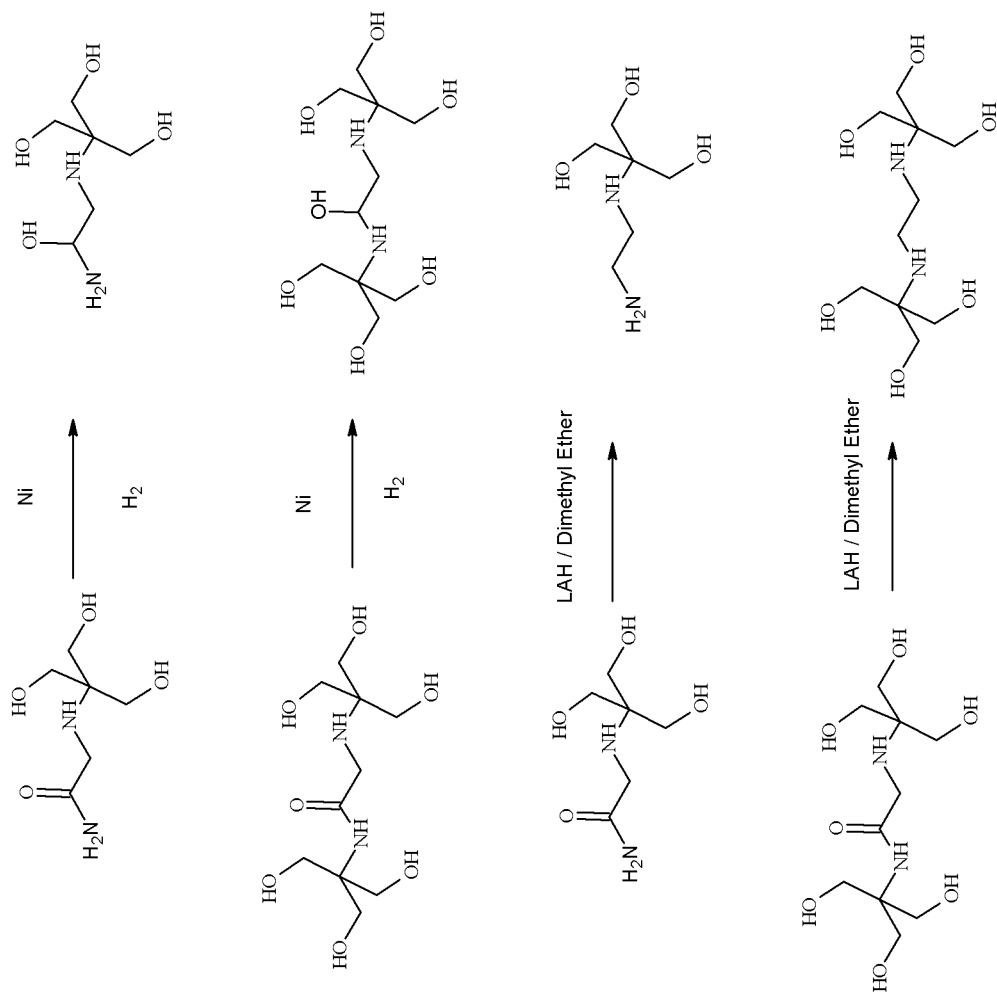
FIG. 73 shows that any of the amidoamine buffers taught herein, maybe reduced to aminoalcohols or diamines.

FIG. 63 shows the synthesis of zwitterionic buffers that are expected to be useful in the treatment of multiple sclerosis (MS) and spinal cord injury by blocking potassium channels. The increased hydrogen bonding available through the sulfonate group is expected to enhance the efficacy over the traditional 4-aminopyridine therapy. While the figure shows only two compounds, one skilled in the art will recognize that any of the amino acid taurates, including, but not limited to those disclosed herein, particularly those of FIGS. 52, 53, 54, and 57. FIGS. 64 and 65 show the synthesis of a further class of amidoamine buffers that are expected to be effective therapies for MS and spinal cord injury due to the pKa and hydrogen bonding. FIGS. 66-68 shows the synthesis of a class of compounds that are excellent amidoamine buffers, particularly useful for electrophoresis and protein focusing. These are also expected to be excellent therapies for MS and spinal cord injury through potassium channel blocking. The more hydrogen bonding variants are expected to have greater efficacy. FIG. 69 shows the synthesis of a further class of amidoamine buffers that are also expected to have utility as MS or spinal cord injury therapies. One skilled in the art will recognize that the amino acids used are not limited to those presented but any amino acid can be utilized and are within the scope of the present invention. In particular, the analogs based on methacrylic and other vinyl acids as the amino acid reacted with 4-aminopyridine are within the scope of the present invention, similar to the analogs presented in FIG. 15 where tromethamine is reacted with various acids to form a family of amino acids. FIGS. 70-72 teach a family of amidoamine buffers. FIG. 73 shows that any of the amidoamines presented herein, may be reduced to the aminoalcohol by reacting with hydrogen in the presence of a catalyst, such as raney nickel or raney cobalt, as well as reduced to the diamine by treatment with lithium aluminum hydride or similarly strong reducing agent.

Figure 74:
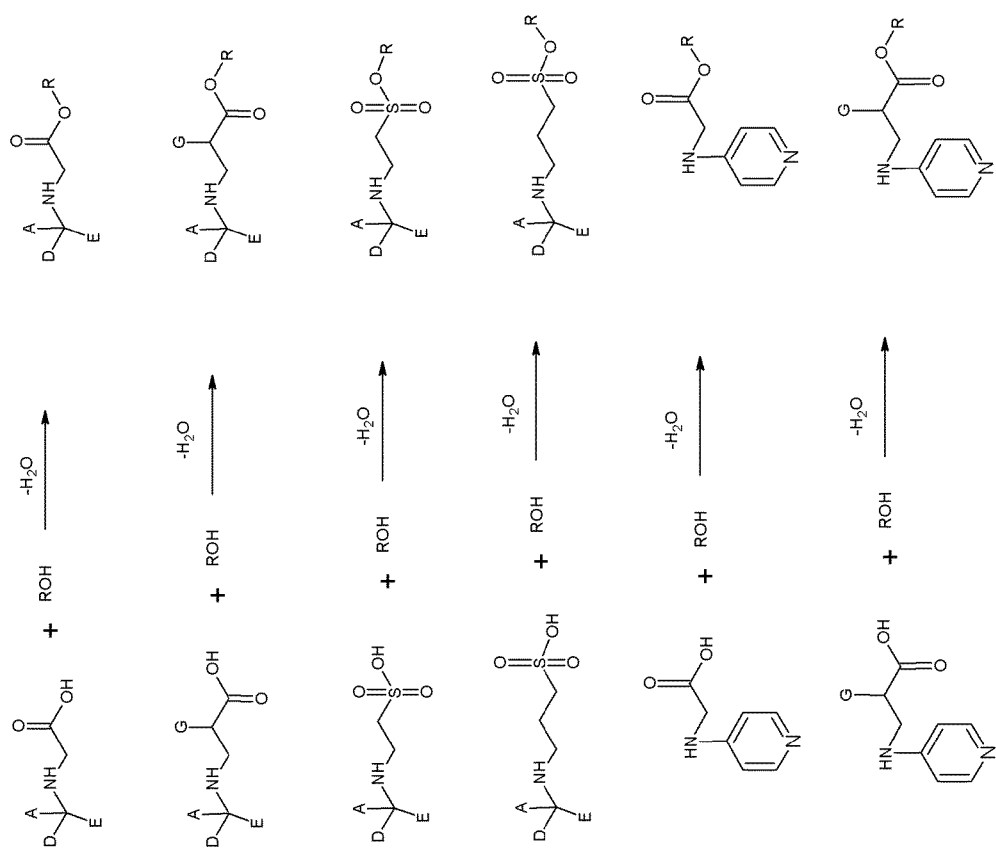
FIG. 74 shows the esterification of the zwitterionic buffers.
Figure 75:
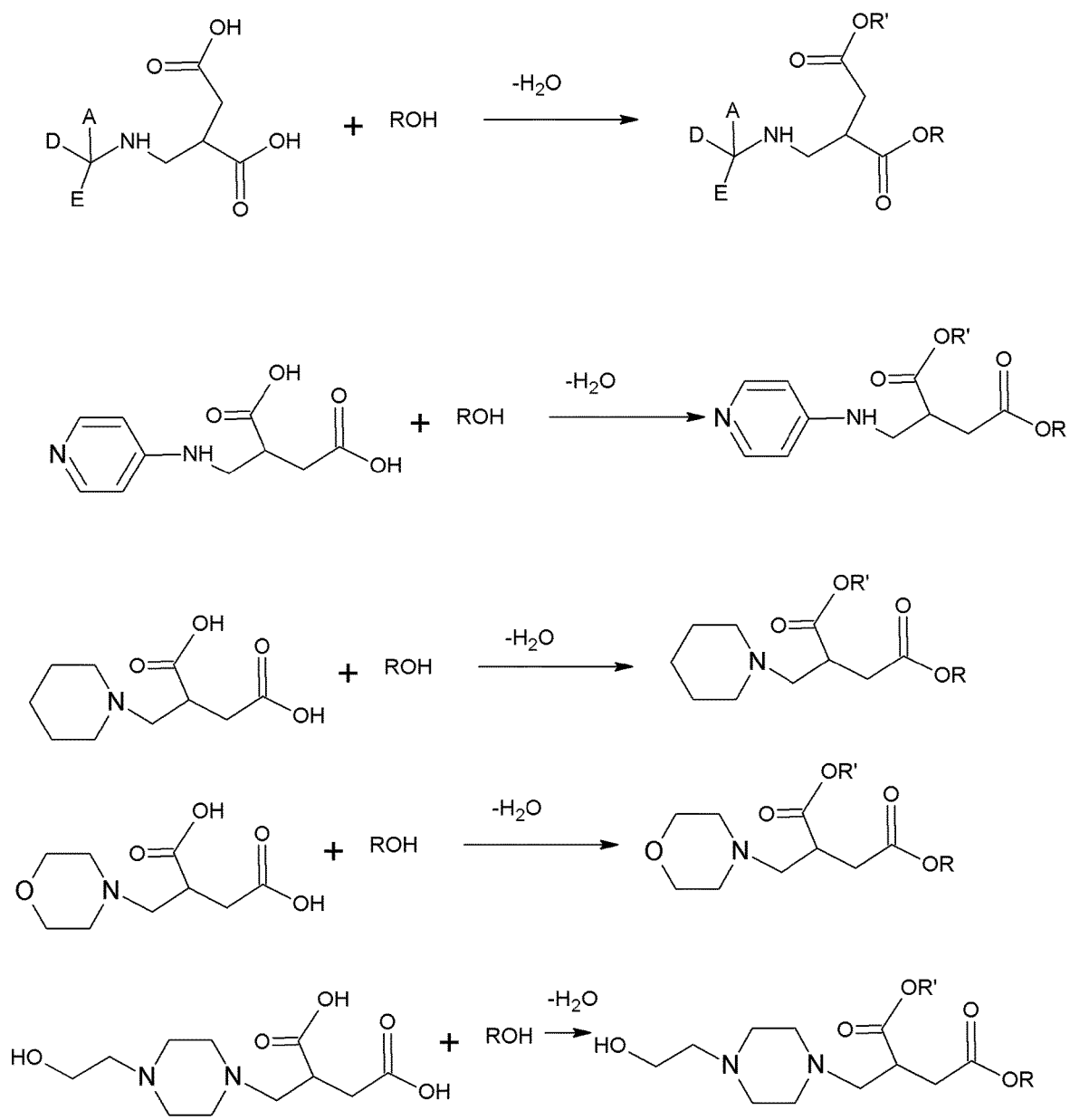
FIG. 75 shows the esterification, mono- and diesterification of the itaconic acid based zwitterionics.

As outlined earlier, one skilled in the art will recognize that the resulting amines can be reacted further with vinyl acids, monochloroacetic acid, sodium vinyl sulfonate, or an oxirane sulfonate to further add acidic character to the zwitterionic buffer. One skilled in the art will recognize that the salts and free acids and free bases of the compounds taught herein are within the scope of the invention. Additionally, to adjust the water solubility, it is useful to alkoxylate of the buffers taught herein, particularly with ethylene oxide, propylene oxide or butylenes oxide or a combination of alkoxylating agents in any amount or ratio to reach the desired result. The resulting alkoxylates will in some cases produce surfactants. Another way to make mild surfactants from the buffers taught is to esterify. FIGS. 74 and 75 show the esterification of the mono- and di-acid functional zwitterionics. It is understood by one skilled in the art that all the zwitterionics taught herein may undergo this reaction in a similar fashion to those explicitly shown. For example, the FIGS. 74 and 75 do not explicitly show the esterification of the products of FIG. 26, but it is understood that the esterification is similar enough to be recognized by one skilled in the art. The 4-aminopyridine derived zwitterionic buffers benefit from esterification in adjusting the bioavailability and water solubility, much as they do from alkoxylation, to improve their efficacy and reduce side effects when used as a therapy for MS, Alzheimer's disease, or other medical use.

Figure 76:
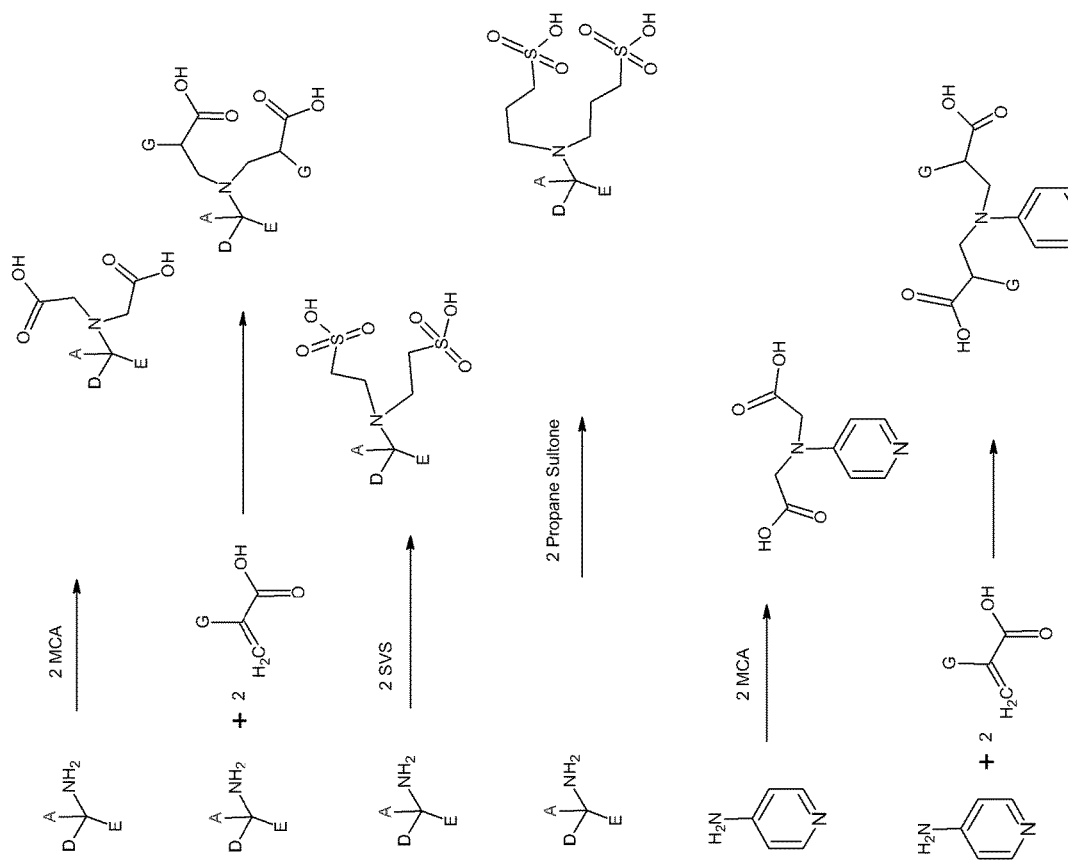
FIG. 76 shows the synthesis of diacid, tertiary amine, zwitterionic buffers.
Figure 77:
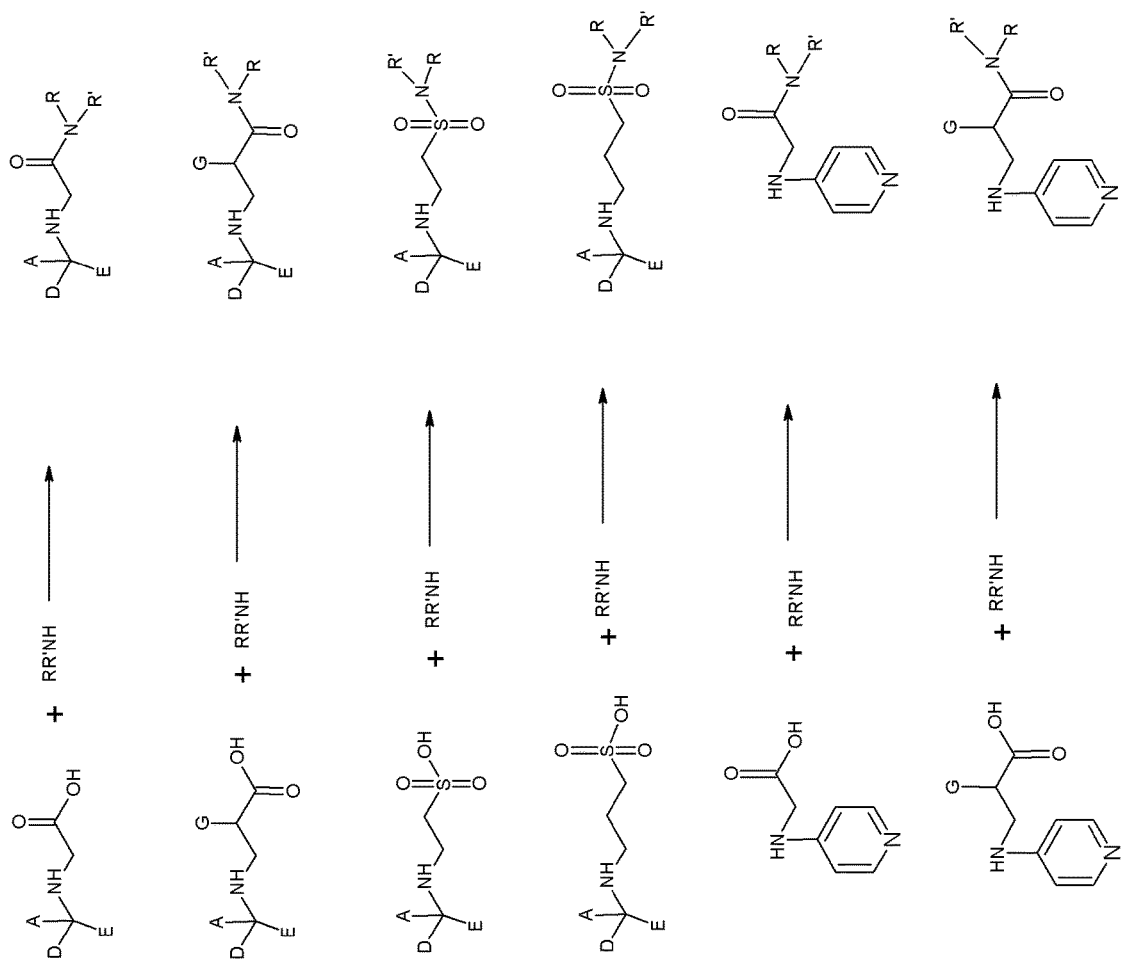
FIG. 77 shows the synthesis of amido amines from zwitterionic buffers, where A, D, and E are independently chosen from, —H, —CH3, —CH2CH3, —CH2OH. G is chosen from —H, —CH3, —CH2CH3, —OH. R and R' are chosen independently from the group alkyl, alkenal, or alkynal, linear or branched, saturated or unsaturated. Additionally, R' may be H.

The primary amines that are the basis for the zwitterionic buffers, may undergo disubstitution to form diacid functional buffers as shown in FIG. 76. These may be mono- or diesterified just as the itaconic acid based buffers in FIG. 75. FIG. 77 expands on the amidoamines that can be synthesized from the zwitterionic buffers. The amidoamine formation may also be carried out by diamines to create dimmers, or with the secondary diamines, such as coco diamine or tallow diamine to produce surfactants that act as corrosion and scale inhibitors.

Figure 78:
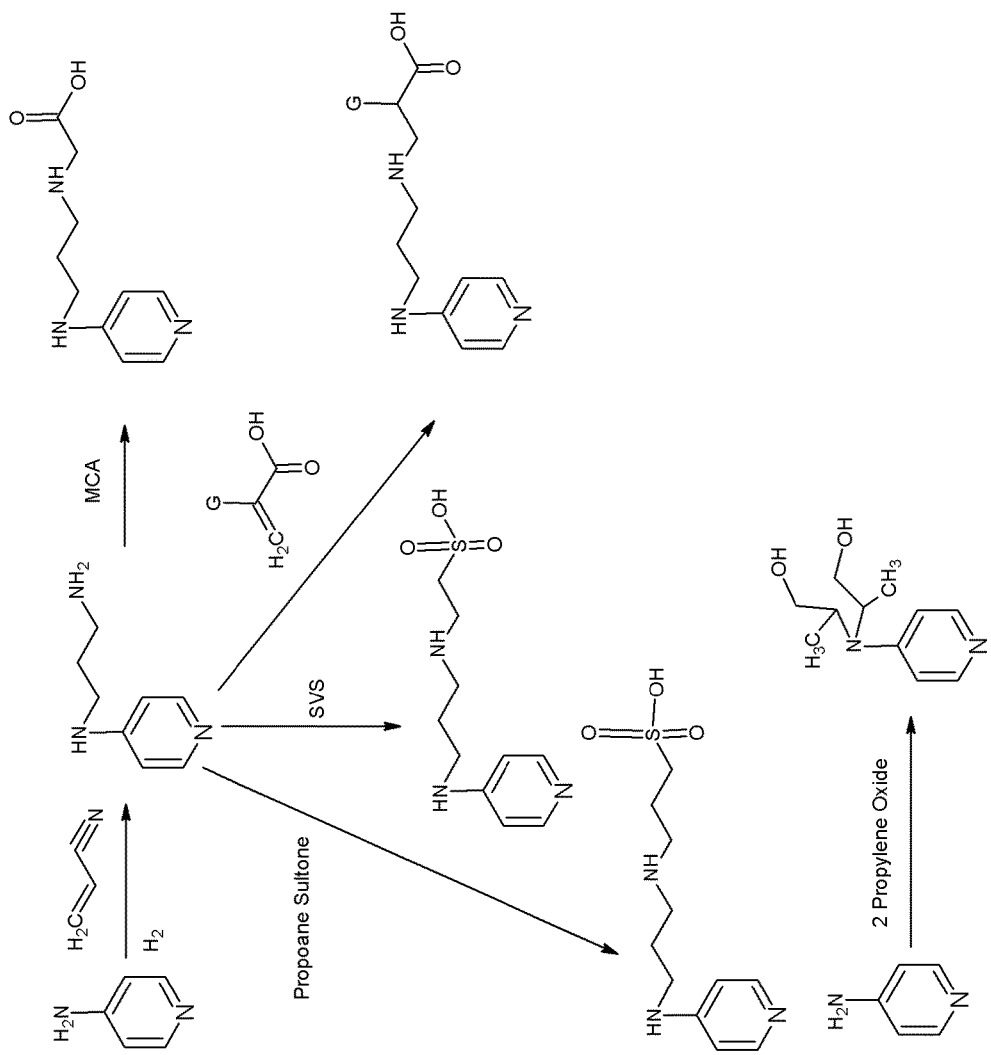
FIG. 78 shows the synthesis of a variety of 4-aminopyridine derivatives that are useful buffers.

FIG. 78 shows the synthesis of a variety of 4-aminopyridine derivatives that are useful buffers. The varying amine strength and water solubility give them unique properties.

Figure 79:
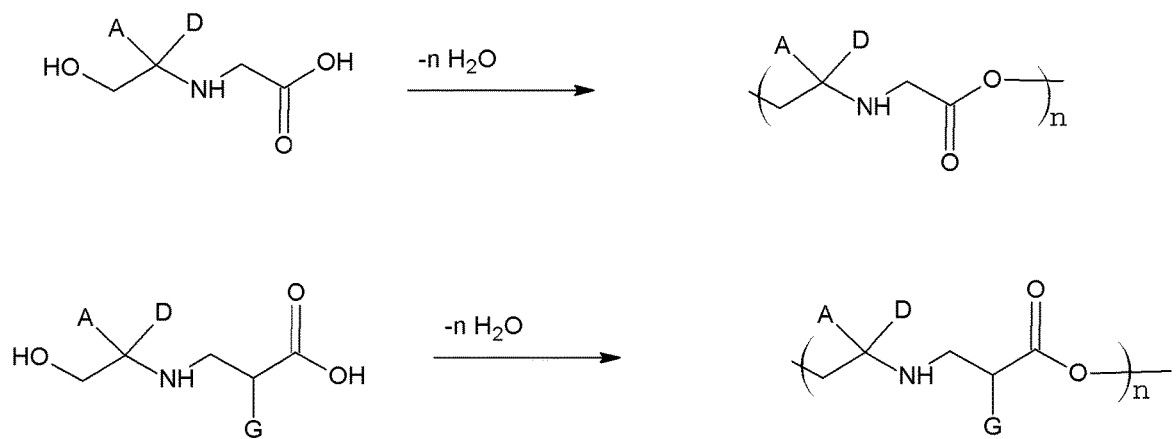
FIG. 79 shows the condensation polymerization of the hydroxyl functional zwitterionics.

FIG. 79 shows the condensation polymerization of the hydroxyl functional zwitterionic buffers. As shown, linear polyesters or polyester prepolymers are produced. By using the buffers with varying hydroxyl numbers, a hydroxyl functional polymer results. When used as a prepolymer, greater cross-linking can be introduced when incorporated into a polyurea, polyurethane, or polyether. If condensed with the itaconic based buffers, such as those in FIG. 42, or other polyacid functional monomers or prepolymers, a 3 dimensional polyester polymer matrix can be achieved.

Figure 80:
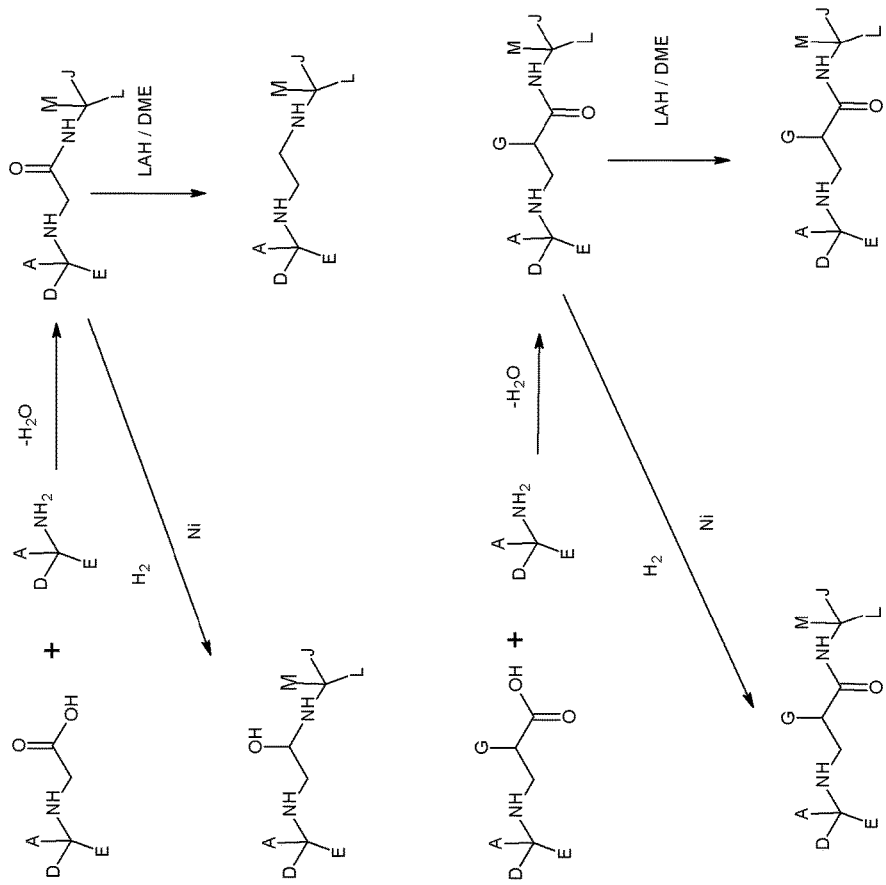
FIG. 80 clarifies the amidoamine to aminoalcohol or diamine synthesis originally outlined in FIG. 73.
Figure 81:
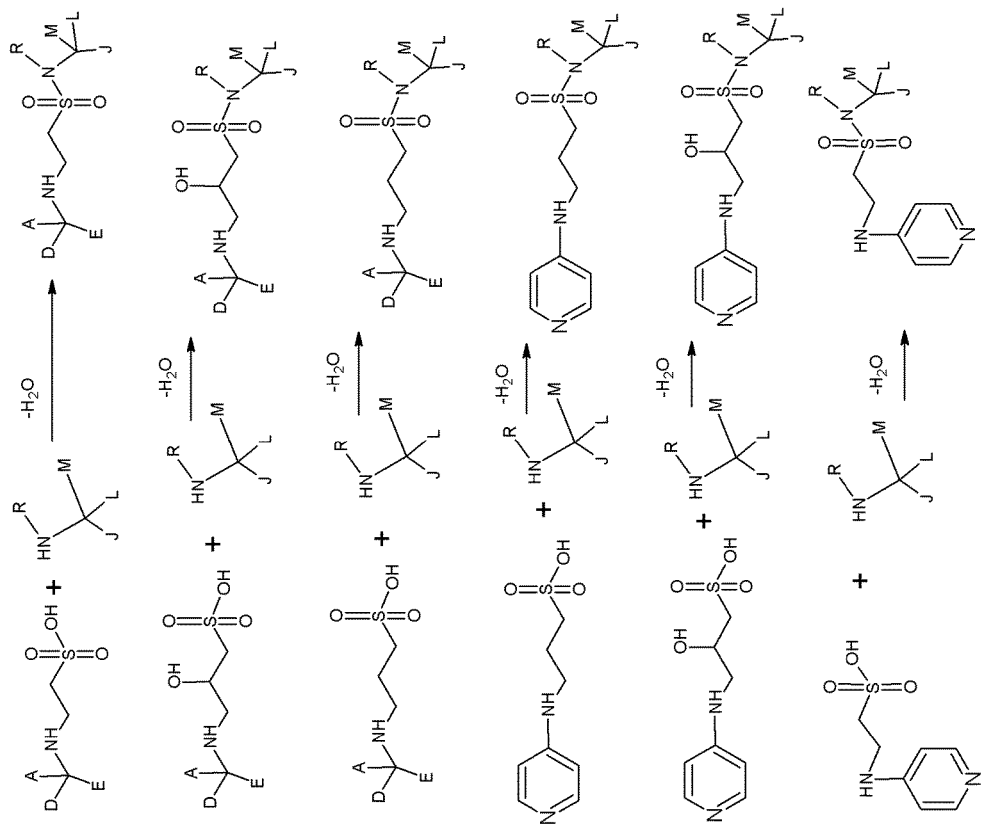
FIG. 81-84 teach the synthesis of sulfonamides from the zwitterionic buffers.
Figure 82:
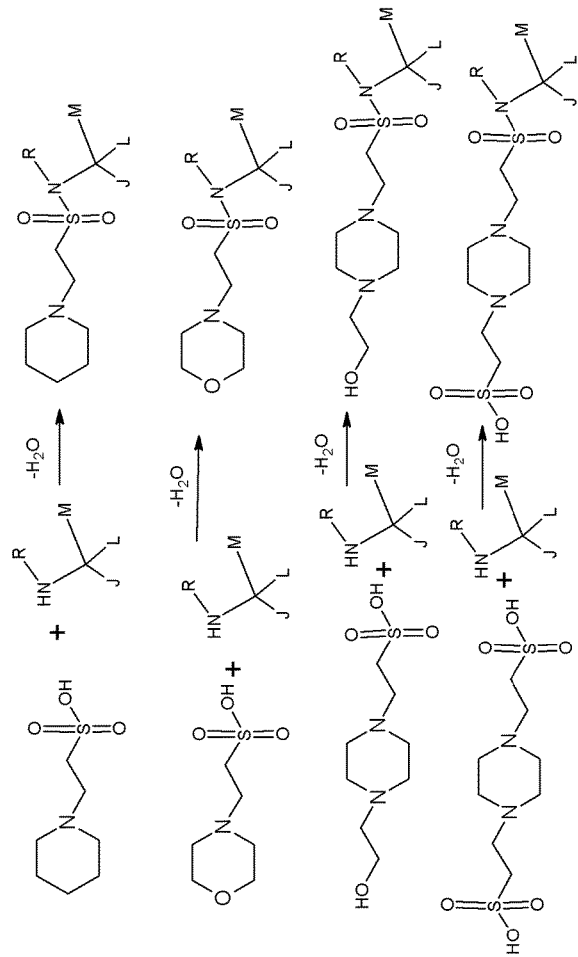
Figure 83:
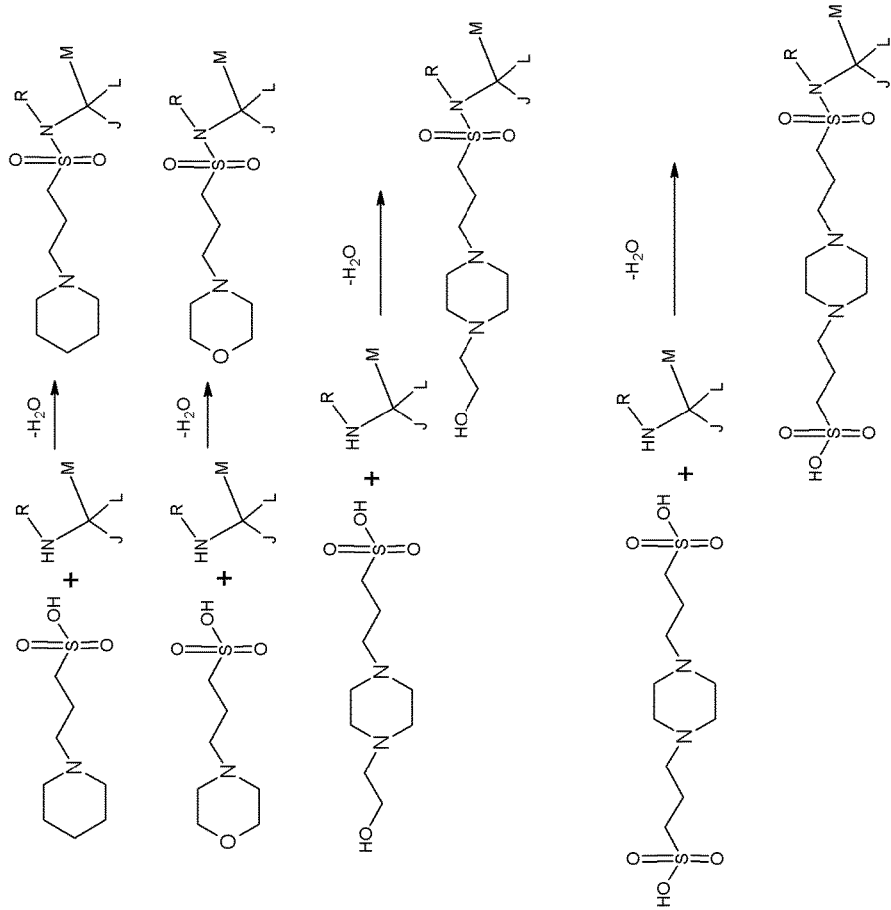
Figure 84:
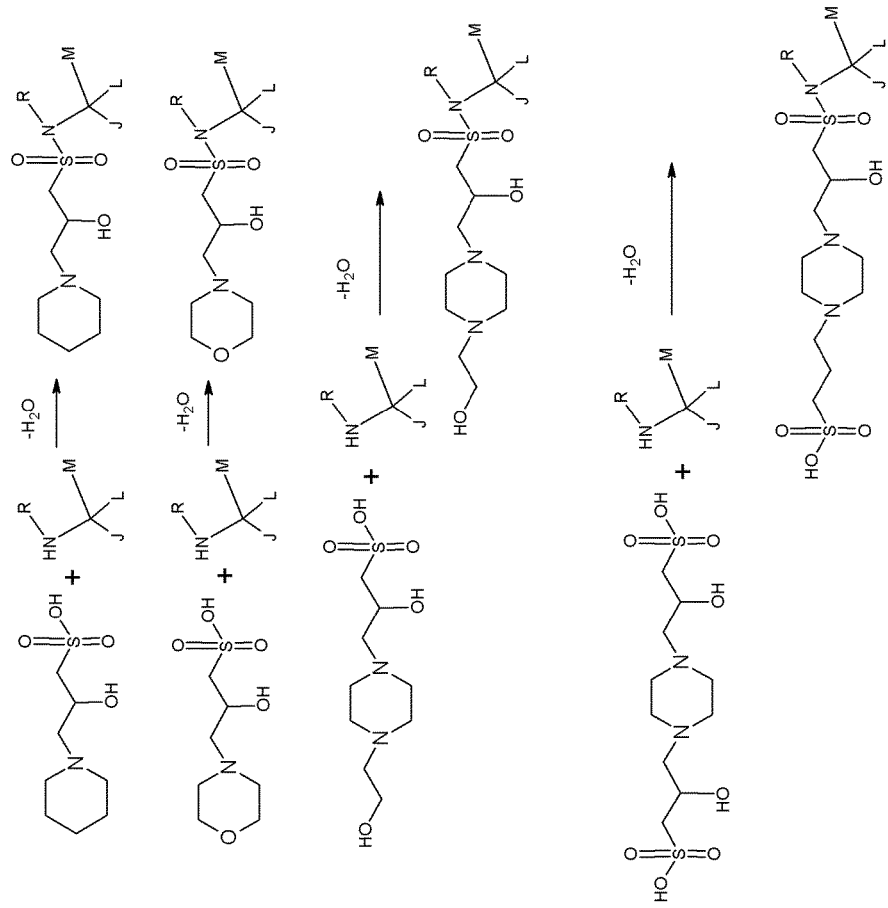

FIG. 80 further clarifies the ability to make diamines from the amides taught herein. In FIG. 80, where G is —OH, it can either remain intact when done under milder reduction conditions, or be converted to —H when harsher conditions, such as when LAH is used. The most useful of these amidoamines and diamines is expected to be those where A=D=E=M=J=L=—CH$_2$OH.

FIGS. 81, 82, 83 and 84 demonstrate how the sulfonate buffers can be converted to sulfonamides. Sulfonamides have a wide range of known biological activity and these sulfonamides are expected to have increased antimicrobial properties versus their related sulfonates or carboxcylic acid functional zwitterionics. It is well known in the art that sulfonamides can be reduced under mild conditions to the sulfonimides, which are within the scope of the invention disclosed herein.

Figure 85:
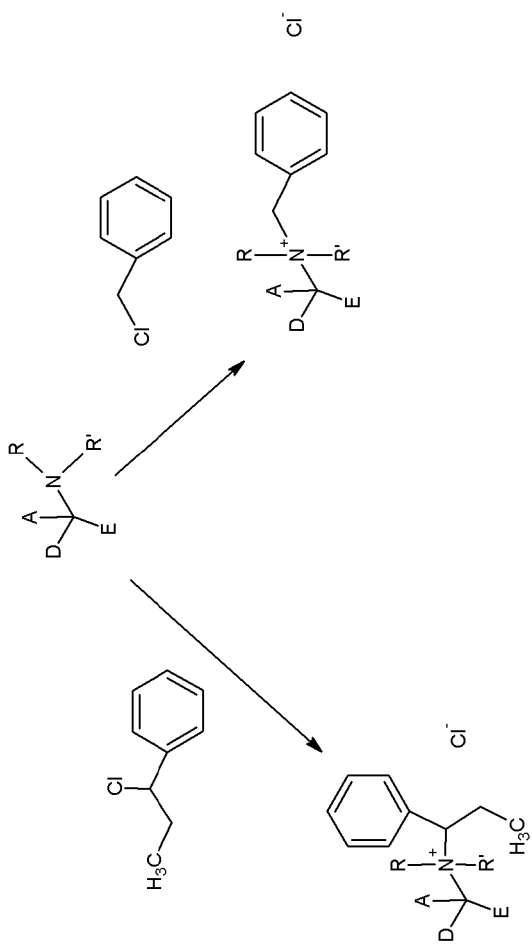
FIG. 85 shows the synthesis of quaternary amine salts from tertiary aminoalcohols where A, D, and E are independently chosen from, —H, —CH3, —CH2CH3, —CH2OH. R and R' are chosen independently and selected from the group alkyl, alkenal, or alkynal, linear or branched, saturated or unsaturated.

FIG. 85 shows the synthesis of quaternary amine salts. These products are particularly useful in diagnostic kits for condution, as well as there antimicrobial properties. The case where A=—CH$_2$OH and D=E=R=R'=—CH$_3$ is the most useful of this class, but the other permutations are useful when the water solubility needs to be increased or decreased.

Figure 86:
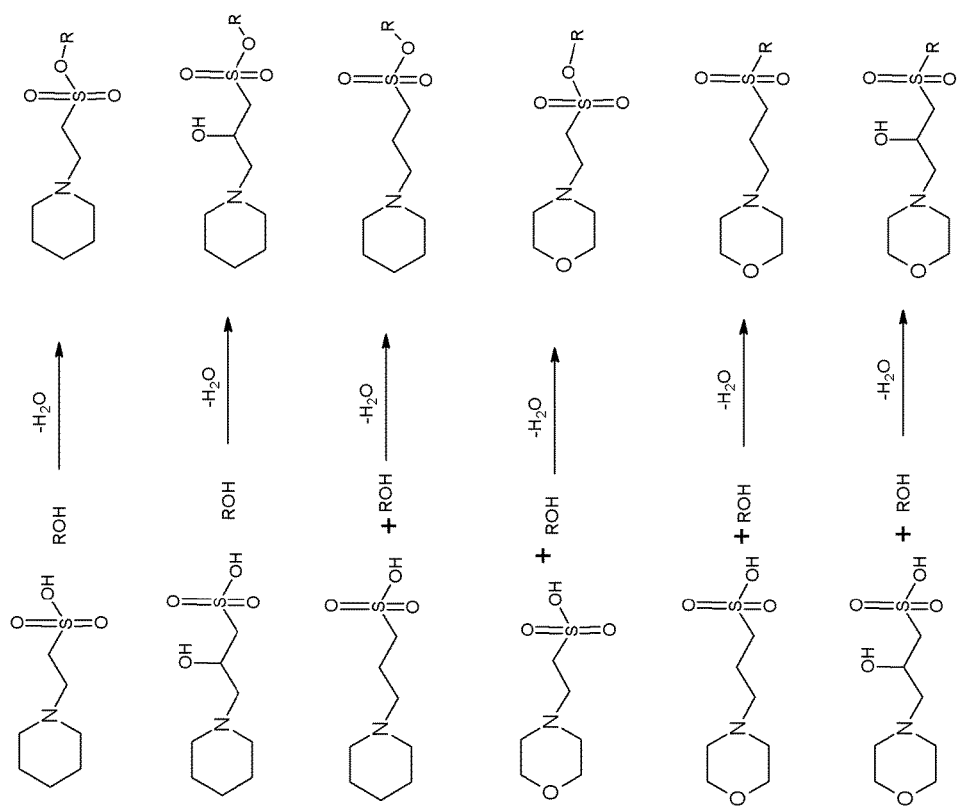
FIG. 86-87 teach the synthesis of sulfonate esters of the zwitterionic buffers.
Figure 87:
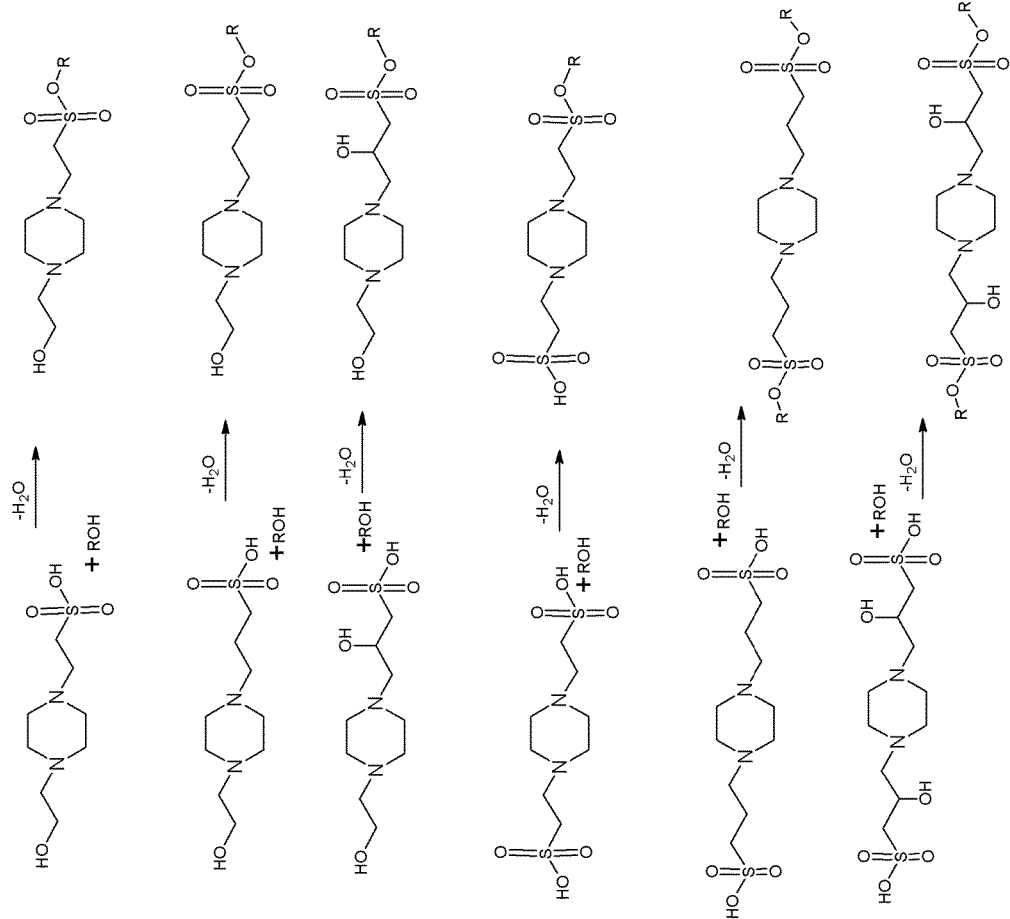
Figure 88:
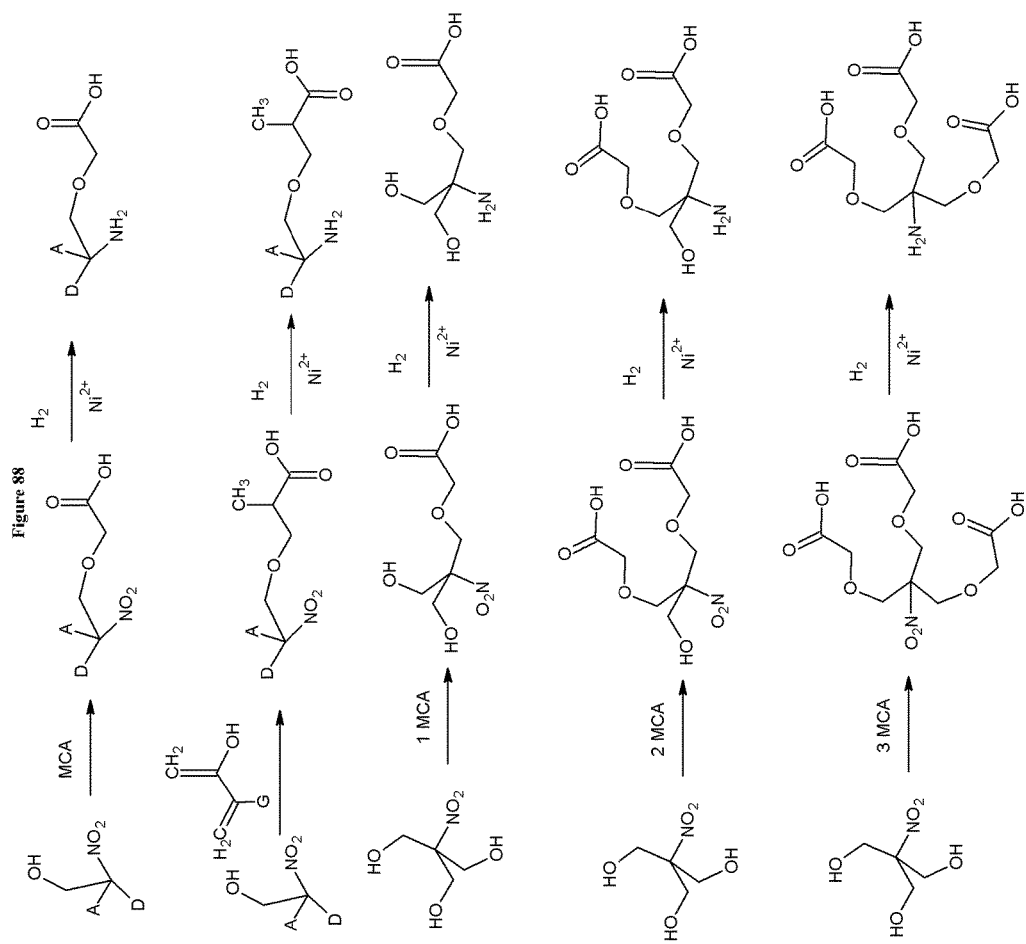
FIG. 88-89 teach the synthesis of amino acid, zwitterionic buffers with primary amine functionality.
Figure 89:
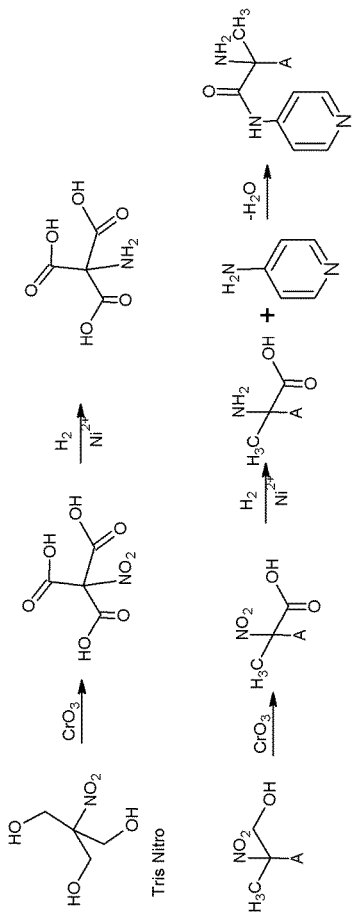

FIGS. 86 and 87 teach the synthesis of sulfonate esters from the zwitterionic buffers. These esters allow for changing the water solubility, while maintaining buffering capacity. FIGS. 88 and 89 teach the synthesis of zwitterionic buffers with primary amino functionality. Again, the 4-aminopyridine moiety containing buffers are promising targets for therapies to treat MS and potentially Alzheimer's disease or other diseases that involve demyelination or other myelin anomalies.

Figure 90:
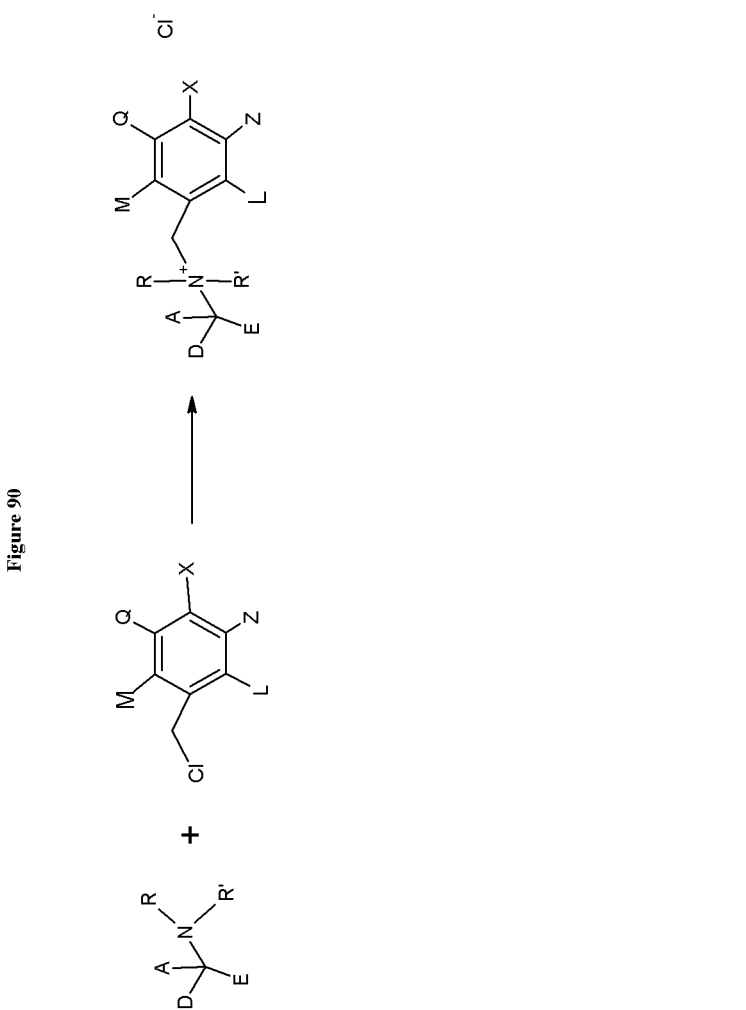
FIG. 90 expands on the quaternary amine salts shown in FIG. 85 where A, D, and E are independently chosen from, —H, —CH3, —CH2CH3, —CH2OH. G is chosen from —H, —CH3, —CH2CH3, —OH. R and R' are chosen independently and selected from the group alkyl, alkenal, or alkynal, linear or branched, saturated or unsaturated. L, M, Q, X, Z are independently chosen from the group —H, —OH, —CH2OH, alkyl, alkenal, or alkynal, linear or branched, saturated or unsaturated.

FIG. 90 expands on the quaternary amine salts shown in FIG. 85.

Figure 91:
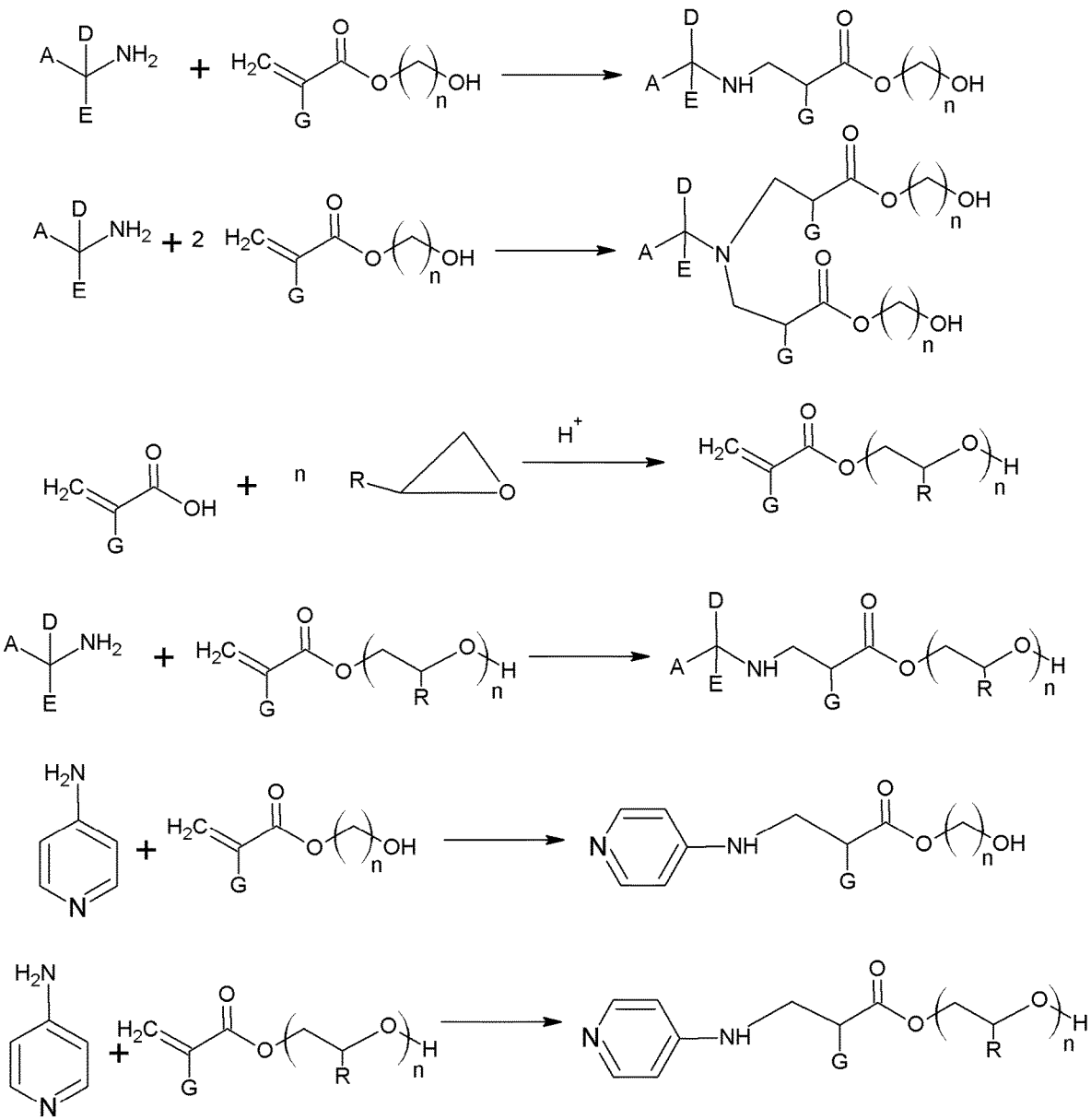
FIGS. 91-92 show the use of acrylate hydroxyesters in the synthesis of biological buffers.
Figure 92:
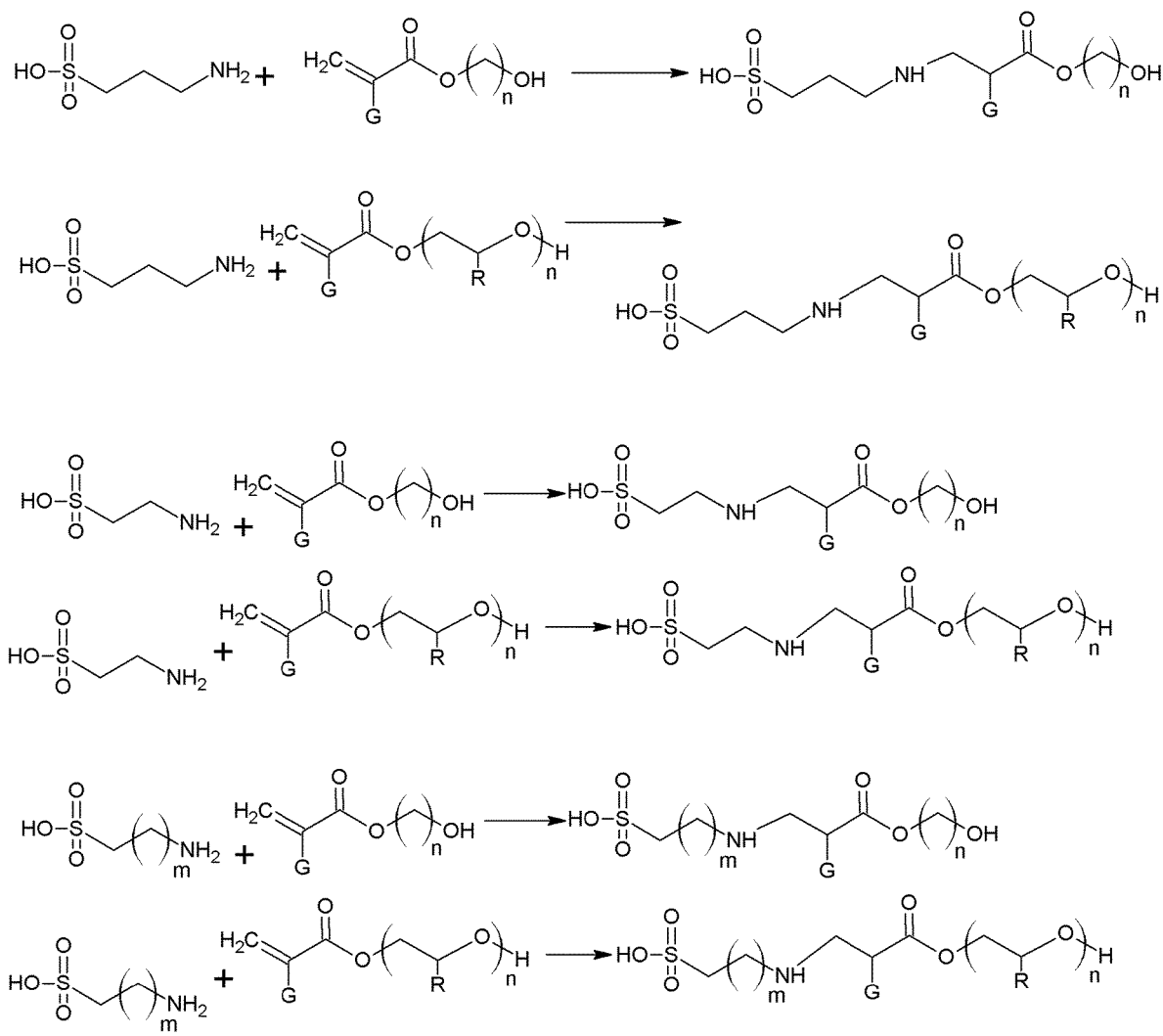

FIGS. 91 and 92 show the synthesis of buffers with adjusted HLB by using hydroxyesters of acrylic acids. In FIG. 91, an example of a disubstituted amine is shown in the second line. This applies for all the amine and acrylate pairs which are within the scope of the present invention. FIG. 91, in addition to showing the hydroxyester acrylates which can be made through acid catylized esterification of the acrylic acid, also show an alkoxylated acrylate. The alkoxylated acrylate can be prepared through acid catalyzed alkoxylation utilizing ethylene oxide, propylene oxide, butylene oxide or any other alkoxylate. The reaction product is a buffer that possesses a wide range of water solubilities. FIG. 91 includes this process.

Figure 93:
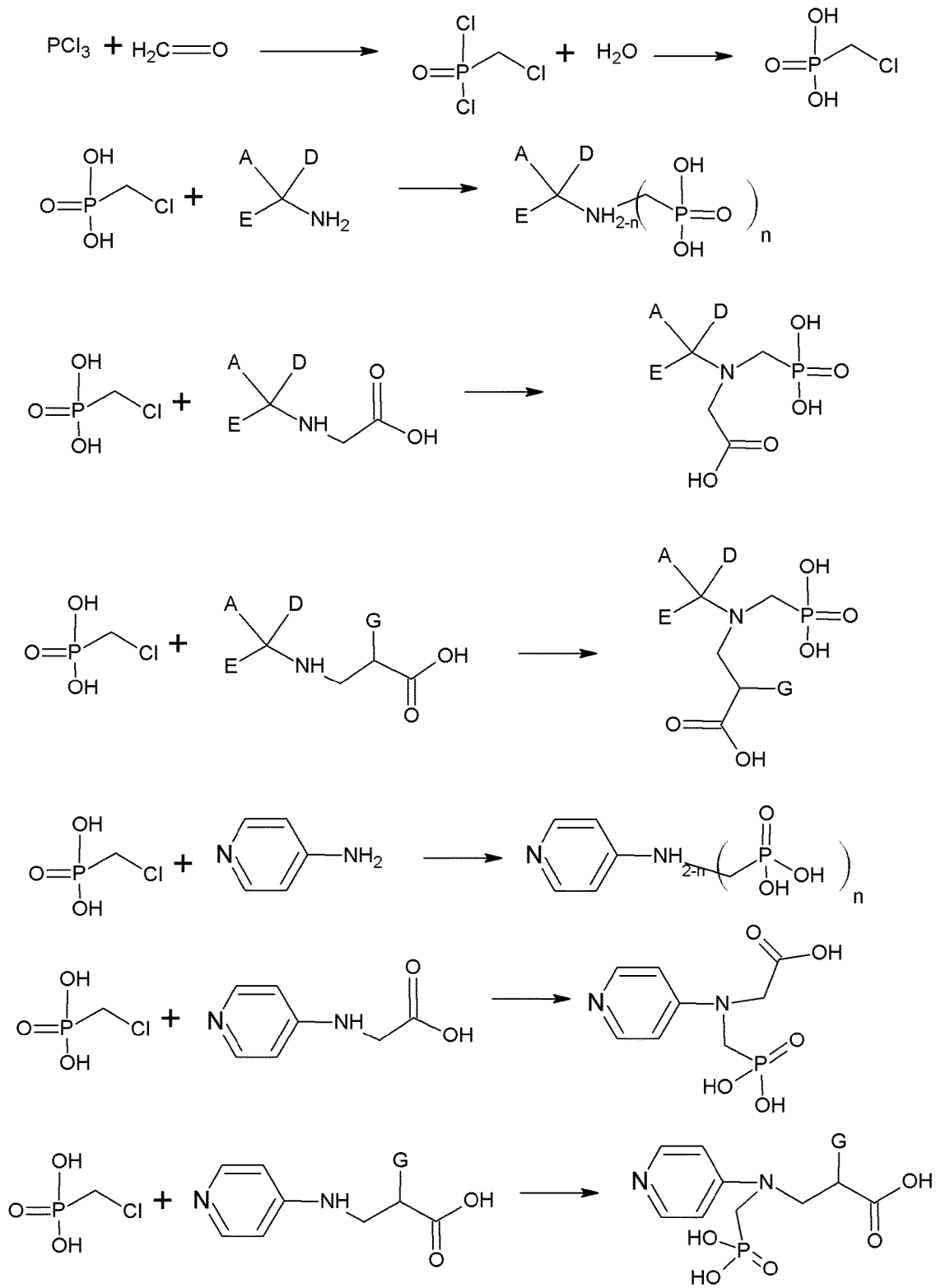
FIG. 93 teaches the synthesis of a family of phosphonates and phosphonate amino acids.

FIG. 93 teaches the synthesis of phosphonates based on aminoalcohols and amino acids, as well as those derived from 4-Aminopyridine. These phosphonates are excellent buffers in their own right, but have other benefits. The phosphonates have a higher solubility profile when salted with divalent cations, such as, calcium, magnesium and zinc. This also results in the molecules being excellent chelants and scale inhibitors. In addition, these phosphonates are expected to be quite biologically active. The amino acid starting materials in FIG. 93 exhibit fungal resistance as well as resistance moss, mold and some bacteria. The 4-Aminopyridine derivatives are biologically active as treatments for MS and other autoimmune diseases, such as rheumatoid arthritis, and conditions effected by abnormal myelination. The phosphonates are expected to extend this efficacy further. In addition, the phosphonates, of the amino acids in particular, are expected to be excellent herbicides.

Figure 94:
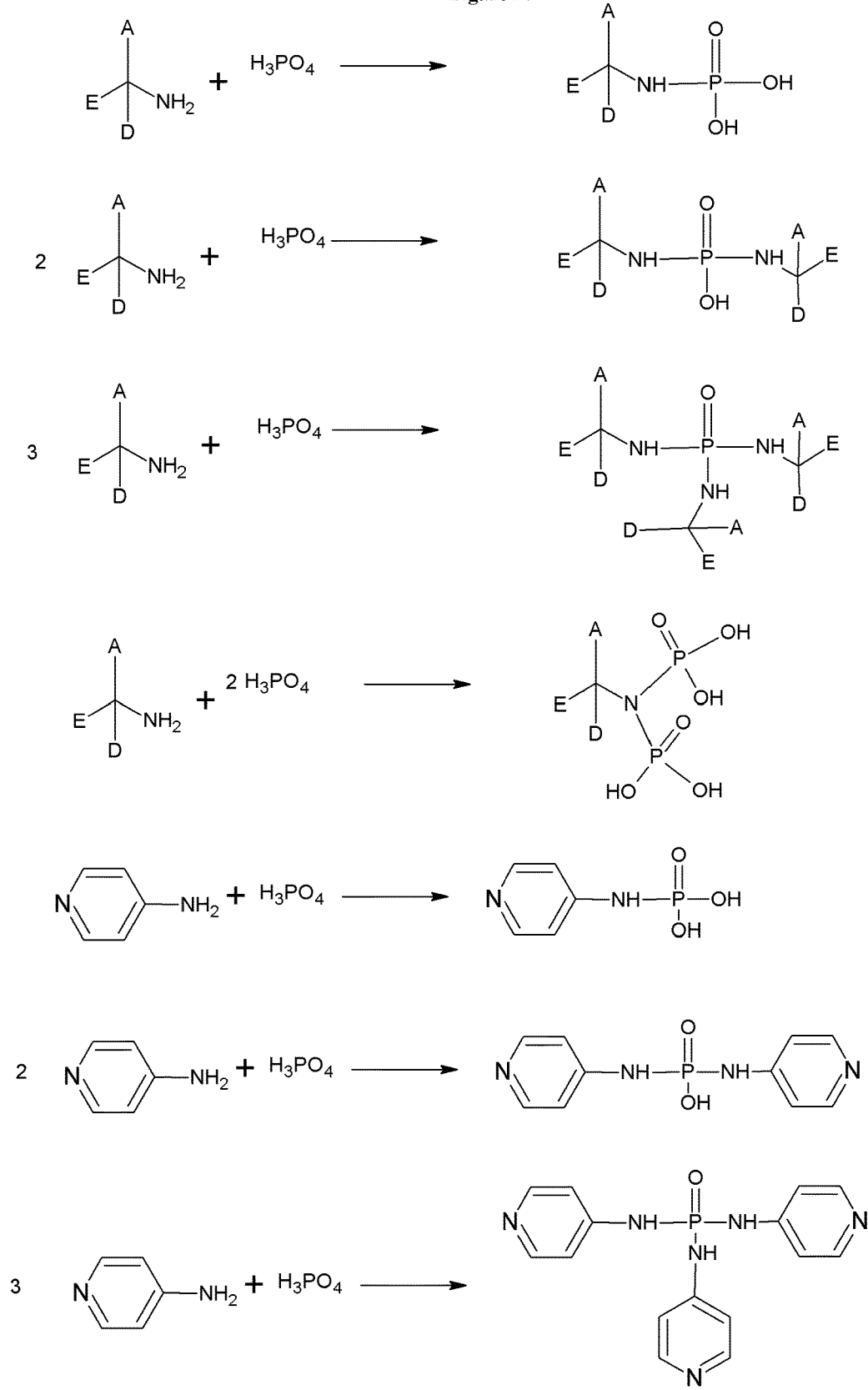
FIG. 94 teaches the synthesis of a family of phosphamides.
Figure 95:
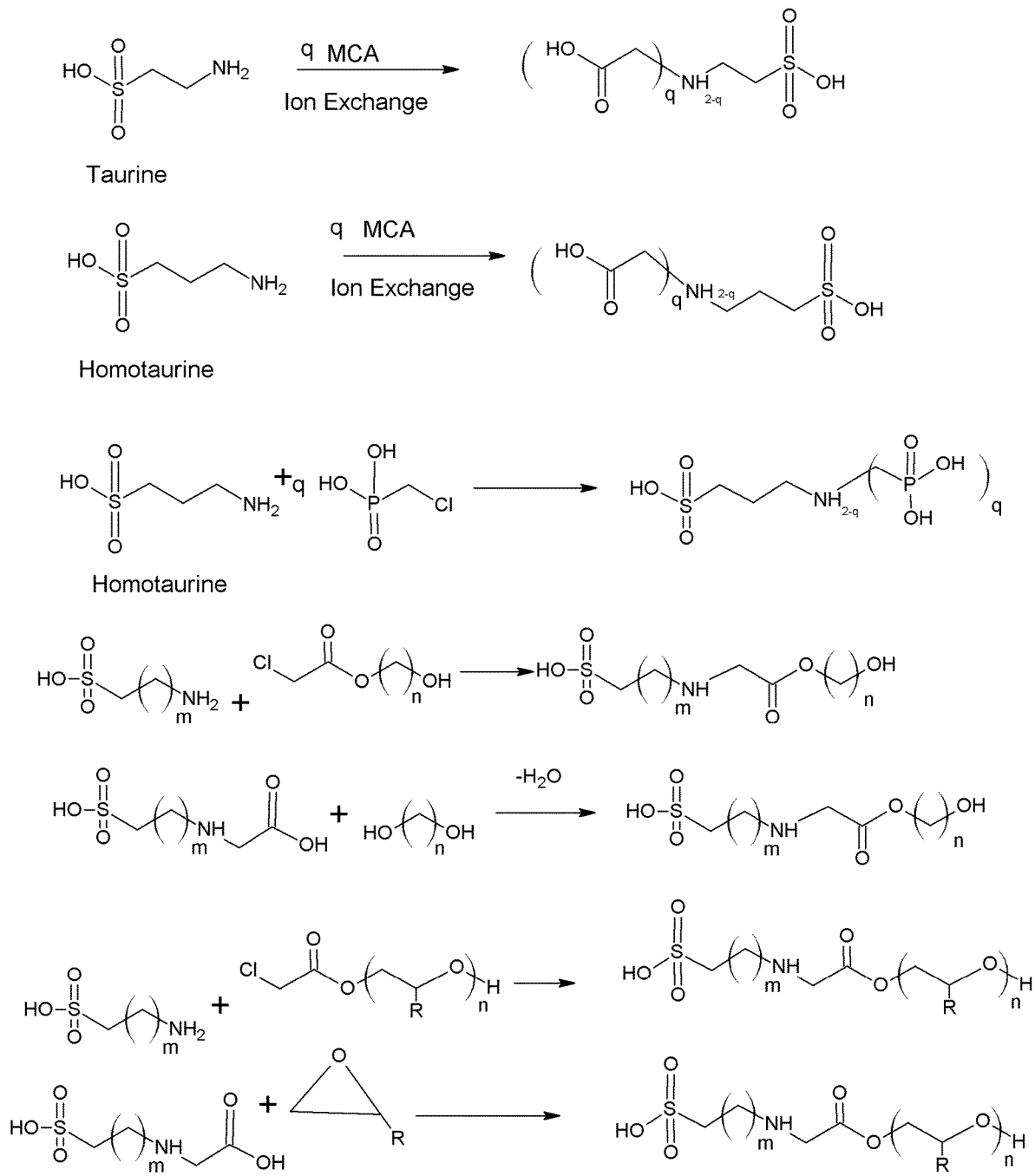
FIG. 95 teaches the synthesis of zwitterionic buffers based on MCA and sulfonic acids.
Figure 96:
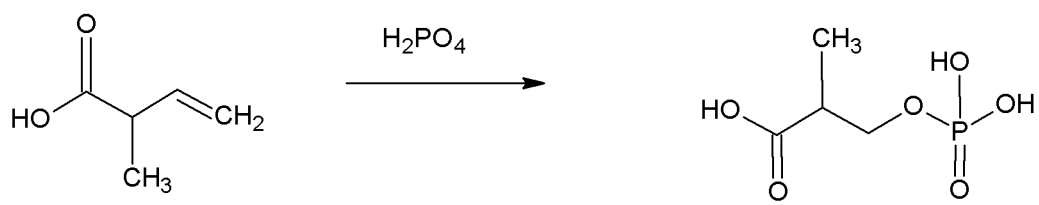
FIG. 96 teaches the synthesis of an enzyme inhibitor.
Figure 97:
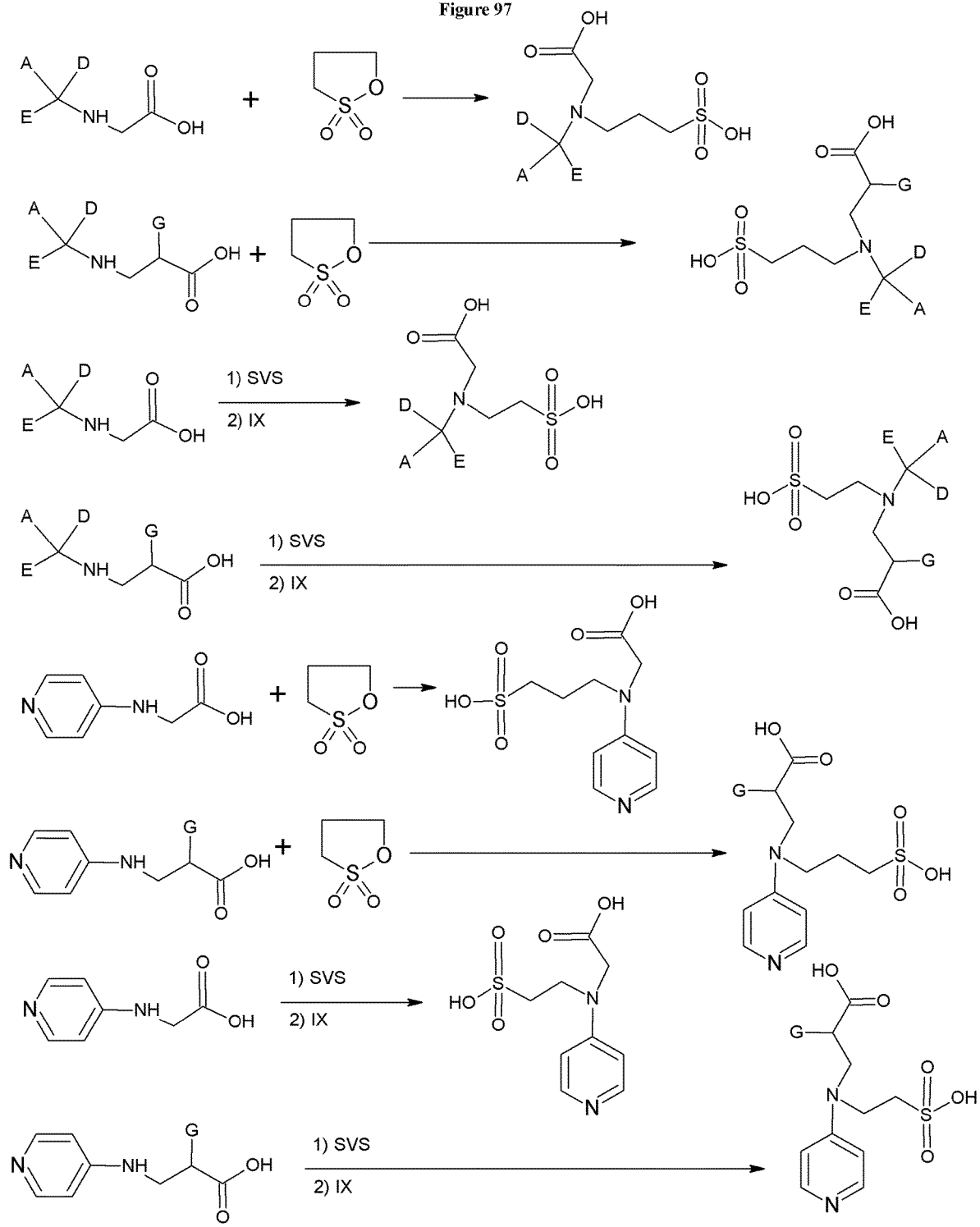
FIG. 97 teaches the synthesis of diacid sulfonic acid buffers.
Figure 98:
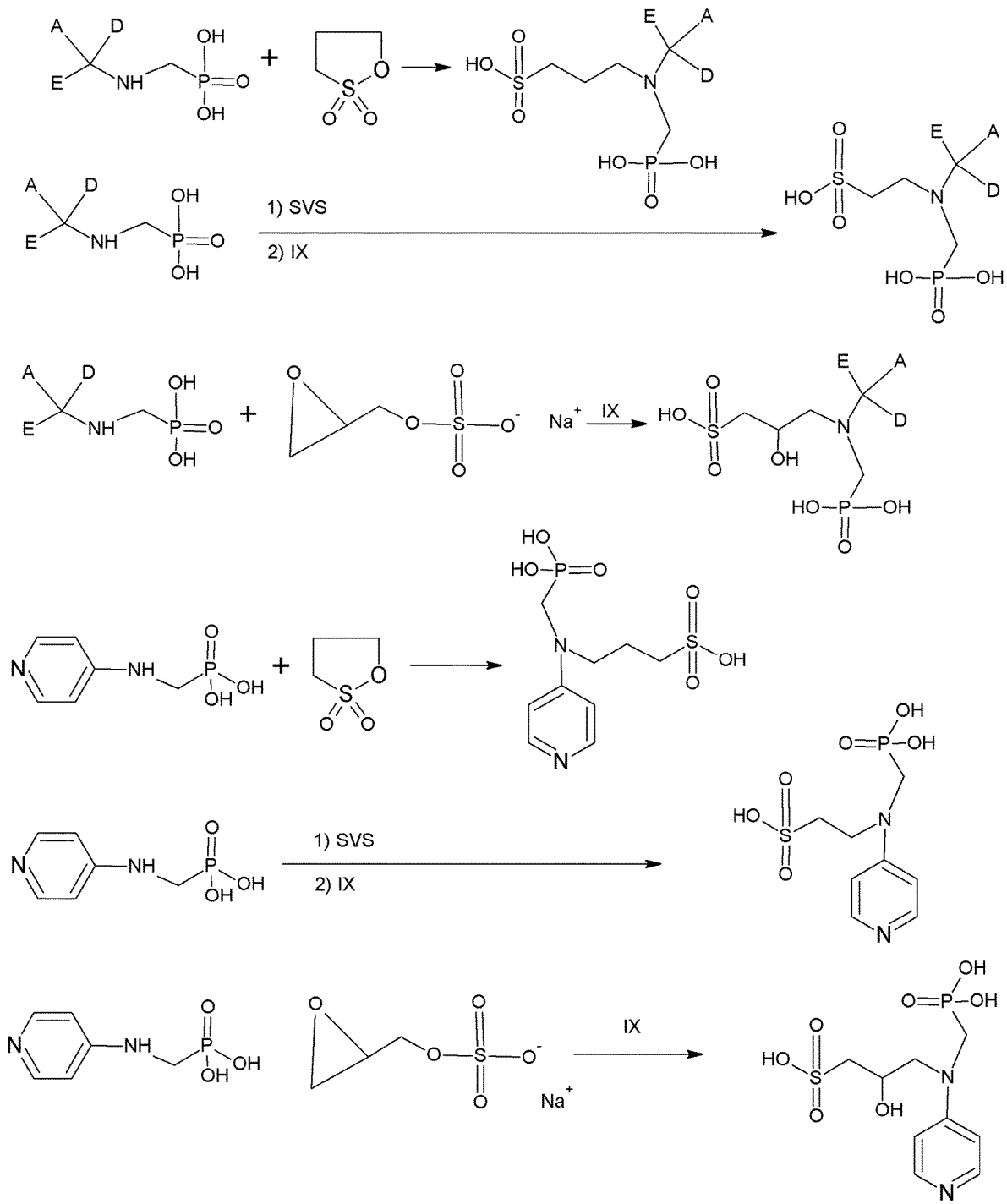
FIG. 98 teaches diacid buffers with sulfonic acid and phosphonate functionality.
Figure 99:
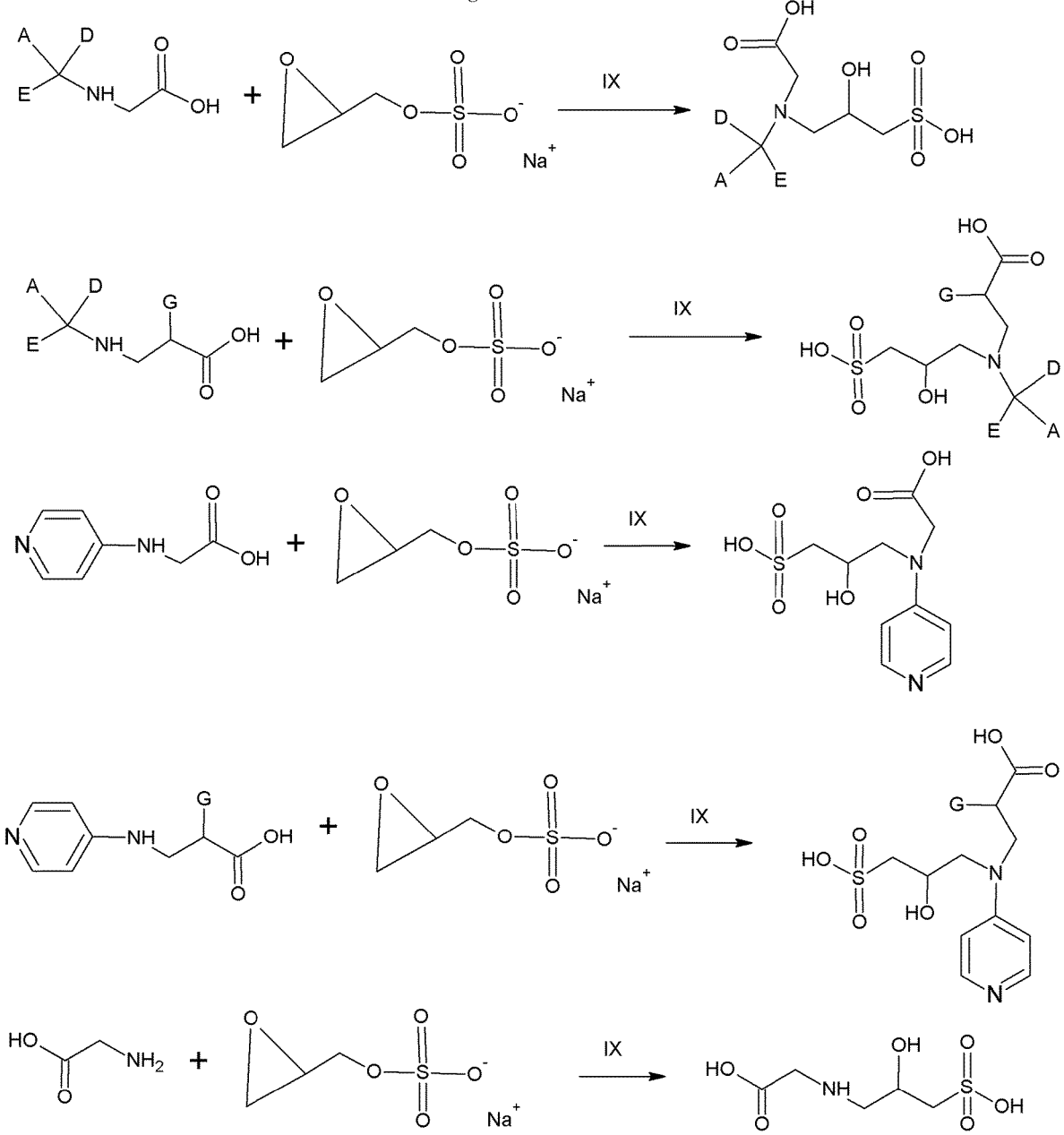
FIG. 99 teaches diacid buffers with sultaine and carboxcylic acid functionality.

The phosphamides of FIG. 94 show great promise as insecticides and insecticide precursors. These phophamides also show promise as chemotherapy agents for treatment of cancers. It is believed that the phosphamides taught are useful therapies for autoimmune diseases by suppressing the immune response to various antigens. FIG. 95 teaches the synthesis of zwitterionic sulfonates based on monochloroacetic acid. FIG. 96 teaches an enzyme inhibitor. FIG. 97 through FIG. 99 teach the synthesis of diacid buffers. These buffers, while useful as buffers also possess unique biological properties, including enzyme inhibition. Thus making these very useful tools in agriculture, diagnostics, and biotechnology. It is understood by one skilled in the art that the amino acid starting materials could be substituted for their esters or alkoxylates, such as in FIGS. 74, 86, 91, 92, thus giving the analogous products.

Figure 100:
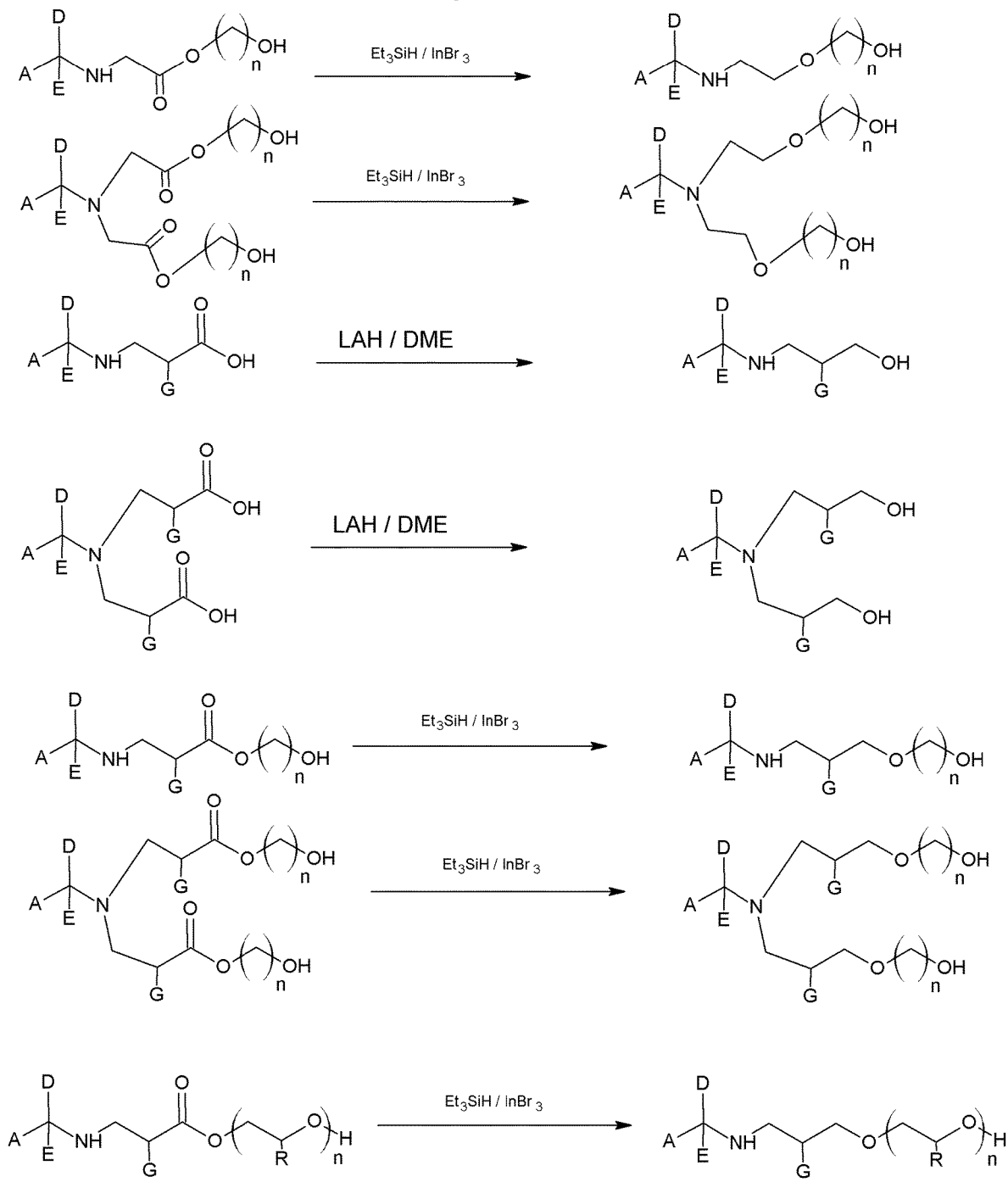
FIG. 100-101 teach the reduction of the zwitterionic buffers to alcohols and ethers.
Figure 101:
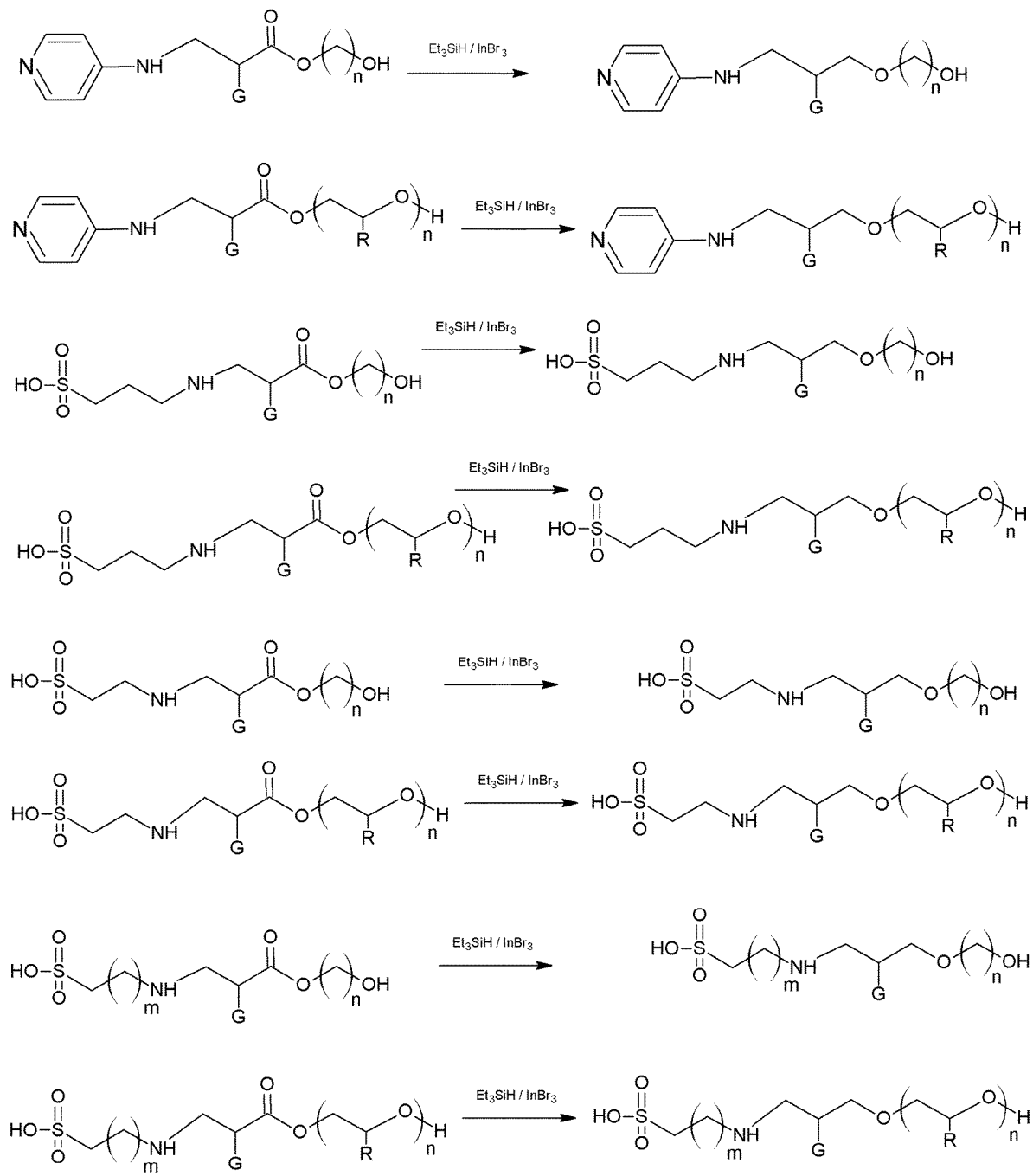
Figure 104:
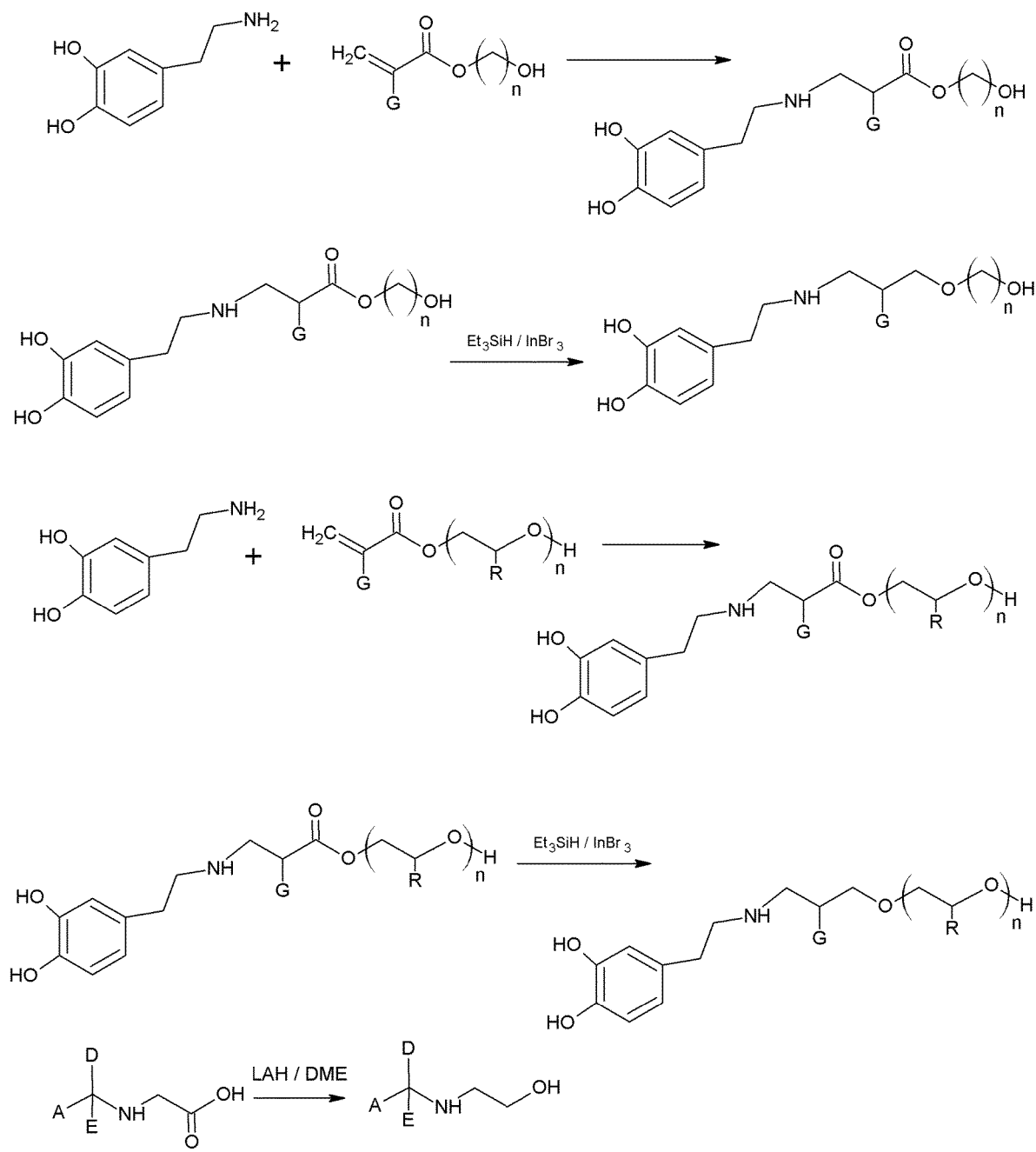

FIG. 100 outlines a family of products that are useful buffers that are primarily liquid and distillable. These products also have wider applications, specifically in removal $H_2S$ from both refinery processes as well as gas and liquid petroleum, products. The reduction of the carbonyl produces compounds that are more stable to the harsh conditions seen in oil and gas recovery and refinery processes. The final molecule at the bottom of FIG. 104 is a hindered amine that has fewer interactions than the primary amine with proteins, improving yield when used to purify proteins. It is a suitable $H_2S$ treating amine as well. Lines 2, 4, and 6 of FIG. 100 are present simply to underscore the fact these amines used as precursors may be mono or disubstituted, as made clear in other sections. This is true for all the primary amine starting materials and the resulting products and the downstream derivatives that result are included within the scope of this invention. FIG. 101 continues to teach the reduction of the zwitterionic buffers and their esters to alcohols and ethers. For the sulfonic acid zwitterions, if the reduction is allowed to run longer or is run under stronger reducing conditions, such as with LAH, the sulfonic acid groups will be converted to thiols. These thiols are also within the scope of the present invention.

Figure 102:
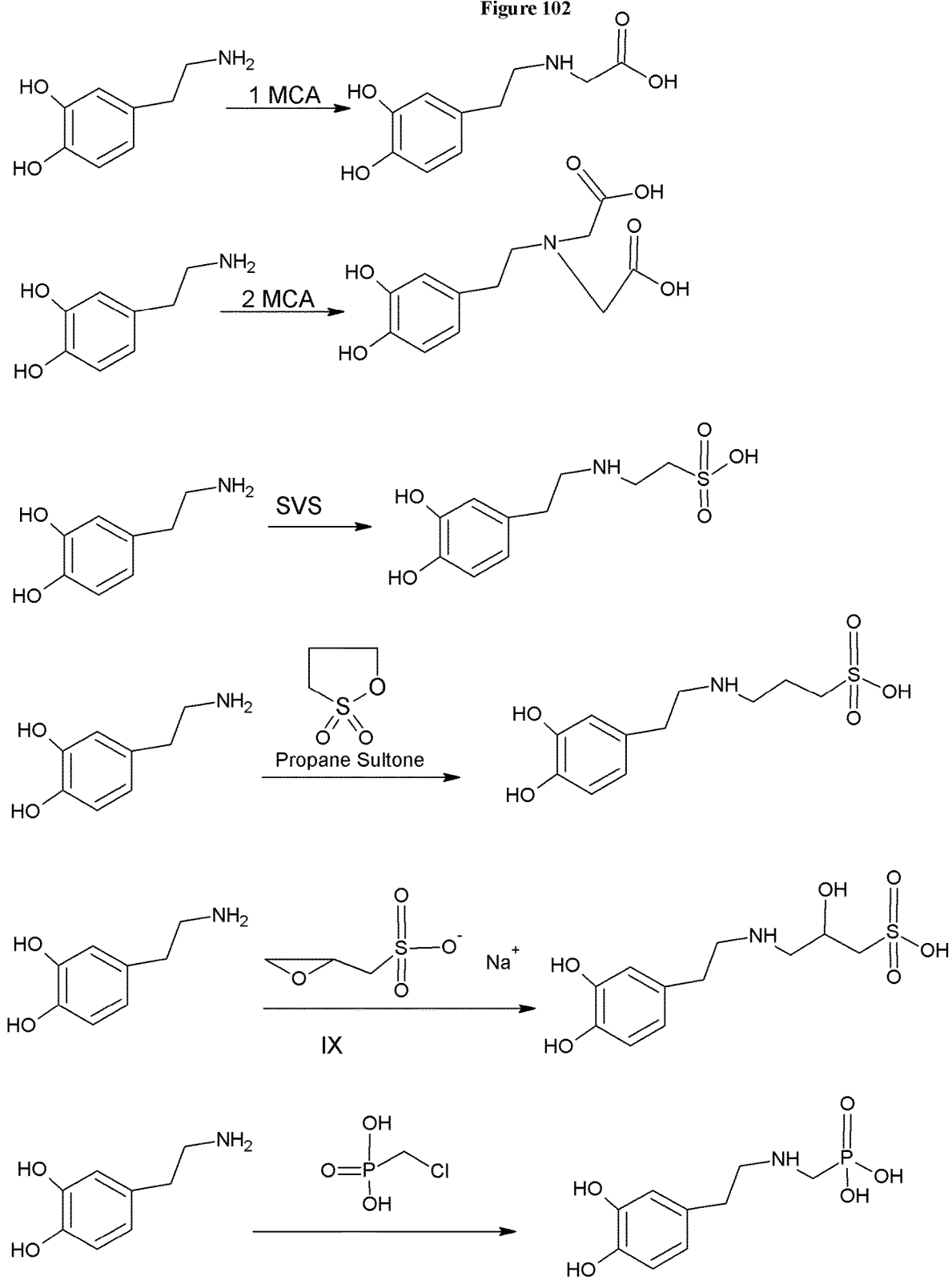
FIG. 102-104 teaches the synthesis of zwitterionic buffers and their reduction to alcohols and ethers.
Figure 103:
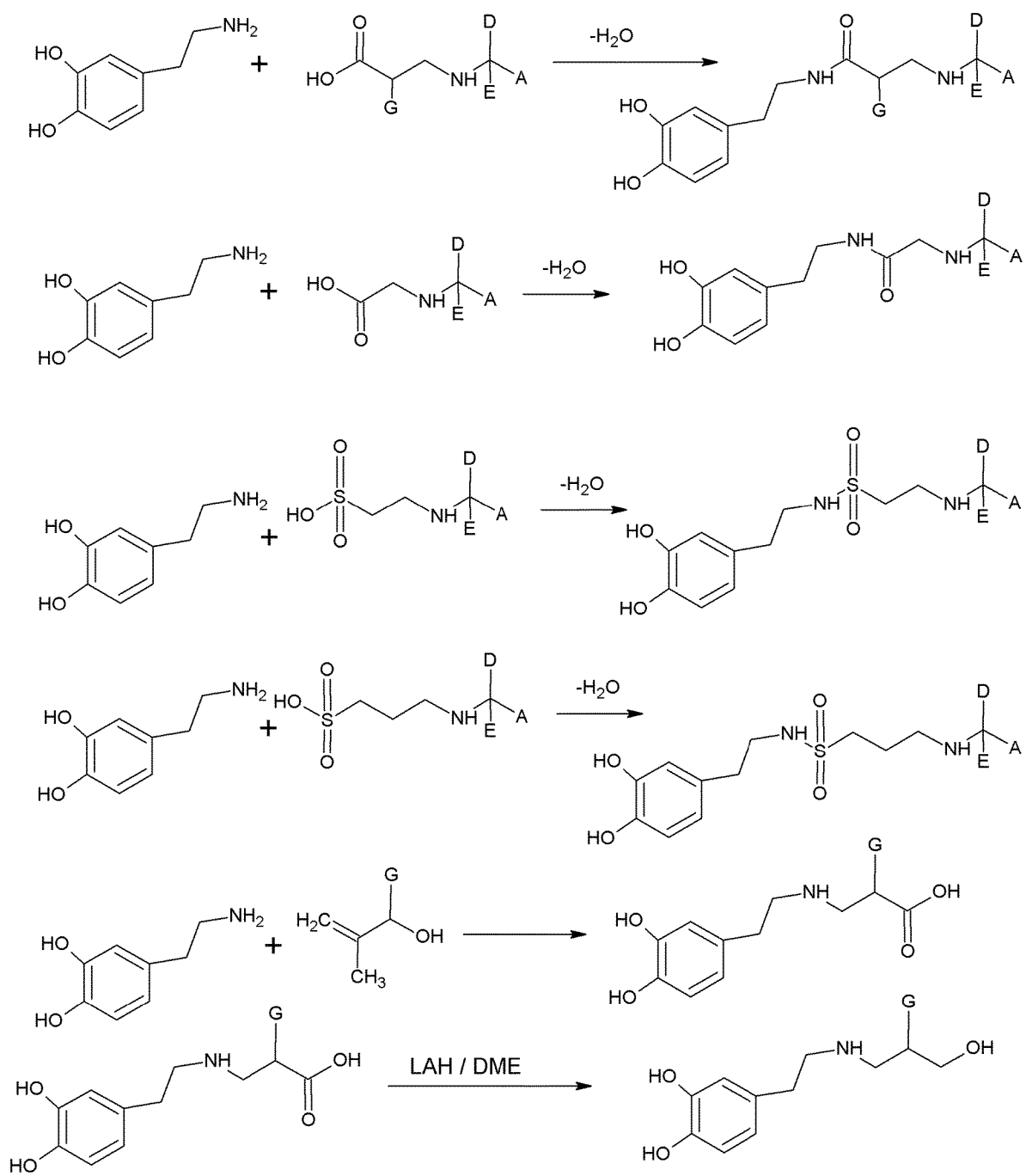
Figure 105:
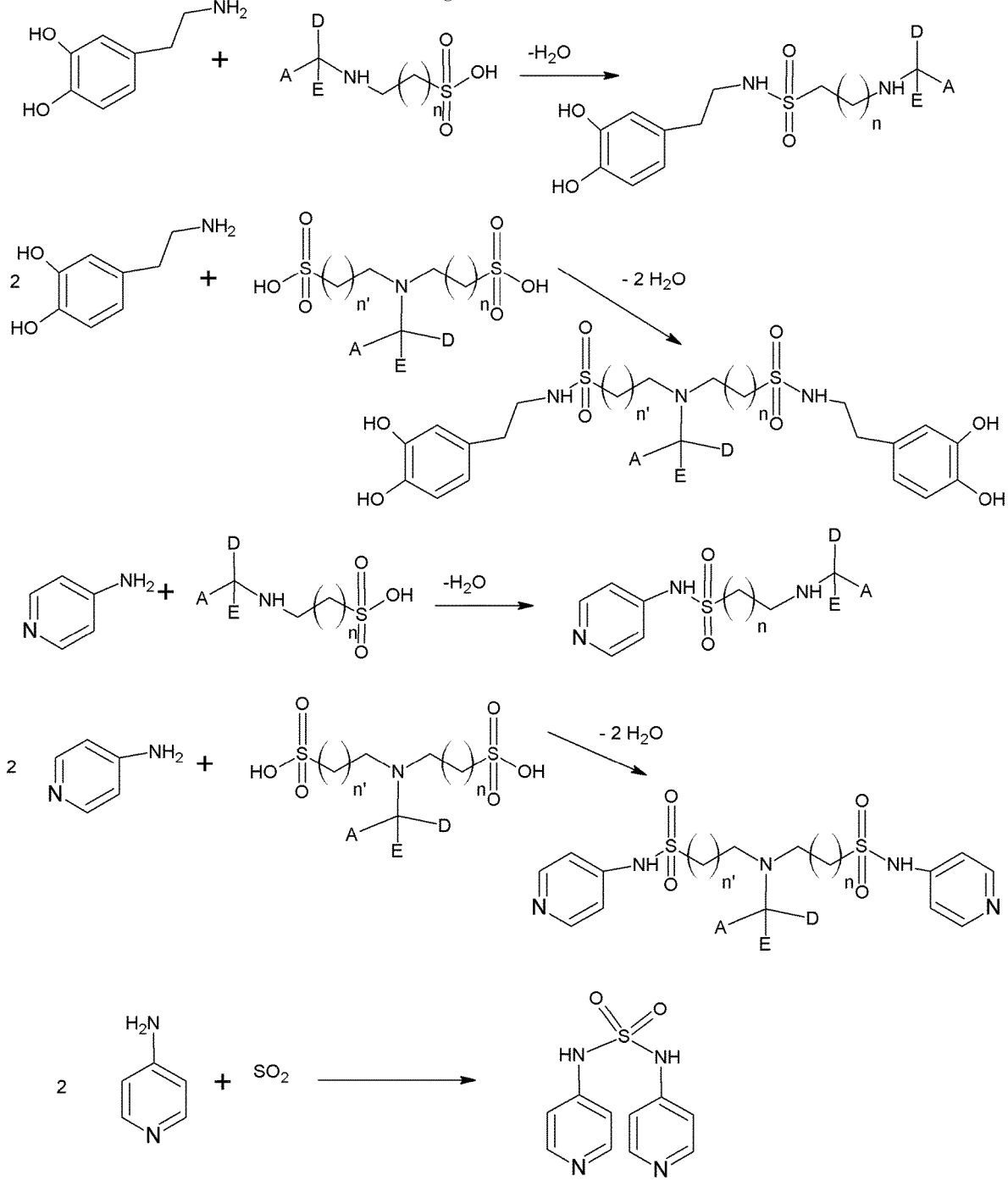
FIG. 105 teaches the synthesis of sulfonamide buffers.

FIG. 102 teaches the synthesis of a range of zwitterionic buffers based on dopamine. These products, and there derivatives are excellent buffers in their own right, but also posses bioactivity, including fungal resistance. FIG. 103 includes sulfonamides that are particularly fungal resistant, as are the zwitterionic buffers taught. FIG. 104 primarily teaches the synthesis of dopamine based zwitterionic buffers and their esters. The esters expand the usefulness of the product by resulting in more hindered buffers so that there are less interactions with proteins that can destabilize their tertiary structure. FIG. 105 teaches the synthesis of sulfonamide and disulfonamide buffers based on the zwitterionic buffers previously taught. In addition to their buffer capability and utility in protein fermentation and purification, the sulfonamide buffers, particularly those based on 4-aminopyridine and dopamine, are expected to have use as therapeutic agents in areas where fungal infection is part of the condition.

Figure 106:
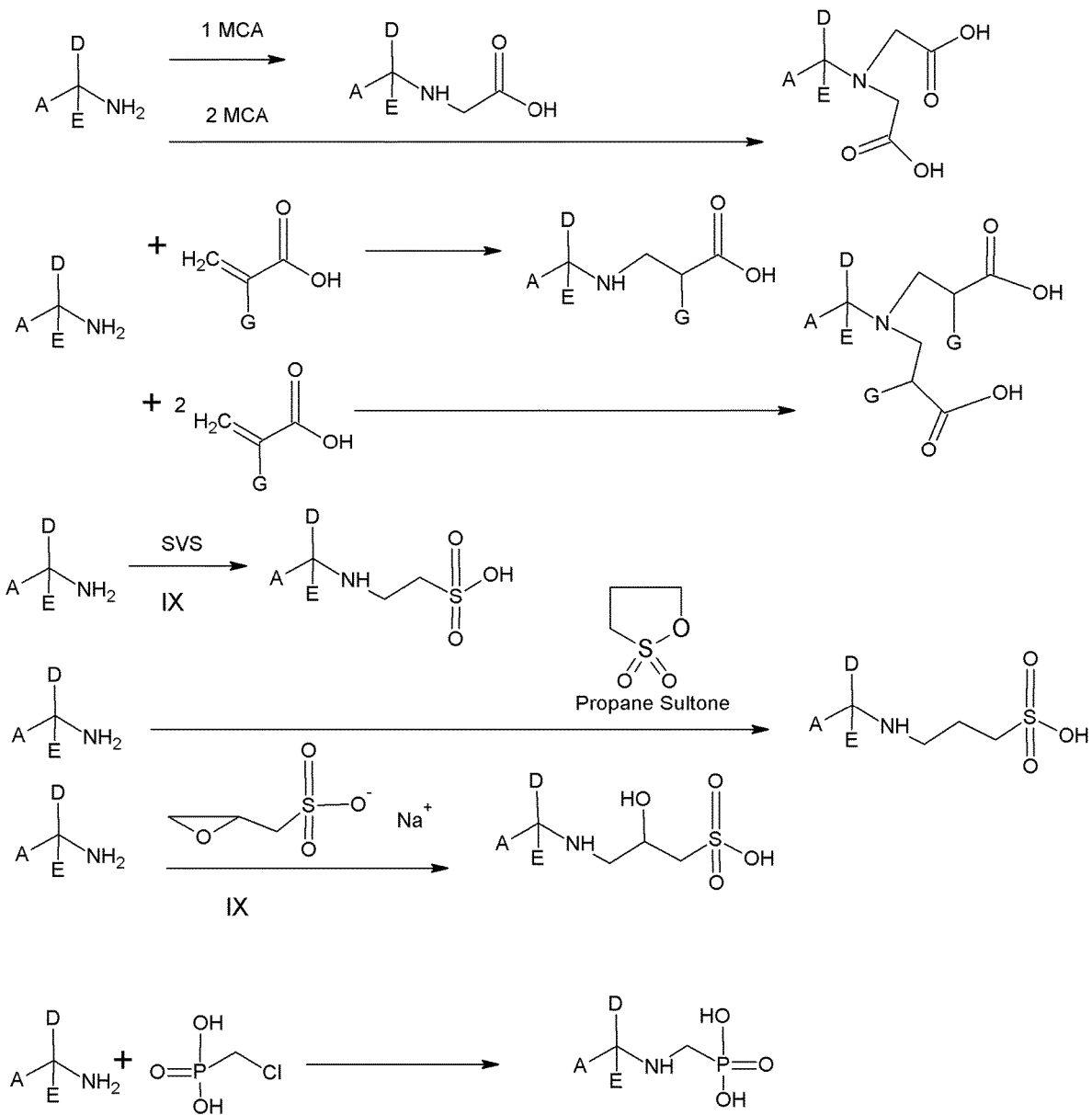
FIG. 106 teaches the synthesis of mono and disubstituted Michael additions to form zwitterionic buffers.
Figure 107:
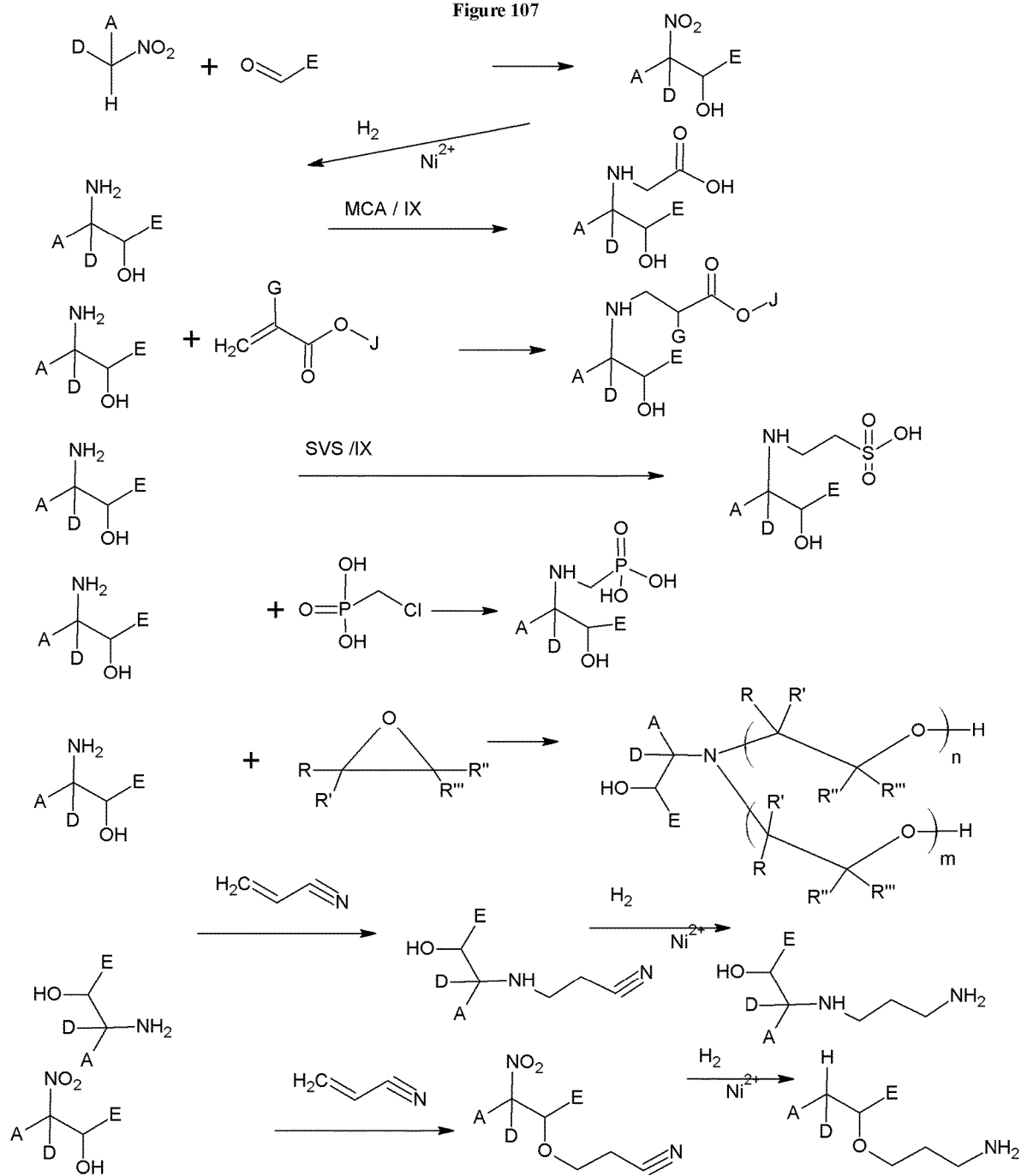
FIG. 107 teaches the synthesis of a new class of amines and aminoalcohols and their derivatives where A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. E is alkyl, saturated or unsaturated, branched or linear with from 2-22 carbons. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R, R', R", R'" are independently chosen from, alkyl, alkenyl, alkynyl, branched or linear. n and m are integers, both may not be zero.
Figure 108:
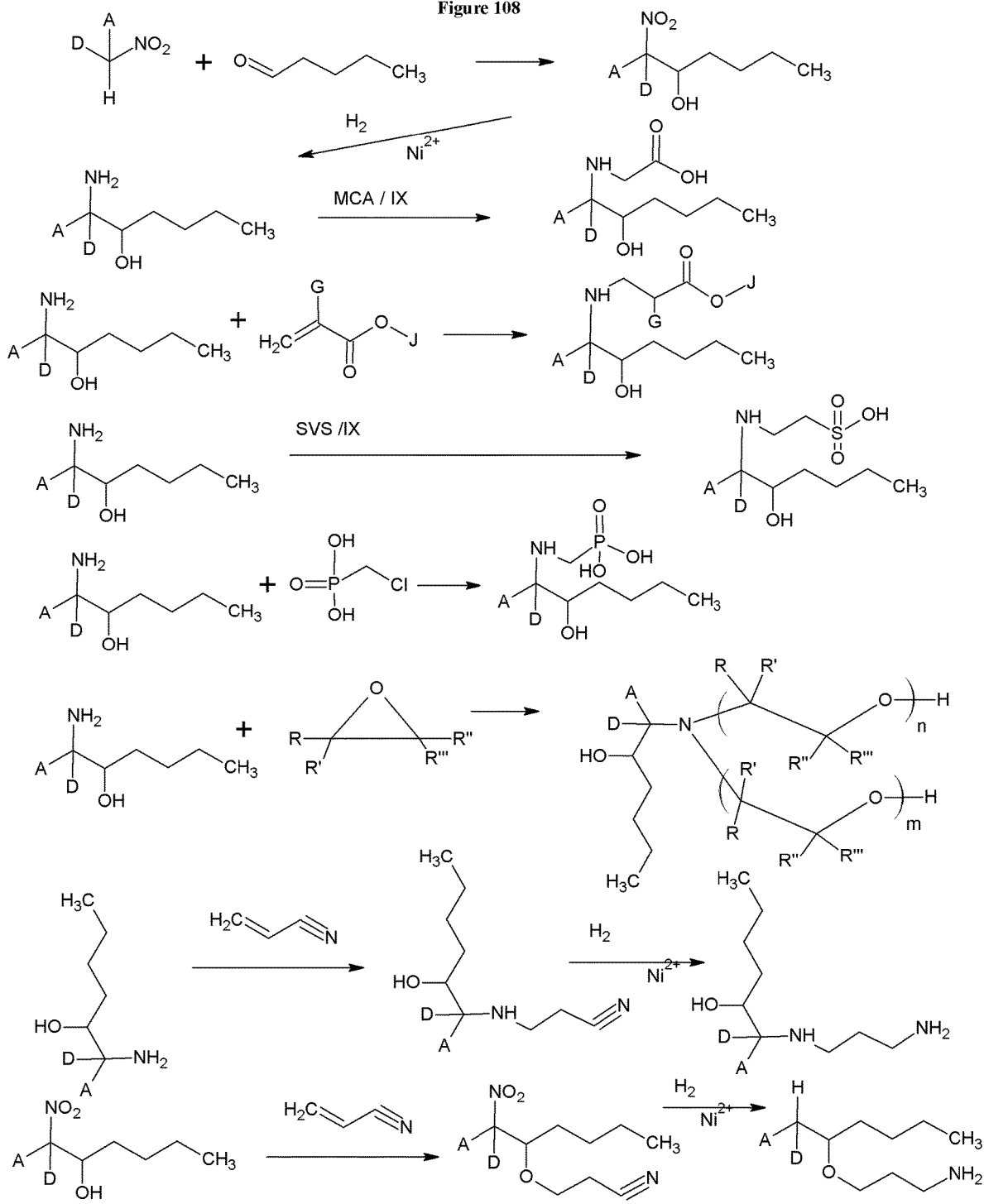
FIG. 108 teaches the synthesis of a new class of amines and aminoalcohols and derivatives of nitro compounds and valeraldehyde. A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R, R', R", R'" are independently chosen from, alkyl, alkenyl, alkynyl, branched or linear. n and m are integers, both may not be zero.
Figure 109:
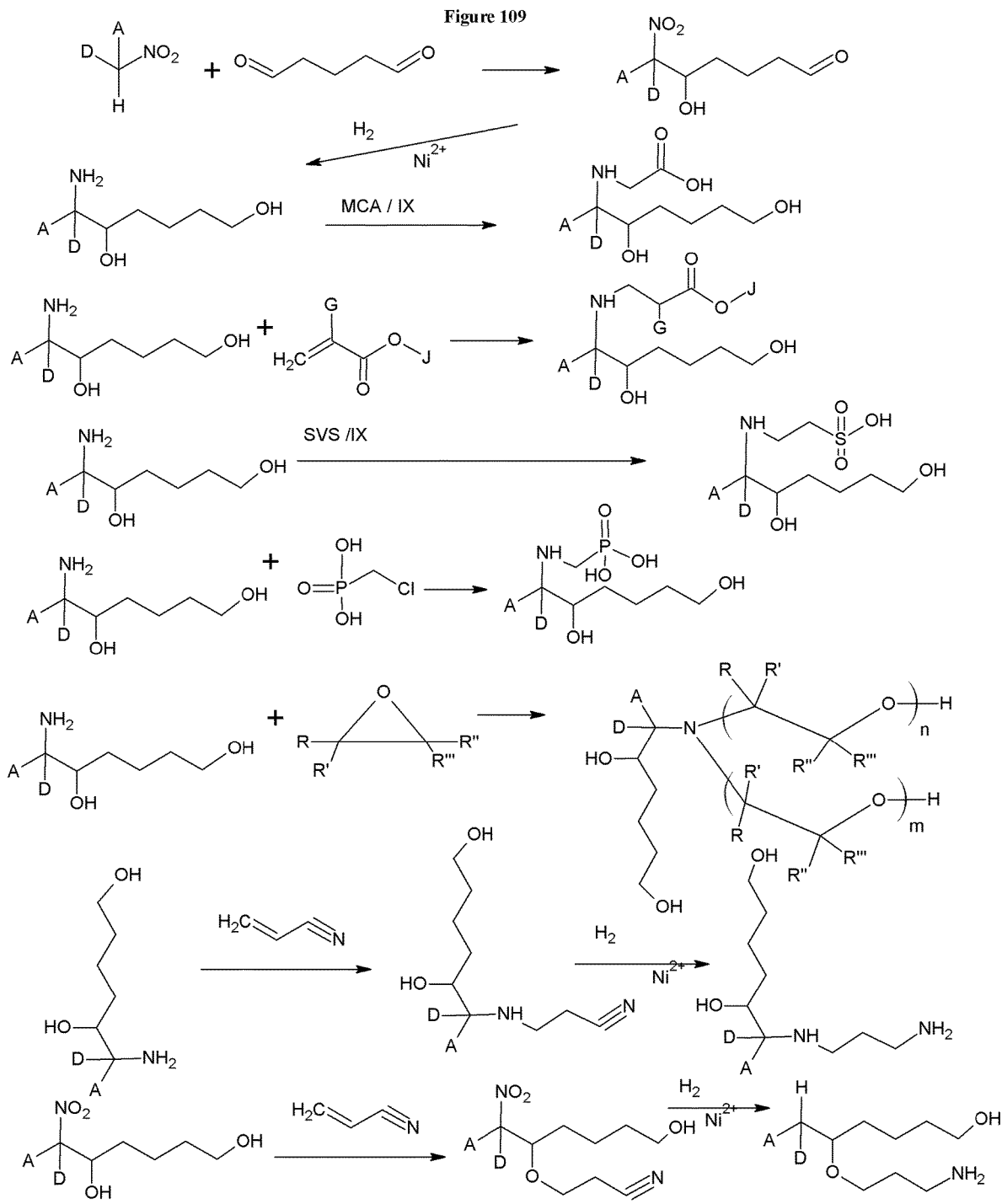
FIG. 109 teaches the synthesis of a new class of aminoalcohols and their derivatives based on monosubstitution of gluteraldehyde and nitro compounds. Where A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. R, R', R", R'" are independently chosen from, alkyl, alkenyl, alkynyl, branched or linear. n and m are integers, both may not be zero.

FIG. 106 demonstrates again the mono or disubtitutions that can take place with primary amines. Both species and there analog derivatives that are taught in this application are within the scope of the present invention. The sulfonic acid buffers may also be synthesized as diacids analogous to the carboxcylic acid diacid analogs in lines 1 and 2 of FIG. 106. They are not explicitly shown because it is obvious to one skilled in the art that these molecules are part of the invention.

FIGS. 107 through 115 and FIG. 120 teach the synthesis of a new class of amines and aminoalcohols, as well as a range of derivatives that are suitable as buffers, monomers antimicrobials, and dispersants. Taught are secondary amino acids based on monochloroacetic acid and acrylic acid type monomers and their esters for both classes, sulfonates, phosphonates, alkoxylates, and polyamines based on acrylonitrile. In the cases where A and/or D are —$CH_2CH_2CN$, subsequent reductions will yield primary amines, that can either be used directly, or further derivatized as other amines in this invention have been, into amides, alkoxylates, reacted with MCA, acrylic acid and its variants, made into phosphonates, and made into sulfonates. While not shown in the figures in every case, the esters (standard esters, phosphate esters, phosphonate esters, and sulfonate esters) of these compounds that result from the reaction of alcohols or polyols are also within the scope of this invention, for linear, branched, saturated or unsaturated alcohols, including polyols such as, but not limited to, EG, PG, BG and polymers or block co-polymers. These derivatives have been adequately within this patent application such that they are included within the scope of this invention.

While in the Figures, mainly the monosubstitution on the primary amine is shown for each type of derivative, it is part of this invention to include the disubstitution, analogous to what is shown in FIG. 76 and similarly throughout this patent application. It is worth pointing out that when reacting acrylonitrile with the nitroalcohols, The secondary alcohol reacts less quickly than the primary alcohol, when present, when A and/or D include a primary alcohol group, as well as the primary alcohol in all molecules in FIG. 109 where the amine starting material for the derivatives contains a primary alcohol. The reaction proceeds analogous to the secondary alcohol shown, as does the reduction, if pursued. An excess of acrylonitrile reacts both the primary and secondary alcohols and at even greater levels, forms nitrile polymer. The primary alcohol groups will also undergo monosubstituted alkoxylation, but at a slower rate than the amine, Less reactive conditions, such as lower temperatures can limit the alkoxylation to the amine. The alkoxylation of the alcohol groups is also part of the invention described.

In the case of the sulfonates, SVS is the only reactant shown, however, the analogous reaction with propane sultone is included as part of this invention. The result, as taught by analogy earlier in this patent application, is an additional carbon between the reactive amine and the —$SO_3H$ group.

Figure 110:
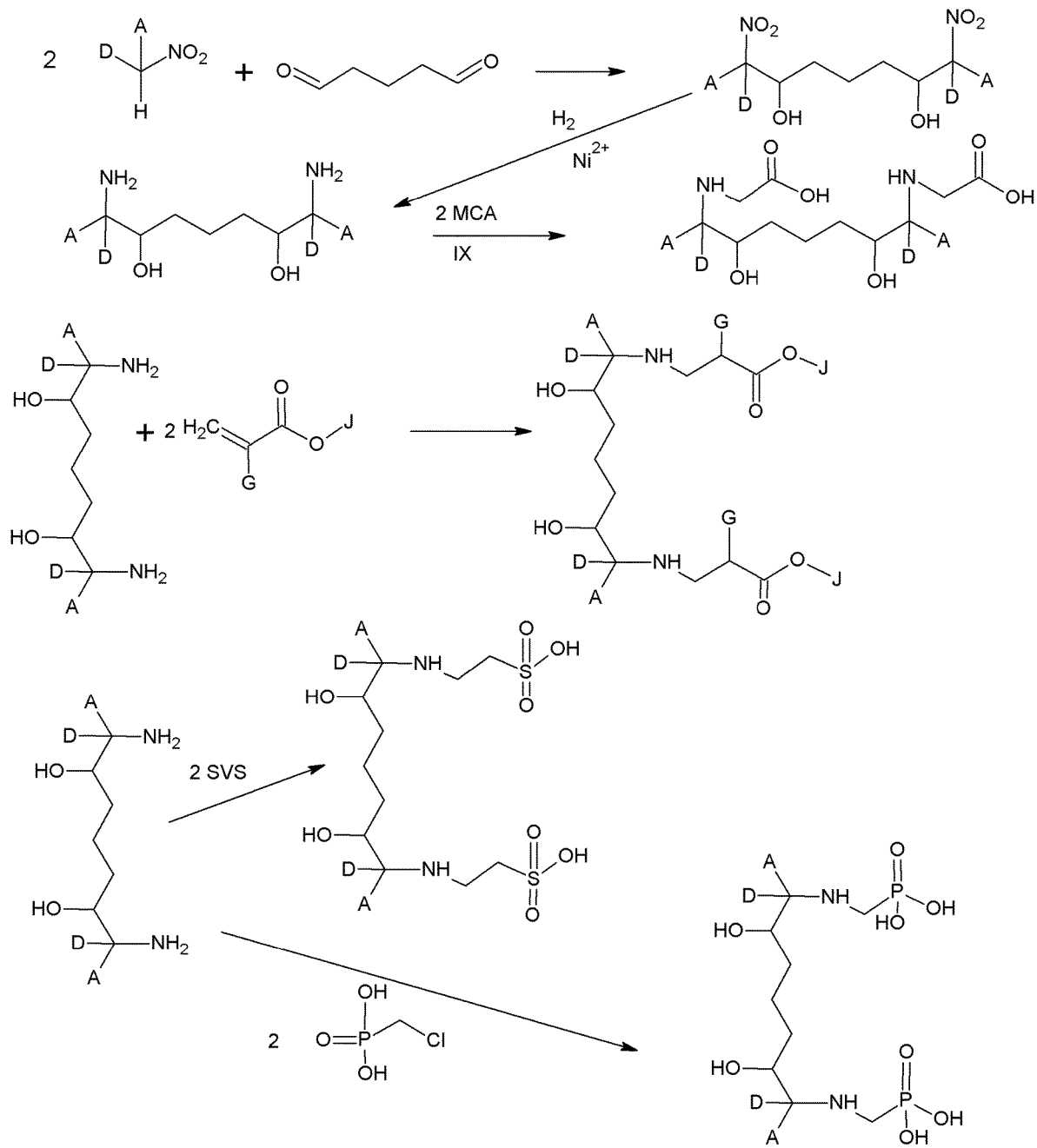
FIG. 110 teaches the synthesis of diamines and their derivatives based on gluteraldehyde and nitro compounds where A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH.
Figure 111:
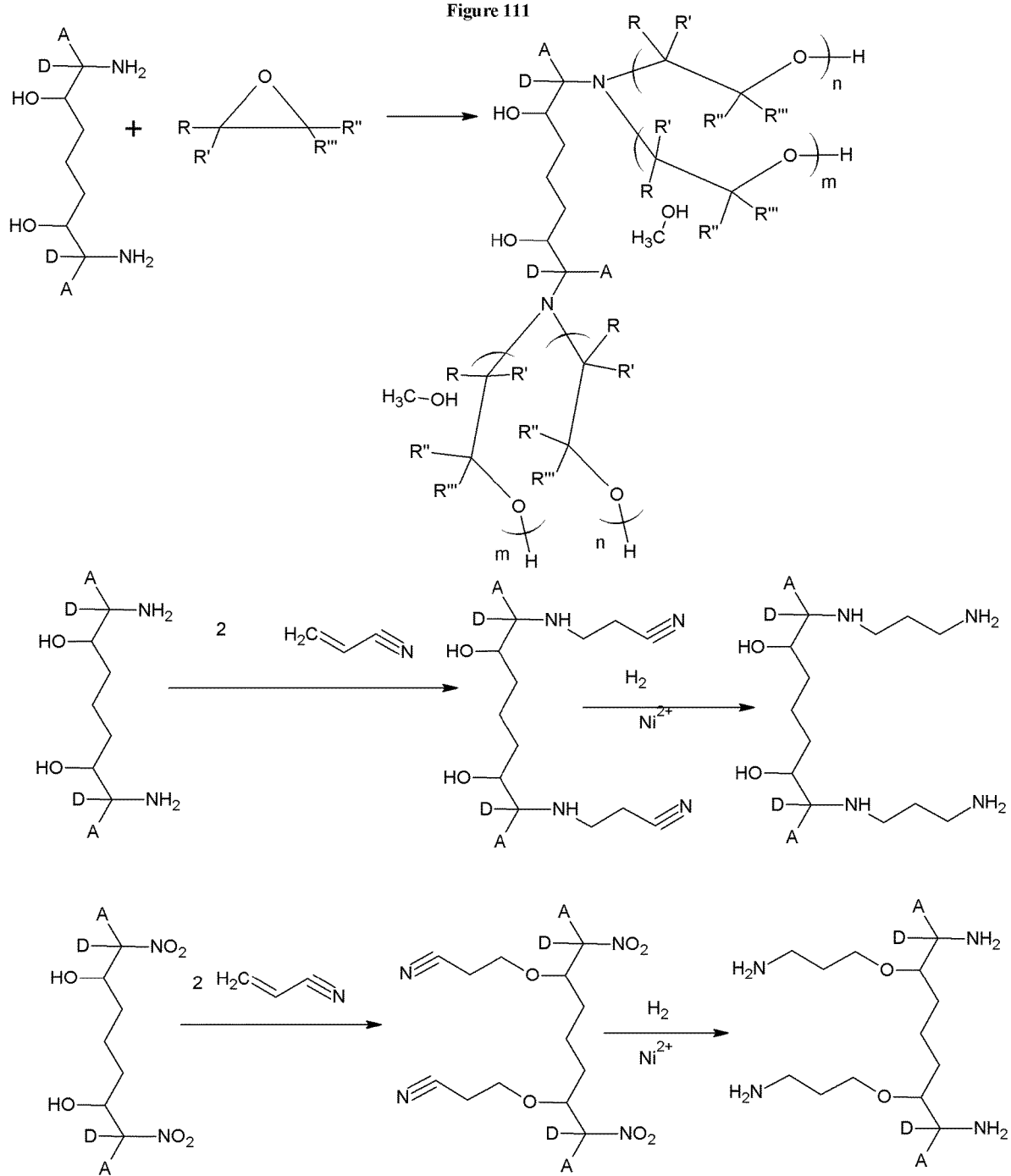
FIG. 111 teaches the synthesis of diamines and their derivatives based on gluteraldehyde and nitro compounds where A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. R, R', R", R'" are independently chosen from, alkyl, alkenyl, alkynyl, branched or linear. n and m are integers, both may not be zero.

FIG. 110 teaches the synthesis of primary diamines from gluteraldehyde and nitro compounds. The figure focuses on the monosubstitution of both of the primary amine groups. However, the invention includes the monosubstitution of just one amine, the disubstitution of both amines, and the disubstitution of one amine and monosubstitution of the other. Further, the invention includes the derivatives where one type of derivative is made on one amine, and another of the described derivative types is made on the other. Likewise, as shown in FIG. 93, the derivations can vary on the individual amine and still be within the scope of this invention. FIG. 111 is a continuation of FIG. 110 in that it teaches more derivatives of the gluteraldehyde based diamines and dinitro compounds. Specifically, alkoxylation and acrylonitrile derivatives.

Figure 112:
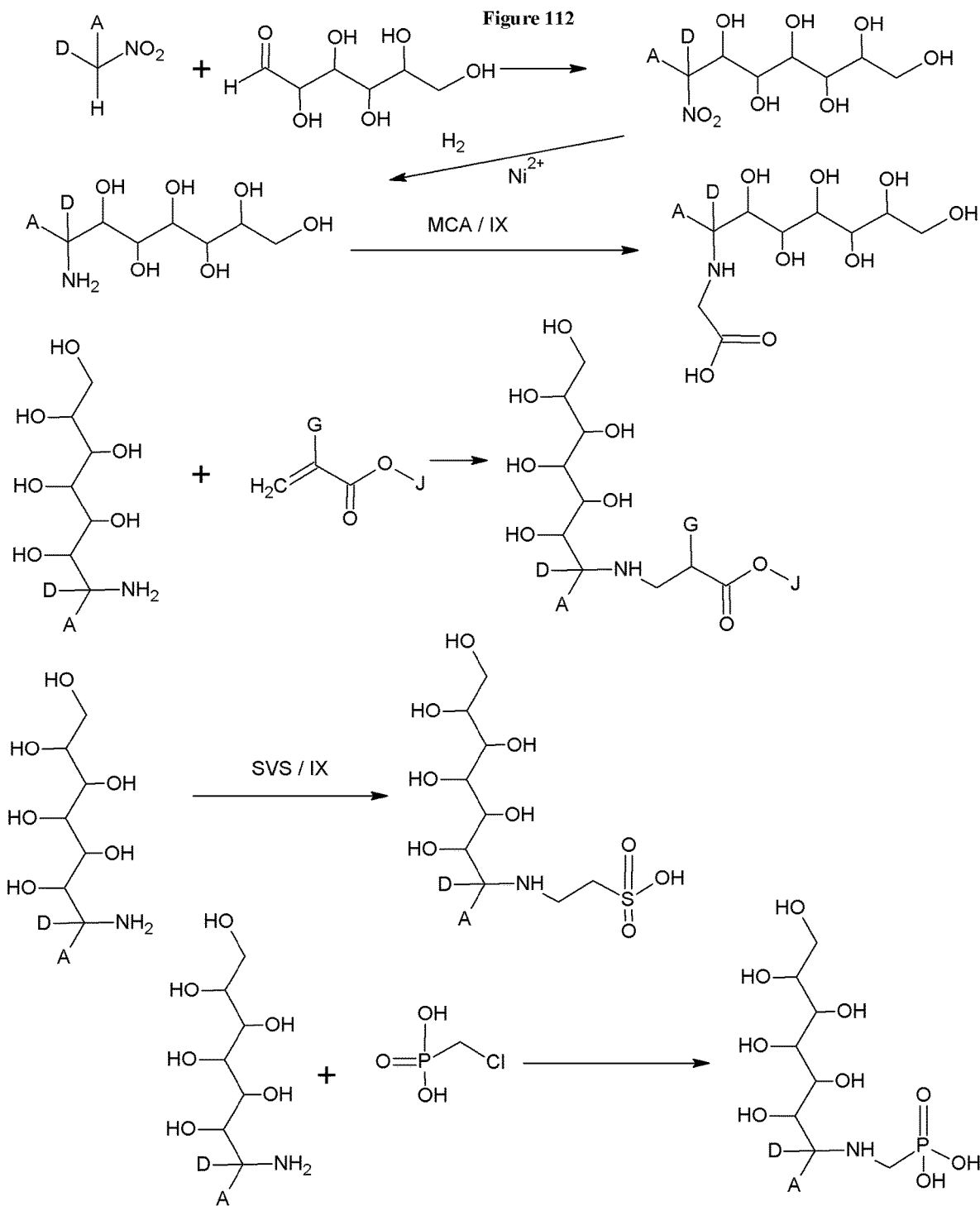
FIG. 112 teaches the synthesis of a class of amino alcohols derived from glucose and nitro compounds and their derivatives where A and D are independently chosen from —H, —CH3, —CH2CH3, —CH2CH2CH3, —CH2OH, —CH2COOH, —CH2CH2COOH, —CH2CH(CH3)COOH, —CH2PO(OH)2. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. n is an integer.
Figure 113:
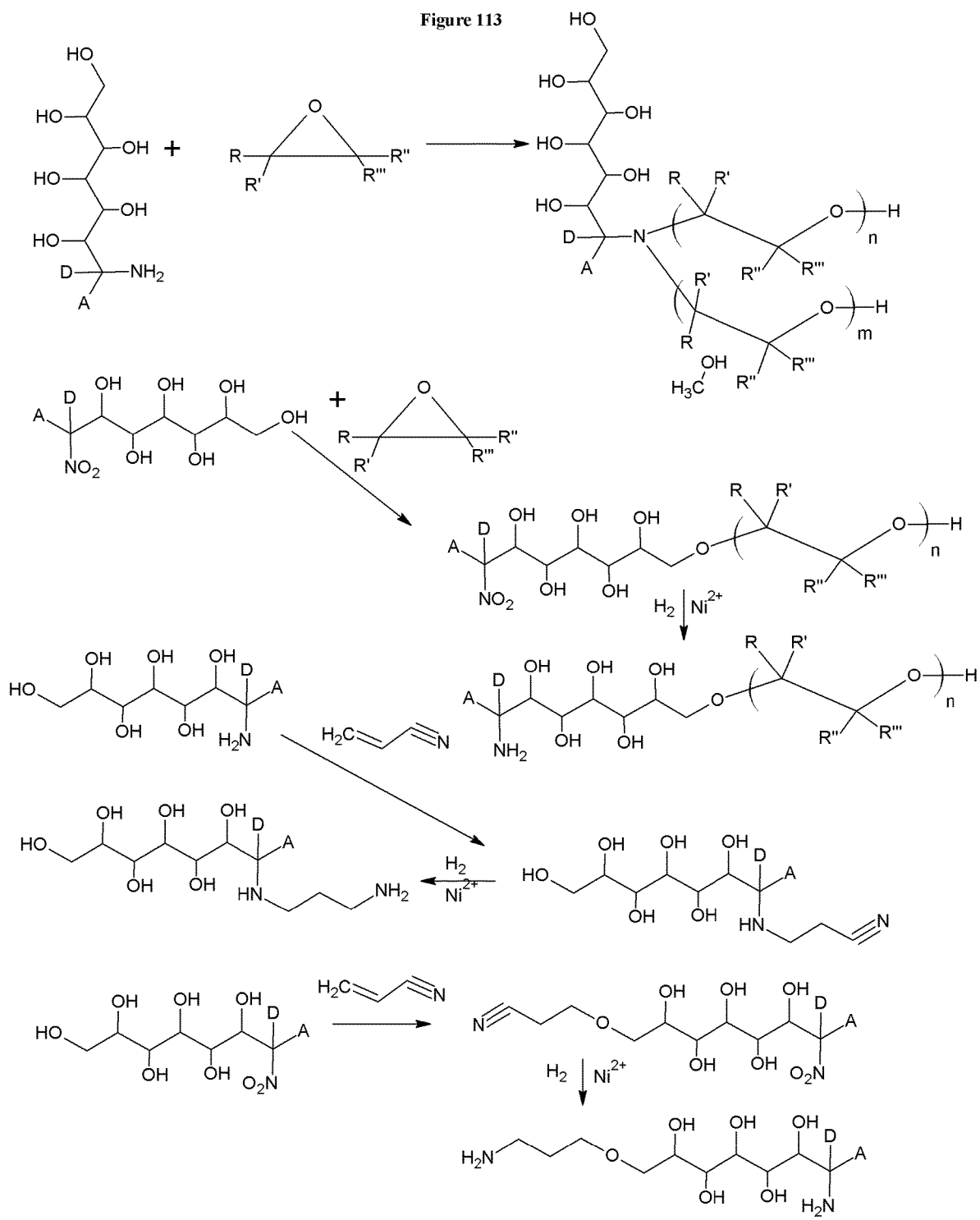
FIG. 113 teaches the synthesis of a class of amino alcohols derived from glucose and nitro compounds and their derivatives.
Figure 119:
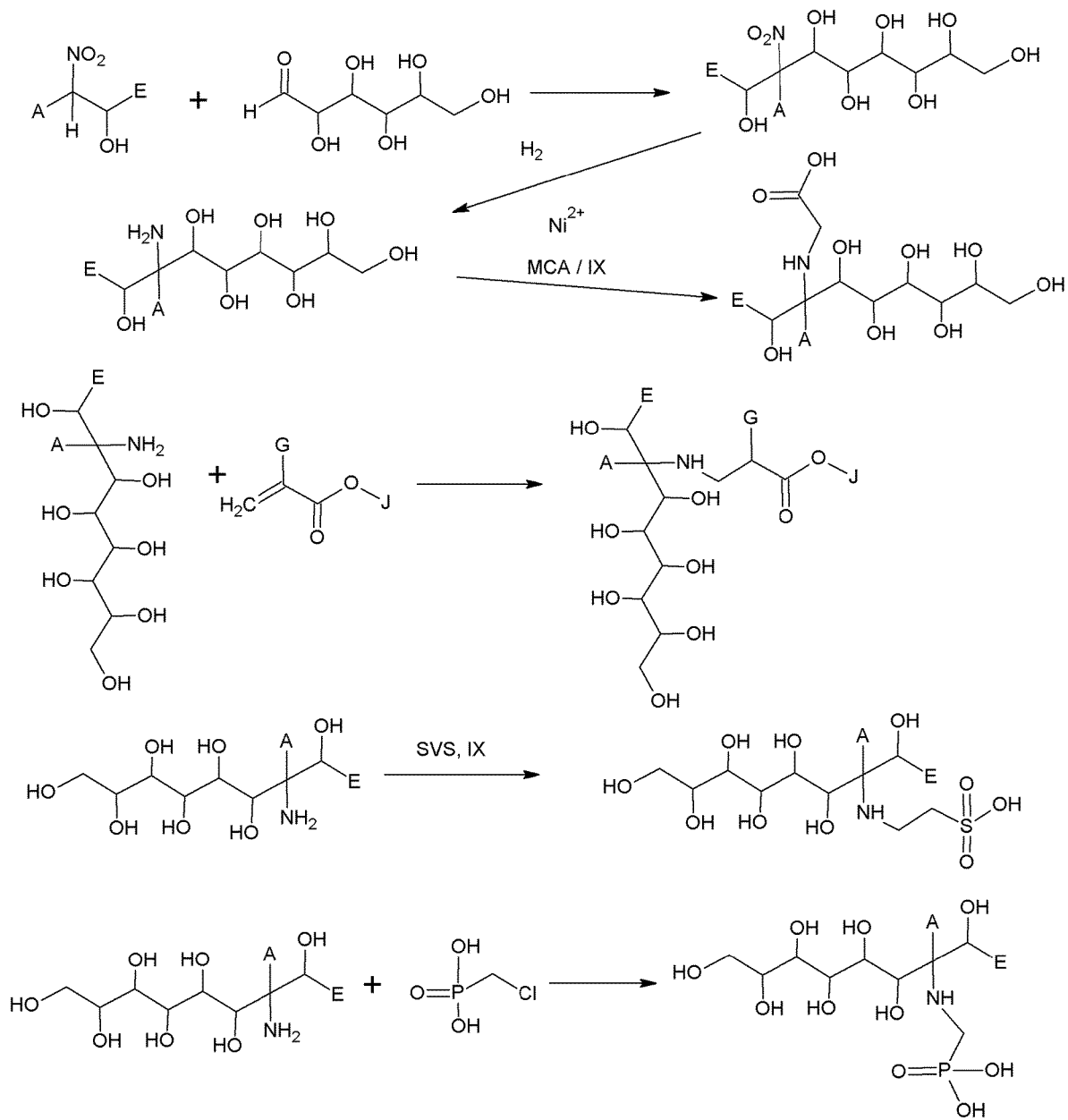
FIG. 119 teaches the synthesis of surfactants based on aldehydes and nitro compounds where A is chosen from —H, —CH3, —CH2CH3, —CH2CH2CH3, —CH2OH, —CH2COOH, —CH2CH2COOH, —CH2CH(CH3)COOH, —CH2PO(OH)2. E is alkyl, saturated or unsaturated, branched or linear with from 1-22 carbons. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH. n is an integer.
Figure 120:
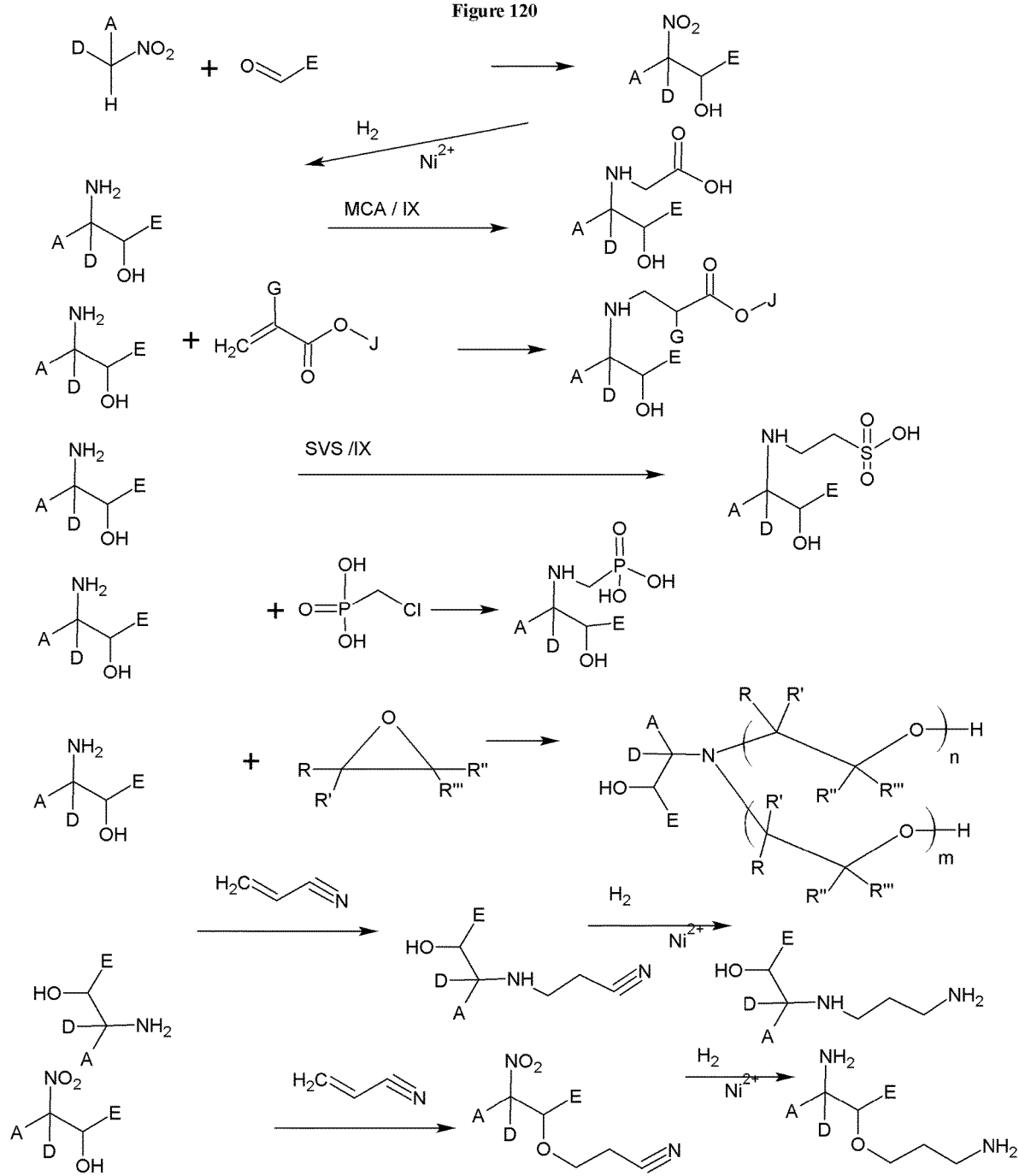
FIG. 120 expands FIG. 107 to cover an additional species where the aldehyde is acetaldehyde in which E —CH$_3$. A and D are independently chosen from —H, —CH3, —CH2CH3, —CH2CH2CH3, —CH2OH, —CH$_2$COOH, —CH$_2$CH$_2$COOH, —CH$_2$CH(CH$_3$)COOH, —CH$_2$PO(OH)$_2$, —CH$_2$CH$_2$CH$_2$CN, E is alkyl, saturated or unsaturated, branched or linear with from 1-22 carbons. G is chosen from —H, —CH3, —CH2CH3, —OH. J is chosen from alkyl, alkenyl, alkynyl, branched or linear, —H, —(CH$_2$CH$_2$O)$_n$H, —(CH$_2$CH$_2$CH$_2$O)$_n$H, —(CH$_2$CH(CH$_3$)O)$_n$H, —(CH$_2$C(CH$_3$)$_2$O)$_n$H. R, R', R", R'" are independently chosen from, alkyl, alkenyl, alkynyl, branched or linear. n and m are integers, both may not be zero.

FIG. 112 teaches the synthesis of a group of aminoalcohols based on glucose. While glucose is taught explicitly in this Figure, all aldehyde terminated sugars can be treated the same way as glucose to yield the analogous amines. Other aldehyde terminated sugars included in this invention, but not limited to are allose, altrose, mannose, gulose, arabinose, xylose, fucose, idose, galactose, talose, ribose, arabinose, xylose, lyxose, erythrose, threose, glyceraldehyde, glycolaldehyde and the related lactic aldehyde. In addition to sugars, flavoring aldehydes and fragrance aldehydes, such as, but not limited to, vanalin, cinnamaldehyde (including butyl and amyl), anisic, 2,4-heptanedienal, isovaleraldehyde, and citral, as well as furfural may undergo this same transformation to make these novel aminoalcohols and their derivatives. It is worth noting that stereochemistry has no effect on this reaction, and therefore all stereo conformers are within the scope of this invention. Where a chiral center is introduced through the formation of the nitroalcohol, the results are racemic, and no stereochemistry in conveyed, nor implied in the structures presented. FIG. 119 expands the invention to make surfactants by reacting glucose, or other aldehydes or aldehyde sugars with the nitro compounds of FIG. 107 and FIG. 120. The invention is not limited to the surfactants from the sugar aldehydes alone, but may be reacted with any of the aldehydes disclosed in this invention, as are the similar derivatives, such as the zwitterionics and phosphonates, which are also taught and within the scope of the invention. The zwitterionic derivatives make very mild, high foaming surfactants that also hold promise as mineral collectors in mining, such as iron ore and other minerals. If D is —H, then a second substitution of the E containing hydroxyl moiety can be achieved, leading to the analogous surfactant with a generally more hydrophobic character. Naturally, these may be reacted with acrylonitrile and reduced to amines or alkoxylated analogously to the glucose or aldehyde sugar aminoalcohols in FIG. 113. As in earlier forms, it is worth pointing out that the zwitterionic surfactants may be mon- or disubstituted at the amine with the acidic functionality. FIG. 113 expands on FIG. 112 by teaching the acrylonitrile and alkoxylate derivatives. For the alkoxylation, the reaction can be significantly isolated to the primary amine group is shown in the first line, however, more aggressive reaction conditions will cause the hydroxyl groups to undergo alkoxylation as well. Leading to a mixture of products. Additionally, it is common among alkoxylators to block copolymerize by reacting with one alkoxylating agent, such as EO, then another, such as PO or BO and repeat the process to achieve the desired HLB. This results in a wide range of products as alkoxylations of this type are not precise and do not yield a single product. This block copolymerization is within the scope of this invention for this and all alkoxylations taught. Further, the primary amine may be retained by performing the alkoxylation on the nitro compound that results in the first line of FIG. 112. After the alkoxylation is complete, the nitro group can be retained, or reduced to the primary amine. Similarly, the reaction with acrylonitrile on the primary amine forming the diamine (which can be derivatized by any of the methods disclosed and included as part of this invention) can also occur on the alcohol groups under more aggressive conditions. Similarly, by reacting the nitro compound with acrylonitrile, the hydroxyls will react with the acrylonitrile, more equivalents of acrylonitrile will result in more hydroxyls being substituted, which can be isolated and used as a reactive intermediate, or reduced to the polyamine. This course produces a high yield of primary amines, verses the secondary and primary amine groups that result from reacting the acrylonitrile with the primary amine. Again, these polyamines undergo the same derivitations as taught in this invention for the other classes of amines taught. FIG. 114 teaches the synthesis of and derivatives of benzaldehyde and nitro compound amines. Again, the alkoxylation can be done on the amine, and largely isolated to the amine, or under more aggressive conditions, on the hydroxyls as well. If alkoxylating the nitro compound, the alkoxylation will be isolated to the alcohol groups present. Reduction of the alkoxylated nitro compound will yield a primary amine. Due to the chiral nature of many of these molecules and their derivation from natural molecules, in addition to being excellent buffers, they are expected to be useful in pharmaceutical and other life science applications as part of drug delivery systems, and some, as therapeutic agents themselves.

FIG. 115 is a continuation of FIG. 114 and teaches the acrylonitrile derivatives. As is the case in previous cases, the acrylonitrile addition can be isolated to the primary amine, mono (shown) or disubstituted, or under more aggressive conditions, also react with any hydroxyls present. The resulting nitrile compounds can readily be reduced to their amine counterparts. Reacting the nitro compound, will result in the hydroxyls being substituted, which can then be reduced, along with the nitro group, which will produce in high yield primary amines and minimal secondary amine formation. These amines can then undergo all the derivatives taught in this invention utilizing the aminoalcohols and are part of this invention.

Figure 116:
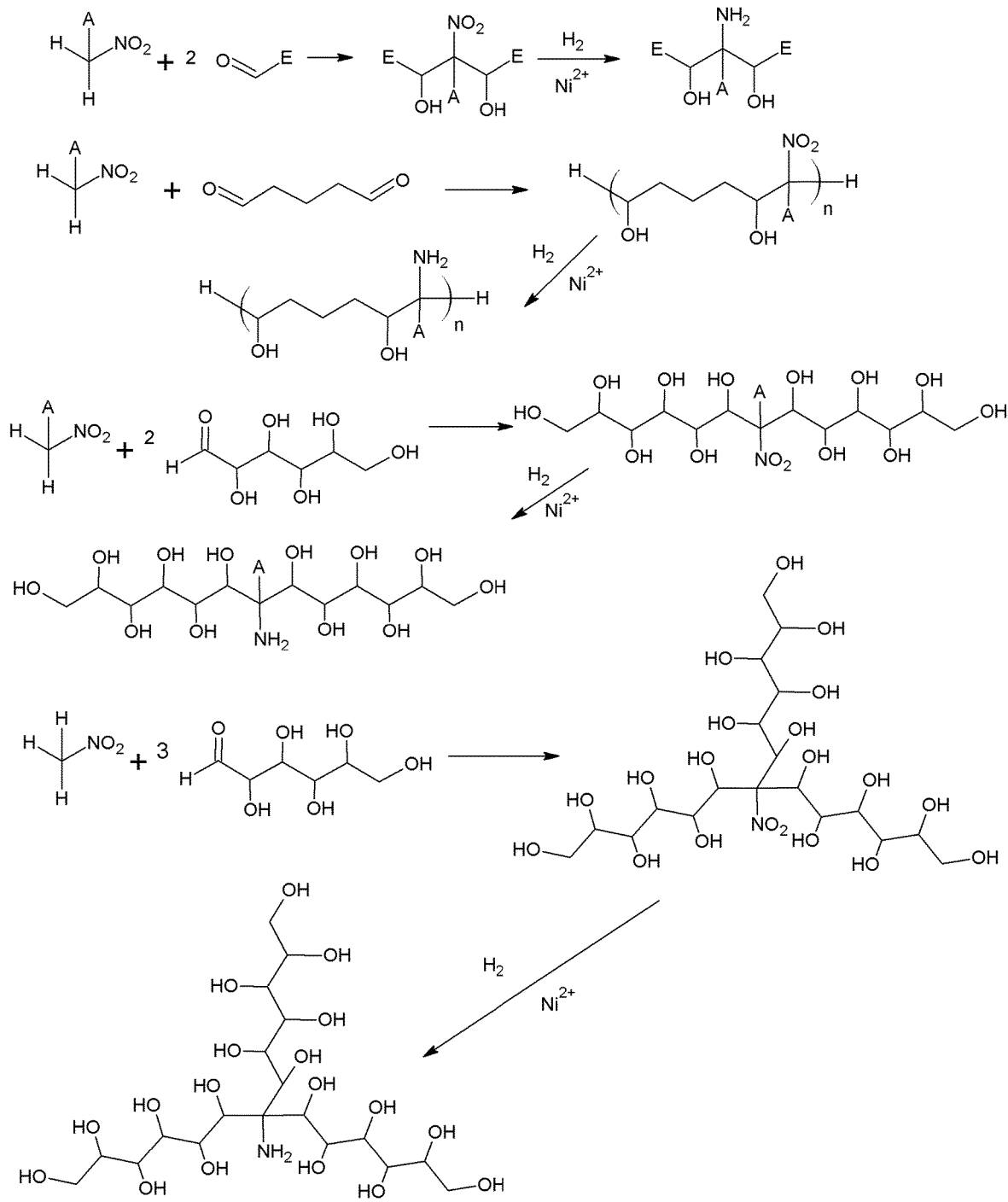
FIG. 116 teaches how dimmers can be formed when using a nitro compound with more than one hydrogen on the nitro containing carbon.
Figure 117:
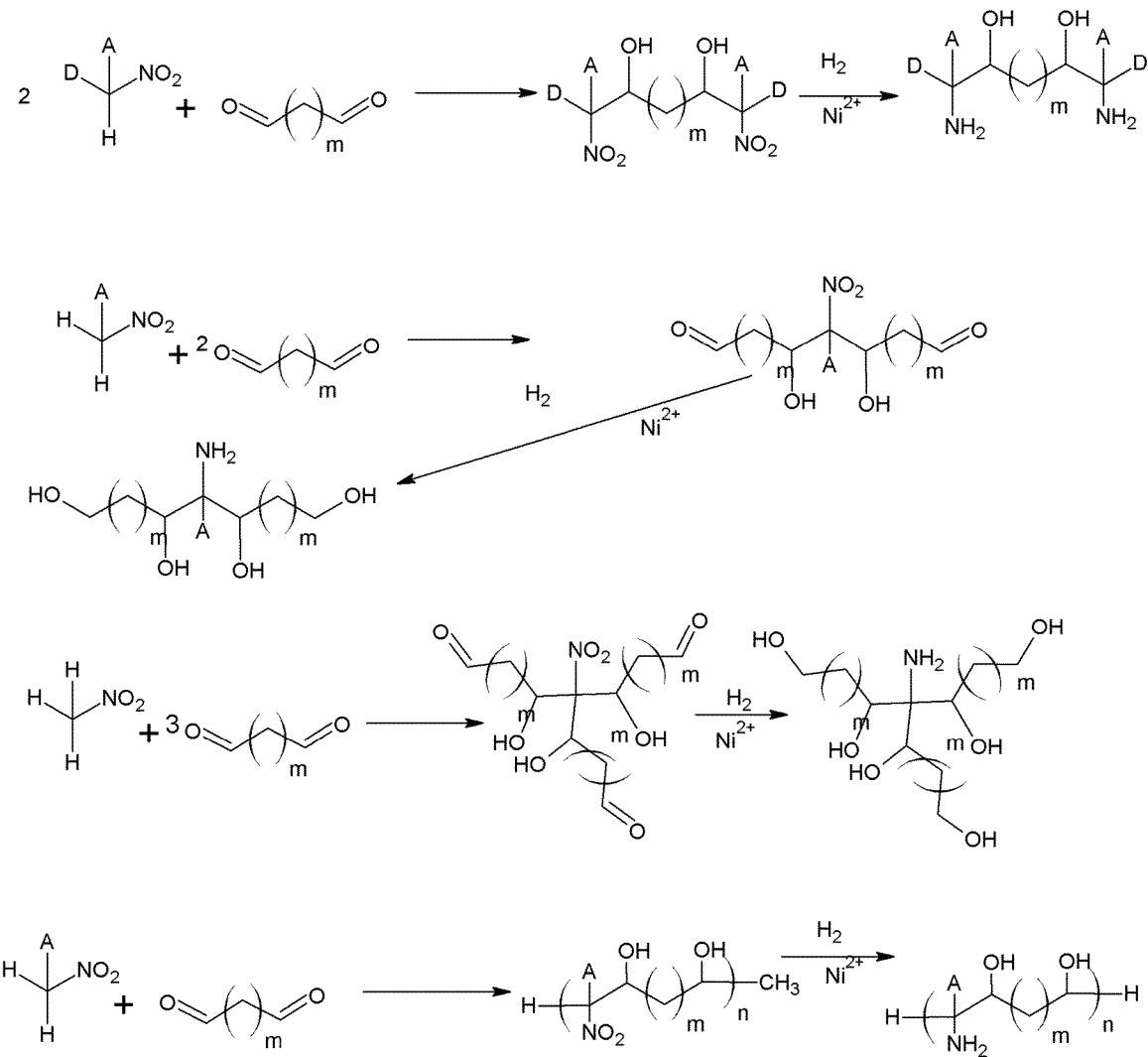
FIG. 117 teaches how dialdehydes can be used to make dimmers and polymers.
Figure 118:
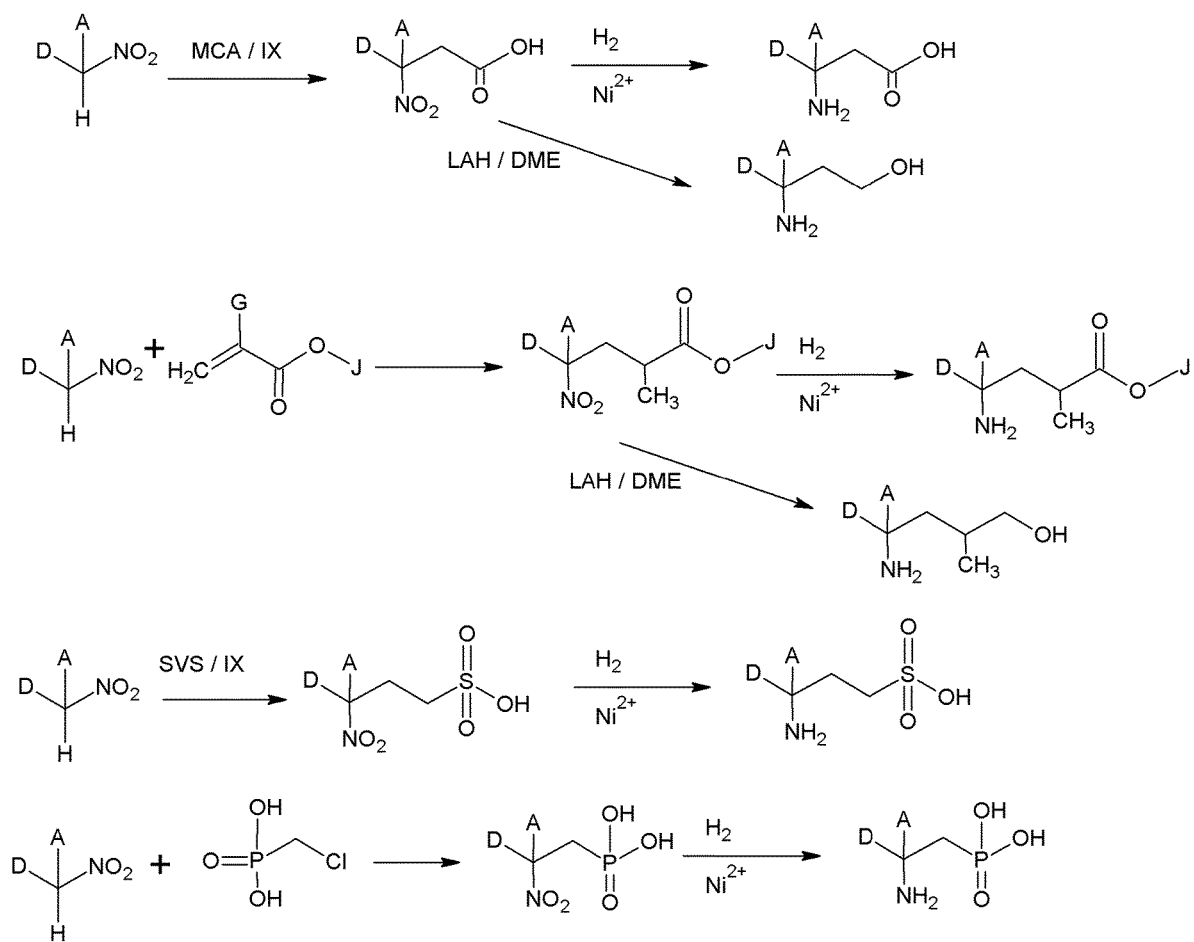
FIG. 118 teaches a novel route to nitro acids and primary amino acids of several types where A and D are independently chosen from —H, —CH3, —CH2CH3, —CH2CH2CH3, —CH2OH. E is alkyl, saturated or unsaturated, branched or linear with from 2-22 carbons. G is chosen from —H, —CH3, —CH2CH3, —OH. J is chosen from alkyl, alkenyl, alkynyl, branched or linear, —H, —(CH2CH2O)nH, —(CH2CH2CH2O)nH, —(CH2CH(CH3)O)nH, —(CH2C(CH3)2O)nH.

FIGS. 116-117 teach the synthesis of dimmers, trimers and polymers when at least two hydrogens are present on the nitro containing carbon, and how polymers may be produced. When more than one hydrogen is present on the carbon containing the nitro group, polymerizartion is always a concern. However, controlling the addition order, rate and temperature can prevent polymer formation. Many of the methoxy containing products can be made by reacting the remaining hydrogen(s) with formaldehyde prior to the reduction to the amine, but using the nitroalcohol is preferred as it leads to much less polymer formation. Particularly in cases where the reaction conditions can not be well controlled. The amines and polyamines taught in the figures are able to undergo all the derivations taught and are part of this invention. Including, but not limited to aminoacid products sulfonic acid products, phosphates, phosphonates, polyamines via acrylonitrile, and alkoxylation. FIG. 118 teaches a novel route to primary amino acids of several types and their nitro precursors. Again, monosubstitution is taught, but the substitution can by di- or tri if sufficient hydrogens are present in the starting nitro compound.

A great deal has been said about the nature of the primary amines that are starting materials for the invention may undergo mono or disubstitution, as shown in FIG. 76. While much of the disclosure focuses on the mono substituted species for clarity, the disubstituted species for each class of molecule or derivative are fully part of this disclosure and their analogous derivatives that have been taught. Further, for all transformations taught, it is within the scope of this invention to include the monosubstituted derivative, then derivatized with another method taught, such as is shown in FIG. 93, line 3 where the amine starting material is the monosubstituted amino acid made with MCA, then the second substitution is made as a phosphonate.

Figure 121:
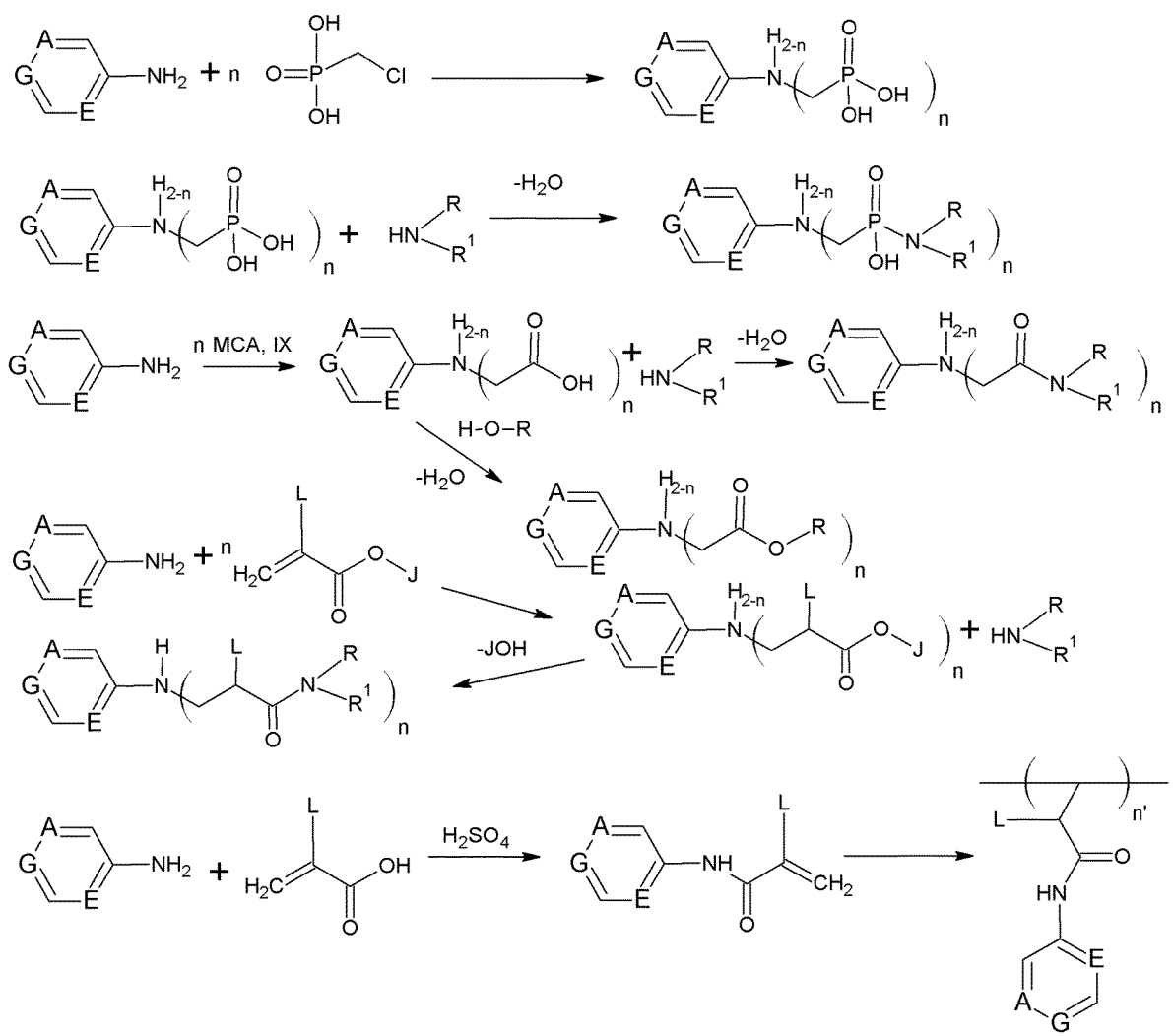
FIG. 121 expands upon the zwitterionic buffers based on 4-aminopyridine to include 2 and 3-aminopyridine to make zwitterionic phosphonate, amino acid buffers, and amides. It builds upon the zwitterionic buffers in teaching a class of pyridine functional monomers, polymers, oligamers, and prepolymers. Where n is 1 or 2. A, G, and E, is chosen from N or C. R, R1 and J are independently chosen from alkyl, saturated or unsaturated, branched or linear, from 1 to 22 carbons, —H, —CH2OH, —CH2CH2OH, —C(Q)(Q')(Q") where Q,Q', and Q" are independently chosen from —H, —CH3, —CH2CH3, —CH2OH, L is chosen from —H, —CH3, —CH2CH3, —OH. L is chosen from —H, —CH3, —CH2CH3, —CH2OH. n' is the standard repeating unit of a polymer, dimer or oligamer.
Figure 122:
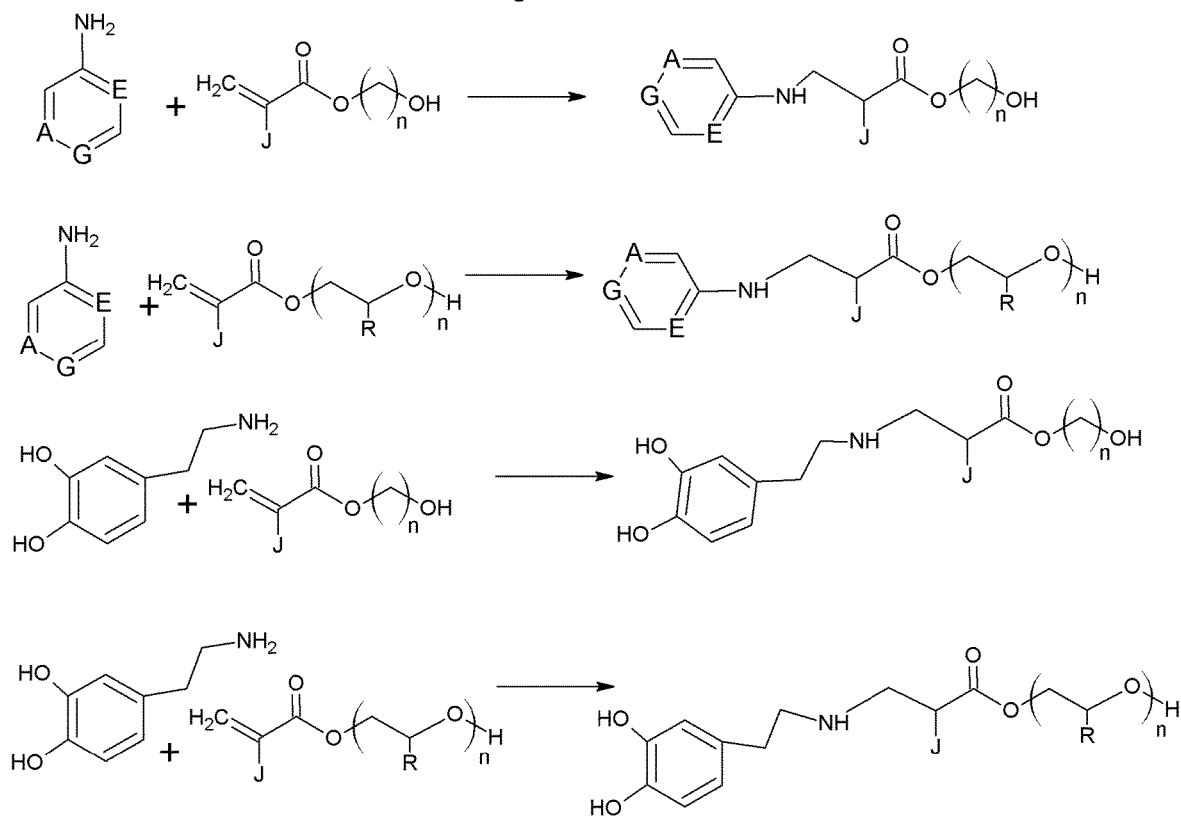
FIG. 122-123 expands upon the zwitterionic buffers based on 4-aminopyridine to include 2 and 3-aminopyridine to make zwitterionic phosphonate, amino acid buffers, and amides. It builds upon the zwitterionic buffers in teaching a class of pyridine functional monomers, polymers, oligamers, and prepolymers.
Figure 123:
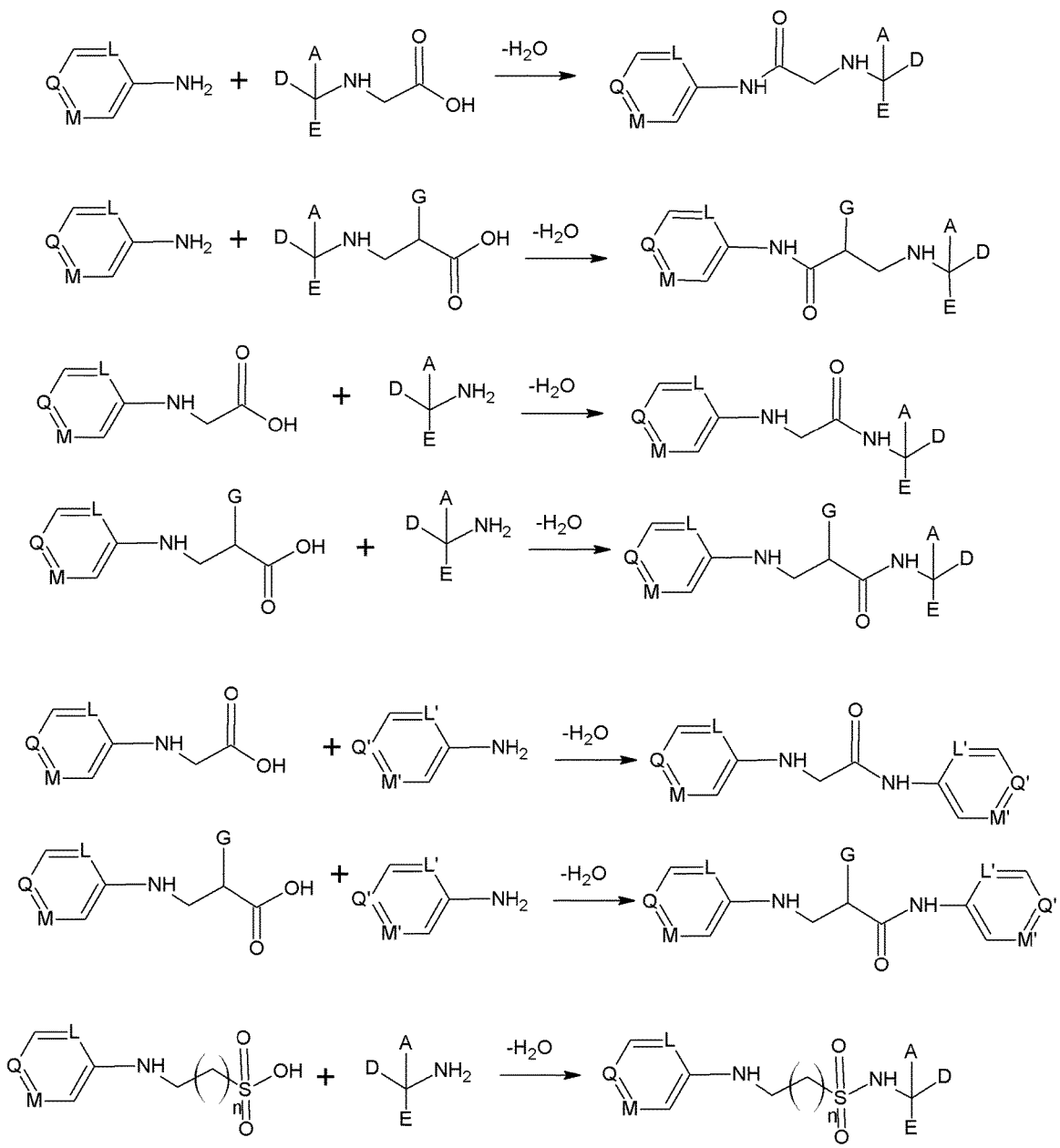
Figure 124:
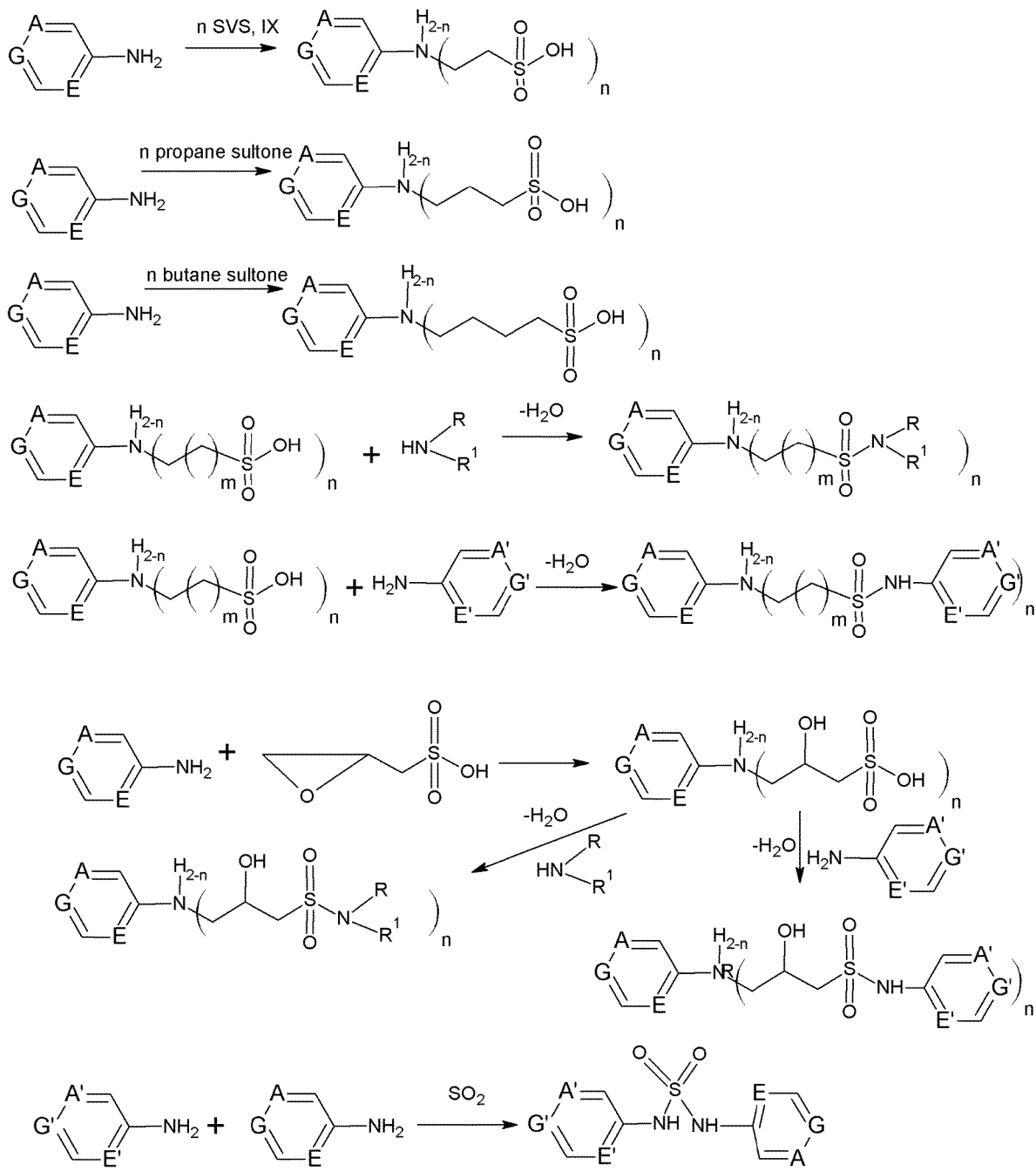
FIG. 124 expands the work with 4-Aminopyridine to include 2-aminopyridine and 3-aminopyridine, as well as introduces sulfamides that act as channel blockers and antibiotics. Where n is 1 or 2. A, A', G, G', E and E', is chosen from N or C. m is an integer from 1 to 6. R, R1 and J are independently chosen from alkyl, saturated or unsaturated, branched or linear, from 1 to 22 carbons, —H, —CH2OH, —CH2CH2OH, —C(Q)(Q')(Q") where Q,Q', and Q" are independently chosen from —H, —CH3, —CH2CH3, —CH2OH, L is chosen from —H, —CH3, —CH2CH3, —OH. n is 1 or 2, m is an integer from 1 to 6.
Figure 125:
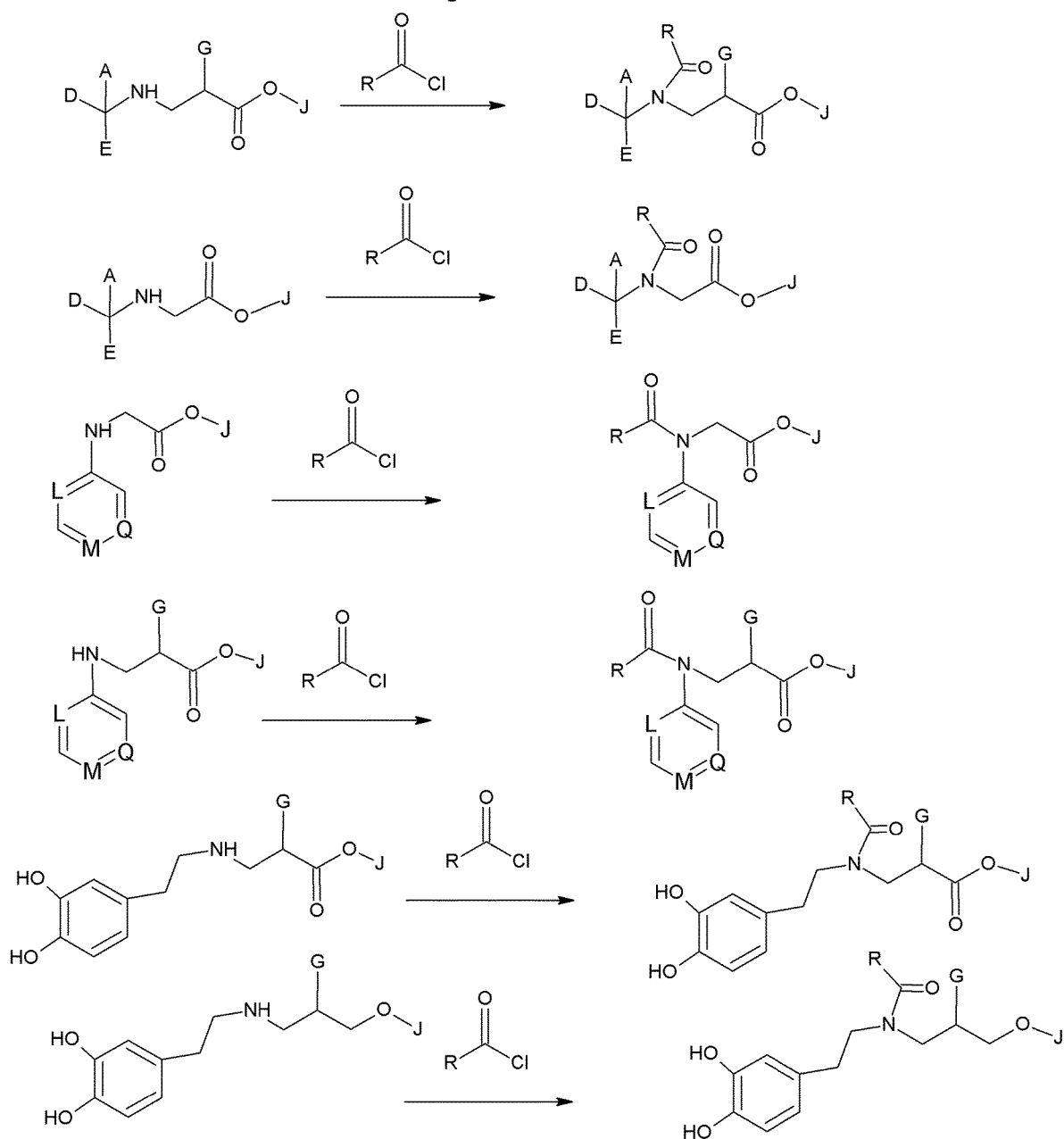
FIG. 125 teaches a series of mild zwitterionic surfactants, where A, D and E are independently chosen from —H, —CH3, —CH2CH3, —CH2CH2CH3, —CH2OH, —CH2COOH, —CH2CH2COOH, —CH2CH(CH3)

FIGS. 121-123 expand on the buffers of 4-aminopyridine to include 2-aminopyridine and 3-aminopyridine. FIG. 121 specifically introduces the monomers and resulting dimers, oligamers, polymers, and copolymers of the monomers. By reacting the acrylate monomer with the aminopyridine under acidic conditions, the ester is formed, while keeping the double bond intact. The resulting monomer can be polymerized with other vinyl group containing monomers, including, but not limited to vinyl chloride, acrylic acid and its esters and the substituted acrylic acids (such as methacrylic acid) and their esters, and ethylene to create amidopyridine functional polymers. In FIGS. 121-123, the carbonyl may be reduced away by the use of lithium aluminum hydride, similar to row 3 in FIG. 100. Alternatively, the allyl alcohol, substituted allyl alcohol (such as methallyl alcohol), or their esters may be substituted for the acrylic acid or substituted acrylic acid or their esters to reach the same molecules. Yields tend to be less, and generally require a stripping step to remove the unreacted components, but requires less capable equipment. This is true for the previous examples, such as FIG. 100, and the other figures where LAH is shown to reduce the carbonyl of an acid or ester to yield the alcohol or ether. FIG. 124 teaches a series of channel blockers/regulators that are based on aminopyridines. Additionally, antibiotic properties are present in diaminopyridine sulfonamides. FIGS. 125-127 teach the synthesis of mild surfactants with bioactivity. FIG. 128 teaches the synthesis of an amino sugar that has antiviral properties in addition to zwitterionic buffering. The reduction in step two must be done with a mild reducing agent to prevent the reduction of the phosphonate while reducing the nitro to the amine. Commercially acceptable results are achieved with Fe powder.

FIG. 129 clarifies some of the FIG. 117 derivatives. The ester and amide derivatives that are present in FIG. 129 are shown as mono esters and mono amides, the esters can be made to the extent of the presence of alcohol groups on the nitro alcohols. The esters and amides need not all have the same alkyl groups. Sequential esterification or amidization with differing alkyl groups can be utilized to produce polyamides, polyesters, and amidoesters that have varying alkyl groups.

The esters can also be made if the amine groups have been derivatized to tertiary amines as already shown in the previous figures, or as amides. The aminoalcohols or amino esters can similarly can be derivatized into amides to the extent that primary amines exist. FIG. 129 only shows the mono amide, but the polyamides are also part of the invention, including the specific case where nitroparaffins are reacted in molar equivalents greater than one to the one of the aldehydes, such as the case of nitromethane shown in FIG. 117. The nitro alcohols and amino alcohols can still be alkoxylated in the same manner as has been shown multiple times in previous figures where the alkoxylating agent adds at the non-tertiary amines or alcohol groups. The primary or secondary amines, as well as the free hydroxyl groups can made to react with acrylonitrile to form nitriles or polynitriles and either used as is, or the nitrile groups reduced to amino groups with sponge metal catalysts and hydrogen or other reducing agents. The resulting polyamines are also useful once alkoxylated. The amides of the diamines make excellent emulsifiers in asphalt emulsions, the polyamines are excellent anti-strips. By reacting with formaldehyde and phosphorous acid as shown in previous figures, produces phosphonates that are excellent corrosion inhibitors. These derivatives that follow the established derivatization are part of the invention.

FIG. 130 teaches the synthesis of ether amino acid buffers that alter the water solubility of the buffers and can also act as surfactants and antifungal compounds useful in a range of applications including paints and coatings, agriculture and mining. FIG. 131 teaches the synthesis of aromatic ring containing fatty nitro compounds and the amines and polyamines that can be obtained from them. In the case where A and/or D are —$CH_2CH_2CN$, when reduction steps occur, primarily to convert —$NO_2$ groups to primary amines, the nitrile will also be reduced to the corresponding primary amine. The addition of additional moles of acrylonitrile can be extended beyond 2 moles and can be added one mole at a time, followed by reduction, to introduce linear polyamines, or multiple moles at a time to create branched polyamines. Additional moles beyond two are part of this invention. These products are useful collectors in mining in both direct or conventional floatation as well as reverse flotation. FIG. 132 and FIG. 133 teach the synthesis of poly primary amines. These poly primary amines are very useful as mining collectors, asphalt emulsifiers, and fuel additives. The amines taught can further be made into higher poly amines by reaction with acrylonitrile followed by reduction with nickel or other catalyst and hydrogen. This can be done with ratios of 2 moles of acrylonitrile to one mole of amine, or 1 to 1. Ratios of greater than 1:1 acrylonitrile: primary amine results in greater branching and disubstitution resulting in a greater proportion of tertiary amine at the acylation site. Further, the alcohol groups may also be reacted with acrylonitrile to form an ether amine moiety. Alcohol and amine groups can similarly be reacted with oxyalkylating agents, the most common being ethylene oxide. Where the figures show ethylene oxide used as an alkoxylating agent, it is understood that any oxyalkylating agent may be used and the analogous product will be produced. Other oxyalkylating agents, include, but are not limited to propylene oxide and butylene oxide. The oxyalkylation can be carried out in steps with alternating oxyalkylating agents to create block copolymer groups. FIG. 134 expands on this idea by teaching that the oxyalkylations described, including the formation of block copolymers of different alkoxylating agents, such as ethylene oxide and propylene oxide can be followed with the reaction of acrylonitrile on the terminal hydroxyl and reduced to the corresponding amine group(s). FIG. 134 further expands on FIG. 132 and FIG. 133 by teaching the oxyalkylation of the amine groups, as well as the subsequent amines formed when the oxyalkylated amine groups are then reacted with acrylonitrile on the terminal hydroxyl and reduced with hydrogen or other reducing agents to form the ether amine groups. While not explicitly shown in FIG. 134, it is understood that the hydroxyl terminated species of A and D, similar to those of FIGS. 132 and 134 can be oxyalkylated prior to addition of acrylonitrile and subsequent reduction to form the ether amines. Similarly, the amines, particularly the amine pendant to the central carbon, can be oxyalkylated with a single or stepwise multiple alkoxylating agents and then optionally reacted with acrylonitrile and reduced to form the ether amine groups. Similarly, these terminal amine groups can be made into higher polyamines by additional stepwise additions of acrylonitrile followed by reductions, or alkoxylated and optionally reacted stepwise with acrylonitrile and reduced to the corresponding polyamines. These stepwise derivations with alkoxylating agents or acrylonitrile followed by reduction can be done in any order in any number of stepwise additions, or singularly in a batch reactor, but a very complicated product will result in this single step approach.

For all the molecules taught herein where a starting material is a carboxcylic acid, an aldehyde, or an acid chloride, the tall oil fatty acid analog, containing the five membered ring, is included, as are the rosin acids analogs. Both generally included under the alkyl cyclic designation.

An additional use for the molecules taught herein is the use in print media to reduce bronzing, similar to that taught in U.S. patent application Ser. No. 12/248,323, which is incorporated by reference. Additionally, the bioactive nature of these molecules makes many of them antimicrobial in nature. The use of these molecules, particularly, but not only, the carboxcylic acid functional molecules and there salts show this property under a wide range of conditions. The use of the molecules disclosed in this invention are also known to exhibit synergistic antimicrobial properties when used in combination with other known antimicrobials. The antimicrobials known to show synergy include, but are not limited to isothiazolinones, carbamates, formaldehyde condensates, formaldehyde donors, phenols, parabens, quaternary ammonium compounds, methylenes, metals and their organic salts, halogenated organics and inorganics, hexetidine, phthalates, sulfonamides and all other antimicrobials. In addition to the other uses for the invention described are as gas scrubbing amines for removal of acid gases, such as $CO_2$, $H_2S$, $CO$ and other acidic gases from industrial processes. They can be used alone, or in combination with other amines, solvents, and all other known means of removing acid gases. Further application of the molecules disclosed herein is the use as dispersants for minerals, pigments, chelation of cations, corrosion inhibition, and the prevention of scale formation. The molecules taught also have great potential as herbicides or adjuvents, particularly when used with other adjuvents, but also alone. Adjuvents that are expected to increase the efficacy, weather used alone or in combinations that may include other surfactants, solvents, or coupling agents include alcohols, amines, ethyleneamines, alkoxylated amines, alkoxylated alcohols, ether amines, alkoxylated etheramines, taurates, sarcosinates, polyethylene glycol, polypropylene glycol, EO/PO block polymers and other non-ionic surfactants, particularly the broad class of alkoxylates. It is also expected that the molecules taught will be tolerated by glyphosate tolerant crops.

Furthermore, the zwitterionic buffers of this invention find use in the electronics industry and other applications that require the precise control of pH while keeping the ionic strength low, or requires that the counter ion be larger than typical mineral acid or mineral base counter ions as conjugate acids or bases. An example is the process of chemical mechanical planarization used in the manufacture of semiconductor wafers. The presence of chlorine or sodium ions poison the n or p holes of the wafer, the use of the zwitterionic buffers here allow for effective buffering and dispersion, while being large enough to be excluded from the n and p holes of the wafer. This same set of properties that are present in the disclosed buffers is also beneficial in paints and coatings as the lack of mineral acids and bases as conjugate acids/conjugate bases reduces the corrosion potential and reduces or eliminates flash rusting of metal substrates. Additional known benefits include: bioactivity, bioresistance/fungal resistance, antimicrobial synergists, dispersion, surfactancy, prevention of print bronzing, emulsion stabilization, ion complex stabilization, cross linking of guar and other hydroxyl functional polymers, bentonite and other clay surface passivation, acid gas or base sequestering (especially hydrogen sulfide). The molecules find use in therapies for diseases and illnesses that target nerves, ion channels, myelin, and form amyloid plaques, as well as antivirals, and therapies for rheumatoid. The molecules are also useful in treating spinal cord injuries by restoring some nerve function by potassium channel blocking. The molecules are also useful in agriculture as adjuvents and surfactants with bioresistant properties that do not increase the biodegradation potential of the final product, and polymer building blocks with asymmetric reactivity. The molecules taught also have the ability to inhibit enzymes, such as 5-enolpyruvylshikimate 3-phosphate synthase. The molecules described also have potential as insecticide and insecticide precursors, and anti-cancer agents, and autoimmune disease therapies, particularly the phosphamides. The aminopyridines in addition to their use as an Alzheimer's therapy, a treatment for neurodiseases or injuries that effect the myelin sheath, and Parkinson's disease, these molecules have shown promise in diabetes treatment of type I or neonatal, as well as pain treatments (local and general anesthetic), arrhythmia and angina treatments, and mucosal dryness.

The diacid buffers are very strong chelators, as are the monoacids. These molecules find utility anywhere strong chelants are valuable, including agriculture, oilfield, hydraulic fracturing, pharmaceuticals and pharmaceutical delivery systems, waste removal, water treatment, personal care, paints and coatings, semiconductor manufacturing, and surface treating. The changes in solubility that occur when complexed versus free zwitterion can be taken advantage of to adjust the availability of the chelated species or the zwitterion, either by timing, hydrophilic/hydrophobic, solids/liquids, liquids/gasses, solids/gasses. The solubility changes can also be taken advantage of to separate ions from solution (gas or liquid) or assist in solvating ions.

Several descriptions and illustrations have been presented to enhance understanding of the present invention. One skilled in the art will know that numerous changes and variations are possible without departing from the spirit of the invention. Each of these changes and variations are within the scope of the present invention.

The invention claimed is:

1. The fuel additive or mining collector of the following structure:

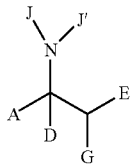

where A and D are independently chosen from —CH3, —CH2CH3, —CH2CH2CH3, —CH2OH, —CH2COOH, —CH2CH2COOH, G is chosen from —O(CH2CH2O)$_n$—(CH2CH(CH3)O)$_m$—(CH2CH(CH2CH3)O)$_q$—(CH2CH2CH2NH)$_r$H; E is chosen from alkyl, saturated or unsaturated, branched or linear, cyclic or acyclic with from 6-22 carbons, J and J' are independently chosen from —H, —(CH2CH2O)n'—(CH2CH(CH3)O)m'—(CH2CH(CH2CH3)O)q'—CH2CH2CH2NH)r'H; wherein, n, n', m, m', q, q', r and r' are non-negative integers; wherein n, m, q and r are not all zero.

2. The fuel additive or mining collector of claim 1 wherein A=D=—CH2OH, E=—C11H23, J=J'=—H, G=—O(CH2CH2O)$_n$—(CH2CH(CH3)O)$_m$—(CH2CH(CH2CH3)O)$_q$—(CH2CH2CH2NH)$_r$H, where n=3, m=q=r=0.

3. The fuel additive or mining collector of claim 1 wherein A=D=—CH3, E=—C11H23, J=J'=—H, G=—O(CH2CH2O)$_n$—(CH2CH(CH3)O)$_m$—(CH2CH(CH2CH3)O)$_q$—(CH2CH2CH2NH)$_r$H, where n=3, m=q=r=0.

4. The fuel additive or mining collector of claim 1 wherein A=D=—CH3, E=—C11H23, J=J'=—H, G=—O(CH2CH2O)$_n$—(CH2CH(CH3)O)$_m$—(CH2CH(CH2CH3)O)$_q$—(CH2CH2CH2NH)$_r$H, where m=3, n=q=r=0.

5. The fuel additive or mining collector of claim 1 wherein A=D=—CH3, E=—C11H23, J=J'=—H, G=—O(CH2CH2O)$_n$—(CH2CH(CH3)O)$_m$—(CH2CH(CH2CH3)O)$_q$—(CH2CH2CH2NH)$_r$H, where n=3, m=q=0, r=1.

6. The fuel additive or mining collector of claim 1 wherein A=D=—CH3, E=—C11H23, J=J'=—H, G=—O(CH2CH2O)$_n$—(CH2CH(CH3)O)$_m$—(CH2CH(CH2CH3)O)$_q$—(CH2CH2CH2NH)$_r$H, where m=3, n=q=0, r=1.

7. The fuel additive or mining collector of claim 1, wherein A and D=—CH3.

8. The fuel additive or mining collector of claim 1, wherein A —CH3 and D=—CH2CH3.

9. The fuel additive or mining collector of claim 1, wherein A and D=—CH2CH3.

10. The fuel additive or mining collector of the following Structure:

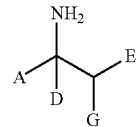

where A and D are independently chosen from —CH3, —CH2CH$_3$, —CH2CH2CH$_3$, —CH2OH, —CH2COOH, —CH2CH2COOH, —CH2CH(CH$_3$)COOH, —CH2PO(OH)$_2$, —(CH2CH2O)$_n$—(CH2CH(CH3)O)$_m$—(CH2CH(CH2CH3)O)$_q$H, —(CH2CH2CH2NH)$_{n'}$H, —CH2O(CH2CH2CH2NH)$_{n''}$H; G is chosen from —O(CH2CH2O)$_{n'''}$—(CH2CH(CH3)O)$_{m'}$—(CH2CH(CH2CH3)O)$_{q'}$H, —O(CH2CH2CH2NH)$_{n''''}$H; E is chosen from alkyl, saturated or unsaturated, branched or linear, cyclic or acyclic with from 6-22 carbons;

wherein n, n, n', n'', n''', n'''', m, m', q and q' are non-negative integers, wherein n, m, and q are not all zero, wherein n''', m', and q' are not all zero, and wherein neither n' nor n'''' is zero.

11. The fuel additive or mining collector of claim 10, wherein A and D=—CH3.

12. The fuel additive or mining collector of claim 10, wherein A —CH3 and D=—CH2CH3.

13. The fuel additive or mining collector of claim 10, wherein A and D=—CH2CH3.

* * * * *